United States Patent
Bennett et al.

(10) Patent No.: US 11,028,180 B2
(45) Date of Patent: Jun. 8, 2021

(54) ANTI-JAGGED1 ANTIGEN BINDING PROTEINS

(71) Applicant: AMGEN INC., Thousand Oaks, CA (US)

(72) Inventors: Brian D. Bennett, Thousand Oaks, CA (US); Chadwick T. King, Thousand Oaks, CA (US); Jonathan Phillips, Thousand Oaks, CA (US)

(73) Assignee: AMGEN INC., Thousand Oaks, CA (US)

( * ) Notice: Subject to any disclaimer, the term of this patent is extended or adjusted under 35 U.S.C. 154(b) by 44 days.

(21) Appl. No.: 15/993,448

(22) Filed: May 30, 2018

(65) Prior Publication Data

US 2019/0023802 A1   Jan. 24, 2019

Related U.S. Application Data

(60) Provisional application No. 62/512,805, filed on May 31, 2017.

(51) Int. Cl.
| | |
|---|---|
| *A61K 39/395* | (2006.01) |
| *C07K 16/22* | (2006.01) |
| *C07K 16/28* | (2006.01) |
| *A61P 37/00* | (2006.01) |
| *C07K 14/52* | (2006.01) |
| *A61K 39/00* | (2006.01) |

(52) U.S. Cl.
CPC ...... *C07K 16/2896* (2013.01); *A61K 39/3955* (2013.01); *A61P 37/00* (2018.01); *C07K 16/22* (2013.01); *A61K 39/39558* (2013.01); *A61K 2039/505* (2013.01); *A61K 2039/545* (2013.01); *C07K 2317/21* (2013.01); *C07K 2317/33* (2013.01); *C07K 2317/34* (2013.01); *C07K 2317/56* (2013.01); *C07K 2317/565* (2013.01); *C07K 2317/76* (2013.01); *C07K 2317/92* (2013.01); *C07K 2319/20* (2013.01)

(58) Field of Classification Search
CPC .......... A61K 2039/505; A61K 39/3955; A61K 39/39558; A61K 39/395; C07K 2317/76; C07K 2317/92; C07K 2317/21; C07K 16/18; C07K 2317/56; C07K 2317/73; C07K 16/22; C07K 2317/565; C07K 2317/54; C07K 16/24
See application file for complete search history.

(56) References Cited

U.S. PATENT DOCUMENTS

| | | | |
|---|---|---|---|
| 3,773,919 A | 11/1973 | Boswell et al. | |
| 4,399,216 A | 8/1983 | Axel et al. | |
| 4,619,794 A | 10/1986 | Hauser | |
| 4,740,461 A | 4/1988 | Kaufman | |
| 4,912,040 A | 3/1990 | Kaufman | |
| 4,946,778 A | 8/1990 | Ladner et al. | |
| 4,959,455 A | 9/1990 | Clark et al. | |
| 4,965,195 A | 10/1990 | Namen et al. | |
| 4,968,607 A | 11/1990 | Dower et al. | |
| 5,011,912 A | 4/1991 | Hopp et al. | |
| 5,260,203 A | 11/1993 | Ladner et al. | |
| 5,292,658 A | 3/1994 | Cormier et al. | |
| 5,418,155 A | 5/1995 | Cormier et al. | |
| 5,530,101 A | 6/1996 | Queen et al. | |
| 5,545,806 A | 8/1996 | Lonberg et al. | |
| 5,545,807 A | 8/1996 | Surani et al. | |
| 5,569,825 A | 10/1996 | Lonberg | |
| 5,585,089 A | 12/1996 | Queen et al. | |
| 5,625,126 A | 4/1997 | Lonberg et al. | |
| 5,633,425 A | 5/1997 | Lonberg et al. | |
| 5,661,016 A | 8/1997 | Lonberg et al. | |
| 5,683,888 A | 11/1997 | Campbell | |
| 5,693,761 A | 12/1997 | Queen et al. | |
| 5,693,762 A | 12/1997 | Queen et al. | |
| 5,741,668 A | 4/1998 | Ward et al. | |
| 5,770,429 A | 6/1998 | Lonberg et al. | |
| 5,777,079 A | 7/1998 | Tsien et al. | |
| 5,789,650 A | 8/1998 | Lonberg et al. | |
| 5,804,387 A | 9/1998 | Cormack et al. | |
| 5,814,318 A | 9/1998 | Lonberg et al. | |
| 5,874,299 A | 2/1999 | Lonberg et al. | |
| 5,874,304 A | 2/1999 | Zolotukhin et al. | |
| 5,876,995 A | 3/1999 | Bryan | |
| 5,877,397 A | 3/1999 | Lonberg et al. | |
| 5,925,558 A | 7/1999 | Tsien et al. | |
| 6,136,952 A * | 10/2000 | Li ........................ | C07K 14/705 435/372 |
| 6,162,963 A | 12/2000 | Kucherlapati et al. | |
| 6,180,370 B1 | 1/2001 | Queen et al. | |

(Continued)

FOREIGN PATENT DOCUMENTS

| | | | |
|---|---|---|---|
| EP | 0 036 676 A1 | 9/1981 | |
| EP | 0 058 481 A1 | 8/1982 | |

(Continued)

OTHER PUBLICATIONS

Lloyd et al. Modelling the human immune response: performance of a 10×11 human antibody repertoire against a broad panel of therapeutically relevant antigens. Protein Engineering Design Selection 22(3): 159-168, 2009.*

Zheng et al. Therapeutic antibody targeting tumor- and osteoblastic niche-derived Jagged 1 sensitizes bone metastasis to chemotherapy. Cancer Cell 32: 731-747, Dec. 2017.*

Ausubel et al., eds., *Current Protocols in Molecular Biology*, Green Publishers Inc. and Wiley and Sons (1994) (Table of Contents Only).

Ausubel, F. M. et al., eds., *Current Protocols in Molecular Biology*, Greene Publishing Associates and Wiley and Sons (1992) (Table of Contents Only).

(Continued)

*Primary Examiner* — Bridget E Bunner
(74) *Attorney, Agent, or Firm* — Jonathan M. Dermott

(57) ABSTRACT

Methods of treating conditions related to lung disease using an antigen binding protein specific for the Jagged1 polypeptide are provided.

11 Claims, 34 Drawing Sheets

Specification includes a Sequence Listing.

(56) References Cited

U.S. PATENT DOCUMENTS

| | | | |
|---|---|---|---|
| 6,255,458 B1 | 7/2001 | Lonberg et al. | |
| 6,270,964 B1 | 8/2001 | Michnick et al. | |
| 6,300,129 B1 | 10/2001 | Lonberg et al. | |
| 6,673,986 B1 | 1/2004 | Kucherlapati et al. | |
| 6,703,198 B1 * | 3/2004 | Li | C07K 14/705 |
| | | | 435/6.11 |
| 6,703,489 B1 | 3/2004 | Ish-Horowicz et al. | |
| 6,713,610 B1 | 3/2004 | Kucherlapati et al. | |
| 8,802,103 B2 | 8/2014 | Gurney et al. | |
| 8,945,569 B2 | 2/2015 | Gurney et al. | |
| 9,127,053 B2 * | 9/2015 | West | A61K 47/6803 |
| 9,518,121 B2 | 12/2016 | Chinn et al. | |
| 9,550,829 B2 * | 1/2017 | French | A61K 47/6849 |
| 9,688,748 B2 * | 6/2017 | West | A61K 39/39558 |
| 9,725,518 B2 | 8/2017 | Banham et al. | |
| 9,982,058 B2 * | 5/2018 | French | A61K 47/6849 |
| 10,011,661 B2 * | 7/2018 | Chinn | A61P 1/00 |
| 10,113,002 B2 * | 10/2018 | Siebel | C07K 16/28 |
| 10,350,216 B2 * | 7/2019 | Kousteni | G01N 33/57426 |
| 10,435,476 B2 * | 10/2019 | Swanson | C07K 16/2896 |
| 2008/0260734 A1 * | 10/2008 | Clarke | A61K 38/005 |
| | | | 424/133.1 |
| 2013/0309246 A1 * | 11/2013 | Kang | C12Q 1/6886 |
| | | | 424/158.1 |
| 2014/0010810 A1 * | 1/2014 | West | C07K 16/2896 |
| | | | 424/134.1 |
| 2014/0314749 A1 * | 10/2014 | French | A61P 1/16 |
| | | | 424/133.1 |
| 2015/0232568 A1 * | 8/2015 | Siebel | C07K 16/2896 |
| | | | 424/139.1 |
| 2015/0329918 A1 * | 11/2015 | Kang | C12Q 1/6886 |
| | | | 424/152.1 |
| 2015/0359799 A1 * | 12/2015 | Kousteni | C07K 16/18 |
| | | | 424/172.1 |
| 2016/0257759 A1 * | 9/2016 | Swanson | C07K 16/2896 |

FOREIGN PATENT DOCUMENTS

| | | |
|---|---|---|
| EP | 0 058 481 B1 | 8/1982 |
| EP | 0 058 481 B2 | 8/1982 |
| EP | 0 088 046 A3 | 7/1983 |
| EP | 0 088 046 B1 | 7/1983 |
| EP | 0 088 046 A2 | 9/1983 |
| EP | 0 036 676 B1 | 7/1984 |
| EP | 0 133 988 A2 | 3/1985 |
| EP | 0 143 949 A1 | 6/1985 |
| EP | 0 143 949 B1 | 6/1985 |
| EP | 0 036 676 B2 | 9/1990 |
| EP | 0 460 846 A1 | 12/1991 |
| EP | 0 460 846 B1 | 12/1991 |
| EP | 0 546 073 A1 | 3/1992 |
| EP | 0 546 073 B1 | 6/1993 |
| EP | 0 546 073 A4 | 4/1994 |
| EP | 3 105 253 B1 | 6/2018 |
| KR | 10-2015 0123049 A | 11/2015 |
| WO | 88/01649 A1 | 3/1988 |
| WO | 90/04036 A1 | 4/1990 |
| WO | 91/10741 A1 | 7/1991 |
| WO | 92/03918 A1 | 3/1992 |
| WO | 92/15673 A1 | 9/1992 |
| WO | 92/22646 A1 | 12/1992 |
| WO | 93/01227 A1 | 1/1993 |
| WO | 93/015722 A1 | 8/1993 |
| WO | 94/02602 A1 | 3/1994 |
| WO | 94/020069 A1 | 9/1994 |
| WO | 95/07463 A1 | 3/1995 |
| WO | 96/33735 A1 | 10/1996 |
| WO | 98/14605 A1 | 4/1998 |
| WO | 98/24893 A1 | 6/1998 |
| WO | 98/26277 A2 | 6/1998 |
| WO | 99/10494 A2 | 3/1999 |
| WO | 99/49019 A2 | 9/1999 |
| WO | 2009/124931 A2 | 10/2009 |
| WO | 2011/063237 A2 | 5/2011 |
| WO | 2014/028446 A1 | 2/2014 |
| WO | 2014/111704 A1 | 7/2014 |
| WO | WO-2015123325 A1 * | 8/2015 |

OTHER PUBLICATIONS

Bianchi, A. A. and Mcgrew, J. T., "High-Level Expression of Full-Length Antibodies Using Trans-Complementing Expression Vectors," *Biotechnol. and Bioeng.*, 84(4):439-444 (2003).

Bootcov, M. R. et al., "MIC-1, a novel macrophage inhibitory cytokine, is a divergent member of the TGF-β superfamily," *Proc. Natl. Acad. Sci. USA*, 94:11514-11519 (1997).

Bowie, J. U. et al., "A Method to Identify Protein Sequences that Fold into a Known three-Dimensional Structure," *Science*, 253:164-170 (1991).

Branden, C. and Tooze, J., eds., *Introduction to Protein Structure*, New York: Garland Publishing (1991) (Table of Contents Only).

Brenner, S. E. et al., "Population statistics of protein structures: lessons from structural classifications," *Curr. Op. Struct. Biol.*, 7:369-376 (1997).

Bruggermann, M. et al., "Designer Mice: The Production of Human Antibody Repertoires in Transgenic Animals," *Year in Immunol.*, 7:33-40 (1993).

Carrillo, H. et al., "The Multiple Sequence Alignment Problem in Biology," *SIAM J. Appl. Math.*, 48(5):1073-1082 (1988).

Chalfie, M. et al., "Green Fluorescent Protein as a Marker for Gene Expression," *Science*, 263:802-805 (1994).

Chen, J. et al., "Immunoglobulin gene rearrangement in B cell deficient mice generated by targeted deletion of the $J_H$ locus," *International Immunology*, 5(6):647-656 (1993).

Cheung, R. C. et al., "Epitope-Specific Antibody Response to the Surface Antigen of Duck Hepatitis B Virus in Infected Ducks," *Virology*, 176:546-552 (1990).

Chothia, C. et al., "Conformations of immunoglobulin hypervariable regions," *Nature*, 342:877-883 (1989).

Chothia, C. and Lesk, A. M., "Canonical Structures for the Hypervariable Regions of Immunoglobulins," *J. Mol. Biol.*, 196:901-917 (1987).

Chou, P. Y. et al., "Prediction of β-Turns," *Biophys. J.*, 26:367-384 (1979).

Chou, P. Y. et al., "Empirical Predictions of Protein Conformation," *Ann. Rev. Biochem.*, 47:251-276 (1978).

Chou, P. Y. et al., "Predictions of the Secondary Structure of Proteins from Their Amino Acid Sequence," *Adv. Enzymol. Relat. Areas Mol. Biol.*, 47:45-148 (1978).

Chou, P. Y. et al., "Conformational Parameters for Amino Acids in Helical, β-Sheet, and Random Coil Regions Calculated from Proteins," *Biochem.*, 13(2):211-222 (1974).

Chou, P. Y. et al., "Prediction of Protein Conformation," *Biochem.*, 13(2):222-245 (1974).

Coligan, John E., ed., *Current Protocols in Immunology*, New York: John Wiley & Sons, Inc. (1994) (Table of Contents Only).

Creighton, Ed., *Proteins: Structure and Molecular Properties*, 2$^{nd}$ ed., W. H. Freeman and Company, N.Y. (1984) (Table of Contents Only).

Danahay et al., "Notch2 is Required for Inflammatory Cytokine-Driven Goblet Cell Metaplasia in the Lung," *Cell Reports*, 10:239-252 (2015).

Dayhoff, M. O., ed, *Atlas of Protein Sequence and Structure*, 5(3):345-352 (1978), Copyright 1979.

Devereux, J. J et al., *Nucl. Acid Res.*, 12(1):387-395, Genetics Computer Group, University of Wisconsin, Madison, WI (1984).

Evans, B. E. et al., "Design of Nonpeptidal Ligands for a Peptide Receptor: Cholecystokinin Antagonists," *J. Med. Chem.* 30:1229-1239 (1987).

Fairlie, W. D., "Expression of a TGF-β superfamily protein, macrophage inhibitory cytokind-1, in the yeast *Pichia pastoris*," *Gene*, 254:67-76 (2000).

Fauchere, J-L. Elements for the Rational Design of Peptide Drugs, *Adv. Drug Res.*, 15:29-69 (1986).

(56) References Cited

OTHER PUBLICATIONS

Fishwild, D. M. et al., "High-avidity human IgGκ monoclonal antibodies from a novel strain of minilocus transgenic mice," *Nature Biotechnology*, 14:845-851 (1996).
GenBank U55762.1, "Cloning vector pEGFP-N1, complete sequence, enhanced green fluorescent protein (egfp) and neomycin phosphotransferase genes, complete cds," Clontech Labs, Inc., http://www.ncbi.nlm.nih.gov/nuccore/U55762|Mar. 4, 2016 19:41 PM], Aug. 22, 2003.
Gennaro, A. R. ed., Remington's Pharmaceutical Sciences, 18$^{th}$ Ed., Mack Publishing Company (1990) (Table of Contents Only).
Goeddel, ed., Methods Enzymol., vol. 185, New York: Academic Press (1990) (Table of Contents Only).
Gribskov, M. et al., *Meth. Enzym.*, Searching Databases, Chap. 9, Profile Analysis, 183:146-159 (1990).
Gribskov, M. et al., "Profile analysis: Detection of distantly related proteins," *Proc. Natl. Acad. Sci.*, 84:4355-4358 (1987).
Gribskov, M. and Devereux, J. eds., *Sequence Analysis Primer*, New York: M. Stockton Press (1991) (Table of Contents Only).
Griffin, A. M. and Griffin, H. G., eds., Computer Analysis of Sequence Data, Part I, New Jersey: Humana Press (1994) (Table of Contents Only).
Harding, F. A. and Lonberg, N., "Class Switching in Human Immunoglobulin Transgenic Mice," *Ann. N. Y. Acad. Sci.*, 764:536-546 (1995).
Harlow, E. and Lane, D., *Antibodies: A Laboratory Manual*, Cold Spring Harbor Laboratory Press, Cold Spring Harbor, NY (1988) (Table of Contents Only).
Haugland, R. P., Molecular Probes Handbook: A Guide to Fluorescent Probes and Labeling Technologies, 11th Ed., Invitrogen by ThermoFisher Scientific (2010) (Table of Contents Only).
Heim, R. et al., "Engineering green fluorescent protein for improved brightness, longer wavelengths and fluorescence resonance energy transfer," *Curr. Biol.*, 6:178-182 (1996).
Henikoff, S. et al., "Amino acid substitution matrices from protein blocks," *Proc. Natl. Acad. Sci. USA*, 89:10915-10919 (1992).
Hinke, S. A., et al., "Identification of a bioactive domain in the amino-terminus of glucose-dependent insulinotropic polypeptide (GIP)", *Biochimica et Biophysica Acta*, 1547:143-155 (2001).
Holm, L. et al., "Protein folds and families: sequence and structure alignments," *Nucl. Acid. Res.*, 27(1):244-247 (1999).
Hoogenboom, H. R. et al., "By-passing Immunisation, Human Antibodies from Synthetic Repertoires of Germline $V_H$ Gene Segments Rearranged in Vitro," *J. Mol. Biol.*, 227:381-388 (1991).
Hopp, T. P. et al., "A Short Polypeptide Marker Sequence Useful for Recombinant Protein Identification and Purification," *Bio/Technology*, 6:1204-1210 (1988).
Ichiki, T. et al., "Regulation of the Expression of Human Cε Germline Transcript," *J. Immunol.*, 150(12):5408-5417 (1993).
Jakobovits, A. et al., "Analysis of homozygous mutant chimeric mice: Deletion of the immunoglobulin heavy-chain joining region blocks B-cell development and antibody production," *Proc. Natl. Acad. Sci. USA*, 90:2551-2555 (1993).
Jakobovits, A. et al., "Germ-line transmission and expression of a human-derived yeast artificial chromosome," *Nature*, 362:255-258 (1993).
Jalkanen, M. et al., "Cell Surface Proteoglycan of Mouse Mammary Epithelial Cells is Shet by Cleavage of Its Matrix-binding Ectodomain from Its Membrane-associated Domain," *J. Cell. Biol.*, 105:3087-3096 (1987).
Jalkanen, M. et al., "Heparan Sulfate Proteoglycans from Mouse Mammary Epithelial Cells: Localization on the Cell Surface with a Monoclonal Antibody," *J. Cell. Biol.*, 101:976-984 (1985).
Jones, D. T., "Progress in protein structure prediction," *Curr. Opin. Struct. Biol.*, 7:377-387 (1997).
Jones, P. T. et al., "Replacing the complementarity-determining regions in a human antibody with those from a mouse," *Nature*, 321:522-525 (1986).

Kabat, E. A. et al., *Sequences of Proteins of Immunological Interest*, 5$^{th}$ Ed., U.S. Department of Health and Human Services, PHS, NIH, NIH Publication No. 91-3242 (1991) (Table of Contents Only).
Kabat, E. A., *Sequences of Proteins of Immunological Interest*, NIH, Bethesda, MD (1987 and 1991) (Table of Contents Only).
Kearney, J. F. et al., "A new mouse myeloma cell line that has lost immunoglobulin expression but permits the construction of antibody-secreting hybrid cell lines," *J. Immunol.*, 123(4):1548-1550 (1979).
Kellermann, S. A. et al., "Antibody discovery: the use of transgenic mice to generate human monoclonal antibodies for therapeutics," *Current Opinion in Biotechnology*, 13:593-597 (2002).
Kennet, R. H. et al., Eds., Monoclonal Antibodies, Hybridomas: A New Dimension in Biological Analyses, Plenum Press, New York (1980) (Table of Contents Only).
Kirkland, T. N. et al., "Analysis of the fine specificity and cross-reactivity of monoclonal anti-lipid A antibodies," *J. Immunol.*, 137:3614-3619 (1986).
Koch, U. et al., "Notch and cancer: a double-edged sword," *Cell. Mol. Life Sci.*, 64:2746-2762 (2007).
Kopan, R. et al., "The Canonical Notch Signaling Pathway: Unfolding the Activation Mechanism," *Cell*, 137:216-233 (2009).
Kostelny, S. A. et al., "Formation of a Bispecific Antibody by the Use of Leucine Zippers," *J. Immunol.*, 148(5):1547-1553 (1992).
Kyte, J. et al., "A Simple Method for Displaying the Hydropathic Character of a Protein," *J. Mol. Biol.*, 157:105-132 (1982).
Langer, R. et al., "Controlled release of macromolecules," *CHEMTECH*, 12:98-105 (1982).
Langer, R. et al., "Biocompatibility of polymeric delivery systems for macromolecules," *J. Biomed. Mater. Res.*, 15:267-277 (1981).
Lesk, A. M., ed., Computational Molecular Biology, New York, Oxford University Press. (1988) (Table of Contents Only).
Livraghi-Butrico, A. et al., "Genetically determined heterogeneity of lung disease in a mouse model of airway mucus obstruction," *Physiol. Genomics*, 44:470-484 (2012).
Longerg, N. and Huszar, D., "Human Antibodies from Transgenic Mice," *Intern. Rev. Immunol.*, 13:65-93 (1995).
Lonberg, N. et al., "Antigen-specific human antibodies from mice comprising four distinct genetic modifications," *Nature*, 368:856-859 (1994).
Lonberg, N. et al., "Transgenic Approaches to Human Monoclonal Antibodies," The Pharmacology of Monoclonal Antibodies, Contributors: R. Balint, et al., M. Rosenberg and G. P. Moore, Eds., Springer-Verlag, Berlin Heidelberg, New York, London, Paris, Tokyo, Hong Kong, Barcelona, Budapest, Chapter 3, 113:49-101 (1994).
Maniatis, T. et al., "Regulation of Inducible and Tissue-Specific Gene Expression," *Science*, 236:1237-1244 (1987).
Marks, J. D. et al., "By-passing Immunization Human Antibodies from V-gene Libraries Displayed on Phage," *J. Mol. Biol.*, 222:581-597 (1991).
Mendez, M. J. et al., "Functional transplant of megabase human immunoglobulin loci recapitulates human antibody response in mice," *Nature Genetics*, 15:146-156 (1997).
Moldenhauer, G. et al., "Identity of HML-1 Antigen on Intestinal Intraepithelial T Cells and of B-ly7 Antigen on Hairy Cell Leukaemia," *Scand. J. Immunol.*, 32:77-82 (1990).
Morel, G. A. et al., "Monoclonal Antibodies to Bovine Serum Albumin: Affinity and Specificity Determinations," *Molec. Immunol.*, 25(1):7-15 (1988).
Moult, J., The current state of the art in protein structure prediction, *Curr. Op. in Biotech.*, 7:422-427 (1996).
Needleman, S. B. et al., "A General Method Applicable to the Search for Similarities in the Amino Acid Sequence of Two Proteins," *J. Mol. Biol.*, 48:443-453 (1970).
NIH Publication No. 02-5215, Third Report of the National Cholesterol Education Program (NCEP) Expert Panel on Detection, Evaluation, and Treatment of the High Blood Cholesterol in Adults (Adult Treatment Panel III) Final Report, National Institutes of Health, pp. 3145-3421 (2002).
Nolan, G. P. et al., "Fluorescence-activated cell analysis and sorting of viable mammalian cells based on β-D-galactosidase activity after transduction of *Escherichia coli* lacZ," *Proc. Natl. Acad. Sci.*, 85:2603-2607 (1988).

(56) References Cited

OTHER PUBLICATIONS

Paul, W. E., ed., *Fundamental Immunology*, 2nd ed., Chapter 7, Evolution of the Immune System, Louis Du Pasquier, pp. 139-165, New York: Raven Press (1989) (Table of Contents Only).
Rathanaswami, P. et al., "High affinity binding measurements of antibodies to cell-surface-expressed antigens," *Analytical Biochemistry*, 373:52-60 (2008).
Riechmann, L. et al., "Reshaping human antibodies for therapy," *Nature*, 332:323-327 (1988).
Rizo, J. and Gierasch, L. M., "Constrained Peptides: Models of Bioactive Peptides and Protein Substructures," *Ann. Rev. Biochem.*, 61:387-418 (1992).
Sambrook, J. et al., *Molecular Cloning: A Laboratory Manual*, 3rd Edition, Cold Spring Harbor Laboratory Press, Cold Spring Harbor, NY (2001) (Table of Contents Only).
Sambrook, J. et al., *Molecular Cloning: A Laboratory Manual*, 2nd ed., Cold Spring Harbor Laboratory, Cold Spring Harbor Laboratory Press, Cold Spring Harbor, NY (1989) (Table of Contents Only).
Sidman, K. R. et al., "Controlled Release of Macromolecules and Pharmaceuticals from Synthetic Polypeptides Based on Glutamic Acid," *Biopolymers*, 22:547-556 (1983).
Sippl, M. J. et al., "Threading thrills and threats," *Structure*, 4(1):15-19 (1996).
Smith, D. W., ed., *Biocomputing: Informatics and Genome Projects*, New York: Academic Press, Inc., (1993) (Table of Contents Only).
Songsivilai, S. and Lachmann, P. J., "Bispecific antibody: a tool for diagnosis and treatment of disease," *Clin. Exp. Immunol.*, 79:315-321 (1990).
Stahli, C. et al., "Distinction of Epitopes by Monoclonal Antibodies," *Methods in Enzymology*, 92:242-253 (1983).
Stauber, R. H., et al., "Development and Applications of Enhanced Green Fluorescent Protein Mutants," Quantum Biotechnologies, Inc., Quebec, Canada, *BioTechniques*, 24(3):462-471 (1998).
Taylor, L. D. et al., "Human immunoglobulin transgenes undergo rearrangement, somatic mutation and class switching in mice that lack endogenous IgM," *International Immunology*, 6(4):579-591 (1994).
Taylor, L. D. et al., "A transgenic mouse that expresses a diversity of human sequence heavy and light chain immunoglobulins," *Nucleic Acids Research*, 20(23):6287-6295 (1992).
Thornton, J. M. et al., "Prediction of progress at last," *Nature*, 354:105-106 (1991).
Tijssen, P. et al., *Laboratory Techniques in Biochemistry and Molecular Biology, Practice and Theory of Enzyme Immunoassays*, vol. 15, R. H. Burdon and P. H. van Knippenberg, Eds., Elsevier, Amsterdam (1993) (Table of Contents Only).
Tuaillon, N. et al., "Biased utilization of $D_{HQ52}$ and $J_H4$ gene segments in a human Ig transgenic minilocus is independent of antigenic selection," *J. Immunol.*, 152:2912-2920 (1994).
Van Heeke, G. and Schuster, S. M., "Expression of Human Asparagine Synthetase in *Escherichia coli*," *J. Biol. Chem.*, 264(10):5503-5509 (1989).
Veber, D. F. and Freidinger, R. M., "The design of metabolically-stable peptide analogs," *TINS*, pp. 392-396 (1985).
Verhoeyen, M. et al., "Reshaping Human Antibodies: Grafting an Antilysozyme Activity," *Science*, 239:1534-1536 (1988).
Von Heijne, G., *Sequence Analysis in Molecular Biology, Treasure Trove or Trivial Pursuit*, New York: Academic Press, Inc. (1987) (Table of Contents Only).
Voss, S. D. et al., "The role of enhancers in the regulation of cell-type-specific transcriptional control," *Trends Biochem. Sci.*, 11:287-289 (1986).
Zola, H., *Monoclonal Antibodies: A Manual of Techniques*, Using Monoclonal Antibodies: Soluble Antigens, Chapter 6, pp. 147-158 (CRC Press, Inc., Boca Raton, Florida) (1987).

* cited by examiner

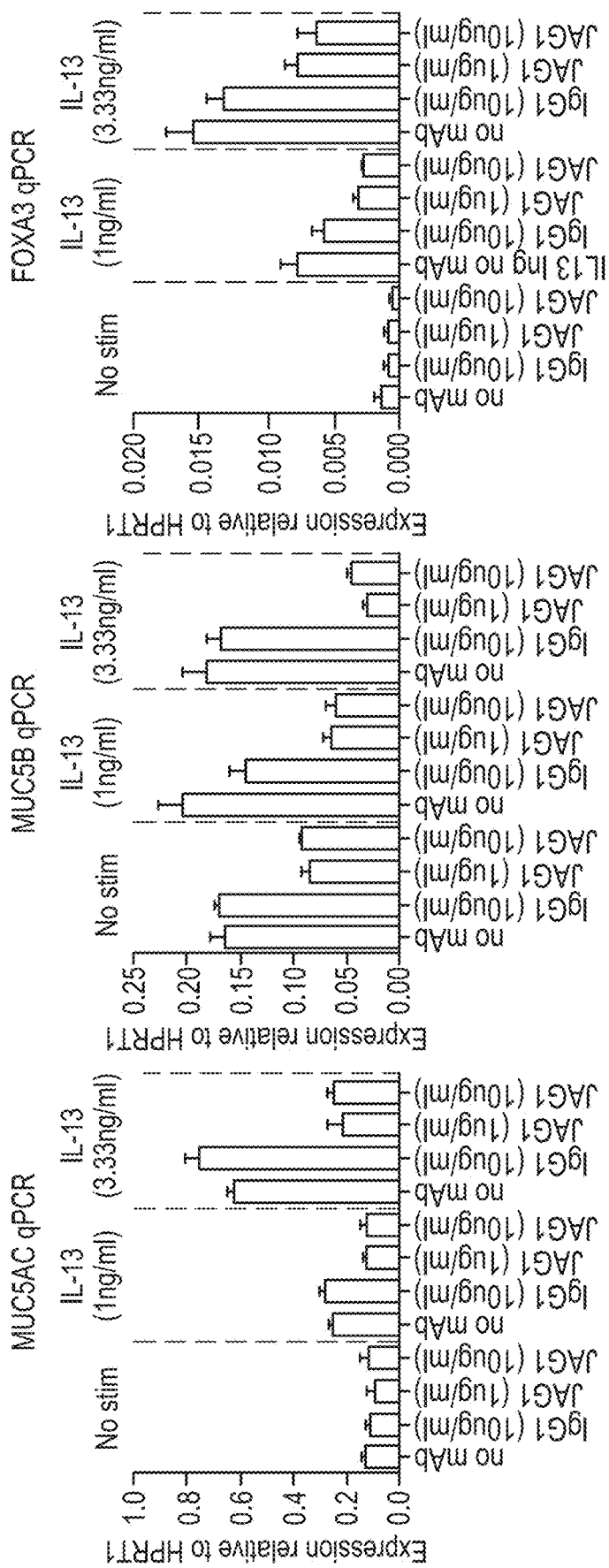

FIG. 3D

**\*HPRT probe** — SEQ ID NO: 359
*Sequence*
5'-/56-FAM/TCCAAAGAT/ZEN/GGTCAAGGTCGCAAG/3IABkFQ/-3'  SEQ ID NO: 360

HPRT primer set
5'-ACTTCCTCCTCCTTTTC-3' → SEQ ID NO: 361
5'-CTTTGCTTTCCTTGGTCAGG-3' → SEQ ID NO: 362

**\*MUC5AC probe** — SEQ ID NO: 363
*Sequence*
5'-/56-FAM/CGTTTGACG/ZEN/GGAAGCAATACACGG/3IABkFQ/-3'  SEQ ID NO: 364

MUC5AC primer set
5'-TACCTGTGCTCTGTGCTTGGAG-3' → SEQ ID NO: 365
5'-AGGGCTTGGTCAGCACATA-3' → SEQ ID NO: 366

**\*MUC5B probe** — SEQ ID NO: 367
*Sequence*
5'-/56-FAM/AACCCGTA/ZEN/GAAGGTGCCATTGT/3IABkFQ/-3'  SEQ ID NO: 368

MUC5B primer set
5'-CCAGAGAGGCAGGTACACAT-3' → SEQ ID NO: 369
5'-GCAGACCTCAGCTGTGTT-3' → SEQ ID NO: 370

| Experimental Group | Drug |
|---|---|
| Group A - Saline/Saline | Vehicle |
| Group B - Saline/Saline | Jag1 (80mpk) |
| Group C - Saline/Saline | Isotype Control (80 mpk) |
| Group D - OVA/OVA | Vehicle |
| Group E - OVA/OVA | Jag1 |
| Group F - OVA/OVA | Isotype Control |
| Group G - OVA/OVA | aTSLP (20mpk) |

Immunization (IP) on day 0 &14
Ab administration (IV) on day 0, 7, 14 & 20
OVA challenge (IH) on day 21, 23, 24 & 26

NRARP Normal Healthy Donor #448751

SCGB1A1 CF Donor #KK030G

MUC5AC CF Donor #KK030G

DNAI2 CF Donor #KK030G

NRARP CF Donor #KK030G

SCGB1A1 COPD Donor #OF3207

MUC5AC COPD Donor #OF3207

DNAI2 COPD Donor #OF3207

NRARP COPD Donor #OF3207

SCGB1A1 Normal Healthy Donor #448751

MUC5AC Normal Healthy Donor #448751

DNAI2 Normal Healthy Donor #448751

NRARP Normal Healthy Donor #448751

SCGB1A1 CF Donor #KK030G

MUC5AC CF Donor #KK030G

DNAI2 CF Donor #KK030G

NRARP CF Donor #KK030G

SCGB1A1 COPD Donor #OF3207

MUC5AC COPD Donor #OF3207

DNAI2 COPD Donor #OF3207

NRARP COPD Donor #OF3207

IL-13 driven model (C57BL/6)

FIG. 20A Nasopharynx
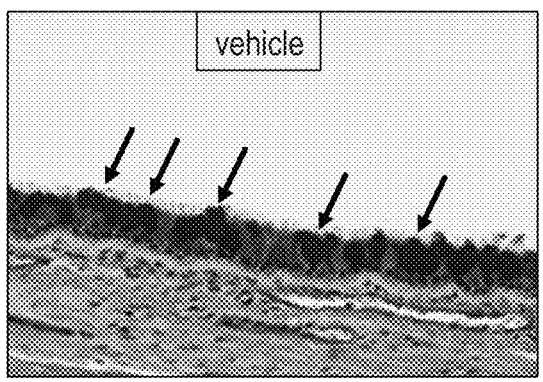
vehicle
FIG. 20B Trachea
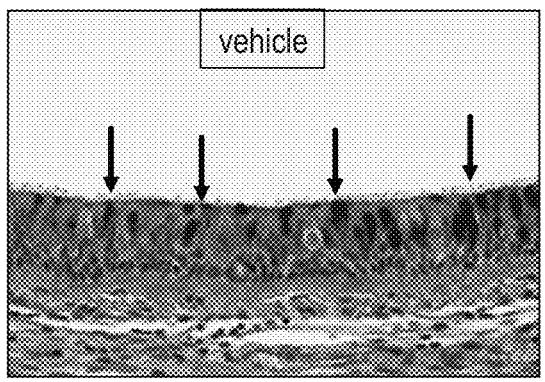
vehicle
FIG. 20C Bronchus
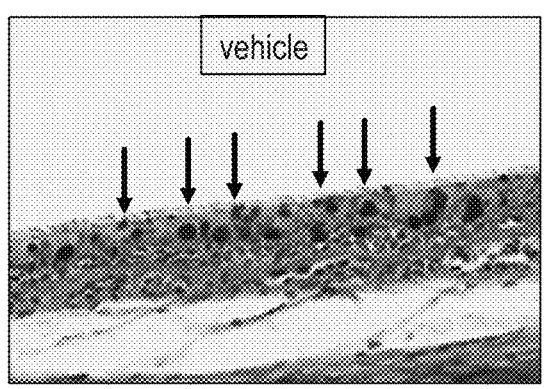
vehicle
FIG. 20D Nasopharynx
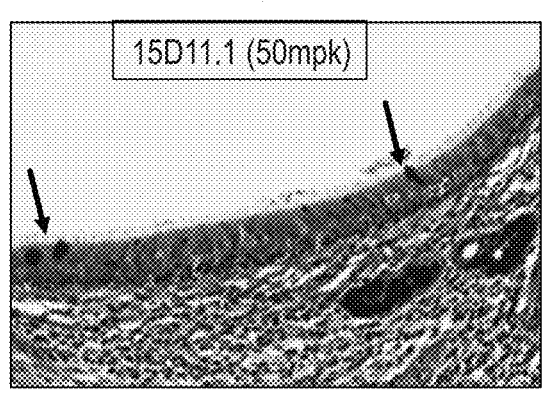
15D11.1 (50mpk)
FIG. 20E Trachea
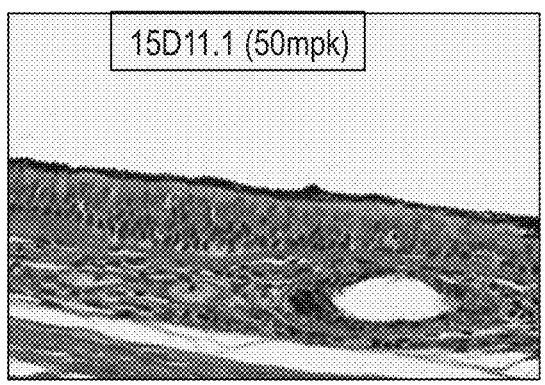
15D11.1 (50mpk)
FIG. 20F Bronchus
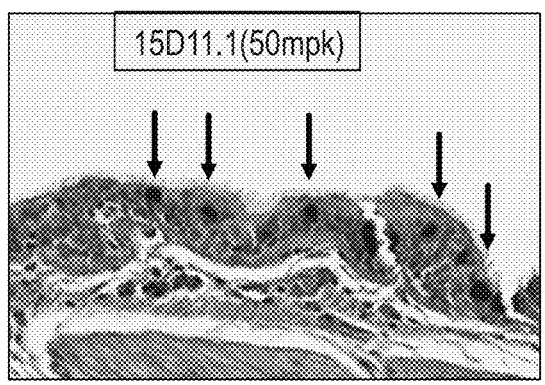
15D11.1 (50mpk)

ANTI-JAGGED1 ANTIGEN BINDING PROTEINS

FIELD OF THE INVENTION

The present disclosure relates to the treatment or amelioration of lung disease using an antigen binding protein specific for Jagged1.

BACKGROUND OF THE INVENTION

The Notch signaling pathway regulates a diverse array of cell functions (Kopan et ah, *Cell* 137, 216-233 (2009)). Four Notch receptors have been identified in mammals, i.e., Notch 1-4, that share basic structural elements that include an extracellular domain, a transmembrane domain, and an intracellular domain. Similarly, the canonical ligands of Notch share certain structural similarities but a number of non-canonical ligands of Notch have also been identified (Kopan et al., *Cell* 137, 216-233 (2009)). The five canonical ligands in mammals are Delta-like 1, Delta-like 3, Delta-like 4, Jagged1 and Jagged2. Binding of a Notch ligand to the extracellular domain of a Notch receptor sets a signaling cascade in motion that begins with proteolytic cleavage at the extracellular S2 site by an alpha secretase of the ADAM (a disintegrin and metalloprotease) family. Cleavage at S2 is followed by proteolytic cleavage by a gamma secretase at the intracellular S3 site, which results in release of the intracellular domain and downstream events that ultimately activate Notch-dependent transcription factors such as Hest and Hey.

Aberrant Notch expression and signaling has been implicated in a number of diseases, including cancer (Koch et al., *Cell. Mol. Life Sci.* 64, 2746-2762 (2007)). It is clear that there continues to be a need for agents that have clinical attributes that are optimal for development as therapeutic agents. The invention described herein meets this need and provides other benefits.

SUMMARY OF THE INVENTION

In one aspect the present invention is directed to a method of treating a subject with a condition related to lung disease, the method comprising administering to the subject a therapeutically effective amount of an antigen binding protein that specifically binds to a protein having an amino acid sequence having at least 90% amino acid sequence identity to an amino acid sequence of a Jagged1. In certain embodiments the subject is human. In certain embodiments the antigen binding protein is administered intravenously, by nebulization, or by subcutaneous injection.

In one aspect the present invention is directed to an antigen binding protein that specifically binds to a protein having an amino acid sequence having at least 90% amino acid sequence identity to an amino acid sequence of a Jagged1.

In certain embodiments the antigen binding protein is a monoclonal antibody, a polyclonal antibody, a recombinant antibody, a human antibody, a humanized antibody, a chimeric antibody, a multispecific antibody, or an antibody fragment thereof. In certain embodiments the antigen binding protein is a Fab fragment, a Fab' fragment, or a F(ab')2 fragment. In certain embodiments the antigen binding protein is a human antibody. In certain embodiments the antigen binding protein is a monoclonal antibody. In certain embodiments the antigen binding protein is of the IgG1-, IgG2- IgG3- or IgG4-type. In certain embodiments the antigen binding protein is coupled to a labeling group.

In certain embodiments the antigen binding protein is an antibody or a fragment thereof. In certain embodiments the antibody comprises a CDRL1, a CDRL2, a CDRL3, a CDRH1, a CDRH2, and a CDRH3, wherein the CDRL1 comprises a sequence selected from the group consisting of SEQ ID NOs: 4, 10, 16, 22, 28, 34, 40, 46, 52, 58, 64, 70, 76, 82, 88, 94, 100, 106, 112, 118, 124, and 130; the CDRL2 comprises a sequence selected from the group consisting of SEQ ID NOs: 5, 11, 17, 23, 29, 35, 41, 47, 53, 59, 65, 71, 77, 83, 89, 95, 101, 107, 113, 119, 125, and 131; the CDRL3 comprises a sequence selected from the group consisting of SEQ ID NOs: 6, 12, 18, 24, 30, 36, 42, 48, 54, 60, 66, 72, 78, 84, 90, 96, 102, 108, 114, 120, 126, and 132; the CDRH1 comprises a sequence selected from the group consisting of SEQ ID NOs: 136, 142, 148, 154, 160, 166, 172, 178, 184, 190, 196, 202, 208, 214, 220, 226, 232, 238, 244, 250, 256, and 262; the CDRH2 comprises a sequence selected from the group consisting of SEQ ID NOs: 137, 143, 149, 155, 161, 167, 173, 179, 185, 191, 197, 203, 209, 215, 221, 227, 233, 239, 245, 251, 257, and 263; and the CDRH3 comprises a sequence selected from the group consisting of SEQ ID NOs: 138, 144, 150, 156, 162, 168, 174, 180, 186, 192, 198, 204, 210, 216, 222, 228, 234, 240, 246, 252, 258, and 264.

In certain embodiments the antibody comprises a CDRL1, a CDRL2, a CDRL3, a CDRH1, a CDRH2, and a CDRH3, wherein each CDRL1, CDRL2, CDRL3, CDRH1, CDRH2, and CDRH3, respectively, comprises a sequence selected from the group consisting of SEQ ID NO: 4, SEQ ID NO: 5, SEQ ID NO: 6, SEQ ID NO: 136, SEQ ID NO: 137, and SEQ ID NO: 138; SEQ ID NO: 10, SEQ ID NO: 11, SEQ ID NO: 12, SEQ ID NO: 142, SEQ ID NO: 143, and SEQ ID NO: 144; SEQ ID NO: 16, SEQ ID NO: 17, SEQ ID NO: 18, SEQ ID NO: 148, SEQ ID NO: 149, and SEQ ID NO: 150; SEQ ID NO: 22, SEQ ID NO: 23, SEQ ID NO: 24, SEQ ID NO: 154, SEQ ID NO: 155, and SEQ ID NO: 156; SEQ ID NO: 28, SEQ ID NO: 29, SEQ ID NO: 30, SEQ ID NO: 160, SEQ ID NO: 161, and SEQ ID NO: 162; SEQ ID NO: 34, SEQ ID NO: 35, SEQ ID NO: 36, SEQ ID NO: 166, SEQ ID NO: 167, and SEQ ID NO: 168; SEQ ID NO: 40, SEQ ID NO: 41, SEQ ID NO: 42, SEQ ID NO: 172, SEQ ID NO: 173, and SEQ ID NO: 174; SEQ ID NO: 46, SEQ ID NO: 47, SEQ ID NO: 48, SEQ ID NO: 178, SEQ ID NO: 179, and SEQ ID NO: 180; SEQ ID NO: 52, SEQ ID NO: 53, SEQ ID NO: 54, SEQ ID NO: 184, SEQ ID NO: 185, and SEQ ID NO: 186; SEQ ID NO: 58, SEQ ID NO: 59, SEQ ID NO: 60, SEQ ID NO: 190, SEQ ID NO: 191, and SEQ ID NO: 192; SEQ ID NO: 64, SEQ ID NO: 65, SEQ ID NO: 66, SEQ ID NO: 196, SEQ ID NO: 197, and SEQ ID NO: 198; SEQ ID NO: 70, SEQ ID NO: 71, SEQ ID NO: 72, SEQ ID NO: 202, SEQ ID NO: 203, and SEQ ID NO: 204; SEQ ID NO: 76, SEQ ID NO: 77, SEQ ID NO: 78, SEQ ID NO: 208, SEQ ID NO: 209, and SEQ ID NO: 210; SEQ ID NO: 82, SEQ ID NO: 83, SEQ ID NO: 84, SEQ ID NO: 214, SEQ ID NO: 215, and SEQ ID NO: 216; SEQ ID NO: 88, SEQ ID NO: 89, SEQ ID NO: 90, SEQ ID NO: 220, SEQ ID NO: 221, and SEQ ID NO: 222; SEQ ID NO: 94, SEQ ID NO: 95, SEQ ID NO: 96, SEQ ID NO: 226, SEQ ID NO: 227, and SEQ ID NO: 228; SEQ ID NO: 100, SEQ ID NO: 101, SEQ ID NO: 102, SEQ ID NO: 232, SEQ ID NO: 233, and SEQ ID NO: 234; SEQ ID NO: 106, SEQ ID NO: 107, SEQ ID NO: 108, SEQ ID NO: 238, SEQ ID NO: 239, and SEQ ID NO: 240; SEQ ID NO: 112, SEQ ID NO: 113, SEQ ID NO: 114, SEQ ID NO: 244, SEQ ID NO: 245, and SEQ ID NO: 246; SEQ ID NO: 118, SEQ ID NO: 119, SEQ ID NO: 120, SEQ ID NO: 250, SEQ ID NO: 251, and SEQ ID NO: 252; SEQ ID NO: 124, SEQ ID NO: 125, SEQ ID NO: 126, SEQ ID NO: 256, SEQ ID NO: 257, and SEQ ID NO: 258; and SEQ ID NO: 130, SEQ ID NO: 131, SEQ ID NO: 132, SEQ ID NO: 262, SEQ ID NO: 263, and SEQ ID NO: 264.

In certain embodiments the antigen binding protein is an antibody or a fragment thereof, and wherein the antibody or fragment thereof comprises a light chain variable region comprising a sequence selected from the group consisting of SEQ ID NOs: 267, 271, 275, 279, 283, 287, 291, 295, 299, 303, 307, 311, 315, 319, 323, 327, 331, 335, 339, 343, 347, and 351 and a heavy chain variable region comprising a sequence selected from the group consisting of SEQ ID NOs: 268, 272, 276, 280, 284, 288, 292, 296, 300, 304, 308, 312, 316, 320, 324, 328, 332, 336, 340, 344, 348, and 352.

In certain embodiments the antigen binding protein is an antibody or a fragment thereof, and wherein the antibody or fragment thereof comprises a combination of a light chain variable region and a heavy chain variable region selected from the group consisting of a light chain variable region comprising SEQ ID NO: 267 and a heavy chain variable region comprising SEQ ID NO: 268; a light chain variable region comprising SEQ ID NO: 271 and a heavy chain variable region comprising SEQ ID NO: 272; a light chain variable region comprising SEQ ID NO: 275 and a heavy chain variable region comprising SEQ ID NO: 276; a light chain variable region comprising SEQ ID NO: 279 and a heavy chain variable region comprising SEQ ID NO: 280; a light chain variable region comprising SEQ ID NO: 283 and a heavy chain variable region comprising SEQ ID NO: 284; a light chain variable region comprising SEQ ID NO: 287 and a heavy chain variable region comprising SEQ ID NO: 288; a light chain variable region comprising SEQ ID NO: 291 and a heavy chain variable region comprising SEQ ID NO: 292; a light chain variable region comprising SEQ ID NO: 295 and a heavy chain variable region comprising SEQ ID NO: 296; a light chain variable region comprising SEQ ID NO: 299 and a heavy chain variable region comprising SEQ ID NO: 300; a light chain variable region comprising SEQ ID NO: 303 and a heavy chain variable region comprising SEQ ID NO: 304; a light chain variable region comprising SEQ ID NO: 307 and a heavy chain variable region comprising SEQ ID NO: 308; a light chain variable region comprising SEQ ID NO: 311 and a heavy chain variable region comprising SEQ ID NO: 312; a light chain variable region comprising SEQ ID NO: 315 and a heavy chain variable region comprising SEQ ID NO: 316; a light chain variable region comprising SEQ ID NO: 319 and a heavy chain variable region comprising SEQ ID NO: 320; a light chain variable region comprising SEQ ID NO: 323 and a heavy chain variable region comprising SEQ ID NO: 324; a light chain variable region comprising SEQ ID NO: 327 and a heavy chain variable region comprising SEQ ID NO: 328; a light chain variable region comprising SEQ ID NO: 331 and a heavy chain variable region comprising SEQ ID NO: 332; a light chain variable region comprising SEQ ID NO: 335 and a heavy chain variable region comprising SEQ ID NO: 336; a light chain variable region comprising SEQ ID NO: 339 and a heavy chain variable region comprising SEQ ID NO: 340; a light chain variable region comprising SEQ ID NO: 343 and a heavy chain variable region comprising SEQ ID NO: 344; a light chain variable region comprising SEQ ID NO: 347 and a heavy chain variable region comprising SEQ ID NO: 348; and a light chain variable region comprising SEQ ID NO: 351 and a heavy chain variable region comprising SEQ ID NO: 352.

In one aspect the present invention is directed to a nucleic acid molecule encoding an antibody or fragment thereof according to the present invention. In one embodiment the nucleic acid molecule is operably linked to a control sequence.

In one aspect the present invention is directed to a vector comprising a nucleic acid molecule according to the present invention.

In one aspect the present invention is directed to a host cell comprising a nucleic acid molecule according to the present invention.

In one aspect the present invention is directed to an antibody or fragment thereof produced by a host cell of the present invention.

In one aspect the present invention is directed to a method of making an antibody or fragment thereof according to the present invention, comprising the step of preparing the antibody or fragment thereof from a host cell that secretes the antibody.

In one aspect the present invention is directed to a pharmaceutical composition comprising at least one antibody or fragment thereof according to the present invention, and a pharmaceutically acceptable excipient.

In one aspect the present invention is directed to an isolated antigen binding protein that competes for binding to human Jagged1 with an antibody or fragment thereof according to the present invention.

BRIEF DESCRIPTION OF THE DRAWINGS

FIGS. 1A through 1D show periodic acid-Schiff/alcian blue staining of unstimulated ALI cultures untreated or treated with IgG1 (10 ug/ml) or anti-Jag-1 15D11.1 (10 ug/ml or 1 ug/ml). FIGS. 1E through 1F show quantification of goblet cell number and percent mucin content of the different treatment groups. Few goblet cells are present in baseline no-stimulation condition and anti-Jag-1 (10 ug/ml) treatment reduced the number of goblet cells below baseline.

FIGS. 2A through 2E show periodic acid-Schiff/alcian blue staining of unstimulated or IL-13 stimulated ALI cultures untreated or treated with IgG1 (10 ug/ml) or anti-Jag-1 15D11.1 (10 ug/ml or 1 ug/ml). FIGS. 2F and 2G-quantification of goblet cell number and percent mucin content of the different treatment groups. Abundant goblet cells are present in the IL-13 stimulation condition and anti-Jag-1 (10 ug/ml or 1 ug/ml) treatment significantly reduced the number of goblet cells and percent mucin content.

FIGS. 3A-3D. FIGS. 3A through 3D show qPCR results for the goblet cell markers MUC5AC; MUC5B and FOXA3 from unstimulated or IL-13 stimulated 3D bronchosphere cultures, untreated or treated with IgG1 (10 ug/ml) or anti-Jag-1 (10 ug/ml or 1 ug/ml). IL-13 induced goblet cell differentiation and anti-Jag-1 treatment (10 ug/ml and 1 ug/ml), but not IgG1 (10 ug/ml) treatment, blocked goblet cell differentiation.

FIG. 4A shows a schematic summary of the OVA challenge study design, FIG. 4B through 4E show Periodic Acid-Schiff staining of lung airways of control, anti-Jag-1 (15D11.1) or anti-TSLP treated mice, FIGS. 4F and 4G quantification of goblet cells and percent mucin content in the airway epithelium of the different treatment groups. The control treated and anti-TSLP treated airways exhibit abundant goblet cells and the anti-Jag-1 treated group show reduced numbers of goblet cells and percent mucin content.

FIG. 5A shows body weight changes for all groups. The mice sensitized without and with OVA are displayed separately in graph FIG. 5B and FIG. 5C.

FIGS. 20A-20F show Dosing of Jag1 antibody inhibits reduced mucin content in the respiratory epithelium of monkeys.

DETAILED DESCRIPTION OF THE INVENTION

Figure 1A:
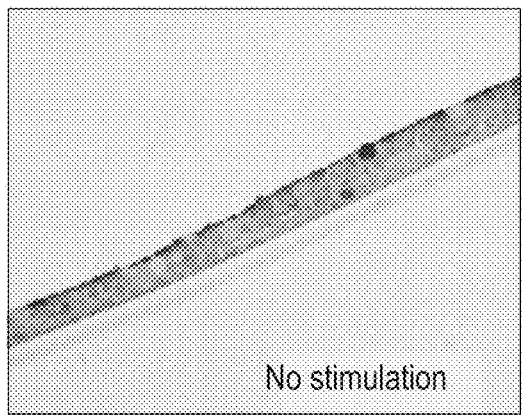
FIGS. 1A-1F.
Figure 1B:
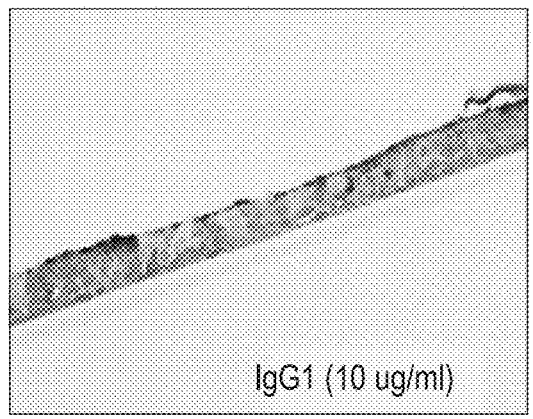
Figure 1C:
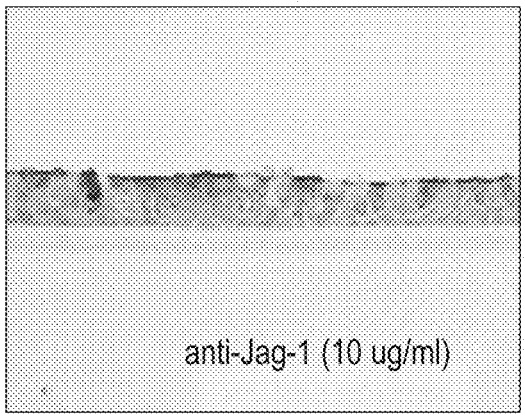
Figure 1D:
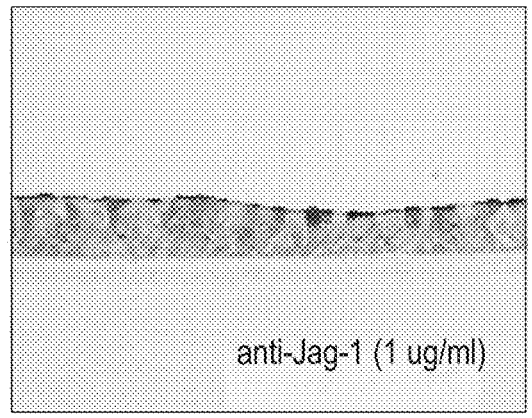
Figure 1E:
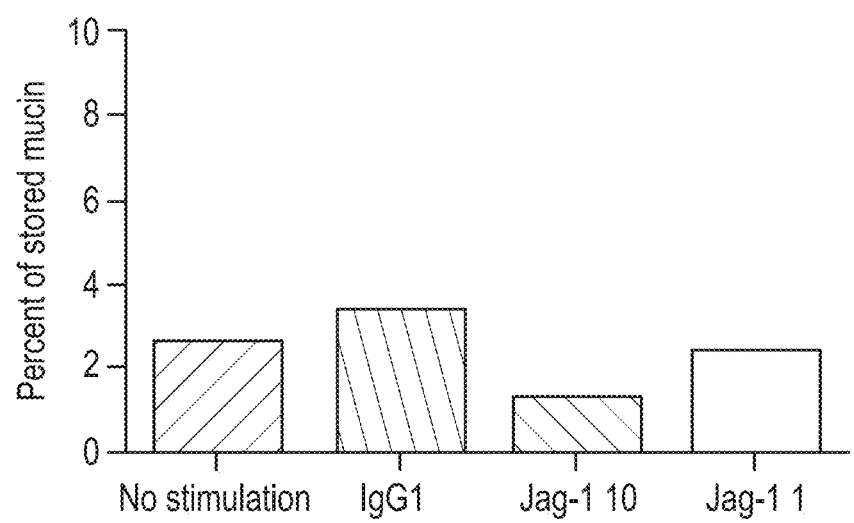
Figure 1F:
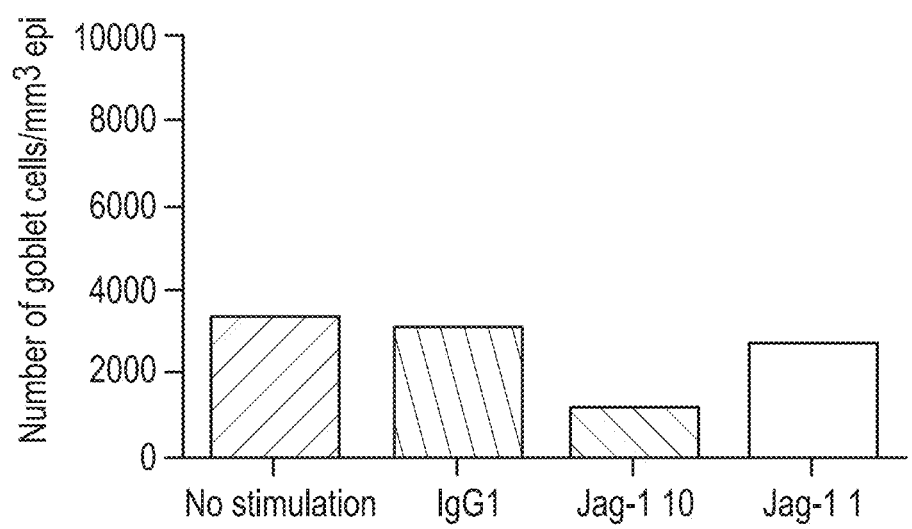
Figure 2A:
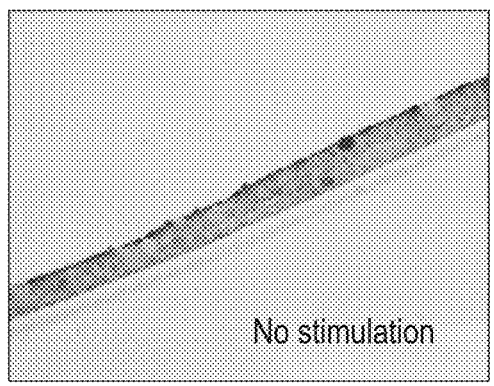
FIGS. 2A-2G.
Figure 2B:
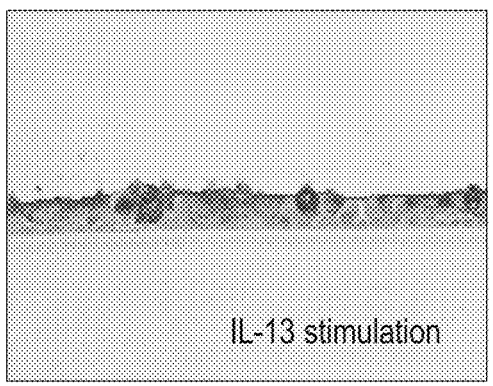
Figure 2C:
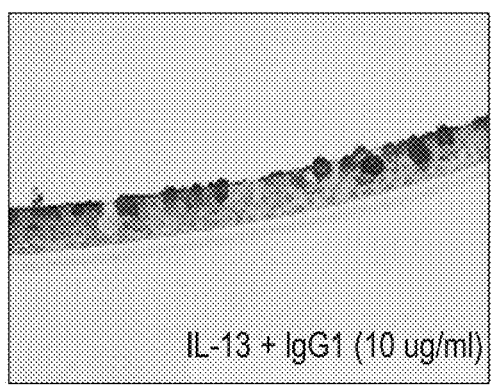
Figure 2D:
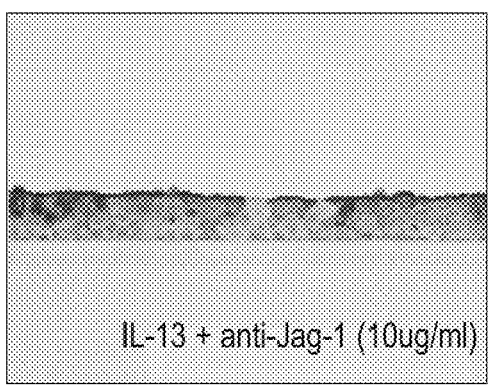
Figure 2E:
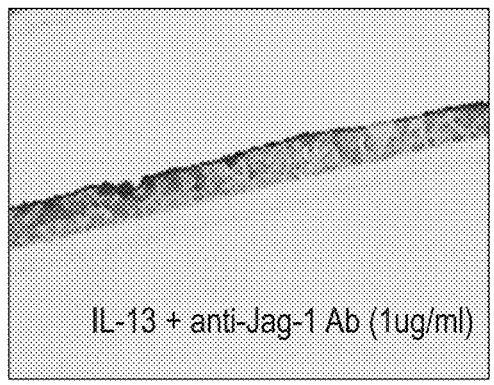
Figure 2F:
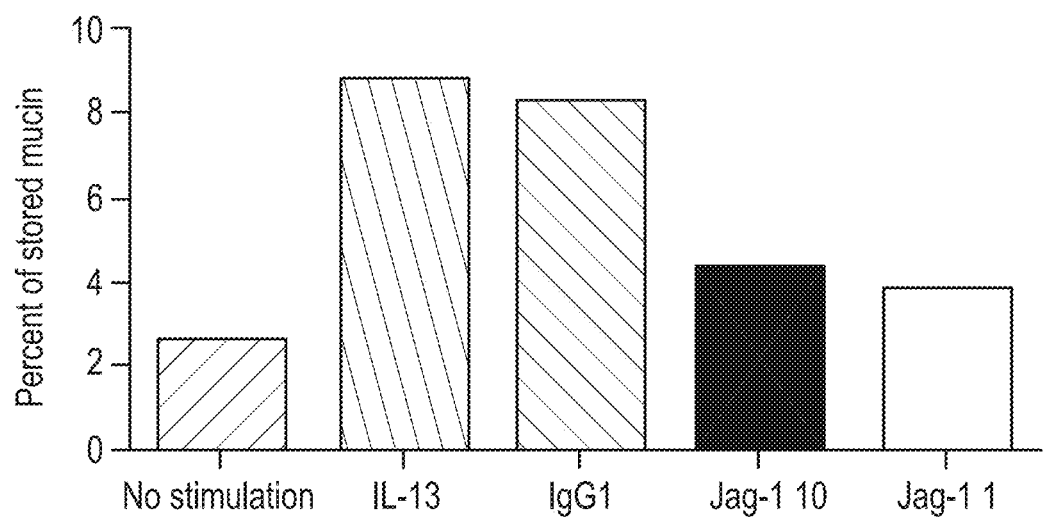
Figure 2G:
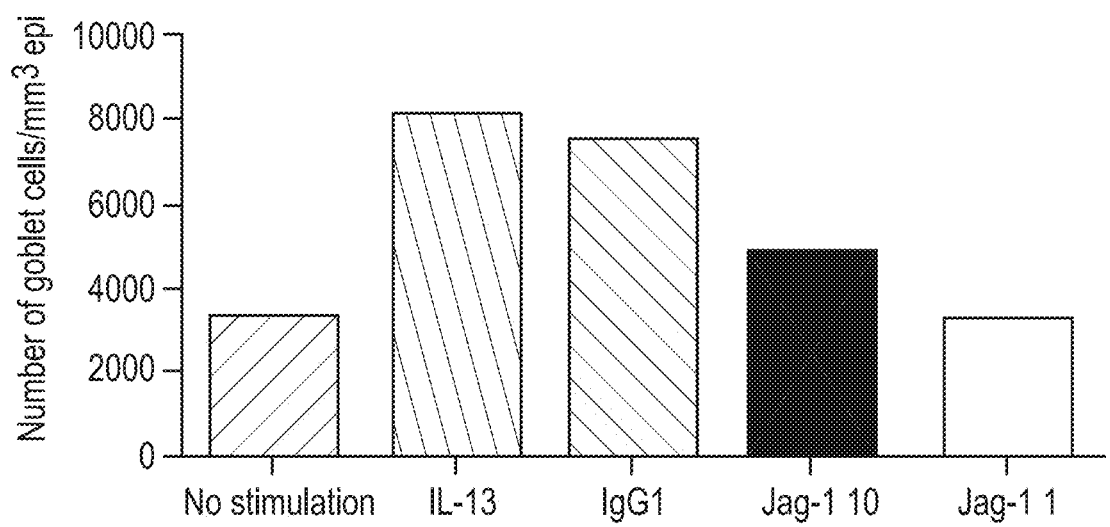
Figure 4A:
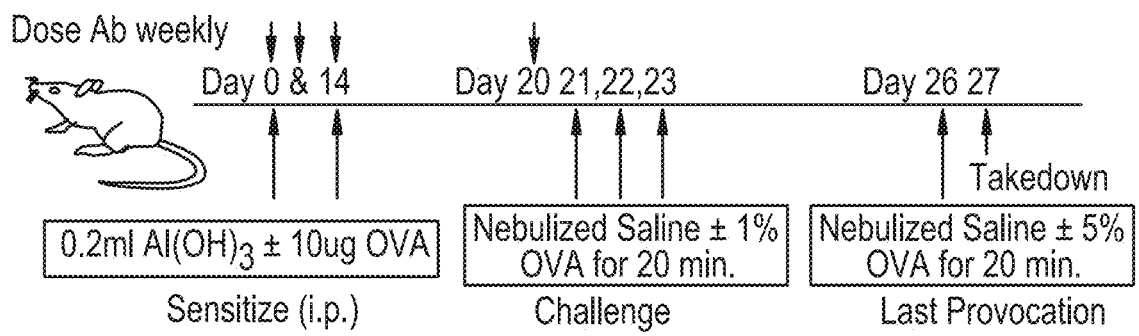
FIGS. 4A-4G.
Figure 4B:
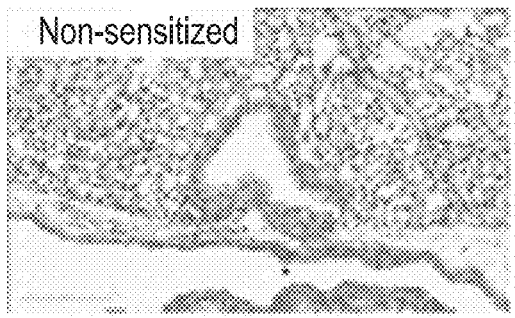
Figure 4C:
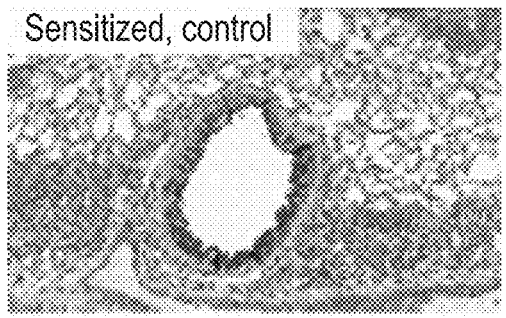
Figure 4D:
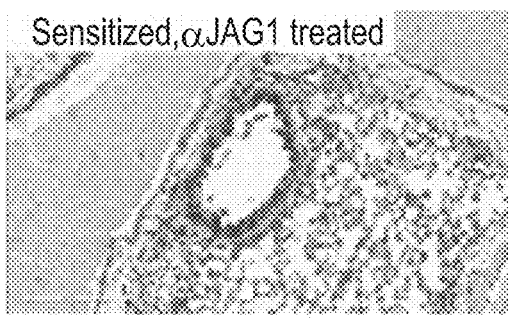
Figure 4E:
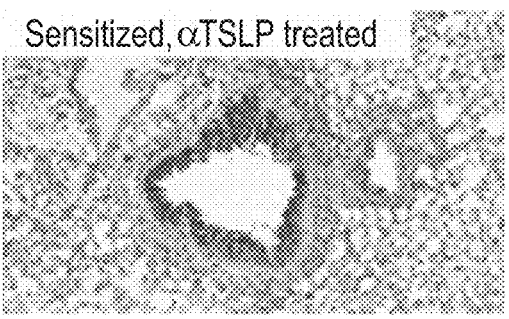
Figure 4F:
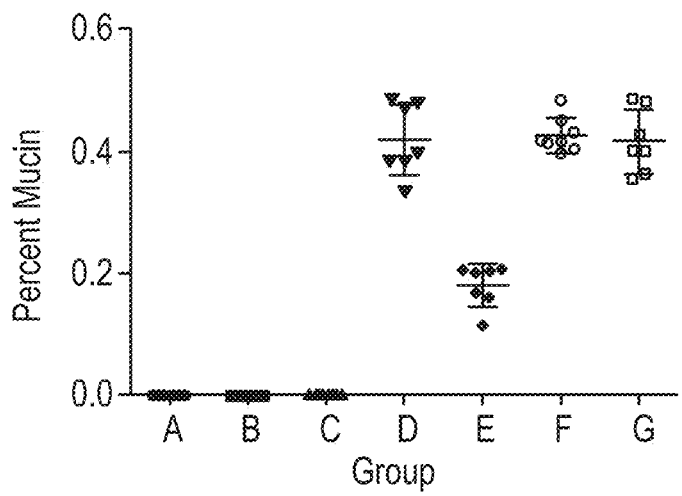
Figure 4G:
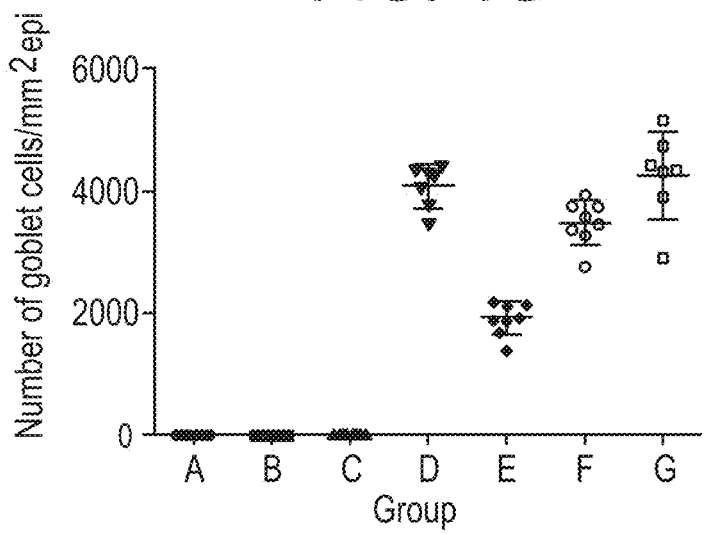

Recombinant polypeptide and nucleic acid methods used herein, including in the Examples, are generally those set forth in Sambrook et al., Molecular Cloning: A Laboratory Manual (Cold Spring Harbor Laboratory Press, 1989) or Current Protocols in Molecular Biology (Ausubel et al., eds., Green Publishers Inc. and Wiley and Sons 1994), both of which are incorporated herein by reference for any purpose.

The section headings used herein are for organizational purposes only and are not to be construed as limiting the subject matter described.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

Generally, nomenclatures used in connection with, and techniques of, cell and tissue culture, molecular biology, immunology, microbiology, genetics and protein and nucleic acid chemistry and hybridization described herein are those well-known and commonly used in the art. The methods and techniques of the present application are generally performed according to conventional methods well known in the art and as described in various general and more specific references that are cited and discussed throughout the present specification unless otherwise indicated. See, e.g., Sambrook et al., Molecular Cloning: A Laboratory Manual, 3rd ed., Cold Spring Harbor Laboratory Press, Cold Spring Harbor, N.Y. (2001), Ausubel et al., Current Protocols in Molecular Biology, Greene Publishing Associates (1992), and Harlow and Lane Antibodies: A Laboratory Manual Cold Spring Harbor Laboratory Press, Cold Spring Harbor, N.Y. (1990), which are incorporated herein by reference. Enzymatic reactions and purification techniques are performed according to manufacturer's specifications, as commonly accomplished in the art or as described herein. The terminology used in connection with, and the laboratory procedures and techniques of, analytical chemistry, synthetic organic chemistry, and medicinal and pharmaceutical chemistry described herein are those well-known and commonly used in the art. Standard techniques can be used for chemical syntheses, chemical analyses, pharmaceutical preparation, formulation, and delivery, and treatment of patients.

It should be understood that this invention is not limited to the particular methodology, protocols, and reagents, etc., described herein and as such may vary. The terminology used herein is for the purpose of describing particular embodiments only, and is not intended to limit the scope of the disclosed, which is defined solely by the claims.

Other than in the operating examples, or where otherwise indicated, all numbers expressing quantities of ingredients or reaction conditions used herein should be understood as modified in all instances by the term "about." The term "about" when used in connection with percentages may mean±1%.

Following convention, as used herein "a" and "an" mean "one or more" unless specifically indicated otherwise.

As used herein, the terms "amino acid" and "residue" are interchangeable and, when used in the context of a peptide or polypeptide, refer to both naturally occurring and synthetic amino acids, as well as amino acid analogs, amino acid mimetics and non-naturally occurring amino acids that are chemically similar to the naturally occurring amino acids.

A "naturally occurring amino acid" is an amino acid that is encoded by the genetic code, as well as those amino acids that are encoded by the genetic code that are modified after synthesis, e.g., hydroxyproline, γ-carboxyglutamate, and O-phosphoserine. An amino acid analog is a compound that has the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs can have modified R groups (e.g., norleucine) or modified peptide backbones, but will retain the same basic chemical structure as a naturally occurring amino acid.

An "amino acid mimetic" is a chemical compound that has a structure that is different from the general chemical structure of an amino acid, but that functions in a manner similar to a naturally occurring amino acid. Examples include a methacryloyl or acryloyl derivative of an amide, β-, γ-, δ-amino acids (such as piperidine-4-carboxylic acid) and the like.

A "non-naturally occurring amino acid" is a compound that has the same basic chemical structure as a naturally occurring amino acid, but is not incorporated into a growing polypeptide chain by the translation complex. "Non-naturally occurring amino acid" also includes, but is not limited to, amino acids that occur by modification (e.g., posttranslational modifications) of a naturally encoded amino acid (including but not limited to, the 20 common amino acids) but are not themselves naturally incorporated into a growing polypeptide chain by the translation complex. A non-limiting lists of examples of non-naturally occurring amino acids that can be inserted into a polypeptide sequence or substituted for a wild-type residue in polypeptide sequence include β-amino acids, homoamino acids, cyclic amino acids and amino acids with derivatized side chains. Examples include (in the L-form or D-form; abbreviated as in parentheses): citrulline (Cit), homocitrulline (hCit), Nα-methylcitrulline (NMeCit), Nα-methylhomocitrulline (Nα-MeHoCit), ornithine (Orn), Nα-Methylornithine (Nα-MeOrn or NMeOrn), sarcosine (Sar), homolysine (hLys or hK), homoarginine (hArg or hR), homoglutamine (hQ), Nα-methylarginine (NMeR), Nα-methylleucine (Nα-MeL or NMeL), N-methylhomolysine (NMeHoK), Nα-methylglutamine (NMeQ), norleucine (Nle), norvaline (Nva), 1,2,3,4-tetrahydroisoquinoline (Tic), Octahydroindole-2-carboxylic acid (Oic), 3-(1-naphthyl)alanine (1-Nal), 3-(2-naphthyl)alanine (2-Nal), 1,2,3,4-tetrahydroisoquinoline (Tic), 2-indanylglycine (IgI), para-iodophenylalanine (pI-Phe), para-aminophenylalanine (4AmP or 4-Amino-Phe), 4-guanidino phenylalanine (Guf), glycyllysine (abbreviated "K(Nε-glycyl)" or "K(glycyl)" or "K(gly)"), nitrophenylalanine (nitrophe), aminophenylalanine (aminophe or Amino-Phe), benzylphenylalanine (benzylphe), γ-carboxyglutamic acid (γ-carboxyglu), hydroxyproline (hydroxypro), p-carboxyl-phenylalanine (Cpa), α-aminoadipic acid (Aad), Nα-methyl valine (NMeVal), N-α-methyl leucine (NMeLeu), Nα-methylnorleucine (NMeNle), cyclopentylglycine (Cpg), cyclohexylglycine (Chg), acetylarginine (acetylarg), α, β-diaminopropionoic acid (Dpr), α, γ-diaminobutyric acid (Dab), diaminopropionic acid (Dap), cyclohexylalanine (Cha), 4-methyl-phenylalanine (MePhe), β, β-diphenyl-alanine (BiPhA), aminobutyric acid (Abu), 4-phenyl-phenylalanine (or biphenylalanine; 4Bip), α-amino-isobutyric acid (Aib), beta-alanine, beta-aminopropionic acid, piperidinic acid, aminocaprioic acid, aminoheptanoic acid, aminopimelic acid, desmosine, diaminopimelic acid, N-ethylglycine, N-ethylaspargine, hydroxylysine, allohydroxylysine, isodesmosine, allo-isoleucine, N-methylglycine, N-methylisoleucine, N-methylvaline, 4-hydroxyproline (Hyp), γ-carboxyglutamate, ε-N,N,N-trimethyllysine, ε-N-acetyllysine, O-phosphoserine, N-acetylserine, N-formylmethionine, 3-methylhistidine, 5-hydroxylysine, ω-methylarginine, 4-Amino-O-Phthalic Acid (4APA), and other similar amino acids, and derivatized forms of any of those specifically listed.

The term "isolated nucleic acid molecule" refers to a single or double-stranded polymer of deoxyribonucleotide or ribonucleotide bases read from the 5' to the 3' end (e.g., a Jagged1 nucleic acid sequence provided herein), or an analog thereof, that has been separated from at least about 50 percent of polypeptides, peptides, lipids, carbohydrates, polynucleotides or other materials with which the nucleic acid is naturally found when total nucleic acid is isolated from the source cells. Preferably, an isolated nucleic acid molecule is substantially free from any other contaminating nucleic acid molecules or other molecules that are found in the natural environment of the nucleic acid that would interfere with its use in polypeptide production or its therapeutic, diagnostic, prophylactic or research use.

The term "isolated polypeptide" refers to a polypeptide (e.g., a Jagged1 polypeptide sequence provided herein or an antigen binding protein of the present invention) that has been separated from at least about 50 percent of polypeptides, peptides, lipids, carbohydrates, polynucleotides, or other materials with which the polypeptide is naturally found when isolated from a source cell. Preferably, the isolated polypeptide is substantially free from any other contaminating polypeptides or other contaminants that are found in its natural environment that would interfere with its therapeutic, diagnostic, prophylactic or research use.

The term "encoding" refers to a polynucleotide sequence encoding one or more amino acids. The term does not require a start or stop codon.

The terms "identical" and percent "identity," in the context of two or more nucleic acids or polypeptide sequences, refer to two or more sequences or subsequences that are the same. "Percent identity" means the percent of identical residues between the amino acids or nucleotides in the compared molecules and is calculated based on the size of the smallest of the molecules being compared. For these calculations, gaps in alignments (if any) can be addressed by a particular mathematical model or computer program (i.e., an "algorithm"). Methods that can be used to calculate the identity of the aligned nucleic acids or polypeptides include those described in Computational Molecular Biology, (Lesk, A. M., ed.), (1988) New York: Oxford University Press; Biocomputing Informatics and Genome Projects, (Smith, D. W., ed.), 1993, New York: Academic Press; Computer Analysis of Sequence Data, Part I, (Griffin, A. M., and Griffin, H. G., eds.), 1994, New Jersey: Humana Press; von Heinje, G., (1987) Sequence Analysis in Molecular Biology, New York: Academic Press; Sequence Analysis Primer, (Gribskov, M. and Devereux, J., eds.), 1991, New York: M. Stockton Press; and Carillo et al., (1988) SIAM J. Applied Math. 48:1073.

In calculating percent identity, the sequences being compared are aligned in a way that gives the largest match between the sequences. The computer program used to determine percent identity is the GCG program package, which includes GAP (Devereux et al., (1984) Nucl. Acid Res. 12:387; Genetics Computer Group, University of Wisconsin, Madison, Wis.). The computer algorithm GAP is used to align the two polypeptides or polynucleotides for which the percent sequence identity is to be determined. The sequences are aligned for optimal matching of their respective amino acid or nucleotide (the "matched span", as determined by the algorithm). A gap opening penalty (which is calculated as 3× the average diagonal, wherein the "average diagonal" is the average of the diagonal of the comparison matrix being used; the "diagonal" is the score or number assigned to each perfect amino acid match by the particular comparison matrix) and a gap extension penalty (which is usually ⅒ times the gap opening penalty), as well as a comparison matrix such as PAM 250 or BLOSUM 62 are used in conjunction with the algorithm. In certain embodiments, a standard comparison matrix (see, Dayhoff et al., (1978) Atlas of Protein Sequence and Structure 5:345-352 for the PAM 250 comparison matrix; Henikoff et al., (1992) Proc. Natl. Acad. Sci. U.S.A. 89:10915-10919 for the BLOSUM 62 comparison matrix) is also used by the algorithm.

Recommended parameters for determining percent identity for polypeptides or nucleotide sequences using the GAP program are the following:

Algorithm: Needleman et al., 1970, J. Mol. Biol. 48:443-453;

Comparison matrix: BLOSUM 62 from Henikoff et al., 1992, supra;

Gap Penalty: 12 (but with no penalty for end gaps)

Gap Length Penalty: 4

Threshold of Similarity: 0

Certain alignment schemes for aligning two amino acid sequences can result in matching of only a short region of the two sequences, and this small aligned region can have very high sequence identity even though there is no significant relationship between the two full-length sequences. Accordingly, the selected alignment method (e.g., the GAP program) can be adjusted if so desired to result in an alignment that spans at least 50 contiguous amino acids of the target polypeptide.

The terms "Jagged1 polypeptide" and "Jagged1 protein" are used interchangeably and mean a naturally-occurring wild-type polypeptide expressed in a mammal, such as a human or a mouse, and includes naturally occurring alleles (e.g., naturally occurring allelic forms of human Jagged1 protein). For purposes of this disclosure, the term "Jagged1 polypeptide" can be used interchangeably to refer to any full-length Jagged1 polypeptide, e.g., SEQ ID NO: 353, which consists of 1218 amino acid residues and which is encoded by the nucleotide sequence SEQ ID NO: 354.

The term "Jagged1 polypeptide" also encompasses a Jagged1 polypeptide in which a naturally occurring Jagged1 polypeptide sequence (e.g., SEQ ID NO: 353) has been modified. Such modifications include, but are not limited to, one or more amino acid substitutions, including substitutions with non-naturally occurring amino acids non-naturally-occurring amino acid analogs and amino acid mimetics.

In various embodiments, a Jagged1 polypeptide comprises an amino acid sequence that is at least about 85 percent identical to a naturally-occurring Jagged1 polypeptide (e.g., SEQ ID NO: 353). In other embodiments, a Jagged1 polypeptide comprises an amino acid sequence that is at least about 90 percent, or about 95, 96, 97, 98, or 99 percent identical to a naturally-occurring Jagged1 polypeptide amino acid sequence (e.g., SEQ ID NOs: 353). Such Jagged1 polypeptides preferably, but need not, possess at least one activity of a wild-type Jagged1 polypeptide, such as the ability to bind a Notch receptor. The present invention also encompasses nucleic acid molecules encoding such Jagged1 polypeptide sequences.

The terms "Jagged1 activity assay" (also referred to as a "Jagged1 functional assay") means an assay that can be used to measure Jagged1 or a Jagged1 receptor (i.e., Notch 1-4) activity in a cellular setting.

The term "Jagged1 binding assay" means an assay that can be used to measure binding of Jagged1 a Notch1-4. In one embodiment, "Jagged1 binding assay" can be an assay using FMAT or FACS that measures fluorescence-labeled Jagged1 binding to Notch 1-4 expressing cells, and Jagged1/Notch 1-4 binding protein's activity can be measured for displacing fluorescence-labeled Jagged1 binding to Notch 1-4 expressing cells. In another embodiment, "Jagged1 binding assay" can be an assay that measures radioactive-labeled Jagged1 binding to Notch 1-4 expressing cells, and Jagged1/Notch 1-4 binding protein's activity can be measured for displacing radioactive labeled Jagged1 binding to Notch 1-4 expressing cells (Biochimica et Biophysica Acta (2001) 1547:143-155).

An "antigen binding protein" as used herein means any protein that specifically binds a specified target antigen, such as a Jagged1 polypeptide (e.g., a human Jagged1 polypeptide such as provided in SEQ ID NO: 353). The term encompasses intact antibodies that comprise at least two full-length heavy chains and two full-length light chains, as well as derivatives, variants, fragments, and mutations thereof. Examples of antibody fragments include Fab, Fab', F(ab')$_2$, and Fv fragments. An antigen binding protein also includes domain antibodies such as nanobodies and scFvs as described further below.

In general, a Jagged1 antigen binding protein is the to "specifically bind" its target antigen Jagged1 when the antigen binding protein exhibits essentially background binding to non-Jagged1 molecules. An antigen binding protein that specifically binds Jagged1 may, however, cross-react with Jagged1 polypeptides from different species. Typically, a Jagged1 antigen binding protein specifically binds human Jagged1 when the dissociation constant (KD) is $\leq 10^{-7}$ M as measured via a surface plasma resonance technique (e.g., BIACore, GE-Healthcare Uppsala, Sweden) or Kinetic Exclusion Assay (KinExA, Sapidyne, Boise, Id.). A Jagged1 antigen binding protein specifically binds human Jagged1 with "high affinity" when the KD is $\leq 5 \times 10^{-9}$ M, and with "very high affinity" when the KD is $\leq 5 \times 10^{-10}$ M, as measured using methods described.

"Antigen binding region" means a protein, or a portion of a protein, that specifically binds a specified antigen. For example, that portion of an antigen binding protein that contains the amino acid residues that interact with an antigen and confer on the antigen binding protein its specificity and affinity for the antigen is referred to as "antigen binding region." An antigen binding region typically includes one or more "complementary binding regions" ("CDRs") of an immunoglobulin, single-chain immunoglobulin, or camelid antibody. Certain antigen binding regions also include one or more "framework" regions. A "CDR" is an amino acid sequence that contributes to antigen binding specificity and affinity. "Framework" regions can aid in maintaining the proper conformation of the CDRs to promote binding between the antigen binding region and an antigen.

A "recombinant protein", including a recombinant Jagged1 antigen binding protein, is a protein made using recombinant techniques, i.e., through the expression of a recombinant nucleic acid as described herein. Methods and techniques for the production of recombinant proteins are well known in the art.

The term "antibody" refers to an intact immunoglobulin of any isotype, or a fragment thereof that can compete with the intact antibody for specific binding to the target antigen, and includes, for instance, chimeric, humanized, fully human, and bispecific antibodies. An "antibody" as such is a species of an antigen binding protein. An intact antibody generally will comprise at least two full-length heavy chains and two full-length light chains. Antibodies may be derived solely from a single source, or may be "chimeric," that is, different portions of the antibody may be derived from two different antibodies as described further below. The antigen binding proteins, antibodies, or binding fragments may be produced in hybridomas, by recombinant DNA techniques, or by enzymatic or chemical cleavage of intact antibodies.

The term "light chain" as used with respect to an antibody or fragments thereof includes a full-length light chain and fragments thereof having sufficient variable region sequence to confer binding specificity. A full-length light chain includes a variable region domain, VL, and a constant region domain, CL. The variable region domain of the light chain is at the amino-terminus of the polypeptide. Light chains include kappa chains and lambda chains.

The term "heavy chain" as used with respect to an antibody or fragment thereof includes a full-length heavy chain and fragments thereof having sufficient variable region sequence to confer binding specificity. A full-length heavy chain includes a variable region domain, VH, and three constant region domains, CH1, CH2, and CH3. The VH domain is at the amino-terminus of the polypeptide, and the CH domains are at the carboxyl-terminus, with the CH3 being closest to the carboxy-terminus of the polypeptide. Heavy chains may be of any isotype, including IgG (including IgG1, IgG2, IgG3 and IgG4 subtypes), IgA (including IgA1 and IgA2 subtypes), IgM and IgE.

The term "immunologically functional fragment" (or simply "fragment") of an antibody or immunoglobulin chain (heavy or light chain), as used herein, is an antigen binding protein comprising a portion (regardless of how that portion is obtained or synthesized) of an antibody that lacks at least some of the amino acids present in a full-length chain but which is capable of specifically binding to an antigen. Such fragments are biologically active in that they bind specifically to the target antigen and can compete with other antigen binding proteins, including intact antibodies, for specific binding to a given epitope.

These biologically active fragments may be produced by recombinant DNA techniques, or may be produced by enzymatic or chemical cleavage of antigen binding proteins, including intact antibodies. Immunologically functional immunoglobulin fragments include, but are not limited to, Fab, Fab', and F(ab')$_2$ fragments.

In another embodiment, Fvs, domain antibodies and scFvs, and may be derived from an antibody of the present invention.

It is contemplated further that a functional portion of the antigen binding proteins disclosed herein, for example, one or more CDRs, could be covalently bound to a second protein or to a small molecule to create a therapeutic agent directed to a particular target in the body, possessing bifunctional therapeutic properties, or having a prolonged serum half-life.

A "Fab fragment" is comprised of one light chain and the CH1 and variable regions of one heavy chain. The heavy chain of a Fab molecule cannot form a disulfide bond with another heavy chain molecule.

An "Fc" region contains two heavy chain fragments comprising the CH2 and CH3 domains of an antibody. The two heavy chain fragments are held together by two or more disulfide bonds and by hydrophobic interactions of the CH3 domains.

An "Fab' fragment" contains one light chain and a portion of one heavy chain that contains the VH domain and the CH1 domain and also the region between the CH1 and CH2 domains, such that an interchain disulfide bond can be formed between the two heavy chains of two Fab' fragments to form an F(ab')2 molecule.

An "F(ab')2 fragment" contains two light chains and two heavy chains containing a portion of the constant region between the CH1 and CH2 domains, such that an interchain disulfide bond is formed between the two heavy chains. A F(ab')2 fragment thus is composed of two Fab' fragments that are held together by a disulfide bond between the two heavy chains.

The "Fv region" comprises the variable regions from both the heavy and light chains, but lacks the constant regions.

"Single chain antibodies" or "scFvs" are Fv molecules in which the heavy and light chain variable regions have been connected by a flexible linker to form a single polypeptide chain, which forms an antigen-binding region. scFvs are discussed in detail in International Patent Application Publication No. WO 88/01649 and U.S. Pat. Nos. 4,946,778 and 5,260,203, the disclosures of which are incorporated by reference.

A "domain antibody" or "single chain immunoglobulin" is an immunologically functional immunoglobulin fragment containing only the variable region of a heavy chain or the variable region of a light chain. Examples of domain antibodies include Nanobodies®. In some instances, two or more VH regions are covalently joined with a peptide linker to create a bivalent domain antibody. The two VH regions of a bivalent domain antibody may target the same or different antigens.

A "bivalent antigen binding protein" or "bivalent antibody" comprises two antigen binding regions. In some instances, the two binding regions have the same antigen specificities. Bivalent antigen binding proteins and bivalent antibodies may be bispecific, see, infra.

A multispecific antigen binding protein" or "multispecific antibody" is one that targets more than one antigen or epitope.

A "bispecific," "dual-specific" or "bifunctional" antigen binding protein or antibody is a hybrid antigen binding protein or antibody, respectively, having two different antigen binding sites. Bispecific antigen binding proteins and antibodies are a species of multispecific antigen binding protein or multispecific antibody and may be produced by a variety of methods including, but not limited to, fusion of hybridomas or linking of Fab' fragments. See, e.g., Songsivilai and Lachmann, 1990, Clin. Exp. Immunol. 79:315-321; Kostelny et al., 1992, J. Immunol. 148:1547-1553. The two binding sites of a bispecific antigen binding protein or antibody will bind to two different epitopes, which may reside on the same or different protein targets.

The term "compete" when used in the context of antigen binding proteins (e.g., antibodies) means competition between antigen binding proteins is determined by an assay in which the antigen binding protein (e.g., antibody or immunologically functional fragment thereof) under test prevents or inhibits specific binding of a reference antigen binding protein to a common antigen (e.g., Jagged1 or a fragment thereof). Numerous types of competitive binding assays can be used, for example: solid phase direct or indirect radioimmunoassay (RIA), solid phase direct or indirect enzyme immunoassay (EIA), sandwich competition assay (see, e.g., Stahli et al., 1983, Methods in Enzymology 9:242-253); solid phase direct biotin-avidin EIA (see, e.g., Kirkland et al., 1986, J. Immunol. 137:3614-3619) solid phase direct labeled assay, solid phase direct labeled sandwich assay (see, e.g., Harlow and Lane, 1988, Antibodies, A Laboratory Manual, Cold Spring Harbor Press); solid phase direct label RIA using I-125 label (see, e.g., Morel et al., 1988, Molec. Immunol. 25:7-15); solid phase direct biotin-avidin EIA (see, e.g., Cheung, et al., 1990, Virology 176: 546-552); and direct labeled RIA (Moldenhauer et al., 1990, Scand. J. Immunol. 32:77-82). Typically, such an assay involves the use of purified antigen bound to a solid surface or cells bearing either of these, an unlabeled test antigen binding protein and a labeled reference antigen binding protein. Competitive inhibition is measured by determining the amount of label bound to the solid surface or cells in the presence of the test antigen binding protein. Usually the test antigen binding protein is present in excess. Additional details regarding methods for determining competitive binding are provided in the examples herein. Usually, when a competing antigen binding protein is present in excess, it will inhibit specific binding of a reference antigen binding protein to a common antigen by at least 40%, 45%, 50%, 55%, 60%, 65%, 70% or 75%. In some instances, binding is inhibited by at least 80%, 85%, 90%, 95%, or 97% or more.

The term "antigen" refers to a molecule or a portion of a molecule capable of being bound by a selective binding agent, such as an antigen binding protein (including, e.g., an antibody), and additionally capable of being used in an animal to produce antibodies capable of binding to that antigen. An antigen may possess one or more epitopes that are capable of interacting with different antigen binding proteins, e.g., antibodies.

The term "epitope" is the portion of a molecule that is bound by an antigen binding protein (for example, an antibody). The term includes any determinant capable of specifically binding to an antigen binding protein, such as an antibody. An epitope can be contiguous or non-contiguous (discontinuous) (e.g., in a polypeptide, amino acid residues that are not contiguous to one another in the polypeptide sequence but that within in context of the molecule are bound by the antigen binding protein). A conformational epitope is an epitope that exists within the conformation of an active protein but is not present in a denatured protein. In certain embodiments, epitopes may be mimetic in that they comprise a three dimensional structure that is similar to an epitope used to generate the antigen binding protein, yet comprise none or only some of the amino acid residues found in that epitope used to generate the antigen binding protein. Most often, epitopes reside on proteins, but in some instances may reside on other kinds of molecules, such as nucleic acids. Epitope determinants may include chemically active surface groupings of molecules such as amino acids, sugar side chains, phosphoryl or sulfonyl groups, and may have specific three dimensional structural characteristics, and/or specific charge characteristics. Generally, antigen binding proteins specific for a particular target antigen will preferentially recognize an epitope on the target antigen in a complex mixture of proteins and/or macromolecules.

As used herein, "substantially pure" means that the described species of molecule is the predominant species present, that is, on a molar basis it is more abundant than any other individual species in the same mixture. In certain embodiments, a substantially pure molecule is a composition wherein the object species comprises at least 50% (on a molar basis) of all macromolecular species present. In other embodiments, a substantially pure composition will comprise at least 80%, 85%, 90%, 95%, 96%, 97%, 98%, or 99% of all macromolecular species present in the composition. In other embodiments, the object species is purified to essential homogeneity wherein contaminating species cannot be detected in the composition by conventional detection methods and thus the composition consists of a single detectable macromolecular species.

The term "treating" refers to any indicia of success in the treatment or amelioration of an injury, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation.

An "effective amount" is generally an amount sufficient to reduce the severity and/or frequency of symptoms, eliminate the symptoms and/or underlying cause, prevent the occurrence of symptoms and/or their underlying cause, and/or improve or remediate the damage that results from or is associated with the disease state (e.g., lung disease). In some embodiments, the effective amount is a therapeutically effective amount or a prophylactically effective amount. A "therapeutically effective amount" is an amount sufficient to remedy a disease state or symptoms, particularly a state or symptoms associated with the disease state, or otherwise prevent, hinder, retard or reverse the progression of the disease state or any other undesirable symptom associated with the disease in any way whatsoever. A "prophylactically effective amount" is an amount of a pharmaceutical composition that, when administered to a subject, will have the intended prophylactic effect, e.g., preventing or delaying the onset (or reoccurrence) of the disease state, or reducing the likelihood of the onset (or reoccurrence) of the disease state or associated symptoms. The full therapeutic or prophylactic effect does not necessarily occur by administration of one dose, and may occur only after administration of a series of doses. Thus, a therapeutically or prophylactically effective amount may be administered in one or more administrations.

The terms "therapeutically effective dose" and "therapeutically effective amount," as used herein, means an amount of a Jagged1 antigen binding protein that elicits a biological or medicinal response in a tissue system, animal, or human being sought by a researcher, physician, or other clinician, which includes alleviation or amelioration of the symptoms of the disease or disorder being treated, i.e., an amount of a Jagged1 antigen binding protein that supports an observable level of one or more desired biological or medicinal response, for example reduced levels of stored mucin and/or reduced goblet cell number per volume of epithelium.

The term "polynucleotide" or "nucleic acid" includes both single-stranded and double-stranded nucleotide polymers. The nucleotides comprising the polynucleotide can be ribonucleotides or deoxyribonucleotides or a modified form of either type of nucleotide. The modifications include base modifications such as bromouridine and inosine derivatives, ribose modifications such as 2',3'-dideoxyribose, and internucleotide linkage modifications such as phosphorothioate, phosphorodithioate, phosphoroselenoate, phosphorodiselenoate, phosphoroanilothioate, phosphoraniladate and phosphoroamidate.

The term "oligonucleotide" means a polynucleotide comprising 200 or fewer nucleotides. In some embodiments, oligonucleotides are 10 to 60 bases in length. In other embodiments, oligonucleotides are 12, 13, 14, 15, 16, 17, 18, 19, or 20 to 40 nucleotides in length. Oligonucleotides may be single stranded or double stranded, e.g., for use in the construction of a mutant gene. Oligonucleotides may be sense or antisense oligonucleotides. An oligonucleotide can include a label, including a radiolabel, a fluorescent label, a hapten or an antigenic label, for detection assays. Oligonucleotides may be used, for example, as PCR primers, cloning primers or hybridization probes.

An "isolated nucleic acid molecule" means a DNA or RNA of genomic, mRNA, cDNA, or synthetic origin or some combination thereof which is not associated with all or a portion of a polynucleotide in which the isolated polynucleotide is found in nature, or is linked to a polynucleotide to which it is not linked in nature. For purposes of this disclosure, it should be understood that "a nucleic acid molecule comprising" a particular nucleotide sequence does not encompass intact chromosomes. Isolated nucleic acid molecules "comprising" specified nucleic acid sequences may include, in addition to the specified sequences, coding sequences for up to ten or even up to twenty other proteins or portions thereof, or may include operably linked regulatory sequences that control expression of the coding region of the recited nucleic acid sequences, and/or may include vector sequences.

Unless specified otherwise, the left-hand end of any single-stranded polynucleotide sequence discussed herein is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA transcript that are 5' to the 5' end of the RNA transcript are referred to as "upstream sequences;" sequence regions on the DNA strand having the same sequence as the RNA transcript that are 3' to the 3' end of the RNA transcript are referred to as "downstream sequences."

The term "control sequence" refers to a polynucleotide sequence that can affect the expression and processing of coding sequences to which it is ligated. The nature of such control sequences may depend upon the host organism. In particular embodiments, control sequences for prokaryotes may include a promoter, a ribosomal binding site, and a transcription termination sequence. For example, control sequences for eukaryotes may include promoters comprising one or a plurality of recognition sites for transcription factors, transcription enhancer sequences, and transcription termination sequences. "Control sequences" can include leader sequences and/or fusion partner sequences.

The term "vector" means any molecule or entity (e.g., nucleic acid, plasmid, bacteriophage or virus) used to transfer protein coding information into a host cell.

The term "expression vector" or "expression construct" refers to a vector that is suitable for transformation of a host cell and contains nucleic acid sequences that direct and/or control (in conjunction with the host cell) expression of one or more heterologous coding regions operatively linked thereto. An expression construct may include, but is not limited to, sequences that affect or control transcription, translation, and, if introns are present, affect RNA splicing of a coding region operably linked thereto.

As used herein, "operably linked" means that the components to which the term is applied are in a relationship that allows them to carry out their inherent functions under suitable conditions. For example, a control sequence in a vector that is "operably linked" to a protein coding sequence is ligated thereto so that expression of the protein coding sequence is achieved under conditions compatible with the transcriptional activity of the control sequences.

The term "host cell" means a cell that has been transformed with a nucleic acid sequence and thereby expresses a gene of interest. The term includes the progeny of the parent cell, whether or not the progeny is identical in morphology or in genetic make-up to the original parent cell, so long as the gene of interest is present.

The terms "polypeptide" or "protein" are used interchangeably herein to refer to a polymer of amino acid residues. The terms also apply to amino acid polymers in which one or more amino acid residues is an analog or mimetic of a corresponding naturally occurring amino acid, as well as to naturally occurring amino acid polymers. The terms can also encompass amino acid polymers that have been modified, e.g., by the addition of carbohydrate residues to form glycoproteins, or phosphorylated. Polypeptides and proteins can be produced by a naturally-occurring and non-recombinant cell; or it is produced by a genetically-engineered or recombinant cell, and comprise molecules having the amino acid sequence of the native protein, or molecules having deletions from, additions to, and/or substitutions of one or more amino acids of the native sequence. The terms "polypeptide" and "protein" specifically encompass Jagged1 antigen binding proteins, antibodies, or sequences that have deletions from, additions to, and/or substitutions of one or more amino acids of an antigen-binding protein. The term "polypeptide fragment" refers to a polypeptide that has an amino-terminal deletion, a carboxyl-terminal deletion, and/or an internal deletion as compared with the full-length protein. Such fragments may also contain modified amino acids as compared with the full-length protein. In certain embodiments, fragments are about five to 500 amino acids long. For example, fragments may be at least 5, 6, 8, 10, 14, 20, 50, 70, 100, 110, 150, 200, 250, 300, 350, 400, or 450 amino acids long. Useful polypeptide fragments include immunologically functional fragments of antibodies, including binding domains.

The term "isolated protein" means that a subject protein (1) is free of at least some other proteins with which it would normally be found, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is operably associated (by covalent or noncovalent interaction) with a polypeptide with which it is not associated in nature, or (6) does not occur in nature. Typically, an "isolated protein" constitutes at least about 5%, at least about 10%, at least about 25%, or at least about 50% of a given sample. Genomic DNA, cDNA, mRNA or other RNA, of synthetic origin, or any combination thereof may encode such an isolated protein. Preferably, the isolated protein is substantially free from proteins or polypeptides or other contaminants that are found in its natural environment that would interfere with its therapeutic, diagnostic, prophylactic, research or other use.

A "variant" of a polypeptide (e.g., an antigen binding protein such as an antibody) comprises an amino acid sequence wherein one or more amino acid residues are inserted into, deleted from and/or substituted into the amino acid sequence relative to another polypeptide sequence. Variants include fusion proteins.

A "derivative" of a polypeptide is a polypeptide (e.g., an antigen binding protein such as an antibody) that has been chemically modified in some manner distinct from insertion, deletion, or substitution variants, e.g., via conjugation to another chemical moiety.

The term "naturally occurring" as used throughout the specification in connection with biological materials such as polypeptides, nucleic acids, host cells, and the like, refers to materials which are found in nature.

A "subject" or "patient" as used herein can be any mammal. In a typical embodiment, the subject or patient is a human.

As disclosed herein, a Jagged1 polypeptide described by the instant disclosure can be engineered and/or produced using standard molecular biology methodology. In various examples, a nucleic acid sequence encoding a Jagged1, which can comprise all or a portion of SEQ ID NO: 353, can be isolated and/or amplified from genomic DNA, or cDNA using appropriate oligonucleotide primers. Primers can be designed based on the nucleic and amino acid sequences provided herein according to standard (RT)-PCR amplification techniques. The amplified Jagged1 nucleic acid can then be cloned into a suitable vector and characterized by DNA sequence analysis.

Oligonucleotides for use as probes in isolating or amplifying all or a portion of the Jagged1 sequences provided herein can be designed and generated using standard synthetic techniques, e.g., automated DNA synthesis apparatus, or can be isolated from a longer sequence of DNA.

The 1218 amino acid sequence of human Jagged1 is:

```
                                           (SEQ ID NO: 353)
MRSPRTRGRS GRPLSLLLAL LCALRAKVCG ASGQFELEIL

SMQNVNGELQ NGNCCGGARN

PGDRKCTRDE CDTYFKVCLK EYQSRVTAGG PCSFGSGSTP

VIGGNTFNLK ASRGNDRNRI

VLPFSFAWPR SYTLLVEAWD SSNDTVQPDS IIEKASHSGM

INPSRQWQTL KQNTGVAHFE

YQIRVTCDDY YYGFGCNKFC RPRDDFFGHY ACDQNGNKTC

MEGWMGRECN RAICRQGCSP

KHGSCKLPGD CRCQYGWQGL YCDKCIPHPG CVHGICNEPW

QCLCETNWGG QLCDKDLNYC

GTHQPCLNGG TCSNTGPDKY QCSCPEGYSG PNCEIAEHAC

LSDPCHNRGS CKETSLGFEC

ECSPGWTGPT CSTNIDDCSP NNCSHGGTCQ DLVNGFKCVC

PPQWTGKTCQ LDANECEAKP

CVNAKSCKNL IASYYCDCLP GWMGQNCDIN INDCLGQCQN

DASCRDLVNG YRCICPPGYA

GDHCERDIDE CASNPCLDGG HCQNEINRFQ CLCPTGFSGN

LCQLDIDYCE PNPCQNGAQC

YNRASDYFCK CPEDYEGKNC SHLKDHCRTT PCEVIDSCTV

AMASNDTPEG VRYISSNVCG

PHGKCKSQSG GKFTCDCNKG FTGTYCHENI NDCESNPCRN

GGTCIDGVNS YKCICSDGWE

GAYCETNIND CSQNPCHNGG TCRDLVNDFY CDCKNGWKGK

TCHSRDSQCD EATCNNGGTC

YDEGDAFKCM CPGGWEGTTC NIARNSSCLP NPCHNGGTCV

VNGESFTCVC KEGWEGPICA

QNTNDCSPHP CYNSGTCVDG DNWYRCECAP GFAGPDCRIN

INECQSSPCA FGATCVDEIN

GYRCVCPPGH SGAKCQEVSG RPCITMGSVI PDGAKWDDDC

NTCQCLNGRI ACSKVWCGPR

PCLLHKGHSE CPSGQSCIPI LDDQCFVHPC TGVGECRSSS

LQPVKTKCTS DSYYQDNCAN

ITFTFNKEMM SPGLTTEHIC SELRNLNILK NVSAEYSIYI

ACEPSPSANN EIHVAISAED

IRDDGNPIKE ITDKIIDLVS KRDGNSSLIA AVAEVRVQRR

PLKNRTDFLV PLLSSVLTVA

WICCLVTAFY WCLRKRRKPG SHTHSASEDN TTNNVREQLN

QIKNPIEKHG ANTVPIKDYE

NKNSKMSKIR THNSEVEEDD MDKHQQKARF AKQPAYTLVD

REEKPPNGTP TKHPNWTNKQ DNRDLESAQS LNRMEYIV
``` and is encoded by the DNA sequence:

```
                                           (SEQ ID NO: 354)
atgcgttccccacggacgcgcggccggtccgggcgcccctaagcctcct gctcgccctgctctgtgccctgcgagccaaggtgtgtgggcctcgggtc agttcgagttggagatcctgtccatgcagaacgtgaacggggagctgcag aacgggaactgctgcggcggcgcccggaacccgggagaccgcaagtgcac ccgcgacgagtgtgacacatacttcaaagtgtgcctcaaggagtatcagt cccgcgtcacggccgggggccctgcagcttcggctcagggtccacgcct gtcatcggggggcaacaccttcaacctcaaggccagccgcggcaacgaccg caaccgcatcgtgctgcctttcagtttcgcctggccgaggtcctatacgt tgcttgtgaggcgtgggattccagtaatgacaccgttcaacctgacagt attattgaaaaggcttctcactcgggcatgatcaacccagccggcagtg gcagacgctgaagcagaacacgggcgttgcccactttgagtatcagatcc gcgtgacctgtgatgactactactatggctttggctgcaataagttctgc cgccccagagatgacttctttggacactatgcctgtgaccagaatggcaa caaaacttgcatggaaggctggatgggccgcgaatgtaacagagctattt gccgacaaggctgcagtcctaagcatgggtcttgcaaactcccaggtgac tgcaggtgccagtacggctggcaaggcctgtactgtgataagtgcatccc acacccgggatgcgtccacggcatctgtaatgagccctggcagtgcctct gtgagaccaactggggcggccagctctgtgacaaagatctcaattactgt gggactcatcagccgtgtctcaacgggggaacttgtagcaacacaggccc tgacaaatatcagtgttcctgccctgagggggtattcaggacccaactgtg aaattgctgagcacgcctgcctctctgatccctgtcacaacagaggcagc tgtaaggagacctccctgggctttgagtgtgagtgttccccaggctggac
```

-continued

```
cggccccacatgctctacaaacattgatgactgttctcctaataactgtt cccacggggcacctgccaggacctggttaacggatttaagtgtgtgtgc ccccacagtggactgggaaaacgtgccagttagatgcaaatgaatgtga ggccaaaccttgtgtaaacgccaaatcctgtaagaatctcattgccagct actactgcgactgtcttcccggctggatgggtcagaattgtgacataaat attaatgactgccttggccagtgtcagaatgacgcctcctgtcgggattt ggttaatggttatcgctgtatctgtccacctggctatgcaggcgatcact gtgagagagacatcgatgaatgtgccagcaacccctgtttggatgggggt cactgtcagaatgaaatcaacagattccagtgtctgtgtcccactggttt ctctggaaacctctgtcagctggacatcgattattgtgagcctaatccct gccagaacggtgcccagtgctacaaccgtgccagtgactatttctgcaag tgccccgaggactatgagggcaagaactgctcacacctgaaagaccactg ccgcacgacccctgtgaagtgattgacagctgcacagtggccatggctt ccaacgacacacctgaagggggtgcggtatatttcctccaacgtctgtggt cctcacgggaagtgcaagagtcagtcgggaggcaaattcacctgtgactg taacaaaggcttcacgggaacatactgccatgaaaatattaatgactgtg agagcaaccccttgtagaaacggtggcacttgcatcgatggtgtcaactcc tacaagtgcatctgtagtgacggctgggaggggggcctactgtgaaaccaa tattaatgactgcagccagaacccctgccacaatgggggcacgtgtcgcg acctggtcaatgacttctactgtgactgtaaaaatgggtggaaaggaaag acctgccactcacgtgacagtcagtgtgatgaggccacgtgcaacaacgg tggcacctgctatgatgaggggatgcttttaagtgcatgtgtcctggcg gctgggaaggaacaacctgtaacatagcccgaaacagtagctgcctgccc aaccctgccataatggggcacatgtgtggtcaacggcgagtcctttac gtgcgtctgcaaggaaggctgggaggggcccatctgtgctcagaatacca atgactgcagccctcatccctgttacaacagcggcacctgtgtggatgga gacaactggtaccggtgcgaatgtgccccgggttttgctgggccgactg cagaataaacatcaatgaatgccagtcttcaccttgtgcctttggagcga cctgtgtggatgagatcaatggctaccggtgtgtctgccctccagggcac agtggtgccaagtgccaggaagtttcagggagaccttgcatcaccatggg gagtgtgataccagatggggccaaatgggatgatgactgtaatacctgcc agtgcctgaatggacggatcgcctgctcaaaggtctggtgtggccctcga ccttgcctgctccacaaagggcacagcgagtgcccagcgggcagagctg catcccatcctggacgaccagtgcttcgtccacccctgcactggtgtgg gcgagtgtcggtcttccagtctccagccggtgaagacaaagtgcacctct gactcctattaccaggataactgtgcgaacatcacatttacctttaacaa ggagatgatgtcaccaggtcttactacggagcacatttgcagtgaattga ggaatttgaatattttgaagaatgtttccgctgaatattcaatctacatc gcttgcgagccttcccttcagcgaacaatgaaatacatgtggccatttc tgctgaagatatacgggatgatgggaacccgatcaaggaaatcactgaca
```

-continued

```
aaataattgatcttgttagtaaacgtgatggaaacagctcgctgattgct gccgttgcagaagtaagagttcagaggcggcctctgaagaacagaacaga tttccttgttcccttgctgagctctgtcttaactgtggcttggatctgtt gcttggtgacggccttctactggtgcctgcggaagcggcggaagccgggc agccacacacactcagcctctgaggacaacaccaccaacaacgtgcggga gcagctgaaccagatcaaaaaccccattgagaaacatggggccaacacgg tccccatcaaggattacgagaacaagaactccaaaatgtctaaaataagg acacacaattctgaagtagaagaggacgacatggacaaacaccagcagaa agcccggtttgccaagcagccggcgtatacgctggtagacagagaagaga agccccccaacggcacgccgacaaaacacccaaactggacaaacaaacag gacaacagagacttggaaagtgcccagagcttaaaccgaatggagtacat cgtatag.
```

As stated herein, the term "Jagged1 polypeptide" encompasses naturally occurring Jagged1 polypeptide sequences, e.g., human amino acid sequence SEQ ID NO: 353. The term "Jagged1 polypeptide," however, also encompasses polypeptides comprising an amino acid sequence that differs from the amino acid sequence of a naturally occurring Jagged1 polypeptide sequence, by one or more amino acids, such that the sequence is at least 85% identical to SEQ ID NO: 353. Jagged1 polypeptides can be generated by introducing one or more amino acid substitutions, either conservative or non-conservative and using naturally or non-naturally occurring amino acids, at particular positions of the Jagged1 polypeptide.

A "conservative amino acid substitution" can involve a substitution of a native amino acid residue (i.e., a residue found in a given position of the wild-type Jagged1 polypeptide sequence) with a nonnative residue (i.e., a residue that is not found in a given position of the wild-type Jagged1 polypeptide sequence) such that there is little or no effect on the polarity or charge of the amino acid residue at that position. Conservative amino acid substitutions also encompass non-naturally occurring amino acid residues that are typically incorporated by chemical peptide synthesis rather than by synthesis in biological systems. These include peptidomimetics, and other reversed or inverted forms of amino acid moieties.

Naturally occurring residues can be divided into classes based on common side chain properties:
(1) hydrophobic: norleucine, Met, Ala, Val, Leu, Ile;
(2) neutral hydrophilic: Cys, Ser, Thr;
(3) acidic: Asp, Glu;
(4) basic: Asn, Gln, His, Lys, Arg;
(5) residues that influence chain orientation: Gly, Pro; and
(6) aromatic: Trp, Tyr, Phe.

Additional groups of amino acids can also be formulated using the principles described in, e.g., Creighton (1984) PROTEINS: STRUCTURE AND MOLECULAR PROPERTIES (2d Ed. 1993), W.H. Freeman and Company. In some instances it can be useful to further characterize substitutions based on two or more of such features (e.g., substitution with a "small polar" residue, such as a Thr residue, can represent a highly conservative substitution in an appropriate context).

Conservative substitutions can involve the exchange of a member of one of these classes for another member of the same class. Non-conservative substitutions can involve the exchange of a member of one of these classes for a member from another class.

Synthetic, rare, or modified amino acid residues having known similar physiochemical properties to those of an above-described grouping can be used as a "conservative" substitute for a particular amino acid residue in a sequence. For example, a D-Arg residue may serve as a substitute for a typical L-Arg residue. It also can be the case that a particular substitution can be described in terms of two or more of the above described classes (e.g., a substitution with a small and hydrophobic residue means substituting one amino acid with a residue(s) that is found in both of the above-described classes or other synthetic, rare, or modified residues that are known in the art to have similar physiochemical properties to such residues meeting both definitions).

Nucleic acid sequences encoding a Jagged1 polypeptide provided herein, including those degenerate to SEQ ID NO: 354, and those encoding polypeptide variants of SEQ ID NO: 353 form other aspects of the instant disclosure.

In order to express the Jagged1 nucleic acid sequences provided herein, the appropriate coding sequence, e.g., SEQ ID NO: 354, can be cloned into a suitable vector and after introduction in a suitable host, the sequence can be expressed to produce the encoded polypeptide according to standard cloning and expression techniques, which are known in the art (e.g., as described in Sambrook, J., Fritsh, E. F., and Maniatis, T. Molecular Cloning: A Laboratory Manual 2nd, ed., Cold Spring Harbor Laboratory, Cold Spring Harbor Laboratory Press, Cold Spring Harbor, N.Y., 1989). The invention also relates to such vectors comprising a nucleic acid sequence according to the invention.

A "vector" refers to a delivery vehicle that (a) promotes the expression of a polypeptide-encoding nucleic acid sequence; (b) promotes the production of the polypeptide therefrom; (c) promotes the transfection/transformation of target cells therewith; (d) promotes the replication of the nucleic acid sequence; (e) promotes stability of the nucleic acid; (f) promotes detection of the nucleic acid and/or transformed/transfected cells; and/or (g) otherwise imparts advantageous biological and/or physiochemical function to the polypeptide-encoding nucleic acid. A vector can be any suitable vector, including chromosomal, non-chromosomal, and synthetic nucleic acid vectors (a nucleic acid sequence comprising a suitable set of expression control elements). Examples of such vectors include derivatives of SV40, bacterial plasmids, phage DNA, baculovirus, yeast plasmids, vectors derived from combinations of plasmids and phage DNA, and viral nucleic acid (RNA or DNA) vectors.

A recombinant expression vector can be designed for expression of a Jagged1 protein in prokaryotic (e.g., *E. coli*) or eukaryotic cells (e.g., insect cells, using baculovirus expression vectors, yeast cells, or mammalian cells). In one embodiment the host cell is a mammalian, non-human host cell. Representative host cells include those hosts typically used for cloning and expression, including *Escherichia coli* strains TOP10F', TOP10, DH10B, DH5a, HB101, W3110, BL21 (DE3) and BL21 (DE3)pLysS, BLUESCRIPT (Stratagene), mammalian cell lines CHO, CHO-K1, HEK293, 293-EBNA pIN vectors (Van Heeke & Schuster, J. Biol. Chem. 264: 5503-5509 (1989); pET vectors (Novagen, Madison Wis.). Alternatively, the recombinant expression vector can be transcribed and translated in vitro, for example using T7 promoter regulatory sequences and T7 polymerase and an in vitro translation system. Preferably, the vector contains a promoter upstream of the cloning site containing the nucleic acid sequence encoding the polypeptide. Examples of promoters, which can be switched on and off, include the lac promoter, the T7 promoter, the trc promoter, the tac promoter and the trp promoter.

Thus, provided herein are vectors comprising a nucleic acid sequence encoding Jagged1 that facilitate the expression of recombinant Jagged1. In various embodiments, the vectors comprise an operably linked nucleotide sequence which regulates the expression of Jagged1. A vector can comprise or be associated with any suitable promoter, enhancer, and other expression-facilitating elements. Examples of such elements include strong expression promoters (e.g., a human CMV IE promoter/enhancer, an RSV promoter, SV40 promoter, SL3-3 promoter, MMTV promoter, or HIV LTR promoter, EF1alpha promoter, CAG promoter), effective poly (A) termination sequences, an origin of replication for plasmid product in *E. coli*, an antibiotic resistance gene as a selectable marker, and/or a convenient cloning site (e.g., a polylinker). Vectors also can comprise an inducible promoter as opposed to a constitutive promoter such as CMV IE. In one aspect, a nucleic acid comprising a sequence encoding a Jagged1 polypeptide which is operatively linked to a tissue specific promoter which promotes expression of the sequence in a metabolically-relevant tissue, such as liver or pancreatic tissue is provided.

In another aspect of the instant disclosure, host cells comprising the Jagged1 nucleic acids and vectors disclosed herein are provided. In various embodiments, the vector or nucleic acid is integrated into the host cell genome, which in other embodiments the vector or nucleic acid is extra-chromosomal.

Recombinant cells, such as yeast, bacterial (e.g., *E. coli*), and mammalian cells (e.g., immortalized mammalian cells) comprising such a nucleic acid, vector, or combinations of either or both thereof are provided. In various embodiments cells comprising a non-integrated nucleic acid, such as a plasmid, cosmid, phagemid, or linear expression element, which comprises a sequence coding for expression of a Jagged1 polypeptide, are provided.

A vector comprising a nucleic acid sequence encoding a Jagged1 polypeptide provided herein can be introduced into a host cell by transformation or by transfection. Methods of transforming a cell with an expression vector are well known.

A Jagged1-encoding nucleic acid can be positioned in and/or delivered to a host cell or host animal via a viral vector. Any suitable viral vector can be used in this capacity. A viral vector can comprise any number of viral polynucleotides, alone or in combination with one or more viral proteins, which facilitate delivery, replication, and/or expression of the nucleic acid of the invention in a desired host cell. The viral vector can be a polynucleotide comprising all or part of a viral genome, a viral protein/nucleic acid conjugate, a virus-like particle (VLP), or an intact virus particle comprising viral nucleic acids and a Jagged1 polypeptide-encoding nucleic acid. A viral particle viral vector can comprise a wild-type viral particle or a modified viral particle. The viral vector can be a vector which requires the presence of another vector or wild-type virus for replication and/or expression (e.g., a viral vector can be a helper-dependent virus), such as an adenoviral vector amplicon. Typically, such viral vectors consist of a wild-type viral particle, or a viral particle modified in its protein and/or nucleic acid content to increase transgene capacity or aid in transfection and/or expression of the nucleic acid (examples of such vectors include the herpes virus/AAV amplicons).

Typically, a viral vector is similar to and/or derived from a virus that normally infects humans. Suitable viral vector particles in this respect, include, for example, adenoviral vector particles (including any virus of or derived from a virus of the adenoviridae), adeno-associated viral vector particles (AAV vector particles) or other parvoviruses and parvoviral vector particles, papillomaviral vector particles, flaviviral vectors, alphaviral vectors, herpes viral vectors, pox virus vectors, retroviral vectors, including lentiviral vectors.

A Jagged1 polypeptide expressed as described herein can be isolated using standard protein purification methods. A Jagged1 polypeptide can be isolated from a cell in which is it naturally expressed or it can be isolated from a cell that has been engineered to express Jagged1, for example a cell that does not naturally express Jagged1.

Protein purification methods that can be employed to isolate a Jagged1 polypeptide, as well as associated materials and reagents, are known in the art. Additional purification methods that may be useful for isolating a Jagged1 polypeptide can be found in references such as Bootcov M R, 1997, Proc. Natl. Acad. Sci. USA 94:11514-9, Fairlie W D, 2000, Gene 254: 67-76.

Antagonist antigen binding proteins that bind Jagged1, including human Jagged1 (hJagged1) are provided herein. In one embodiment, the human Jagged1 has the sequence as such as set forth in SEQ ID NO: 353.

The antigen binding proteins provided are polypeptides into which one or more complementary determining regions (CDRs), as described herein, are embedded and/or joined. In some antigen binding proteins, the CDRs are embedded into a "framework" region, which orients the CDR(s) such that the proper antigen binding properties of the CDR(s) are achieved. Certain antigen binding proteins described herein are antibodies or are derived from antibodies. In other antigen binding proteins, the CDR sequences are embedded in a different type of protein scaffold. The various structures are further described below.

The antigen binding proteins that are disclosed herein have a variety of utilities. The antigen binding proteins, for instance, are useful in specific binding assays, affinity purification of Jagged1, and in screening assays to identify other antagonists of Jagged1 activity. Other uses for the antigen binding proteins include, for example, diagnosis of Jagged1-associated diseases or conditions and screening assays to determine the presence or absence of Jagged1. Given that the antigen binding proteins that are provided are antagonists, the Jagged1 antigen binding proteins have value in therapeutic methods in which it is useful to treat lung disease, reduce mucin levels, and reduce goblet cell levels. Accordingly, in one aspect the present invention is directed to a method inhibiting the differentiation of secretory cells in a subject, the method comprising administering to the subject a therapeutically effective amount of an antigen binding protein that specifically binds to a protein having the amino acid sequence consisting of SEQ ID NO: 353. In one embodiment, the antigen binding protein comprises the CDRS and/or the VH and VL disclosed in the present application.

A variety of selective binding agents useful for modulating the activity of Jagged1 are provided. These agents include, for instance, antigen binding proteins that contain an antigen binding domain (e.g., scFvs, domain antibodies, and polypeptides with an antigen binding region) and specifically bind to a Jagged1 polypeptide, in particular human Jagged1.

In general the antigen binding proteins that are provided typically comprise one or more CDRs as described herein (e.g., 1, 2, 3, 4, 5 or 6). In some instances, the antigen binding protein comprises (a) a polypeptide structure and (b) one or more CDRs that are inserted into and/or joined to the polypeptide structure. The polypeptide structure can take a variety of different forms. For example, it can be, or comprise, the framework of a naturally occurring antibody, or fragment or variant thereof, or may be completely synthetic in nature. Examples of various polypeptide structures are further described below.

In certain embodiments, the polypeptide structure of the antigen binding proteins is an antibody or is derived from an antibody. Accordingly, examples of certain antigen binding proteins that are provided include, but are not limited to, monoclonal antibodies, bispecific antibodies, minibodies, domain antibodies such as Nanobodies®, synthetic antibodies (sometimes referred to herein as "antibody mimetics"), chimeric antibodies, humanized antibodies, human antibodies, antibody fusions, and portions or fragments of each, respectively. In some instances, the antigen binding protein is an immunological fragment of a complete antibody (e.g., a Fab, a Fab', a F(ab')2). In other instances the antigen binding protein is a scFv that uses CDRs from an antibody of the present invention.

In one embodiment, a Jagged1 antigen binding protein has one or more of the following activities:

(a) binds human Jagged1 such that KD is ≤200 nM, is ≤150 nM, is ≤100 nM, is ≤50 nM, is ≤10 nM, is ≤5 nM, is ≤2 nM, or is ≤1 nM, e.g., as measured via a surface plasma resonance or kinetic exclusion assay technique.

(b) has a half-life in human serum of at least 3 days;

Some antigen binding proteins that are provided have an on-rate (ka) for Jagged1 of at least $10^4$/M×seconds, at least $10^5$/M×seconds, or at least $10^6$/M×seconds as measured, for instance, as described below. Certain antigen binding proteins that are provided have a slow dissociation rate or off-rate. Some antigen binding proteins, for instance, have a kd (off-rate) of $1\times10^{-2}$ $s^{-1}$, or 1×, or $1\times10^{-4}$ $s^{-1}$, or $1\times10^{-5}$ $s^{-1}$. In certain embodiments, the antigen binding protein has a KD (equilibrium binding affinity) of less than 25 pM, 50 pM, 100 pM, 500 pM, 1 nM, 5 nM, 10 nM, 25 nM or 50 nM.

Depending on the assay, the binding of an antigen binding protein to its target can also be measured as an EC50 (the concentration of antigen binding protein that gives a half-maximal response when bound to target). An EC50 for an anti-Jagged1 antigen binding protein of the present invention can be determined by incubating different concentrations of antigen binding protein with cells expressing Jagged1. Anti-Jagged1 antigen binding proteins of the present invention can have EC50s less 200 nM, 150 nM, 125 nM, 100 nM, 90 nM, 80 nM, 70 nM, 60 nM, 50 nM, 40 nM, or 30 nM.

An IC50 (the half maximal inhibitory concentration: a measure of the effectiveness of an antigen binding protein in inhibiting a specific biological or biochemical function) can also be used to measure the activity of anti-Jagged1 antigen binding protein. An IC 50 can be measured using a functional assay. For example, cell-bound or soluble Jagged1 ligand can be used to activate a Notch receptor expressed by a cell wherein the Notch receptor pathway activation can be measured using a reporter gene, such as luciferase. In one embodiment the Notch receptor expressed by the reporter cell is Notch 2. Anti-Jagged1 antigen binding proteins of the present invention can have IC50s less 200 nM, 150 nM, 125 nM, 100 nM, 90 nM, 80 nM, 70 nM, 60 nM, 50 nM, 40 nM, 30 nM, 20 nM, 15 nM, 10 nM, 9 nM, 8 nM, 7 nM, 6 nM, 5 nM, 4 nM, 3 nM, or 2 nM.

In another aspect, an antigen-binding protein is provided having a half-life of at least one day in vitro or in vivo (e.g., when administered to a human subject). In one embodiment, the antigen binding protein has a half-life of at least three days. In various other embodiments, the antigen binding protein has a half-life of 4, 5, 6, 7, 8, 9, 10, 15, 20, 25, 30, 40, 50, or 60 days or longer. In another embodiment, the antigen binding protein is derivatized or modified such that it has a longer half-life as compared to the underivatized or unmodified antibody. In another embodiment, the antigen binding protein contains point mutations to increase serum half-life. Further details regarding such mutant and derivatized forms are provided below.

Some of the antigen binding proteins that are provided have the structure typically associated with naturally occurring antibodies. The structural units of these antibodies typically comprise one or more tetramers, each composed of two identical couplets of polypeptide chains, though some species of mammals also produce antibodies having only a single heavy chain. In a typical antibody, each pair or couplet includes one full-length "light" chain (in certain embodiments, about 25 kDa) and one full-length "heavy" chain (in certain embodiments, about 50-70 kDa). Each individual immunoglobulin chain is composed of several "immunoglobulin domains", each consisting of roughly 90 to 110 amino acids and expressing a characteristic folding pattern. These domains are the basic units of which antibody polypeptides are composed. The amino-terminal portion of each chain typically includes a variable domain that is responsible for antigen recognition. The carboxy-terminal portion is more conserved evolutionarily than the other end of the chain and is referred to as the "constant region" or "C region". Human light chains generally are classified as kappa and lambda light chains, and each of these contains one variable domain and one constant domain. Heavy chains are typically classified as mu, delta, gamma, alpha, or epsilon chains, and these define the antibody's isotype as IgM, IgD, IgG, IgA, and IgE, respectively. IgG has several subtypes, including, but not limited to, IgG1, IgG2, IgG3, and IgG4. IgM subtypes include IgM, and IgM2. IgA subtypes include IgA1 and IgA2. In humans, the IgA and IgD isotypes contain four heavy chains and four light chains; the IgG and IgE isotypes contain two heavy chains and two light chains; and the IgM isotype contains five heavy chains and five light chains. The heavy chain C region typically comprises one or more domains that may be responsible for effector function. The number of heavy chain constant region domains will depend on the isotype. IgG heavy chains, for example, each contain three C region domains known as CH1, CH2 and CH3. The antibodies that are provided can have any of these isotypes and subtypes. In certain embodiments, the Jagged1 antibody is of the IgG1, IgG2, or IgG4 subtype. The terms "Jagged1 antibody" and "anti-Jagged1 antibody" are used interchangeably throughout this application and figures. Both terms refer to an antibody that binds to Jagged1.

In full-length light and heavy chains, the variable and constant regions are joined by a "J" region of about twelve or more amino acids, with the heavy chain also including a "D" region of about ten more amino acids. See, e.g. Fundamental Immunology, 2nd ed., Ch. 7 (Paul, W., ed.) 1989, New York: Raven Press (hereby incorporated by reference in its entirety for all purposes). The variable regions of each light/heavy chain pair typically form the antigen binding site.

For the antibodies provided herein, the variable regions of immunoglobulin chains generally exhibit the same overall structure, comprising relatively conserved framework regions (FR) joined by three hypervariable regions, more often called "complementarity determining regions" or CDRs. The CDRs from the two chains of each heavy chain/light chain pair mentioned above typically are aligned by the framework regions to form a structure that binds specifically with a specific epitope on Jagged1. From N-terminal to C-terminal, naturally-occurring light and heavy chain variable regions both typically conform with the following order of these elements: FR1, CDR1, FR2, CDR2, FR3, CDR3 and FR4. A numbering system has been devised for assigning numbers to amino acids that occupy positions in each of these domains. This numbering system is defined in Kabat Sequences of Proteins of Immunological Interest (1987 and 1991, NIH, Bethesda, Md.), or Chothia & Lesk, 1987, J. Mol. Biol. 196:901-917; Chothia et al., 1989, Nature 342:878-883.

The sequence information for specific antibodies prepared and identified as described in the Examples below is summarized in TABLE 1. Thus, in an embodiment, an antigen binding protein is an antibody with the CDR, variable domain and light and heavy chain sequences as specified in one of the rows of TABLE 1.

SEQ ID NOs have been assigned to variable light chain, variable heavy chain, light chain, heavy chain, CDRL1, CDRL2, CDRL3, CDRH1, CDRH2, and CDRH3 sequences of the antibodies and fragments thereof of the present invention and are shown in TABLE 1. SEQ ID NOs have also been assigned to polynucleotides encoding the variable light chain, variable heavy chain, light chain, heavy chain, CDRL1, CDRL2, CDRL3, CDRH1, CDRH2, and CDRH3 sequences of the antibodies and fragments thereof of the present invention and are shown in TABLE 2. The antigen binding proteins of the present invention can be identified by SEQ ID NO, but also by construct name (e.g., 15D11.1) or identifier number (e.g., iPS:480499).

The various light chain and heavy chain variable regions provided herein are depicted in TABLE 3. Each of these variable regions may be attached to a heavy or light chain constant regions to form a complete antibody heavy and light chain, respectively. Furthermore, each of the so generated heavy and light chain sequences may be combined to form a complete antibody structure.

TABLE 1

| | Amino acid SEQ ID NOs. | | | | | | | | |
|---|---|---|---|---|---|---|---|---|---|
| Ref # | Antibody | VL | VH | CDRL1 | CDRL2 | CDRL3 | CDRH1 | CDRH2 | CDRH3 |
| iPS: 480496 | 17B3.1 | 3 | 4 | 92 | 93 | 94 | 224 | 225 | 226 |
| iPS: 480499 | 15D11.1 | 7 | 8 | 98 | 99 | 100 | 230 | 231 | 232 |
| iPS: 480522 | 4F5.1 | 11 | 12 | 104 | 105 | 106 | 236 | 237 | 238 |
| iPS: 481499 | 1A12.1 | 15 | 16 | 110 | 111 | 112 | 242 | 243 | 244 |
| iPS: 480526 | 6B1.1 | 19 | 20 | 116 | 117 | 118 | 248 | 249 | 250 |

TABLE 1-continued

Amino acid SEQ ID NOs.

| Ref # | Antibody | VL | VH | CDRL1 | CDRL2 | CDRL3 | CDRH1 | CDRH2 | CDRH3 |
|---|---|---|---|---|---|---|---|---|---|
| iPS: 480529 | 1G9.1 | 23 | 24 | 122 | 123 | 124 | 254 | 255 | 256 |
| iPS: 480533 | 6E12.1 | 27 | 28 | 128 | 129 | 130 | 260 | 261 | 262 |
| iPS: 480548 | 9G5.1 | 31 | 32 | 134 | 135 | 136 | 266 | 267 | 268 |
| iPS: 480551 | 5A12.1 | 35 | 36 | 140 | 141 | 142 | 272 | 273 | 274 |
| iPS: 480555 | 6B11.1 | 39 | 40 | 146 | 147 | 148 | 278 | 279 | 280 |
| iPS: 480558 | 8C8.1 | 43 | 44 | 152 | 153 | 154 | 284 | 285 | 286 |
| iPS: 480561 | 8G12.1 | 47 | 48 | 158 | 159 | 160 | 290 | 291 | 292 |
| iPS: 480572 | 9D3.1_LC1 | 51 | 52 | 164 | 165 | 166 | 296 | 297 | 298 |
| iPS: 480573 | 9D3.1_LC2 | 55 | 56 | 170 | 171 | 172 | 302 | 303 | 304 |
| iPS: 481500 | 6C9.1 | 59 | 60 | 176 | 177 | 178 | 308 | 309 | 310 |
| iPS: 481501 | 4E2.1 | 63 | 64 | 182 | 183 | 184 | 314 | 315 | 316 |
| iPS: 481983 | 3D5.1 | 67 | 68 | 188 | 189 | 190 | 320 | 321 | 322 |
| iPS: 481984 | 5D11.1 | 71 | 72 | 194 | 195 | 196 | 326 | 327 | 328 |
| iPS: 481989 | 1H1.1 | 75 | 76 | 200 | 201 | 202 | 332 | 333 | 334 |
| iPS: 480570 | 9E8.1 | 79 | 80 | 206 | 207 | 208 | 338 | 339 | 340 |
| iPS: 480538 | 2B6.1 | 83 | 84 | 212 | 213 | 214 | 344 | 345 | 346 |
| iPS: 480569 | 1D2.1 | 87 | 88 | 218 | 219 | 220 | 350 | 351 | 352 |

TABLE 2

Nucleic acid SEQ ID NOs.

| Ref # | Antibody | VL | VH | CDRL1 | CDRL2 | CDRL3 | CDRH1 | CDRH2 | CDRH3 |
|---|---|---|---|---|---|---|---|---|---|
| iPS: 480496 | 17B3.1 | 1 | 2 | 89 | 90 | 91 | 221 | 222 | 223 |
| iPS: 480499 | 15D11.1 | 5 | 6 | 95 | 96 | 97 | 227 | 228 | 229 |
| iPS: 480522 | 4F5.1 | 9 | 10 | 101 | 102 | 103 | 233 | 234 | 235 |
| iPS: 481499 | 1A12.1 | 13 | 14 | 107 | 108 | 109 | 239 | 240 | 241 |
| iPS: 480526 | 6B1.1 | 17 | 18 | 113 | 114 | 115 | 245 | 246 | 247 |
| iPS: 480529 | 1G9.1 | 21 | 22 | 119 | 120 | 121 | 251 | 252 | 253 |
| iPS: 480533 | 6E12.1 | 25 | 26 | 125 | 126 | 127 | 257 | 258 | 259 |
| iPS: 480548 | 9G5.1 | 29 | 30 | 131 | 132 | 133 | 263 | 264 | 265 |
| iPS: 480551 | 5A12.1 | 33 | 34 | 137 | 138 | 139 | 269 | 270 | 271 |
| iPS: 480555 | 6B11.1 | 37 | 38 | 143 | 144 | 145 | 275 | 276 | 277 |
| iPS: 480558 | 8C8.1 | 41 | 42 | 149 | 150 | 151 | 281 | 282 | 283 |
| iPS: 480561 | 8G12.1 | 45 | 46 | 155 | 156 | 157 | 287 | 288 | 289 |
| iPS: 480572 | 9D3.1_LC1 | 49 | 50 | 161 | 162 | 163 | 293 | 294 | 295 |
| iPS: 480573 | 9D3.1_LC2 | 53 | 54 | 167 | 168 | 169 | 299 | 300 | 301 |
| iPS: 481500 | 6C9.1 | 57 | 58 | 173 | 174 | 175 | 305 | 306 | 307 |
| iPS: 481501 | 4E2.1 | 61 | 62 | 179 | 180 | 181 | 311 | 312 | 313 |
| iPS: 481983 | 3D5.1 | 65 | 66 | 185 | 186 | 187 | 317 | 318 | 319 |
| iPS: 481984 | 5D11.1 | 69 | 70 | 191 | 192 | 193 | 323 | 324 | 325 |
| iPS: 481989 | 1H1.1 | 73 | 74 | 197 | 198 | 199 | 329 | 330 | 331 |
| iPS: 480570 | 9E8.1 | 77 | 78 | 203 | 204 | 205 | 335 | 336 | 337 |
| iPS: 480538 | 2B6.1 | 81 | 82 | 209 | 210 | 211 | 341 | 342 | 343 |
| iPS: 480569 | 1D2.1 | 85 | 86 | 215 | 216 | 217 | 247 | 348 | 349 |

TABLE 3

Exemplary Variable Light and Variable Heavy Regions: Nucleic Acid ("NA") and Amino Acid ("AA") Sequences

| ips: 480496 | 17B3.1 | NA | GACATCCAGATGACCCAGTCTCCATCTTCCGTGTCTGCA TCTGTAGGAGACAGAGTCACCATCACTTGTCGGGCGAGT CAGGGTATTAGCGACTGGTTAGCCTGGTATCAGCAGAAA CCAGGGAAAGCCCCTAAGCTCCTGATCTTTGCTGCATCC AGTTTGCAAAGTGGGGTCCCATCCAGGTTCAGCGGCAGT GAATCTGGGACAGATTTCACTCTCACCATCAGCAGCCTG CAGCCTGAAGATTTTGCAACTTACTATTGTCAACAGGCT AACAGTTTCCCGATCACCTTCGGCCAAGGGACACGACTG GAGATTCAA (SEQ ID NO: 1) | CAGGTGCAGCTGGTGGAGTCTGGGGGAGGCGTGGTCCA GCCTGGGAGGTCCCTGAGACTCTCCTGTGCAGCGTCGG ATTCACCTTCAGTAGTTATGGCATGCACTGGGTCCGCCA GGCTCCAGGCAAGGGGCTGGAGTGGGTGGCAGTTATAT GGTATGATGGAAGTAATGAATACTATGCAGACTCCGTGA AGGGCCGATTCACCATCTCCAGAGACAATTCCAAGAAC ACGCTGTATCTGCAAATGAACAGCCTGAGAGCCGAGGA CACGGCTGTGTATTACTGTGCGAGACATGACCACAGTCA CTACGGTTTTGACTACTGGGGCCAGGGAACCCTGGTCAC CGTATCCTCA (SEQ ID NO: 2) |
|---|---|---|---|---|
| | | AA | DIQMTQSPSSVSASVGDRVTITCRASQGISDWLAWYQQKP GKAPKLLIFAASSLQSGVPSRFSGSESGTDFTLTISSLQPED FATYYCQQANSFPITFGQGTRLEIQ (SEQ ID NO: 3) | QVQLVESGGGVVQPGRSLRLSCAASGFTFSSYGMHWVRQ APGKGLEWVAVIWYDGSNEYYADSVKGRFTISRDNSKNTL YLQMNSLRAEDTAVYYCARHDHSYGFDYWGQGTLVTV SS (SEQ ID NO: 4) |

TABLE 3-continued

Exemplary Variable Light and Variable Heavy Regions: Nucleic Acid ("NA") and Amino Acid ("AA") Sequences

| iPS: 480499 | 15D11.1 | NA | CAGTCTGCCCTGACTCAGCCTGCCTCCGTGTCTGGGTCTC CTGGACAGTCGATCACCATCTCCTGCACTGGAACCAGCA GTGCCGTTGGTGGTCATAACTTTGTCTCCTGGTACCAAC AGTACCCAGGCAAAGCCCCCAAACTCATGATTTATGAGG TCAGTAATCGGCCCTCAGGGGTTTCTACTCGCTTCTCTGG CTCCAAGTCTGGCAACACGGCCTCCCTGACCATCTCTGG GCTCCAGGCTGAGGACGAGGCTGATTATTACTGCAGCTC TTATACAAGCAGCAGCACTTGGGTGTTCGGCGGAGGGA CCAGGCTGACCGTCCTA (SEQ ID NO: 5) | CAGGTCACCTTGAAGGAGTCTGGTCCTGTGCTGGTGAAA CCCACAGAGACCCTCACGCTGACCTGCACCGTCTCTGGG TTCTCACTCAGCAATGCTGAAATGGGTGTGAGCTGGATC CGTCAGCCCCCAGGGAAGGCCCTGGAGTGGCTTGCACA CCTTTTTTCGAATGACGAAAATCCTACAGCACATCTCT GAAGAGCAGGCTCACCATCTCCAAGGACACCTCCAAAA GCCAGGTGGTCCTTACCATGACCGACCTGGACCCTGTGG ACACAGCCACCTATTACTGTGCACGGTCGTTTAACTGGA ACTACGACTTTGACTACTGGGGCCAGGGAACCCTGGTCA CCGTCTCCTCA (SEQ ID NO: 6) |
|---|---|---|---|---|
| | | AA | QSALTQPASVSGSPGQSITISCTGTSSAVGGHNFVSWYQQY PGKAPKLMIYEVSNRPSGVSTRFSGSKSGNTASLTISGLQAE DEADYYCSSYTSSSTWVFGGGTRLTVL (SEQ ID NO: 7) | QVTLKESGPVLVKPTETLTLTCTVSGFSLSNAEMGVSWIR QPPGKALEWLAHLFSNDEKSYSTSLKSRLTISKDTSKSQV VLTMTDLDPVDTATYYCARSFNWNYDFDYWGQGTLVTVSS (SEQ ID NO: 8) |
| iPS: 480522 | 4F5.1 | NA | GAAATAGTGATGACGCAGTCTCCAGCCACCCTGTCTGTG TCTCCAGGGGAAAGAGCCACCCTCTCCTGCAGGGCCAGT CAGAGTGTTAGGAGCAACTTAGCCTGGTACCAGCAGAA AGCTGGCCAGGCTCCCAGGCTCCTCATCGATGGTGCATC CACCAGGGCCACTGGCATAACAGCCAGGTTCAGTGGCA GTGGGTCTGGGACAGAGTTCACTCTCACCATCAGCAGCC TGCAGTCTGAAGATTTTGCAGTTTATTACTGTCAGCAGT ATAATAACTGGCCTACTTTCGGCCCTGGGACCAAAGTGG ATATCAAA (SEQ ID NO: 9) | CAGCTGCAGCTGCAGGAGTCGGGCCCAGGACTGGTGAA GCCTTCGGAGACCCTGTCCCTCACCTGCACTGTCTCTGGT GGCTCCATCAGCAGTGGTAGTTACTACTGGGGCTGGATC CGCCAGCCCCCAGGGAAGGGGCTGGAGTGGATTGGGAG TATCTATTATGGTGGGAACACCTACTACAACCCGTCCCT CAAGAGTCGAGTCACCATATCCATAGACACGTCCAAGA ACCAGTTCTCCCTGAAGCTGAGCTCTGTGACCGCCGCAG ACACGGCTGTGTATTACTGTGCGGGAGAACTGCGGAGG GCTTTTGATATCTGGGGCCAAGGGACAATGGTCACCGTC TCTTCA (SEQ ID NO: 10) |
| | | AA | EIVMTQSPATLSVSPGERATLSCRASQSVRSNLAWYQQKA GQAPRLLIDGASTRATGITARFSGSGSGTEFTLTISSLQSED FAVYYCQQYNNWPTFGPGTKVDIK (SEQ ID NO: 11) | QLQLQESGPGLVKPSETLSLTCTVSGGSISSGSYMGWIRQ PPGKGLEWIGSIYYGGNTYYNPSLKSRVTISIDTSKNQFS LKLSSVTAADTAVYYCAGELRRAFDIWGQGTMVTVSS (SEQ ID NO: 12) |
| iPS: 481499 | 1A12.1 | NA | AATTTTATGCTGACTCAGCCCCACTCTGTGTCGGAGTCTC CGGGGAAGACGGTAACCATCTCCTGCACCCGCAGCAGT GACAGCATTGCCAGCAACTATGTGCAGTGGTACCAGCA GCGCCCGGGCAGTTCCCCCACCACTGTGATCTTTGAGGA TAACCAAAGACCCTCTGGGGTCCCTGATCGGTTCTCTGG CTCCATCGACAGCCTCCTCCAACTCTGCCTCCCTCACCATC TCTGGACTGAAGCCTGAAGATGAAGCTGACTACTACTGT CAGTCTTATGATAGCAGCAATCATGTGGTATTCGGCGGA GGGACCAAGCTGACCGTCCTA (SEQ ID NO: 13) | CAGGTGCAGCTGGTGGAGTCTGGGGGAGGCGTGGTCCA GCCTGGGAGGTCCCTGAGACTCTCCTGTGCAGCGTCTGG ATTCACCTTCAGTTACTATGGCATGCACTGGGTCCGCCA GGCTCCAGGCAAGGGGCTGGAGTGGGTGGCAGTTATAT GGTATGATGGAAGTAATAAATACTATGCAGACTCCGTGA AGGGCCGATTCACCATCTCCAGAGACAATTCCAAGAAC ACGCTGTATCTGCAAATGAACAGCCTGAGAGCCGAGGA CACGGCTGTGTATTACTGTGCGAGAGATCATGACTACGG TGTCCTGTACTACTTTGACTACTGGGGCCAGGGAACCCT GGTCACCGTCTCCTCA (SEQ ID NO: 14) |
| | | AA | NFMLTQPHSVSESPGKTVTISCTRSSDSIASNYVQWYQQRP GSSPTTVIFEDNQRPSGVPDRFSGSIDSSSNSASLTISGLKP EDEADYYCQSYDSSNHVVFGGGTKLTVL (SEQ ID NO: 15) | QVQLVESGGGVVQPGRSLRLSCAASGFTFSYYGMHWVRQ APGKGLEWVAVIWYDGSNKYYADSVKGRFTISRDNSKNT LYLQMNSLRAEDTAVYYCARDHDYGVLYYFDWGQGTL VTVSS (SEQ ID NO: 16) |
| iPS: 480526 | 6B1.1 | NA | TCCTTTGAACTGACACAGCCACCCTCGGTGTCAGTGTCC CCAGGACAGACGGCCAGGATCACCTGCTCTGGAGATGC ATTGCCAAAGCAATATGCTTATTGGTACCGGCAGAAGCC AGGCCAGGCCCCTGTACTGGTAATATATAAAGACAGTG AGAGGCCCTCAGGGATCCATGAGCGATTCTCTGGCTCCA CCTCAGGGACAACAGTCACGTTGACCATCAGTGGAGTCC AGGCAGAAGACGAGGCTGACTATTACTGTCAATCAACA GACAGAAGAGGTACTGTGTTCGGCGGAGGGACCAAGTT GACCGTCCTA (SEQ ID NO: 17) | CAGATCACCTTGAAGGAGTCTGGTCCTACGCTGGTGAAA CCCACACAGACCCTCACGCTGACCTGCACCTTCTCTGGG TTCTCACTCAGCACTAGTGGAGTGGGTGTGGGCTGGATC CGTCAGCCCCCAGGAAAGGCCCTGGAGTGGCTTGCACTC ATTTATTGGAATGATGATAAGCGCTACAGCCCATCTCTG AAGAGCAGGCTCACCATCACCAAGGACACCTCCAAAA CCAGGTGGTCCTTACAATGACCAACATGGACCCTGTGGA CACAGCCACATATTACTGTGCACACAGACATGGCTACGA TAGGATGCGTGATGCTTTTGATATCTGGGGCCAAGGGAC AATGGTCACCGTCTCTTCA (SEQ ID NO: 18) |
| | | AA | SFELTQPPSVSVSPGQTARITCSGDALPKQYAYWYRQKPGQ APVLVIYKDSERPSGIHERFSGSTSGTTVTLTISGVQAEDEA DYYCQSTDRRGTVFGGGTKLTVL (SEQ ID NO: 19) | QITLKESGPTLVKPTQTLTLTCTFSGFSLSTSGVGVGWIR QPPGKALEWLALIYWNDDKRYSPSLKSRLTITKDTSKNQV VLTNITNMDPVDTATYYCAHRHGYDRMRDAFDIWGQGTMV TVSS (SEQ ID NO: 20) |
| iPS: 480529 | 1G9.1 | NA | GAAATTGTGTTGACGCAGTCTCCAGACACCCTGTCTTTG TCTCCAGGGGAAAGAGCCACCCTCTCCTGCAGGGCCAGT CAGATTTTTAGCAGCAGTTACTTAGCCTGGTACCAGCAG AAACCTGGCCAGGCTCCCAGGCTCCTCATCTCTGGTGCA TCCAGCAGGGCCACTGGCATCCCAGACAGGTTCAGTGGC AGTGGGTCTGGGACAGACTTCACTCTCACCATCAGCAG ACTGGAGCCTGAGGATTTTGCAGTGTATTACTGTCAGCAG TATGGTAGCTCATGCAGTTTTGGCCAGGGGACCAAGCTG GAGATCAAA (SEQ ID NO: 21) | CAGGTGCAGTTGGTGCAGTCTGGGGCTGAGGTGAAGAA GCCTGGGGCCTCAGTGAAGGTTTCCTGCAAGGCATCTGG ATACACCTTCACCAGCTACTTTATACACTGGGTGCGACA GGCCCCTGGACAAGGGCTTGAGTGGATGGGAATAATCA ACCCTAGTGGTGGTAGCACAAGCTACGCACAGAAGTTCC AGGGCAGAGTCACCATGACCAGGGACACGTCCACGAGT ACAGTCTACATGGAGCTTAGCAGCCTGAGATCTGAGGAC ACGGCCGTGTATTACTGTGCGAGAGATCAGGAGGGAGC AGTGGCTGGTACAGACTACTACTTCTACGGTATGGACGT CTGGGGCCAAGGGACCACGGTCACCGTCTCCTCA (SEQ ID NO: 22) |

TABLE 3-continued

Exemplary Variable Light and Variable Heavy Regions: Nucleic Acid ("NA") and Amino Acid ("AA") Sequences

| | | | | |
|---|---|---|---|---|
| | | AA | EIVLTQSPDTLSLSPGERATLSCRASQIFSSSYLAWYQQKPG QAPRLLISGASSRATGIPDRFSGSGSGSDFTLTISRLEPEDF AVYYCQQYGSSCSFGQGTKLEIK (SEQ ID NO: 23) | QVQLVQSGAEVKKPGASVKVSCKASGYTFTSYFIHWVRQ APGQGLEWMGIINPSGGSTSYAQKFQGRVTNITRDTSTST VYMELSSLRSEDTAVYYCARDQEGAVAGTDYYFYGMDVW GQGTTVTVSS (SEQ ID NO: 24) |
| iPS: 480533 | 6E12.1 | NA | GATATTGTGATGACTCAGTCTCCACTCTCCCTGCCCGTCA CCCCTGGAGAGCCGGCCTCCATCTCCTGCAGGTCTAGTC AGAGCCTCCTACATAGTCATGGATACAGCTATTTGAATT GGTACCTGCAGAAGCCAGGGCAGTCTCCACAGCTCCTGA TCCATTTGGGTTCTAATCGGGCCTCCGGGGTCCCTGACA GGTTCAGTGGCAGTGGATCAGGCACAGAATTTACACTGA GAATCAGCAGAGTGGAGGCTGAGGATGTTGGGGTTTATT ACTGCATGCAAGTTCTGCTAACTCCGATCACCCTCGGCC AAGGGACACGACTGGAGATTAAA (SEQ ID NO: 25) | CAGGTGCAGCTGGTGGAGTCTGGGGGAGGCGTGGTCCA GCCTGGGAGGTCCCTGAGACTCTCCTGTGCAGCCTCTGG ATTCACCTTCAGTAGCTATGGCATGCACTGGGTCCGCCA GGCTCCAGGCAAGGGGCTGGAGTGGGTGGCAGTTATAT CATATGATGGAAATAATAAATACTATGCAGACTCCGTGA AGGGCCGATTCACCATCTCCAGAGACAATTCCAAGACCA CGCTGTATCTGCAAATGAACAGCCTGAGACCTGAGGAC ACGGCTGTGTTTTACTGTGCGAGAGATGCCAGTGGGAGC TCCCTCTACCTTGACTACTGGGGCCAGGGAACCCTGGTC ACCGTCTCCTCA (SEQ ID NO: 26) |
| | | AA | QVQLVESGGGVVQPGRSLRLSCAASGFTFSSYGMHWVRQ APGKGLEWVAVISYDGNNKYYADSVKGRFTISRDNSKTTL AEDVGVYYCMQVLLTPITLGQGTRLEIK (SEQ ID NO: 27) | DIVMTQSPLSLPVTPGEPASISCRSSQSLLHSHGYSYLNW YLQKPGQSPQLLIHLGSNRASGVPDRFSGSGSGTEFTLRI SRVEYLQMNSLRPEDTAVFYCARDASGSSLYLDYWGQGTL VTVSS (SEQ ID NO: 28) |
| iPS: 480548 | 9G5.1 | NA | GATATTGTGATGACTCAGTCTCCACTCTCCCTGCCCGTCA CCCCTGGAGAGCCGGCCTCCATCTCCTGCAGGTCTAGTC AGAGCCTCCTACATAGTCATGGATACAACTATTTGAATT GGTACCTGCAGAAGCCAGGGCAGTCTCCACACCTCCTGA TCTATTTGGGTTCTAATCGGGCTCCGGGGTCCCTGACA GGTTCAGTGGCAGTGGATCAGGCACAGAATTTACACTGA AAATCAGCAGAGTGGAGGCTGAGGATGTTGGGGTTTATT ACTGCATGCAAGTTCTACAAACTCCGATCACCCTCGGCC AAGGGACACGACTGGAGATTAAA (SEQ ID NO: 29) | CAGGTGCAGCTGGTGGAGTCTGGGGGAGGCGTGGTCCA GCCTGGGAGGTCCCTGAGACTCTCCTGTGCAGCCTCTGG ATTCACCTTCAGTAGCTATGGCATGCACTGGGTCCGCCA GGCTCCAGGCAAGGGGCTGGAGTGGGTGGCAGTTATAT CATATGATGGAAGTAAAAAATACTATGCAGACTCCGTG AAGGGCCGATTCACCATCTCCAGAGACAATTCCAAGAA CACGCTGTATCTGCAAATGAACAGCCTGAGAGCTGAGG ACACGGCTGTGTATTACTGTGCGAGAGATGCCAGTGGGA GCTCCCTCTACTCTGACTACTGGGGCCAGGGAATCCTGG TCACCGTCTCCTCA (SEQ ID NO: 30) |
| | | AA | DIVMTQSPLSLPVTPGEPASISCRSSQSLLHSHGYNYLNWY LQKPGQSPHLLIYLGSNRASGVPDRFSGSGSGTEFTLKISRV EEADVGVYYCMQVLQTPITLGQGTRLEIK (SEQ ID NO: 31) | QVQLVESGGGVVQPGRSLRLSCAASGFTFSNYGMHWVRQ APGKGLEWVAVISYDGSKKYYADSVKGRFTISRDNSKNTL YLQMNSLRAEDTAVYYCARDASGSSLYSDYWGQGILVTV SS (SEQ ID NO: 32) |
| iPS: 480551 | 5A12.1 | NA | GATATTGTGATGACTCAGTCTCCACTCTCCCTGCCCGTCA CCCCTGGAGAGCCGGCCTCCATCTCCTGCAGGTCTAGTC AGGGCCTCCTACATAGTCATGGATACCACTATTTGAATT GGTACCTGCAGAAGCCAGGGCAGTCTCCACAGCTCCTGA TCTATTTGGGTTCTAATCGGGCCTCCGGGGTCCCTGACA GGTTCAGTGGCAGTGGATCAGGCACAGAATTTACACTGA AAATCAGCAGAGTGGAGGCTGAGGATGTTGGGGTTTATT ACTGCATGCAAGTTCTACAAACTCCGATCACCCTCGGCC AAGGGACACGACTGGAGATTAAA (SEQ ID NO: 33) | CAGGTGCAGCTGGTGGAGTCTGGGGGAGGCGTGGTCCA GCCTGGGAGGTCCCTGAGACTCTCCTGTGCAGCCTCTGG ATTCACCTTCAGTAGCTATGGCATGCACTGGGTCCGCCA GGCTCCAGGCAAGGGGCTGGAGTGGGTGACAGTTATAT CAAAAGATGGAAGTTATAAATACTATGCGGACTCCGTG AAGGGCCGATTCACCATCTCCAGAGACAATTCCAAGAA CACGCTGTATCTGCAAATGAACAGCCTGAGAGCTGAGG ACACGGCTGTGTATTACTGTGCGAGGGATGCCAGTGGGA GCTCCCTCTACTTAGACTACTGGGGCCAGGGTACCCTGG TCACCGTCTCCTCA (SEQ ID NO: 34) |
| | | AA | DIVMTQSPLSLPVTPGEPASISCRSSQGLLHSHGYHYLNWY LQKPGQSPQLLIYLGSNRASGVPDRFSGSGSGTEFTLKISRV EEADVGVYYCMQVLQTPITLGQGTRLEK (SEQ ID NO: 35) | QVQLVESGGGVVQPGRSLRLSCAASGFTFSSYGMHWVRQ APGKGLEWVTVISKDGSYKYYADSVKGRFTISRDNSKNTL YLQMNSLRAEDTAVYYCARDASGSSLYLDWGQGTLVTV SS (SEQ ID NO: 36) |
| iPS: 480555 | 6B11.1 | NA | CAGTCTGTGCTGACTCAGCCACCCTCAGCGTCTGGGACC CCCGGGCAGAGGGTCACCATCTCTTGTTCTGGAAGCAGC TCCAACATCGGAAGAAATACTGTAAACTGGTACCAGCA GCTCCCAGGAACGGCCCCCAAACTCCTCATCTATAGTAA TAATCAGCGGCCCTCAGGGGTCCCTGACCGATTCTCTGG CTCCAAGTCTGGCACCTCAGTCTCCCTGGCCATCAGTGG GCTCCAGTCTGAGGATGAGGCTGATTATTACTGTGCAGC ATGGGATGACAGCCTGAATGGTGTGGTATTCGGCGGAG GGACCAAGTTGACCGTCCTA (SEQ ID NO: 37) | CAGGTGCAGCTGGTGGAGTCTGGGGGAGGCGTGGTCCA GCCTGGGAGGTCCCTGAGACTCTCCTGTGCAGCGTCTGG ATTCACCTTCAGTAGCTATGGCATGCACTGGGTCCGCCA GGCTCCAGGCAAGGGGCTGGAGTGGGTGGCAGTTATAT GGTATGATGGAAGTAATAAATACCATGCAGACTCCGTG AAGGGCCGATTCACCATCTCCAGAGACAATTCCAAGGA CACGCTGTATCTGCAAATGAACAGCCTGAGAGCTGAGG ACACGGCTGTGTATTACTGTGCGGGGGACTTTGCTTACT TCTACTACGGTATGGACGTCTGGGGCCAAGGGACCACG GTCACCGTCTCCTCA (SEQ ID NO: 38) |
| | | AA | QSVLTQPPSASGTPGQRVTISCSGSSSNIGRNTVNWYQQLP GTAPKLLIYSNNQRPSGVPDRFSGSKSGTSVSLAISGLQSED EADYYCAAWDDSLNGVVFGGGTKLTVL (SEQ ID NO: 39) | QVQLVESGGGVVQPGRSLRLSCAASGFTFSSYGMHWVRQ APGKGLEWVAVIWYDGSNKYHADSVKGRFTISRDNSKDT LYLQMNSLRAEDTAVYYCAGDFAYFYYGMDVWGQGTTV TVSS (SEQ ID NO: 40) |
| iPS: 480558 | 8C8.1 | NA | TCCTATGAGCTGACCCAGCCACCCTCGGTGTCAGTGTCC CCAGGACAGACGGCCAGGATCACCTGCTCTGGAGATGC TTTGCCAAGGCAATATACTTATTGGTACCAGCAGAAACC | CAGATCACCTTGAAGGAGTCTGGTCCTACGCTGGTGAAA CCCACACAGACCCTCACGCTGACCTGCACCTTCTCTGGG TTCTCACTCAGCACTAGTGGAGTGGGTGTGGGCTGGATC |

TABLE 3-continued

Exemplary Variable Light and Variable Heavy Regions: Nucleic Acid ("NA") and Amino Acid ("AA") Sequences

| | | | | |
|---|---|---|---|---|
| | | | AGGCCAGGCCCCTGTTCTGGTGATATTTAAAGACACTGC GAGGCCCTCAGGGATCCCTGAGCGATTCTCTGGCTCCAG CTCAGGGACAACAGTCACGTTGACCATCAGTGGAGTCCA GGCAGAAGACGAGGCTGACTATTACTGTCAATAACAG ACAGAAGTGGTACTGTGTTCGGCGGAGGGACCAAGCTG ACCGTCCTA (SEQ ID NO: 41) | CGTCAGCCCCCAGGAAAGGCCCTGGAGTGGCTTGCACTC ATTTATTGGAATGATGATAAGCGCTACAGCCCATCTCTG AAGAGCAGGCTCACCATCACCAAGGACACCTCCAAAAA CCAGGTGGTCCTTACAATGACCAACATGGACCCTGTGGA CACAGCCACATATTACTGTGCACACAGACATGGCTACGA TAGGATGCGTGATGCTTTTGATATCTGGGGCCAAGGGAC AATGGTCACCGTCTCTTCA (SEQ ID NO: 42) |
| | | AA | SYELTQPPSVSVSPGQTARITCSGDALPRQYTYWYQQKPG QAPVLVIFKDTARPSGIPERFSGSSSGTTVTLTISGVQAEDE ADYYCQSTDRSGTVFGGGTKLTVL (SEQ ID NO: 43) | QITLKESGPTLVKPTQTLTLTCTFSGFSLSTSGVGVGWIR QPPGKALEWLALIYWNDDKRYSPSLKSRLTITKDTSKNQV VLTNITNMDPVDTATYYCAHRHGYDRMRDAFDIWGQGTMV TVSS (SEQ ID NO: 44) |
| iPS: 480561 | 8G12.1 | NA | GAAATTGTGATGACCCAGACTCCATTCTCTCTGTCCGTC ACCCCTGGACAGCCGGCCTCCATCTCCTGCAAGTCTAGT CAGAGCCTCCTGCATAGTAGTGGAAAGACCTATTTGTAT TGGTACCTGCAGAAGCCAGGCCAGCCTCCACAGCTCCTG ATCTATGAAGTTTCCAACCGGTTCTCTGGAGTGCCAGAT AGGTTCAGTGGCAGCGGGTCAGGGACAGATTTCACACT GAAAATCAGCCGGGTGGAGGCTGAGGATGTTGGGGTTT ATTTCTGCATGCAAAGTATACAGCTTCCGTGGACGTTCG GCCAAGGGACCAAGGTGGAAATCAAA (SEQ ID NO: 45) | CAGGTGCAGCTGCAGGAGTCGGGCCCAGGACTGGTGAA GCCTTCCCAGACCCTGTCCCTCACCTGCACTGTCTCTGGT GGCTCCATCAACAGTGGTGGTTACTACTGGAGCTGGATC CGCCAGCACCCAGGGAAGGGCCTGGAGTGGATTGGGTA CATCTCTTACAGTGGGAGCACCTACTACAACCCGTCCCT CAAGAGTCGAGTTACCATATCAGTAGACACGTCTAAGA ACCAGTTCTCCCTGAGGCTGAGCTCTGTGACTGCCGCGG ACACGGCCGTGTATTACTGTGCGAGAGAGAGCCCTACG GTGACTACGGCTTTTGATATCTGGGGCCAAGGGACAAAG GTCACCGTCTCTTCA (SEQ ID NO: 46) |
| | | AA | EIVMTQTPFSLSVTPGQPASISCKSSQSLLHSSGKTYLWYL QKPGQPPQLLIYEVSNRFSGVPDRFSGSGSGTDFTLKISRVE AEDVGVYFCMQSIQLPWTFGQGTKVEIK (SEQ ID NO: 47) | QVQLQESGPGLVKPSQTLSLTCTVSGGSINSGGYMSWIRQ HPGKGLEWIGYISYSGSTYYNPSLKSRVTISVDTSKNQFS LRLSSVTAADTAVYYCARESPTVTTAFDIWGQGTKVTVSS (SEQ ID NO: 48) |
| iPS: 480572 | 9D3.1_ LC1 | NA | GACATCCAGTTGACCCAGTCTCCATCCTCCCTGTGTGCA TCTGTAGGAGACAGAGTCACCATCACTTGCCGGGTGAGT CAGGACATTAACAGTTATTTAAATTGGTGTCGGCAGAAA CCAGGGAAAGTTCCTCAGTTCCTGATCTATAGTGCATCC AATTTGCAATCTGGAGTCCCATCTCGGTTCAGTGGCAGT GGATCTGGGACAGATTTCACTCTCACTTTCAGCGGCCTG CAGACTGAATATGTTGCACGTTATTACGGTCAACGGACT TACAATGCCCTTCCGACGTTCGGCCTAGGGACCAGGGCG GAAATCAAA (SEQ ID NO: 49) | CAGGTGCAGCTGCAGGAGTCGGGCCCAGGACTGGTGAA GCCTTCACAGACCCTGTCCCTCACCTGCACTGTCTCTGGT GGCTCCATCAGCAGTGGTGGTTACGACTGGAGCTGGATC CGCCAGCACCCAGGGAAGGGCCTGGAGTGGATTGGGAA CATTTATTACAGTGGGAGGACCTACTACAACCCGTCCCT CAAGAGTCGAATTACCATATCAGTAGACACGTCTAAGA ACCAGTTCTCCCTGAAGCTGAGGTCTGTGACTGCCGCGG ACACGGCCGTGTATTACTGTGCGAGAGATCGCCCTTATG GAGGTAATTCCGGCTACTACTACGGTATGGACGTCTGGG GCCAAGGGACCACGGTCACCGTCTCCCCA (SEQ ID NO: 50) |
| | | AA | DIQLTQSPSSLCASVGDRVTITCRVSQDINSYLNWCRQKPG KVPQFLIYSASNLQSGVPSRFSGSGSGTDFTLTFSGLQTEYV ARYYGQRTYNALPTFGLGTRAEIK (SEQ ID NO: 51) | QVQLQESGPGLVKPSQTLSLTCTVSGGSISSGGYDWSWIR QHPGKGLEWIGNIYYSGRTYYNPSLKSRITISVDTSKNQF SLLRSVTAADTAVYYCARDRPYGGNSGYYYGMDVWGQGTT KVTVSP (SEQ ID NO: 52) |
| iPS: 480573 | 9D3.1_ LC2 | NA | GAAATTGTGTTGACGCAGTCTCCAGGCACCCTGTCTTTG TCTCCAGGGGAAAGAGCCACCCTCTCCTGCAGGGCCAGT CAGACTATTAGCAGCAGCTACTTAGCCTGGTACCAGCAG AGACCTGGCCAGGCTCCCAGGCTCCTTATGTATGGTGCA TCCAACAGGGTCATTGGCATCCCAGTCAGGTTCAGTGGC GGTGGGTGTGGGACAGACTTCACTTTCACCATCAGCAGA CTGGATCCTGAAGATTTTGCAGTGTATTACTGTCAGCAG TATGGTAACTCACCCATGTGCAGTTTTGGCCAGGGGACC AAGGTGGAGATCAAA (SEQ ID NO: 53) | CAGGTGCAGCTGCAGGAGTCGGGCCCAGGACTGGTGAA GCCTTCACAGACCCTGTCCCTCACCTGCACTGTCTCTGGT GGCTCCATCAGCAGTGGTGGTTACGACTGGAGCTGGATC CGCCAGCACCCAGGGAAGGGCCTGGAGTGGATTGGGAA CATTTATTACAGTGGGAGGACCTACTACAACCCGTCCCT CAAGAGTCGAATTACCATATCAGTAGACACGTCTAAGA ACCAGTTCTCCCTGAAGCTGAGGTCTGTGACTGCCGCGG ACACGGCCGTGTATTACTGTGCGAGAGATCGCCCTTATG GAGGTAATTCCGGCTACTACTACGGTATGGACGTCTGGG GCCAAGGGACCACGGTCACCGTCTCCCCA (SEQ ID NO: 54) |
| | | AA | EIVLTQSPGTLSLSPGERATLSCRASQTISSSYLAWYQQRPG QAPRLLMYGASNRVIGIPVRFSGGGCGTDFTFTISRLDPEDF AVYYCQQYGNSPMCSFGQGTKVEIK (SEQ ID NO: 55) | QVQLQESGPGLVKPSQTLSLTCTVSGGSISSGGYDWSWIR QHPGKGLEWIGNIYYSGRTYYNPSLKSRITISVDTSKNQF SLKLRSVTAADTAVYYCARDRPYGGNSGYYYGMDVWGQGT TVTVSP (SEQ ID NO: 56) |
| iPS: 481500 | 6C9.1 | NA | GAAATAGTGATGACGCAGTCTCCAGCCACCCTGTCTGTG TCTCCAGGGGAGAGAGCCACCCTCTCCTGCAGGGCCAGT CAGAGTGTTAGGAGCAACTTAGCCTGGTACCAGCAGAA ACCTGGCCAGGCTCCCAGGCTCCTCATCGATGGTGCATC CACCAGGGCCACTGGTATCACAGCCAGGTTCAGTGGCA GTGGGTCTGGGACAGAGTTCACTCTCACCATCAGCAGCC TGCAGTCTGAAGATTTTGCAGTTTATTACTGTCAGCAGT ATAATAACTGGCCTACTTTCGGCCCTGGGACCAAAGTGG ATATCAAA (SEQ ID NO: 57) | CAGCTGCAGCTGCAGGAGTCGGGCCCAGGACTGGTGAA GCCTTCGGAGACCCTGTCCCTCACCTGCACTGTCTCTGGT GGCTCCATCAGCAGTAGTAGTTACTATTGGGGCTGGATC CGCCAGCCCCCAGGGAAGGGCTGGAGTGGATTGGGAG TATCTATTATGGTGGGAACACCTACTACAACCCGTCCCT CAAGAGTCGAGTCACCATATCCGTAGACACGTCCAAGA ACCAGTTCTCCCTGAAGCTGAGCTCTGTGACCGCCGCAG ACACGGCCGTGTATTACTGTGCGGGAGAACTGCCGAGG GCTTTTGATATCTGGGGCCAAGGGACAATGGTCACCGTC TCTTCA (SEQ ID NO: 58) |

TABLE 3-continued

Exemplary Variable Light and Variable Heavy Regions: Nucleic Acid ("NA") and Amino Acid ("AA") Sequences

| | | | | |
|---|---|---|---|---|
| | | AA | EIVMTQSPATLSVSPGERATLSCRASQSVRSNLAWYQQKP GQAPRLLIDGASTRATGITARFSGSGSGTEFTLTISSLQSE DFAVYYCQQYNNWPTFGPGTKVDIK (SEQ ID NO: 59) | QLQLQESGPGLVKPSETLSLTCTVSGGSISSSSYYWGWIR QPPGKGLEWIGSIYYGGNTYYNPSLKSRVTISVDTSKNQF SLKLSSVTAADTAVYYCAGELRRAFDIWGQGTMVTVSS (SEQ ID NO: 60) |
| iPS: 481501 | 4E2.1 | NA | GAAATAGTGATGACGCAGTCTCCAGCCACCCTGTCTGTG TCTCCAGGGGAAAGAGCCACCCTCTCCTGCAGGGCCAGT CAGAGTGTTAGGAGCAACTTAGCCTGGTACCAGCAGAAA ACCTGGCCAGGCTCCCAGGCTCCTCATCGATGGTGCATC CACCAGGGCCACTGGCATCACAGCCAGGTTCAGTGGCA GTGGGTCTGGGACAGAGTTCACTCTCACCATCAGCAGCC TGCAGTCTGAAGATTTTGCAGTTTATTACTGTCAGCAGT ATAATAATTGGCCTACTTTCGGCCCTGGGACCAAAGTGG ATATCAAA (SEQ ID NO: 61) | CAGCTGCAGCTGCAGGAGTCGGGCCCAGGACTGGTGAA GCCTTCGGAGACCCTGTCCCTCACCTGCACTGTCTCTGGT GGCTCCATCAGCAGTGGTAGTTACTACTGGGGCTGGATC CGCCAGCCCCCAGGGAAGGGGCTGGAGTGGATTGGGAG TATCTATTATGGTGGGAACACCTACTACAACCCGTCCCT CAAGAGTCGAGTCACCATATCCGTAGACACGTCCAAGA ACCAGTTCTCCCTGAAGCTGAGCTCTGTGACCGCCGCAG ACACGGCTGTGTATTACTGTGCGGGAGAACTGCGGAGG GCTTTTGATATCTGGGGCCAAGGGACAATGGTCACCGTC TCTTCA (SEQ ID NO: 62) |
| | | AA | EIVMTQSPATLSVSPGERATLSCRASQSVRSNLAWYQQKP GQAPRLLIDGASTRATGITARFSGSGSGTEFTLTISSLQSE DFAVYYCQQYNNWPTFGPGTKVDIK (SEQ ID NO: 63) | QLQLQESGPGLVKPSETLSLTCTVSGGSISSGSYMGWIRQ PPGKGLEWIGSIYYGGNTYYNPSLKSRVTISVDTSKNQFS LKLSSVTAADTAVYYCAGELRRAFDIWGQGTMVTVSS (SEQ ID NO: 64) |
| iPS: 481983 | 3D5.1 | NA | GACATCCAGATGACCCAGTCTCCGTCCTCCCTGTGTGCA TCTGTAGGAGACAGAGTCACCATCTCTTGCCGGGCAAGT CAGGACATTAGAAATGATTTAGGCTGGTATCAGCAGAA ACCAGGGAAAGCCCCTAAGCGCCTGATTTATGTTGCATC CAGTTTGCAAAGTGGGGTCCCATCAAGGTTCAGCGGCAG TGGATTTGGGACAGAATTCACTCTCACAATCAGCAGCCT GCAGCGTGAAGATTTTGCAACTTATTACTGTCTACAGCA TAATATTTACCCGTGCAGTTTTGGCCAGGGGACCAAGCT GGAGATCAAA (SEQ ID NO: 65) | CAGGTGCAGCTGGTGGAGTCTGGGGGAGGCGTGGTCCA GCCTGGGAGGTCCCTGAGACTCTCCTGTGCAGCCTCTGG ATTCACCTTCAGTAGCTTTGGCATGCACTGGGTCCGCCA GGCTCCAGGCAAGGGGCTGGAGTGGGTGGCAATTTTATC ATTTGATGGAAATAATAAATACTATGCAGACTCCGTGAA GGGCCGATTCACCATCTCCAGAGACAATTCCAAGAACAC GGTGTATCTGCAAATGAACAGCCTGAGAGCTGAGGACA CGGCTGTGTATTACTGTGCGAGAGAGGGGGGTATAACT GGAACTGACTTTGACTACTGGGGCCAGGGAACCCTG GTCACCGTCTCCTCA (SEQ ID NO: 66) |
| | | AA | DIQMTQSPSSLCASVGDRVTISCRASQDIRNDLGWYQQKPG KAPKRLIYVASSLQSGVPSRFSGSGFGTEFTLTISSLQRED FATYYCLQHNIYPCSFGQGTKLEIK (SEQ ID NO: 67) | QVQLVESGGGVVQPGRSLRLSCAASGFTFSSFGMHWVRQ APGKGLEWVAILSFDGNNKYYADSVKGRFTISRDNSKNTV YLQMNSLRAEDTAVYYCAREGGYNWNYDFDWGQGTLV TVSS (SEQ ID NO: 68) |
| iPS: 481984 | 5D11.1 | NA | TCTTCTGAGCTGACTCAGGACCCTGCTGTGTCTGTGGCCT TGGGACAGACAGTCAGGATCACATGTCAAGGAGACAGC CTCAGAACCTATTATGCAAGCTGGTACCAGCAGAAGCCA GGACAGGCCCCTGTACTTGTCATCTATGGTAAAAACATC CGGCCCTCAGGGATCCCAGACCGATTCTCTGCCTCCAGG TCAGGAAATACAGCTGCCTTGACCATCACTGGGGCTCAG GCGGAAGATGAGGCTGACTATTACTGTAACTCCCGGGAC AGCAGTGGTGACCATGTGATATTCGGCGGAGGGACCAA GGTGACCGTCCTA (SEQ ID NO: 69) | CAGGTGCAACTGCAGGAGTCGGGCCCAGGACTGGTGAA GCCTTCGGAGACCCTGTCCCTCACCTGCACTGTCTCTGGT GGCTCCGTCAGCAGTGGTGGTGACTACTGGAGCTGGATC CGGCAGCCCCCAGGGAAGGGACTGGAGTGGATTGGTTA TATCTATTACACTGGGAGCACCTACAACCCCTCCCT CAAGAGTCGAGTCACCATATCAGTAGACACGTTCAAGC ACCAGTTCTCCGTGAATCTGACCTCTGTGACCGCTGCGG ACACGGCCGTGTATTATTGTGCGAGATCGGGTGTAGCAA TGGCTCGCTTTGACTACTGGGGCCAGGGAACCCTGGTCA CCGTCTCCTCA (SEQ ID NO: 70) |
| | | AA | SSELTQDPAVSVALGQTVRITCQGDSLRTYYASWYQQKPG QAPVLVIYGKNIRPSGIPDRFSASRSGNTAALTITGAQAEDE ADYYCNSRDSSGDHVIFGGGTKVTVL (SEQ ID NO: 71) | QVQLQESGPGLVKPSETLSLTCTVSGGSVSSGGDYWSWIR QPPGKGLEWIGYIYYTGSTYNPSLKSRVTISVDTFKHQF SVNLTSVTAADTAVYYCARSGVAMARFDWGQGTLVTVSS (SEQ ID NO: 72) |
| iPS: 481989 | 1H1.1 | NA | AATTTTATGCTGACTCAGCCCCACTCTGTGTCGGAGTCTC CGGGGAAGACGGTAACCATCTCCTGCACCCGCAGCAGT GGCAGCATTGTCAGCAACTATGTGCAGTGGTACCAACAG CGCCCGGGCAGTTCCCCCACCATTGTGATCTATGAGGAT AATCAAAGACCCTCTGGGGTCCCTGATCGGTTCTCTGGC TCCATCGACAGCTCCTCGAACTCTGCCTCCCTCACCATCT CTGGACTGAAGACTGAGGACGAGGCTGACTACTATTGTC AGTCTTATGATAGCAGCAATCAGGTGTTCGGCGGAGGG ACCAAGCTGACCGTCCTA (SEQ ID NO: 73) | CAGGTGCAGCTGCAGGAGTCGGGCCCAGGACTGGTGAA GCCTTCACAGACCCTGTCCCTCATCTGCACTGTCTCTGGT GGCTCCATCAGCAGTGGTGGCTACCACTGGAGCTGGATC CGCCAGCACCCAGGGAAGGGCCTGGAGTGGATTGGGTA CATCTATTACAGTGGGAGCACCTACTACAACCCGTCCCT CAAGAGTCGAGTTACCATATCAGTAGACACGTCTAAGA ACCAGTTCTCCCTGAAGCTGAGCTCTGTGACTGCCGCGG ACACGGCCGTATATTACTGTGCGAGAGACTACGGTG GTAAAGGGGTACTTCGATCTCTGGGGCCGTGGCACCCTG GTCACTGTCTCCTCA (SEQ ID NO: 74) |
| | | AA | NFMLTQPHSVSESPGKTVTISCTRSSGSIVSNYVQWYQQRP GSSPTIVIYEDNQRPSGVPDRFSGSIDSSSNSASLTISGLKT EDEADYYCQSYDSSNQVFGGGTKLTVL (SEQ ID NO: 75) | QVQLQESGPGLVKPSQTLSLICTVSGGSISSGGYHWSWIR QHPGKGLEWIGYIYYSGSTYYNPSLKSRVTISVDTSKNQF SLKLSSVTAADTAVYYCARETTVVKGYFDLWGRGTLVTVS S (SEQ ID NO: 76) |
| iPS: 480570 | 9E8.1 | NA | CAGTCTGTGCTGACTCAGCCACCCTCAGCGTCTGGGACC CCCGGGCAGAGGGTCACCATCTCTTGTTCTGGAAGCAGC TCCAACATCGGAAGTAATTATGTATTCTGGTACCAGCAG CTCCCAGGAACGGCCCCCAAACTCCTCATCTTTAGGAAT AATCAGCGGCCCTCAGGGGTCCCTGACCGATTCTTTGGC TCCAAGTCTGGCACCTCAGCCTCCTGGCCATCAGTGGG CTCCGGTCCGAGGATGAGGCTGATTATTACTGTGCAGCA | GAGGTGCAGCTGGTGGAGTCTGGGGGAGGCTTGGTAAA GCCTGGGGGGTCCCTTAGACTCTCCTGTGCAGCCTCTGG ATTCACTTTCAGTTACGCCTGGATGGGCTGGGTCCGCCA GGCTCCAGGGAAGGGCTGGAGTGGATTGGCCGTATTA AAAGCAAAACTGATGGTGGGACAACAGACTACGCTGCA CCCGTGAAAGGCAGATTCACCATCTCAAGAGATGATTCA AAAAACACGCTGTATCTGCAAATGAACAGCCTGAAAAC |

TABLE 3-continued

Exemplary Variable Light and Variable Heavy Regions: Nucleic Acid ("NA") and Amino Acid ("AA") Sequences

| Ref # | antibody | Type | Light | Heavy |
|---|---|---|---|---|
| | | | TGGGATGACAGCCTGAGTGGTTGGGTGTTCGGCGGAGG GACCAAGCTGACCGTCCTA (SEQ ID NO: 77) | CGAGGACACAGCCGTGTATTACTGTACCACAGATGGGG CACTGGCCCCCACGGCTACTGGGGCCAGGGAACCCTG GTCACCGTCTCCTCA (SEQ ID NO: 78) |
| | | AA | QSVLTQPPSASGTPGQRVTISCSGSSSNIGSNYVFWYQQLPG TAPKLLIFRNNQRPSGVPDRFFGSKSGTSASLAISGLRSEDE ADYYCAAWDDSLSGWVFGGGTKLTVL (SEQ ID NO: 79) | EVQLVESGGGLVKPGGSLRLSCAASGFTFSYAWMGWVRQ APGKGLEWIGRIKSKTDGGFIDYAAPVKGRFTISRDDSKN TLYLQMNSLKTEDTAVYYCTTDGALAPHGYWGQGTLVTVS S (SEQ ID NO: 80) |
| iPS: 480538 | 2B6.1 | NA | GAAATAGTGATGACGCAGTCTCCAGCCACCCTGTCTGTG TCTCCAGGGGATAGAGCCACCCTCTCCTGCAGGGCCAGT CAGAGTGTTAGAAGCAACTTAGCCTGGTACCAGCAGAAA ACCTGGCCAGGCTCCCAGGCTCCTCATCTATGGTGCATC CACCAGGGCCACTGGTATCCCAGCCAGGTTCAGTGGCAG TGGGTCTGGGACAGAGTTCACTCTCACCATCAGCAGCCT GCAGTCTGAAGATTTTGCAGTTTATTACTGTCAGCAATA CACTGACTGGCCCACTTTCGGCGGAGGGACCAAGGTGG AGATCAAA (SEQ ID NO: 81) | CAGGTGCAGCTGCAGGAGTCGGGCCCAGGACTGGTGAA GCCTTCACAGACCCTGTCCCTCACCTGCACTGTCTCTGGT GGCTCCATCAGCAGTGGTGGTTACTTCTGGAGCTGGATC CGCCAGCACCCAGGGAAGGGCCTGGAGTGGATTGGGTA CATCTATTACAGTGGGAGCACCTACTACAACCCGTCCCT CAAGAGTCGAGTTACCATATCAGTAGACACGTCTAAGA ACCAGTTCTCCCTGAAGCTGAGCTCTGTGACTGCCGCGG ACACGGCCGTGTATTACTGTGCGAGATGGGGAGCAGCA GCCGGCTTTGACTATTGGGGCCAGGGAACCCTGGTCACC GTCTCCTCA (SEQ ID NO: 82) |
| | | AA | EIVMTQSPATLSVSPGDRATLSCRASQSVRSNLAWYQQKP GQAPRLLIYGASTRATGIPARFSGSGSGTEFTLTISSLQSED FAVYYCQQYTDWPTFGGGTKVEIK (SEQ ID NO: 83) | QVQLQESGPGLVKPSQTLSLTCTVSGGSISSGGYFWSWIR QHPGKGLEWIGYIYYSGSTYYNPSLKSRVTISVDTSKNQF SLKLSSVTAADTAVYYCARWGAAAGFDYWGQGTLVTVSS (SEQ ID NO: 84) |
| iPS: 480569 | 1D2.1 | NA | GATATTGTGATGACTCAGTCTCCACTCTCCCTGCCCGTCA CCCCTGGAGAGCCGGCCTCCATCTCCTGCAGGTCTAGTC AGAGCCTCCTACATAGTCATGGATACAGCTATTTGAATT GGTACCTGCAGAAGCCAGGGCAGTCTCCACAGCTCCTGA TCCATTTGGGTTCTAATCGGGCCTCCGGGGTCCCTGACA GGTTCAGTGGCAGTGGATCAGGCACAGAATTTACACTGA GAATCAGCAGAGTGGAGGCTGAGGATGTTGGGGTTTATT ATTGCATGCAAGTTCTGCTAACTCCGATCACCCTCGGCC AAGGGACACGACTGGAGATTAAA (SEQ ID NO: 85) | CAGGTGCAGCTGGTGGAGTCTGGGGGAGGCGTGGTCCA GCCTGGGAGGTCCCTGAGACTCTCCTGTGCAGCCTCTGG ATTCACCTTCAGTAGCTATGGCATGCACTGGGTCCGCCA GGCTCCAGGCAAGGGGCTGGAGTGGGTGGCAGTTATAT CATATGATGGAAATAATAAATACTATGCAGACTCCGTGA AGGGCCGATTCACCATCTCCAGAGACAATTCCAAGAAC ACGCTGTATCTGCAAATGAACAGCCTGAGAGCTGAGGA CACGGCTGTGTATTACTGTGCGAGAGATGCCAGTGGGAG CTCCCTCTACCTTGACTACTGGGGCCAGGGAACCCTGGT CACCGTCTCCTCA (SEQ ID NO: 86) |
| | | AA | DIVMTQSPLSLPVTPGEPASISCRSSQSLLHSHGYSYLNWYL QKPGQSPQLLIHLGSNRASGVPDRFSGSGSGTEFTLRISRVE AEDVGVYYCMQVLLTPITLGQGTRLEIK (SEQ ID NO: 87) | QVQLVESGGGVVQPGRSLRLSCAASGFTFSSYGMHWVRQ APGKGLEWVAVISYDGNNKYYADSVKGRFTISRDNSKNTL YLQMNSLRAEDTAVYYCARDASGSSLYLDYWGQGTLVTV SS (SEQ ID NO: 88) |

Table 4. Exemplary CDRL1, CDRL2, CDRL3, CDRH1, CDRH2, and CDRH3 NucleicAcid ("NA") and Amino Acid ("AA") Sequences Table 4A. Exemplary CDRL1, CDRL2, and CDRL3 Nucleic Acid ("NA") and Amino Acid ("AA") Sequences

| Ref # | antibody | Type | CDRL1 | CDRL2 | CDRL3 |
|---|---|---|---|---|---|
| iPS:480496 | 17B3.1 | NA | CGGGCGAGTCAGGGTATTAGC GACTGGTTAGCC (SEQ ID NO: 89) | GCTGCATCCAGTTTGCAAAGT (SEQ ID NO: 90) | CAACAGGCTAACAGTTTCCCG ATCACC (SEQ ID NO: 91) |
| | | AA | RASQGISDWLA (SEQ ID NO: 92) | AASSLQS (SEQ ID NO: 93) | QQANSFPIT (SEQ ID NO: 94) |
| iPS:480499 | 15D11.1 | NA | ACTGGAACCAGCAGTGCCGTT GGTGGTCATAACTTTGTCTCC (SEQ ID NO: 95) | GAGGTCAGTAATCGGCCCTCA (SEQ ID NO: 96) | AGCTCTTATACAAGCAGCAGC ACTTGGGTG (SEQ ID NO: 97) |
| | | AA | TGTSSAVGGHNFVS (SEQ ID NO: 98) | EVSNRPS (SEQ ID NO: 99) | SSYTSSSTWV (SEQ ID NO: 100) |
| iPS:480522 | 4F5.1 | NA | AGGGCCAGTCAGAGTGTTAGG AGCAACTTAGCC (SEQ ID NO: 101) | GGTGCATCCACCAGGGCCACT (SEQ ID NO: 102) | CAGCAGTATAATAACTGGCCT ACT (SEQ ID NO: 103) |
| | | AA | RASQSVRSNLA (SEQ ID NO: 104) | GASTRAT (SEQ ID NO: 105) | QQYNNWPT (SEQ ID NO: 106) |
| iPS:481499 | 1A12.1 | NA | ACCCGCAGCAGTGACAGCATT GCCAGCAACTATGTGCAG (SEQ ID NO: 107) | GAGGATAACCAAAGACCCTCT (SEQ ID NO: 108) | CAGTCTTATGATAGCAGCAAT CATGTGGTA (SEQ ID NO: 109) |
| | | AA | TRSSDSIASNYVQ (SEQ ID NO: 110) | EDNQRPS (SEQ ID NO: 111) | QSYDSSNHVV (SEQ ID NO: 112) |

-continued

| iPS:480526 | 6B1.1 | NA | TCTGGAGATGCATTGCCAAAG CAATATGCTTAT (SEQ ID NO: 113) | AAAGACAGTGAGAGGCCCTC A (SEQ ID NO: 114) | CAATCAACAGACAGAAGAGG TACTGTG (SEQ ID NO: 115) |
| --- | --- | --- | --- | --- | --- |
| | | AA | SGDALPKQYQY (SEQ ID NO: 116) | KDSERPS (SEQ ID NO: 117) | QSTDRRGTV (SEQ ID NO: 118) |
| iPS:480529 | 1G9.1 | NA | AGGGCCAGTCAGATTTTTAGC AGCAGTTACTTAGCC (SEQ ID NO: 119) | GGTGCATCCAGCAGGGCCACT (SEQ ID NO: 120) | CAGCAGTATGGTAGCTCATGC AGT (SEQ ID NO: 121) |
| | | AA | RASQIFSSSYLA (SEQ ID NO: 122) | GASSRAT (SEQ ID NO: 123) | QQYGSSCS (SEQ ID NO: 124) |
| iPS:480533 | 6E12.1 | NA | AGGTCTAGTCAGAGCCTCCTA CATAGTCATGGATACAGCTAT TTGAAT (SEQ ID NO: 125) | TTGGGTTCTAATCGGGCCTCC (SEQ ID NO: 126) | ATGCAAGTTCTGCTAACTCCG ATCACC (SEQ ID NO: 127) |
| | | AA | RSSSLLHSHGYSYLN (SEQ ID NO: 128) | LGSNRAS (SEQ ID NO: 129) | MQVLLTPIT (SEQ ID NO: 130) |
| iPS:480548 | 9G5.1 | NA | AGGTCTAGTCAGAGCCTCCTG CATAGTCATGGATACAACTAT TTGAAT (SEQ ID NO: 131) | TTGGGTTCTAATCGGGCCTCC (SEQ ID NO: 132) | ATGCAAGTTCTACAAACTCCG ATCACC (SEQ ID NO: 133) |
| | | AA | RSSQSLLHSHGYNYLN (SEQ ID NO: 134) | LGSNRAS (SEQ ID NO: 135) | MQVLQTPIT (SEQ ID NO: 136) |
| iPS:480551 | 5A12.1 | NA | AGGTCTAGTCAGGGCCTCCTG CATAGTCATGGATACCACTAT TTGAAT (SEQ ID NO: 137) | TTGGGTTCTAATCGGGCCTCC (SEQ ID NO: 138) | ATGCAAGTTCTACAAACTCCG ATCACC (SEQ ID NO: 139) |
| | | AA | RSSQGLLHSHGYHYLN (SEQ ID NO: 140) | LGSNRAS (SEQ ID NO: 141) | MQVLQTPIT (SEQ ID NO: 142) |
| iPS:480555 | 6B11.1 | NA | TCTGGAAGCAGCTCCAACATC GGAAGAAATACTGTAAAC (SEQ ID NO: 143) | AGTAATAATCAGCGGCCCTCA (SEQ ID NO: 144) | GCAGCATGGGATGACAGCCTG AATGGTGTGGTA (SEQ ID NO: 145) |
| | | AA | SGSSSNIGRNTVN (SEQ ID NO: 146) | SNNQRPS (SEQ ID NO: 147) | AAWDDSLNGVV (SEQ ID NO: 148) |
| iPS:480558 | 8C8.1 | NA | TCTGGAGATGCTTTGCCAAGG CAATATACTTAT (SEQ ID NO: 149) | AAAGACACTGCGAGGCCCTCA (SEQ ID NO: 150) | CAATCAACAGACAGAAGTGG TACTGTG (SEQ ID NO: 151) |
| | | AA | SGDALPRQYTY (SEQ ID NO: 152) | KDTARPS (SEQ ID NO: 153) | QSTDRSGTV (SEQ ID NO: 154) |
| iPS:480561 | 8G12.1 | NA | AAGTCTAGTCAGAGCCTCCTG CATAGTAGTGGAAAGACCTAT TTGTAT (SEQ ID NO: 155) | GAAGTTTCCAACCGGTTCTCT (SEQ ID NO: 156) | ATGCAAAGTATACAGCTTCCG TGGACG (SEQ ID NO: 157) |
| | | AA | KSSQSLLHSSGKTYLY (SEQ ID NO: 158) | EVSNRFS (SEQ ID NO: 159) | MQSIQLPWT (SEQ ID NO: 160) |
| iPS:480572 | 9D3.1_ LC1 | NA | CGGGTGAGTCAGGACATTAAC AGTTATTTAAAT (SEQ ID NO: 161) | AGTGCATCCAATTTGCAATCT (SEQ ID NO: 162) | CAACGGACTTACAATGCCCTT CCGACG (SEQ ID NO: 163) |
| | | AA | RVSQDINSYLN (SEQ ID NO: 164) | SASNLQS (SEQ ID NO: 165) | QRTYNALPT (SEQ ID NO: 166) |
| iPS:480573 | 9D3.1_ LC | NA | AGGGCCAGTCAGACTATTAGC AGCAGCTACTTAGCC (SEQ ID NO: 167) | GGTGCATCCAACAGGGTCATT (SEQ ID NO: 168) | CAGCAGTATGGTAACTCACCC AGTGCCAGT (SEQ ID NO: 169) |
| | | AA | RASQTISSSYLA (SEQ ID NO: 170) | GASNRVI (SEQ ID NO: 171) | QQYGNSPMCS (SEQ ID NO: 172) |
| iPS:481500 | 6C9.1 | NA | AGGGCCAGTCAGAGTGTTAGG AGCACTTAGCC (SEQ ID NO: 173) | GGTGCATCCACCAGGGCCACT (SEQ ID NO: 174) | CAGCAGTATAATAACTGGCCT ACT (SEQ ID NO: 175) |
| | | AA | RASQSVRSNLA (SEQ ID NO: 176) | GASTRAT (SEQ ID NO: 177) | QQYNNWPT (SEQ ID NO: 178) |
| iPS:481501 | 4E2.1 | NA | AGGGCCAGTCAGAGTGTTAGG AGCAACTTAGCC (SEQ ID NO: 179) | GGTGCATCCACCAGGGCCACT (SEQ ID NO: 180) | CAGCAGTATAATAATTGGCCT ACT (SEQ ID NO: 181) |
| | | AA | RASQSVRSNLA (SEQ ID NO: 182) | GASTRAT (SEQ ID NO: 183) | QQYNNWPT (SEQ ID NO: 184) |

| | | | | | |
|---|---|---|---|---|---|
| iPS481983 | 3D5.1 | NA | CGGGCAAGTCAGGACATTAG AAATGATTTAGGC (SEQ ID NO: 185) | GTTGCATCCAGTTTGCAAAGT (SEQ ID NO: 186) | CTACAGCATAATATTTACCCG TGCAGT (SEQ ID NO: 187) |
| | | AA | RASQDIRNDLG (SEQ ID NO: 188) | VASSLQS (SEQ ID NO: 189) | LQHNIYPCS (SEQ ID NO: 190) |
| iPS:481984 | 5D11.1 | NA | CAAGGAGACAGCCTAGAAC CTATTATGCAAGC (SEQ ID NO: 191) | GGTAAAAACATCCGGCCCTCA (SEQ ID NO: 192) | AACTCCCGGGACAGCAGTGGT GACCATGTGATA (SEQ ID NO: 193) |
| | | AA | QGDSLRTYYAS (SEQ ID NO: 194) | GKINRPS (SEQ ID NO: 195) | NSRDSSGDHVI (SEQ ID NO: 196) |
| iPS:481989 | 1H1.1 | NA | ACCCGCAGCAGTGGCAGCATT GTCAGCAACTATGTGCAG (SEQ ID NO: 197) | GAGGATAATCAAAGACCCTCT (SEQ ID NO: 198) | CAGTCTTATGATAGCAGCAAT CAGGTG (SEQ ID NO: 199) |
| | | AA | TRSSGSIVSNYVQ (SEQ ID NO: 200) | EDNQRPS (SEQ ID NO: 201) | QSYDSSNQV (SEQ ID NO: 202) |
| iPS:480570 | 9E8.1 | NA | TCTGGAAGCAGCTCCAACATC GGAAGTAATTATGTATTC (SEQ ID NO: 203) | AGGAATAATCAGCGGCCCTCA (SEQ ID NO: 204) | GCAGCATGGGATGACAGCCTG AGTGGTTGGGTG (SEQ ID NO: 205) |
| | | AA | SGSSSNIGSNYVF (SEQ ID NO: 206) | RNNQRPS (SEQ ID NO: 207) | AAWDDSLSGWV (SEQ ID NO: 208) |
| iPS:480538 | 2B6.1 | NA | AGGGCCAGTCAGAGTGTTAGA AGCAACTTAGCC (SEQ ID NO: 209) | GGTGCATCCACCAGGGCCACT (SEQ ID NO: 210) | CAGCAATACACTGACTGGCCC ACT (SEQ ID NO: 211) |
| | | AA | RASQSVRSNLA (SEQ ID NO: 212) | GASTRAT (SEQ ID NO: 213) | QQYTDWPT (SEQ ID NO: 214) |
| iPS:480569 | 1D2.1 | NA | AGGTCTAGTCAGAGCCTCCTA CATAGTCATGGATACAGCTAT TTGAAT (SEQ ID NO: 215) | TTGGGTTCTAATCGGGCCTCC (SEQ ID NO: 216) | ATGCAAGTTCTGCTAACTCCG ATCACCC (SEQ ID NO: 217) |
| | | AA | RSSQSLLHSHGYSYLN (SEQ ID NO: 218) | LGSNRAS (SEQ ID NO: 219) | MQVLLTPIT (SEQ ID NO: 220) |

Table 4B. Exemplary CDRH1, CDRH2, CDRH3 Nucleotide and Amino Acid Sequences

| Ref # | antibody | Type | CDRH1 | CDRH2 | CDRH3 |
|---|---|---|---|---|---|
| iPS:480496 | 17B3.1 | NA | AGTTATGGCATGCAC | GTTATATGGTATGATGGAAGT AATAATACTATGCAGACTCC GTGAAGGGC | CATGACCACAGTCACTACGGT TTTGACTAC |
| | | | (SEQ ID NO: 221) | (SEQ ID NO: 222) | (SEQ ID NO: 223) |
| | | AA | SYGMH (SEQ ID NO: 224) | VIWYDGSNEYYADSVKG (SEQ ID NO: 225) | HDHSHYGFDY (SEQ ID NO: 226) |
| iPS:480499 | 15D11.1 | NA | AATGCTGAAATGGGTGTGAGC | CACCTTTTTTCGAATGACGAA AAATCCTACAGCACATCTCTG AAGAGC | TCGTTTAACTGGAACTACGAC TTTGACTAC |
| | | | (SEQ ID NO: 227) | (SEQ ID NO: 228) | (SEQ ID NO: 229) |
| | | AA | NAEMGVS (SEQ ID NO: 230) | HLFSNDEKSYSTSLKS (SEQ ID NO: 231) | SFNWNYDFDY (SEQ ID NO: 232) |
| iPS:480522 | 4F5.1 | NA | AGTGGTAGTTACTACTGGGGC | AGTATCTATTATGGTGGGAAC ACCTACTACAACCCGTCCCTC AAGAGT | GAACTGCGGAGGGCTTTTGAT ATC |
| | | | (SEQ ID NO: 233) | (SEQ ID NO: 234) | (SEQ ID NO: 235) |
| | | AA | SGSYYWG (SEQ ID NO: 236) | SIYYGGNTYYNPSLKS (SEQ ID NO: 237) | ELRRAFDI (SEQ ID NO: 238) |
| iPS:481499 | 1A12.1 | NA | TACTATGGCATGCAC | GTTATATGGTATGATGGAAGT AATAAATACTATGCAGACTCC GTGAAGGGC | GATCATGACTACGGTGTCCTG TACTACTTTGACTAC |
| | | | (SEQ ID NO: 239) | (SEQ ID NO: 240) | (SEQ ID NO: 241) |
| | | AA | YYGMH (SEQ ID NO: 242) | VIWYDGSNKYYADSVKG (SEQ ID NO: 243) | DHDYGVLYYFDY (SEQ ID NO: 244) |
| iPS:480526 | 6B1.1 | NA | ACTAGTGGAGTGGTGTGGGC | CTCATTATTGGAATGATGAT AAGCGCTACAGCCCATCTCTG AAGAGC | AGACATGGCTACGATAGGATG CGTGATGCTTTTGATATC |
| | | | (SEQ ID NO: 245) | (SEQ ID NO: 246) | (SEQ ID NO: 247) |
| | | AA | TSGVGVG (SEQ ID NO: 248) | LIYWNDDKRYSPSLKS (SEQ ID NO: 249) | RHGYDRMRDAFDI (SEQ ID NO: 250) |

| | | | | | |
|---|---|---|---|---|---|
| iPS:480529 | 1G9.1 | NA | AGCTACTTTATACAC | ATAATCAACCCTAGTGGTGGT AGCACAAGCTACCGCACAGAA GTTCCAGGGC | GATCAGGAGGGAGCAGTGGC TGGTACAGACTACTACTTCTA CGGTATGGACGTC |
| | | | (SEQ ID NO: 251) | (SEQ ID NO: 252) | (SEQ ID NO: 253) |
| | | AA | SYFIH | IINPSGGSTSYAQKRQG | DQEGAVAGTDYYFYGMDV |
| | | | (SEQ ID NO: 254) | (SEQ ID NO: 255) | (SEQ ID NO: 256) |
| iPS:480533 | 6E12.1 | NA | AGCTATGGCATGCAC | GTTATATCATATGATGGAAAT AATAAATACTATGCAGACTCC GTGAAGGGC | GATGCCAGTGGGAGCTCCCTC TACCTTGACTAC |
| | | | (SEQ ID NO: 257) | (SEQ ID NO: 258) | (SEQ ID NO: 259) |
| | | AA | SYGMH | VISYDGNNKYYADSVKG | DASGSSLYLDY |
| | | | (SEQ ID NO: 260) | (SEQ ID NO: 261) | (SEQ ID NO: 262) |
| iPS:480548 | 9G5.1 | NA | AACTATGGCATGCAC | GTTATATCATATGATGGAAGT AAAAAATACTATGCAGACTCC GTGAAGGGC | GATGCCAGTGGGAGCTCCCTC TACTCTGACTAC |
| | | | (SEQ ID NO: 263) | (SEQ ID NO: 264) | (SEQ ID NO: 265) |
| | | AA | NYGMH | VISYDGSKKYYADSVKG | DASGSSLYSDY |
| | | | (SEQ ID NO: 266) | (SEQ ID NO: 267) | (SEQ ID NO: 268) |
| iPS:480551 | 5A12.1 | NA | AGCTATGGCATGCAG | GTTATATCAAAAGATGGAAGT TATAAATACTATGCGGACTCC GTGAAGGGC | GATGCCAGTGGGAGCTCCCTC TACTTAGACTAC |
| | | | (SEQ ID NO: 269) | (SEQ ID NO: 270) | (SEQ ID NO: 271) |
| | | AA | SYGMH | VISKDGSYKYYADSVKG | DASGSSLYLDY |
| | | | (SEQ ID NO: 272) | (SEQ ID NO: 273) | (SEQ ID NO: 274) |
| iPS:480555 | 6B11.1 | NA | AGCTATGGCATGCAG | GTTATATGGTATGATGGAAGT AATAAATACCATGCAGACTCC GTGAAGGGC | GACTTTGCTTACTTCTACTACG GTATGGACGTC |
| | | | (SEQ ID NO: 275) | (SEQ ID NO: 276) | (SEQ ID NO: 277) |
| | | AA | SYGMH | VIWYDGSNKYHADSVKG | DFAYFYYGMDV |
| | | | (SEQ ID NO: 278) | (SEQ ID NO: 279) | (SEQ ID NO: 280) |
| iPS:480558 | 8C8.1 | NA | ACTAGTGGAGTGGGTGTGGGC | CTCATTTATTGGAATGATGAT AAGCGCTACAGCCCATCTCTG AAGAGC | AGACATGGCTACGATAGGATG CGTGATGCTTTTGATATC |
| | | | (SEQ ID NO: 281) | (SEQ ID NO: 282) | (SEQ ID NO: 283) |
| | | AA | TSGVGVG | LIY6WNDKRYSPSLKS | RHGYDRMRDAFDI |
| | | | (SEQ ID NO: 284) | (SEQ ID NO: 285) | (SEQ ID NO: 286) |
| iPS:480561 | 8G12.1 | NA | AGTGGTGGTTACTACTGGAGC | TACATCTCTTACAGTGGGAGC ACCTACTACAACCCGTCCCTC AAGAGT | GAGAGCCCTACGGTGACTACG GCTTTTGATATC |
| | | | (SEQ ID NO: 287) | (SEQ ID NO: 288) | (SEQ ID NO: 289) |
| | | AA | SGGYYWS | YISYSGSTYYNPSLKS | ESPTVTTAFDI |
| | | | (SEQ ID NO: 290) | (SEQ ID NO: 291) | (SEQ ID NO: 292) |
| ips:480572 | 9D3.1_ LC1 | NA | AGTGGTGGTTACGACTGGAGC | AACATTTATTACAGTGGGAGG ACCTACTACAACCCGTCCCTC AAGAGT | GATCGCCCTTATGGAGGTAAT TCCGGCTACTACTACGGTATG GACGTC |
| | | | (SEQ ID NO: 293) | (SEQ ID NO: 294) | (SEQ ID NO: 295) |
| | | AA | SGGYDWS | NIYYSGRTYYNPSLKS | DRPYGGNSGYYYGMDV |
| | | | (SEQ ID NO: 296) | (SEQ ID NO: 297) | (SEQ ID NO: 298) |
| iPS:480573 | 9D3.1_ LC | NA | AGTGGTGGTTACGACTGGAGC | AACATTTATTACAGTGGGAGG ACCTACTACAACCCGTCCCTC AAGAGT | GATCGCCCTTATGGAGGTAAT TCCGGCTACTACTACGGTATG GACGTC |
| | | | (SEQ ID NO: 299) | (SEQ ID NO: 300) | (SEQ ID NO: 301) |
| | | AA | SGGYDWS | NIYYSGRTYYNPSLKS | DRPYGGNSGYYYGMDV |
| | | | (SEQ ID NO: 302) | (SEQ ID NO: 303) | (SEQ ID NO: 304) |
| iPS:481500 | 6C9.1 | NA | ATGAGTAGTTACTATTGGGGC | AGTATCTATTATGGTGGGAAC ACCTACTACAACCCGTCCCTC AAGAGT | GAACTGCGGAGGGCTTTTGAT ATC |
| | | | (SEQ ID NO: 305) | (SEQ ID NO: 306) | (SEQ ID NO: 307) |
| | | AA | SSSYYWG | SIYYGGNTYYNPSLKS | ELRRAFDI |
| | | | (SEQ ID NO: 308) | (SEQ ID NO: 309) | (SEQ ID NO: 310) |
| iPS:481501 | 4E2.1 | NA | ATGAGTAGTTACTATTGGGGC | AGTATCTATTATGGTGGGAAC ACCTACTACAACCCGTCCCTC AAGAGT | GAACTGCGGAGGGCTTTTGAT ATC |
| | | | (SEQ ID NO: 311) | (SEQ ID NO: 312) | (SEQ ID NO: 313) |
| | | AA | SGSYYWG | SIYYGGNTYYNPSLKS | ELRRAFDI |
| | | | (SEQ ID NO: 314) | (SEQ ID NO: 315) | (SEQ ID NO: 316) |

| | | | | | |
|---|---|---|---|---|---|
| iPS481983 | 3D5.1 | NA | AGCTTTGGCATGCAC | ATTTTATCATTTGATGGAAAT AATAAATACTATGCAGACTCC GTGAAGGGC | GAGGGGGGGTATAACTGGAA CTACGACTTTGACTAC |
| | | | (SEQ ID NO: 317) | (SEQ ID NO: 318) | (SEQ ID NO: 319) |
| | | AA | SFGMH | ILSFDGNNKYYADSVKG | EGGYNWNYDFDY |
| | | | (SEQ ID NO: 320) | (SEQ ID NO: 321) | (SEQ ID NO: 322) |
| iPS:481984 | 5D11.1 | NA | AGTGGTGGTGACTACTGGAGC | TATATCTATTACACTGGGAGC ACCAACTACAACCCCTCCCTC AAGAGT | TCGGGTGTAGCAATGGCTCGC TTTGACTAC |
| | | | (SEQ ID NO: 323) | (SEQ ID NO: 324) | (SEQ ID NO: 325) |
| | | AA | SGGDYWS | YIYYTGSNTYNPSLKS | SGVAMARFDY |
| | | | (SEQ ID NO: 326) | (SEQ ID NO: 327) | (SEQ ID NO: 328) |
| iPS:481989 | 1H1.1 | NA | AGTGGTGGCTACCACTGGAGC | TACATCTATTACAGTGGGAGC ACCTACTACAACCCGTCCCTC AAGAGT | GAGACTACGGTGGTAAAGGG GTACTTCGATCTC |
| | | | (SEQ ID NO: 329) | (SEQ ID NO: 330) | (SEQ ID NO: 331) |
| | | AA | SGGYHWS | YIYYSGSTYYNPSLKS | ETTVVKGYFDL |
| | | | (SEQ ID NO: 332) | (SEQ ID NO: 333) | (SEQ ID NO: 334) |
| iPS:480570 | 9E8.1 | NA | TACGCCTGGATGGGC | CGTATTAAAAGCAAAACTGAT GGTGGGACAACAGACTACGCT GCACCCGTGAAAGGC | GATGGGGCACTGGCCCCCCAC GGCTAC |
| | | | (SEQ ID NO: 335) | (SEQ ID NO: 336) | (SEQ ID NO: 337) |
| | | AA | YAWMG | RIKSKTDGGTTDYAAPVKG | DGALAPHGY |
| | | | (SEQ ID NO: 338) | (SEQ ID NO: 339) | (SEQ ID NO: 340) |
| iPS:480538 | 2B6.1 | NA | AGTGGTGGTTACTTCTGGAGC | TACATCTATTACAGTGGGAGC ACCTACTACAACCCGTCCCTC AAGAGT | TGGGGAGCAGCAGCCGGCTTT GACTAT |
| | | | (SEQ ID NO: 341) | (SEQ ID NO: 342) | (SEQ ID NO: 343) |
| | | AA | SGGYFWS | YIYYSGSTYYNPSLKS | WGAAAGFDY |
| | | | (SEQ ID NO: 344) | (SEQ ID NO: 345) | (SEQ ID NO: 346) |
| iPS:480569 | 1D2.1 | NA | AGCTATGGCATGCAC | GTTATATCATATGATGGAAAT AATAAATACTATGCAGACTCC GTGAAGGGC | GATGCCAGTGGGAGCTCCCTC TACCTTGACTAC |
| | | | (SEQ ID NO: 347) | (SEQ ID NO: 348) | (SEQ ID NO: 349) |
| | | AA | SYGMH | VISYDGNNKYYADSVKG | DASGSSLYLDY |
| | | | (SEQ ID NO: 350) | (SEQ ID NO: 351) | (SEQ ID NO: 352) |

In one embodiment the antibody or fragment thereof comprises a light chain variable region comprising a sequence selected from the group consisting of SEQ ID NOs: 267, 271, 275, 279, 283, 287, 291, 295, 299, 303, 307, 311, 315, 319, 323, 327, 331, 335, 339, 343, 347, and 351. In one embodiment the antibody or fragment thereof comprises a heavy chain variable region comprising a sequence selected from the group consisting of SEQ ID NOs: 268, 272, 276, 280, 284, 288, 292, 296, 300, 304, 308, 312, 316, 320, 324, 328, 332, 336, 340, 344, 348, and 352. In one embodiment the antibody or fragment thereof comprises a light chain variable region comprising a sequence selected from the group consisting of SEQ ID NOs: 267, 271, 275, 279, 283, 287, 291, 295, 299, 303, 307, 311, 315, 319, 323, 327, 331, 335, 339, 343, 347, and 351 and a heavy chain variable region comprising a sequence selected from the group consisting of SEQ ID NOs: 268, 272, 276, 280, 284, 288, 292, 296, 300, 304, 308, 312, 316, 320, 324, 328, 332, 336, 340, 344, 348, and 352. In one embodiment the antibody or fragment thereof comprises a combination of light chain variable region and a heavy chain variable region selected from the group consisting of a light chain variable region comprising SEQ ID NO: 267 and a heavy chain variable region comprising SEQ ID NO: 268; a light chain variable region comprising SEQ ID NO: 271 and a heavy chain variable region comprising SEQ ID NO: 272; a light chain variable region comprising SEQ ID NO: 275 and a heavy chain variable region comprising SEQ ID NO: 276; a light chain variable region comprising SEQ ID NO: 279 and a heavy chain variable region comprising SEQ ID NO: 280; a light chain variable region comprising SEQ ID NO: 283 and a heavy chain variable region comprising SEQ ID NO: 284; a light chain variable region comprising SEQ ID NO: 287 and a heavy chain variable region comprising SEQ ID NO: 288; a light chain variable region comprising SEQ ID NO: 291 and a heavy chain variable region comprising SEQ ID NO: 292; a light chain variable region comprising SEQ ID NO: 295 and a heavy chain variable region comprising SEQ ID NO: 296; a light chain variable region comprising SEQ ID NO: 299 and a heavy chain variable region comprising SEQ ID NO: 300; a light chain variable region comprising SEQ ID NO: 303 and a heavy chain variable region comprising SEQ ID NO: 304; a light chain variable region comprising SEQ ID NO: 307 and a heavy chain variable region comprising SEQ ID NO: 308; a light chain variable region comprising SEQ ID NO: 311 and a heavy chain variable region comprising SEQ ID NO: 312; a light chain variable region comprising SEQ ID NO: 315 and a heavy chain variable region comprising SEQ ID NO: 316; a light chain variable region comprising SEQ ID NO: 319 and a heavy chain variable region comprising SEQ ID NO: 320; a light chain variable region comprising SEQ ID NO: 323 and a heavy chain variable region comprising SEQ ID NO: 324; a light chain variable region comprising SEQ ID NO: 327 and a heavy chain variable region comprising SEQ ID NO: 328; a light chain variable region comprising SEQ ID NO: 331 and a heavy chain variable region comprising SEQ ID NO: 332; a light chain variable region comprising SEQ ID NO: 335 and a heavy chain variable region comprising SEQ ID NO: 336; a light chain variable region comprising SEQ ID NO: 339 and a heavy chain variable region comprising SEQ ID NO: 340; a light chain variable region comprising SEQ ID NO: 343 and a heavy chain variable region comprising SEQ ID NO: 344; a light chain variable region comprising SEQ ID NO: 347 and a heavy chain variable region comprising SEQ ID NO: 348; and a light chain variable region comprising SEQ ID NO: 351 and a heavy chain variable region comprising SEQ ID NO: 352.

In one embodiment the antibody or fragment thereof comprises a light chain variable region encoded by a polynucleotide sequence selected from the group consisting of SEQ ID NOs: 265, 269, 273, 277, 281, 285, 289, 293, 297, 301, 305, 309, 313, 317, 321, 325, 329, 333, 337, 341, 345, and 349. In one embodiment the antibody or fragment thereof comprises a heavy chain variable region encoded by a polynucleotide selected from the group consisting of SEQ ID NOs: 266, 270, 274, 278, 282, 286, 290, 294, 298, 302, 306, 310, 314, 318, 322, 326, 330, 334, 338, 342, 346, and 350. In one embodiment the antibody or fragment thereof comprises a light chain variable region encoded by a polynucleotide sequence selected from the group consisting of SEQ ID NOs: 265, 269, 273, 277, 281, 285, 289, 293, 297, 301, 305, 309, 313, 317, 321, 325, 329, 333, 337, 341, 345, and 349 and a heavy chain variable region encoded by a polynucleotide sequence selected from the group consisting of SEQ ID NOs: 266, 270, 274, 278, 282, 286, 290, 294, 298, 302, 306, 310, 314, 318, 322, 326, 330, 334, 338, 342, 346, and 350. In one embodiment the antibody or fragment thereof comprises a combination of light chain variable region and a heavy chain variable region selected from the group consisting of a light chain variable region encoded by a polynucleotide sequence comprising SEQ ID NO: 265 and a heavy chain variable region encoded by a polynucleotide sequence comprising SEQ ID NO: 266; a light chain variable region encoded by a polynucleotide sequence comprising SEQ ID NO: 269 and a heavy chain variable region encoded by a polynucleotide sequence comprising SEQ ID NO: 270; a light chain variable region encoded by a polynucleotide sequence comprising SEQ ID NO: 273 and a heavy chain variable region encoded by a polynucleotide sequence comprising SEQ ID NO: 274; a light chain variable region encoded by a polynucleotide sequence comprising SEQ ID NO: 277 and a heavy chain variable region encoded by a polynucleotide sequence comprising SEQ ID NO: 278; a light chain variable region encoded by a polynucleotide sequence comprising SEQ ID NO: 281 and a heavy chain variable region encoded by a polynucleotide sequence comprising SEQ ID NO: 282; a light chain variable region encoded by a polynucleotide sequence comprising SEQ ID NO: 285 and a heavy chain variable region encoded by a polynucleotide sequence comprising SEQ ID NO: 286; a light chain variable region encoded by a polynucleotide sequence comprising SEQ ID NO: 289 and a heavy chain variable region encoded by a polynucleotide sequence comprising SEQ ID NO: 290; a light chain variable region encoded by a polynucleotide sequence comprising SEQ ID NO: 293 and a heavy chain variable region encoded by a polynucleotide sequence comprising SEQ ID NO: 294; a light chain variable region encoded by a polynucleotide sequence comprising SEQ ID NO: 297 and a heavy chain variable region encoded by a polynucleotide sequence comprising SEQ ID NO: 298; a light chain variable region encoded by a polynucleotide sequence comprising SEQ ID NO: 301 and a heavy chain variable region encoded by a polynucleotide sequence comprising SEQ ID NO: 302; a light chain variable region encoded by a polynucleotide sequence comprising SEQ ID NO: 305 and a heavy chain variable region encoded by a polynucleotide sequence comprising SEQ ID NO: 306; a light chain variable region encoded by a polynucleotide sequence comprising SEQ ID NO: 309 and a heavy chain variable region encoded by a polynucleotide sequence comprising SEQ ID NO: 310; a light chain variable region encoded by a polynucleotide sequence comprising SEQ ID NO: 313 and a heavy chain variable region encoded by a polynucleotide sequence comprising SEQ ID NO: 314; a light chain variable region encoded by a polynucleotide sequence comprising SEQ ID NO: 317 and a heavy chain variable region encoded by a polynucleotide sequence comprising SEQ ID NO: 318; a light chain variable region encoded by a polynucleotide sequence comprising SEQ ID NO: 321 and a heavy chain variable region encoded by a polynucleotide sequence comprising SEQ ID NO: 322; a light chain variable region encoded by a polynucleotide sequence comprising SEQ ID NO: 325 and a heavy chain variable region encoded by a polynucleotide sequence comprising SEQ ID NO: 326; a light chain variable region encoded by a polynucleotide sequence comprising SEQ ID NO: 329 and a heavy chain variable region encoded by a polynucleotide sequence comprising SEQ ID NO: 330; a light chain variable region encoded by a polynucleotide sequence comprising SEQ ID NO: 333 and a heavy chain variable region encoded by a polynucleotide sequence comprising SEQ ID NO: 334; a light chain variable region encoded by a polynucleotide sequence comprising SEQ ID NO: 337 and a heavy chain variable region encoded by a polynucleotide sequence comprising SEQ ID NO: 338; a light chain variable region encoded by a polynucleotide sequence comprising SEQ ID NO: 341 and a heavy chain variable region encoded by a polynucleotide sequence comprising SEQ ID NO: 342; a light chain variable region encoded by a polynucleotide sequence comprising SEQ ID NO: 345 and a heavy chain variable region encoded by a polynucleotide sequence comprising SEQ ID NO: 346; and a light chain variable region encoded by a polynucleotide sequence comprising SEQ ID NO: 349 and a heavy chain variable region encoded by a polynucleotide sequence comprising SEQ ID NO: 350.

Some antigen binding proteins comprise a variable light domain and a variable heavy domain as listed in one of the rows for one of the antibodies listed in TABLE 3. In some instances, the antigen binding protein comprises two identical variable light domains and two identical variable heavy domains from one of the antibodies listed in TABLE 3. Some antigen binding proteins that are provided comprise a variable light domain and a variable heavy domain as listed in one of the rows for one of the antibodies listed in TABLE 3, except that one or both of the domains differs from the sequence specified in the table at only 1, 2, 3, 4, 5, 6, 7, 8, 9, 10, 11, 12, 13, 14 or 15 amino acid residues, wherein each such sequence difference is independently either a single amino acid deletion, insertion or substitution, with the deletions, insertions and/or substitutions resulting in no more than 1, 2, 3, 4, 5, 6, 7, 8, 9, 10, 11, 12, 13, 14 or 15 amino acid changes relative to the variable domain sequences specified in TABLE 3. In one embodiment, the antigen binding protein comprises a variable region sequence from Table 3, but with the N-terminal methionine deleted. Other antigen binding proteins also comprise a variable light domain and a variable heavy domain as listed in one of the rows for one of the antibodies listed in TABLE 3, except that one or both of the domains differs from the sequence specified in the table in that the heavy chain variable domain and/or light chain variable domain comprises or consists of a sequence of amino acids that has at least 70%, 75%, 80%, 85%, 90%, 95%, 96%, 97%, 98%, or 99% sequence identity to the amino acid sequences of the heavy chain variable domain or light chain variable domain sequences as specified in TABLE 3.

In another aspect, the antigen binding protein consists just of a variable light or variable heavy domain from an antibody listed in TABLE 3. In still another aspect, the antigen binding protein comprises two or more of the same variable heavy domains or two or more of the same variable light domains from those listed in TABLE 3. Such domain antibodies can be fused together or joined via a linker as described in greater detail below. The domain antibodies can also be fused or linked to one or more molecules to extend the half-life (e.g., PEG or albumin).

Other antigen binding proteins that are provided are variants of antibodies formed by combination of the heavy and light chains shown in TABLE 3 and comprise light and/or heavy chains that each have at least 70%, 75%, 80%, 85%, 90%, 95%, 96%, 97%, 98% or 99% identity to the amino acid sequences of these chains. In some instances, such antibodies include at least one heavy chain and one light chain, whereas in other instances the variant forms contain two identical light chains and two identical heavy chains.

The various combinations of heavy chain variable regions may be combined with any of the various combinations of light chain variable regions.

In a further embodiment, the isolated antigen binding protein provided herein is a human antibody comprising a sequence as set forth in TABLE 3 and is of the IgG$_1$-, IgG$_2$-IgG$_3$- or IgG$_4$-type.

The antigen binding proteins disclosed herein are polypeptides into which one or more CDRs are grafted, inserted and/or joined. An antigen binding protein can have 1, 2, 3, 4, 5 or 6 CDRs. An antigen binding protein thus can have, for example, one heavy chain CDR1 ("CDRH1"), and/or one heavy chain CDR2 ("CDRH2"), and/or one heavy chain CDR3 ("CDRH3"), and/or one light chain CDR1 ("CDRL1"), and/or one light chain CDR2 ("CDRL2"), and/or one light chain CDR3 ("CDRL3"). Some antigen binding proteins include both a CDRH3 and a CDRL3. Specific light and heavy chain CDRs are identified in TABLEs 4A and 4B, respectively.

Complementarity determining regions (CDRs) and framework regions (FR) of a given antibody may be identified using the system described by Kabat et al. in Sequences of Proteins of Immunological Interest, 5th Ed., US Dept. of Health and Human Services, PHS, NIH, NIH Publication no. 91-3242, 1991. Certain antibodies that are disclosed herein comprise one or more amino acid sequences that are identical or have substantial sequence identity to the amino acid sequences of one or more of the CDRs presented in TABLES 4A and 4B. These CDRs use the system described by Kabat et al. as noted above.

The structure and properties of CDRs within a naturally occurring antibody has been described, supra. Briefly, in a traditional antibody, the CDRs are embedded within a framework in the heavy and light chain variable region where they constitute the regions responsible for antigen binding and recognition. A variable region comprises at least three heavy or light chain CDRs, see, supra (Kabat et al., 1991, *Sequences of Proteins of Immunological Interest*, Public Health Service N.I.H., Bethesda, Md.; see also Chothia and Lesk, 1987, *J. Mol. Biol.* 196:901-917; Chothia et al., 1989, *Nature* 342: 877-883), within a framework region (designated framework regions 1-4, FR1, FR2, FR3, and FR4, by Kabat et al., 1991, supra; see also Chothia and Lesk, 1987, supra). The CDRs provided herein, however, may not only be used to define the antigen binding domain of a traditional antibody structure, but may be embedded in a variety of other polypeptide structures, as described herein.

In one embodiment the antibody or fragment thereof comprises a CDRL1, a CDRL2, a CDRL3, a CDRH1, a CDRH2, and a CDRH3. In one embodiment the antibody or fragment thereof comprises a CDRL1 comprising a sequence selected from the group consisting of SEQ ID NOs: 4, 10, 16, 22, 28, 34, 40, 46, 52, 58, 64, 70, 76, 82, 88, 94, 100, 106, 112, 118, 124, and 130. In one embodiment the antibody or fragment thereof comprises a CDRL2 comprising a sequence selected from the group consisting of SEQ ID NOs: 5, 11, 17, 23, 29, 35, 41, 47, 53, 59, 65, 71, 77, 83, 89, 95, 101, 107, 113, 119, 125, and 131. In one embodiment the antibody or fragment thereof comprises a CDRL3 comprising a sequence selected from the group consisting of SEQ ID NOs: 6, 12, 18, 24, 30, 36, 42, 48, 54, 60, 66, 72, 78, 84, 90, 96, 102, 108, 114, 120, 126, and 132. In one embodiment the antibody or fragment thereof comprises a CDRH1 comprising a sequence selected from the group consisting of SEQ ID NOs: 136, 142, 148, 154, 160, 166, 172, 178, 184, 190, 196, 202, 208, 214, 220, 226, 232, 238, 244, 250, 256, and 262. In one embodiment the antibody or fragment thereof comprises a CDRH2 comprising a sequence selected from the group consisting of SEQ ID NOs: 137, 143, 149, 155, 161, 167, 173, 179, 185, 191, 197, 203, 209, 215, 221, 227, 233, 239, 245, 251, 257, and 263. In one embodiment the antibody or fragment thereof comprises a CDRH3 comprising a sequence selected from the group consisting of SEQ ID NOs: 138, 144, 150, 156, 162, 168, 174, 180, 186, 192, 198, 204, 210, 216, 222, 228, 234, 240, 246, 252, 258, and 264. In one embodiment the antibody or fragment thereof comprises a CDRL1, a CDRL2, a CDRL3, a CDRH1, a CDRH2, and a CDRH3, wherein each CDRL1, CDRL2, CDRL3, CDRH1, CDRH2, and CDRH3, respectively, comprises a sequence selected from the group consisting of SEQ ID NO: 4, SEQ ID NO: 5, SEQ ID NO: 6, SEQ ID NO: 136, SEQ ID NO: 137, and SEQ ID NO: 138; SEQ ID NO: 10, SEQ ID NO: 11, SEQ ID NO: 12, SEQ ID NO: 142, SEQ ID NO: 143, and SEQ ID NO: 144; SEQ ID NO: 16, SEQ ID NO: 17, SEQ ID NO: 18, SEQ ID NO: 148, SEQ ID NO: 149, and SEQ ID NO: 150; SEQ ID NO: 22, SEQ ID NO: 23, SEQ ID NO: 24, SEQ ID NO: 154, SEQ ID NO: 155, and SEQ ID NO: 156; SEQ ID NO: 28, SEQ ID NO: 29, SEQ ID NO: 30, SEQ ID NO: 160, SEQ ID NO: 161, and SEQ ID NO: 162; SEQ ID NO: 34, SEQ ID NO: 35, SEQ ID NO: 36, SEQ ID NO: 166, SEQ ID NO: 167, and SEQ ID NO: 168; SEQ ID NO: 40, SEQ ID NO: 41, SEQ ID NO: 42, SEQ ID NO: 172, SEQ ID NO: 173, and SEQ ID NO: 174; SEQ ID NO: 46, SEQ ID NO: 47, SEQ ID NO: 48, SEQ ID NO: 178, SEQ ID NO: 179, and SEQ ID NO: 180; SEQ ID NO: 52, SEQ ID NO: 53, SEQ ID NO: 54, SEQ ID NO: 184, SEQ ID NO: 185, and SEQ ID NO: 186; SEQ ID NO: 58, SEQ ID NO: 59, SEQ ID NO: 60, SEQ ID NO: 190, SEQ ID NO: 191, and SEQ ID NO: 192; SEQ ID NO: 64, SEQ ID NO: 65, SEQ ID NO: 66, SEQ ID NO: 196, SEQ ID NO: 197, and SEQ ID NO: 198; SEQ ID NO: 70, SEQ ID NO: 71, SEQ ID NO: 72, SEQ ID NO: 202, SEQ ID NO: 203, and SEQ ID NO: 204; SEQ ID NO: 76, SEQ ID NO: 77, SEQ ID NO: 78, SEQ ID NO: 208, SEQ ID NO: 209, and SEQ ID NO: 210; SEQ ID NO: 82, SEQ ID NO: 83, SEQ ID NO: 84, SEQ ID NO: 214, SEQ ID NO: 215, and SEQ ID NO: 216; SEQ ID NO: 88, SEQ ID NO: 89, SEQ ID NO:

90, SEQ ID NO: 220, SEQ ID NO: 221, and SEQ ID NO: 222; SEQ ID NO: 94, SEQ ID NO: 95, SEQ ID NO: 96, SEQ ID NO: 226, SEQ ID NO: 227, and SEQ ID NO: 228; SEQ ID NO: 100, SEQ ID NO: 101, SEQ ID NO: 102, SEQ ID NO: 232, SEQ ID NO: 233, and SEQ ID NO: 234; SEQ ID NO: 106, SEQ ID NO: 107, SEQ ID NO: 108, SEQ ID NO: 238, SEQ ID NO: 239, and SEQ ID NO: 240; SEQ ID NO: 112, SEQ ID NO: 113, SEQ ID NO: 114, SEQ ID NO: 244, SEQ ID NO: 245, and SEQ ID NO: 246; SEQ ID NO: 118, SEQ ID NO: 119, SEQ ID NO: 120, SEQ ID NO: 250, SEQ ID NO: 251, and SEQ ID NO: 252; SEQ ID NO: 124, SEQ ID NO: 125, SEQ ID NO: 126, SEQ ID NO: 256, SEQ ID NO: 257, and SEQ ID NO: 258; and SEQ ID NO: 130, SEQ ID NO: 131, SEQ ID NO: 132, SEQ ID NO: 262, SEQ ID NO: 263, and SEQ ID NO: 264.

In one embodiment the antibody or fragment thereof comprises a CDRL1, a CDRL2, a CDRL3, a CDRH1, a CDRH2, and a CDRH3 encoded by a polynucleotide. In one embodiment the antibody or fragment thereof comprises a CDRL1 encoded by a polynucleotide sequence selected from the group consisting of SEQ ID NOs: 1, 7, 13, 19, 25, 31, 37, 43, 49, 55, 61, 67, 73, 79, 85, 91, 97, 103, 109, 115, 121, and 127. In one embodiment the antibody or fragment thereof comprises a CDRL2 encoded by a polynucleotide sequence selected from the group consisting of SEQ ID NOs: 2, 8, 14, 20, 26, 32, 38, 44, 50, 56, 62, 68, 74, 80, 86, 92, 98, 104, 110, 116, 122, and 128. In one embodiment the antibody or fragment thereof comprises a CDRL3 encoded by a polynucleotide sequence selected from the group consisting of SEQ ID NOs: 3, 9, 15, 21, 27, 33, 39, 45, 51, 57, 63, 69, 75, 81, 87, 93, 99, 105, 111, 117, 123, and 129. In one embodiment the antibody or fragment thereof comprises a CDRH1 encoded by a polynucleotide sequence selected from the group consisting of SEQ ID NOs: 133, 139, 145, 151, 157, 163, 169, 175, 181, 187, 193, 199, 205, 211, 217, 223, 229, 235, 241, 247, 253, and 259. In one embodiment the antibody or fragment thereof comprises a CDRH2 encoded by a polynucleotide sequence selected from the group consisting of SEQ ID NOs: 134, 140, 146, 152, 158, 164, 170, 176, 182, 188, 194, 200, 206, 212, 218, 224, 230, 236, 242, 248, 254, and 260. In one embodiment the antibody or fragment thereof comprises a CDRH3 encoded by a polynucleotide sequence selected from the group consisting of SEQ ID NOs: 135, 141, 147, 153, 159, 165, 171, 177, 183, 189, 195, 201, 207, 213, 219, 225, 231, 237, 243, 249, 255, and 261. In one embodiment the antibody or fragment thereof comprises a CDRL1, a CDRL2, a CDRL3, a CDRH1, a CDRH2, and a CDRH3, wherein each CDRL1, CDRL2, CDRL3, CDRH1, CDRH2, and CDRH3, respectively, is encoded by a sequence comprising a sequence selected from the group consisting of SEQ ID NO: 1, SEQ ID NO: 2, SEQ ID NO: 3, SEQ ID NO: 133, SEQ ID NO: 134, and SEQ ID NO: 135; SEQ ID NO: 7, SEQ ID NO: 8, SEQ ID NO: 9, SEQ ID NO: 139, SEQ ID NO: 140, and SEQ ID NO: 141; SEQ ID NO: 13, SEQ ID NO: 14, SEQ ID NO: 15, SEQ ID NO: 145, SEQ ID NO: 146, and SEQ ID NO: 147; SEQ ID NO: 19, SEQ ID NO: 20, SEQ ID NO: 21, SEQ ID NO: 151, SEQ ID NO: 152, and SEQ ID NO: 153; SEQ ID NO: 25, SEQ ID NO: 26, SEQ ID NO: 27, SEQ ID NO: 157, SEQ ID NO: 158, and SEQ ID NO: 159; SEQ ID NO: 31, SEQ ID NO: 32, SEQ ID NO: 33, SEQ ID NO: 163, SEQ ID NO: 164, and SEQ ID NO: 165; SEQ ID NO: 37, SEQ ID NO: 38, SEQ ID NO: 39, SEQ ID NO: 169, SEQ ID NO: 170, and SEQ ID NO: 171; SEQ ID NO: 43, SEQ ID NO: 44, SEQ ID NO: 45, SEQ ID NO: 175, SEQ ID NO: 176, and SEQ ID NO: 177; SEQ ID NO: 49, SEQ ID NO: 50, SEQ ID NO: 51, SEQ ID NO: 181, SEQ ID NO: 182, and SEQ ID NO: 183; SEQ ID NO: 55, SEQ ID NO: 56, SEQ ID NO: 57, SEQ ID NO: 187, SEQ ID NO: 188, and SEQ ID NO: 189; SEQ ID NO: 61, SEQ ID NO: 62, SEQ ID NO: 63, SEQ ID NO: 193, SEQ ID NO: 194, and SEQ ID NO: 195; SEQ ID NO: 67, SEQ ID NO: 68, SEQ ID NO: 69, SEQ ID NO: 199, SEQ ID NO: 200, and SEQ ID NO: 201; SEQ ID NO: 73, SEQ ID NO: 74, SEQ ID NO: 75, SEQ ID NO: 205, SEQ ID NO: 206, and SEQ ID NO: 207; SEQ ID NO: 79, SEQ ID NO: 80, SEQ ID NO: 81, SEQ ID NO: 211, SEQ ID NO: 212, and SEQ ID NO: 213; SEQ ID NO: 85, SEQ ID NO: 86, SEQ ID NO: 87, SEQ ID NO: 217, SEQ ID NO: 218, and SEQ ID NO: 219; SEQ ID NO: 91, SEQ ID NO: 92, SEQ ID NO: 93, SEQ ID NO: 223, SEQ ID NO: 224, and SEQ ID NO: 225; SEQ ID NO: 97, SEQ ID NO: 98, SEQ ID NO: 99, SEQ ID NO: 229, SEQ ID NO: 230, and SEQ ID NO: 231; SEQ ID NO: 103, SEQ ID NO: 104, SEQ ID NO: 105, SEQ ID NO: 235, SEQ ID NO: 236, and SEQ ID NO: 237; SEQ ID NO: 109, SEQ ID NO: 110, SEQ ID NO: 111, SEQ ID NO: 241, SEQ ID NO: 242, and SEQ ID NO: 243; SEQ ID NO: 115, SEQ ID NO: 116, SEQ ID NO: 117, SEQ ID NO: 247, SEQ ID NO: 248, and SEQ ID NO: 249; SEQ ID NO: 121, SEQ ID NO: 122, SEQ ID NO: 123, SEQ ID NO: 253, SEQ ID NO: 254, and SEQ ID NO: 255; and SEQ ID NO: 127, SEQ ID NO: 128, SEQ ID NO: 129, SEQ ID NO: 259, SEQ ID NO: 260, and SEQ ID NO: 261.

In another aspect, an antigen binding protein includes 1, 2, 3, 4, 5, or 6 variant forms of the CDRs listed in TABLES 4A and 4B, each having at least 80%, 85%, 90%, 95%, 96%, 97%, 98%, or 99% sequence identity to a CDR sequence listed in TABLES 4A and 4B. Some antigen binding proteins include 1, 2, 3, 4, 5, or 6 of the CDRs listed in TABLES 4A and 4B, each or collectively differing by no more than 1, 2, 3, 4 or 5 amino acids from the CDRs listed in this table.

In various other embodiments, the antigen binding protein is derived from such antibodies. For instance, in one aspect, the antigen binding protein comprises 1, 2, 3, 4, 5 or all 6 of the CDRs listed in one of the rows for any particular antibody listed in TABLES 4A and 4B. In another aspect, an antigen binding protein includes 1, 2, 3, 4, 5, or 6 variant forms of the CDRs listed in one of the rows for an antibody in TABLES 4A and 4B, each CDR having at least 80%, 85%, 90%, 95%, 96%, 97%, 98%, or 99% sequence identity to a CDR sequence listed in TABLES 4A and 4B. Some antigen binding proteins include 1, 2, 3, 4, 5, or 6 of the CDRs listed in one of the rows of TABLES 4A and 4B, each differing by no more than 1, 2, 3, 4 or 5 amino acids from the CDRs listed in these tables. In another aspect, the antigen binding protein comprises all 6 of the CDRS listed in a row of TABLES 4A and 4B and the total number of amino acid changes to the CDRs collectively is no more than 1, 2, 3, 4, or 5 amino acids.

In still another aspect, antigen-binding proteins containing the CDRs, and/or variable domains listed in TABLES 3, 4A, and 4B is a monoclonal antibody, a chimeric antibody, a humanized antibody, a human antibody, a multispecific antibody, or an antibody fragment of the foregoing. In another embodiment, the antibody fragment of the isolated antigen-binding proteins provided herein is a Fab fragment, a Fab' fragment, an F(ab')$_2$ fragment, an Fv fragment, a diabody, or a scFv based upon an antibody with the sequences as listed in TABLES 3, 4A, and 4B.

In yet another aspect, the isolated antigen-binding protein provided in TABLES 3, 4A, and 4B can be coupled to a labeling group and can compete for binding to Jagged1 with an antigen binding protein of one of the isolated antigen-binding proteins provided herein.

In another embodiment, antigen binding proteins are provided that compete with one of the exemplified antibodies or functional fragments described above for specific binding to a human Jagged1 (e.g., SEQ ID NO: 353). Such antigen binding proteins may bind to the same epitope as one of the antigen binding proteins described herein, or to an overlapping epitope. Antigen binding proteins and fragments that compete with the exemplified antigen binding proteins are expected to show similar functional properties. The exemplified antigen binding proteins and fragments include those described above, including those with variable region domains and CDRs included in TABLES 3, 4A, and 4B. Thus, as a specific example, the antigen binding proteins that are provided include those that compete with an antibody having:

all 6 of the CDRs listed for any antibody listed in TABLES 4A and 4B; or a VH and a VL listed for any antibody listed in TABLE 3.

The antigen binding proteins that are provided include monoclonal antibodies that bind to Jagged1. Monoclonal antibodies may be produced using any technique known in the art, e.g., by immortalizing spleen cells harvested from the transgenic animal after completion of the immunization schedule. The spleen cells can be immortalized using any technique known in the art, e.g., by fusing them with myeloma cells to produce hybridomas. Myeloma cells for use in hybridoma-producing fusion procedures preferably are non-antibody-producing, have high fusion efficiency, and enzyme deficiencies that render them incapable of growing in certain selective media which support the growth of only the desired fused cells (hybridomas). Examples of suitable cell lines for use in mouse fusions include Sp-20, P3-X63/Ag8, P3-X63-Ag8.653, NS1/1.Ag 4 1, Sp210-Ag14, FO, NSO/U, MPC-11, MPC11-X45-GTG 1.7 and S194/5XXO Bul; examples of cell lines used in rat fusions include R210.RCY3, Y3-Ag 1.2.3, IR983F and 4B210. Other cell lines useful for cell fusions are U-266, GM1500-GRG2, LICR-LON-HMy2 and UC729-6.

In some instances, a hybridoma cell line is produced by immunizing an animal (e.g., a transgenic animal having human immunoglobulin sequences) with a Jagged1 immunogen; harvesting spleen cells from the immunized animal; fusing the harvested spleen cells to a myeloma cell line, thereby generating hybridoma cells; establishing hybridoma cell lines from the hybridoma cells, and identifying a hybridoma cell line that produces an antibody that binds a Jagged1 polypeptide. Such hybridoma cell lines, and anti-Jagged1 monoclonal antibodies produced by them, are aspects of the present application.

Monoclonal antibodies secreted by a hybridoma cell line can be purified using any technique known in the art. Hybridomas or mAbs may be further screened to identify mAbs with particular properties, such as the ability to increase Jagged1 activity.

Chimeric and humanized antibodies based upon the foregoing sequences are also provided. Monoclonal antibodies for use as therapeutic agents may be modified in various ways prior to use. One example is a chimeric antibody, which is an antibody composed of protein segments from different antibodies that are covalently joined to produce functional immunoglobulin light or heavy chains or immunologically functional portions thereof. Generally, a portion of the heavy chain and/or light chain is identical with or homologous to a corresponding sequence in antibodies derived from a particular species or belonging to a particular antibody class or subclass, while the remainder of the chain(s) is/are identical with or homologous to a corresponding sequence in antibodies derived from another species or belonging to another antibody class or subclass. For methods relating to chimeric antibodies, see, for example, U.S. Pat. No. 4,816,567; and Morrison et al., 1985, Proc. Natl. Acad. Sci. USA 81:6851-6855, which are hereby incorporated by reference. CDR grafting is described, for example, in U.S. Pat. Nos. 6,180,370, 5,693,762, 5,693,761, 5,585,089, and 5,530,101.

Generally, the goal of making a chimeric antibody is to create a chimera in which the number of amino acids from the intended patient species is maximized. One example is the "CDR-grafted" antibody, in which the antibody comprises one or more complementarity determining regions (CDRs) from a particular species or belonging to a particular antibody class or subclass, while the remainder of the antibody chain(s) is/are identical with or homologous to a corresponding sequence in antibodies derived from another species or belonging to another antibody class or subclass. For use in humans, the variable region or selected CDRs from a rodent antibody often are grafted into a human antibody, replacing the naturally-occurring variable regions or CDRs of the human antibody.

One useful type of chimeric antibody is a "humanized" antibody. Generally, a humanized antibody is produced from a monoclonal antibody raised initially in a non-human animal. Certain amino acid residues in this monoclonal antibody, typically from non-antigen recognizing portions of the antibody, are modified to be homologous to corresponding residues in a human antibody of corresponding isotype. Humanization can be performed, for example, using various methods by substituting at least a portion of a rodent variable region for the corresponding regions of a human antibody (see, e.g., U.S. Pat. Nos. 5,585,089, and 5,693,762; Jones et al., 1986, *Nature* 321:522-525; Riechmann et al., 1988, Nature 332:323-27; Verhoeyen et al., 1988, *Science* 239: 1534-1536).

In one aspect, the CDRs of the light and heavy chain variable regions of the antibodies provided herein are grafted to framework regions (FRs) from antibodies from the same, or a different, phylogenetic species. For example, the CDRs of the heavy and light chain variable regions $V_H1$, $V_H2$, $V_H3$, $V_H4$, $V_H5$, $V_H6$, $V_H7$, $V_H8$, $V_H9$, $V_H10$, $V_H11$, $V_H12$ and/or $V_L1$, and $V_L2$ can be grafted to consensus human FRs. To create consensus human FRs, FRs from several human heavy chain or light chain amino acid sequences may be aligned to identify a consensus amino acid sequence. In other embodiments, the FRs of a heavy chain or light chain disclosed herein are replaced with the FRs from a different heavy chain or light chain. In one aspect, rare amino acids in the FRs of the heavy and light chains of Jagged1 antibodies are not replaced, while the rest of the FR amino acids are replaced. A "rare amino acid" is a specific amino acid that is in a position in which this particular amino acid is not usually found in an FR. Alternatively, the grafted variable regions from the one heavy or light chain may be used with a constant region that is different from the constant region of that particular heavy or light chain as disclosed herein. In other embodiments, the grafted variable regions are part of a single chain Fv antibody.

In certain embodiments, constant regions from species other than human can be used along with the human variable region(s) to produce hybrid antibodies.

Fully human Jagged1 antibodies are also provided. Methods are available for making fully human antibodies specific for a given antigen without exposing human beings to the antigen ("fully human antibodies"). One specific means provided for implementing the production of fully human antibodies is the "humanization" of the mouse humoral immune system. Introduction of human immunoglobulin (Ig) loci into mice in which the endogenous Ig genes have been inactivated is one means of producing fully human monoclonal antibodies (mAbs) in mouse, an animal that can be immunized with any desirable antigen. Using fully human antibodies can minimize the immunogenic and allergic responses that can sometimes be caused by administering mouse or mouse-derived mAbs to humans as therapeutic agents.

Fully human antibodies can be produced by immunizing transgenic animals (usually mice) that are capable of producing a repertoire of human antibodies in the absence of endogenous immunoglobulin production. Antigens for this purpose typically have six or more contiguous amino acids, and optionally are conjugated to a carrier, such as a hapten. See, e.g., Jakobovits et al., 1993, *Proc. Natl. Acad. Sci. USA* 90:2551-2555; Jakobovits et al., 1993, *Nature* 362:255-258; and Bruggermann et al., 1993, *Year in Immunol.* 7:33. In one example of such a method, transgenic animals are produced by incapacitating the endogenous mouse immunoglobulin loci encoding the mouse heavy and light immunoglobulin chains therein, and inserting into the mouse genome large fragments of human genome DNA containing loci that encode human heavy and light chain proteins. Partially modified animals, which have less than the full complement of human immunoglobulin loci, are then cross-bred to obtain an animal having all of the desired immune system modifications. When administered an immunogen, these transgenic animals produce antibodies that are immunospecific for the immunogen but have human rather than murine amino acid sequences, including the variable regions. For further details of such methods, see, for example, WO96/33735 and WO94/02602. Additional methods relating to transgenic mice for making human antibodies are described in U.S. Pat. Nos. 5,545,807; 6,713,610; 6,673,986; 6,162,963; 5,545,807; 6,300,129; 6,255,458; 5,877,397; 5,874,299 and 5,545,806; in PCT publications WO91/10741, WO90/04036, and in EP 546073B1 and EP 546073A1.

The transgenic mice described above, referred to herein as "HuMab" mice, contain a human immunoglobulin gene minilocus that encodes unrearranged human heavy ([mu] and [gamma]) and [kappa] light chain immunoglobulin sequences, together with targeted mutations that inactivate the endogenous [mu] and [kappa] chain loci (Lonberg et al., 1994, *Nature* 368:856-859). Accordingly, the mice exhibit reduced expression of mouse IgM or [kappa] and in response to immunization, and the introduced human heavy and light chain transgenes undergo class switching and somatic mutation to generate high affinity human IgG [kappa] monoclonal antibodies (Lonberg et al., supra.; Lonberg and Huszar, 1995, *Intern. Rev. Immunol.* 13: 65-93; Harding and Lonberg, 1995, *Ann. N. Y Acad. Sci.* 764:536-546). The preparation of HuMab mice is described in detail in Taylor et al., 1992, *Nucleic Acids Research* 20:6287-6295; Chen et al., 1993, *International Immunology* 5:647-656; Tuaillon et al., 1994, *J. Immunol.* 152:2912-2920; Lonberg et al., 1994, *Nature* 368:856-859; Lonberg, 1994, *Handbook of Exp. Pharmacology* 113:49-101; Taylor et al., 1994, *International Immunology* 6:579-591; Lonberg and Huszar, 1995, *Intern. Rev. Immunol.* 13:65-93; Harding and Lonberg, 1995, *Ann. N.Y Acad. Sci.* 764:536-546; Fishwild et al., 1996, *Nature Biotechnology* 14:845-851; the foregoing references are hereby incorporated by reference in their entirety for all purposes. See, further U.S. Pat. Nos. 5,545,806; 5,569,825; 5,625,126; 5,633,425; 5,789,650; 5,877,397; 5,661,016; 5,814,318; 5,874,299; and 5,770,429; as well as U.S. Pat. No. 5,545,807; International Publication Nos. WO 93/1227; WO 92/22646; and WO 92/03918, the disclosures of all of which are hereby incorporated by reference in their entirety for all purposes. Technologies utilized for producing human antibodies in these transgenic mice are disclosed also in WO 98/24893, and Mendez et al., 1997, Nature Genetics 15:146-156, which are hereby incorporated by reference. For example, the HCo7 and HCo12 transgenic mice strains can be used to generate human monoclonal antibodies against Jagged1. Further details regarding the production of human antibodies using transgenic mice are provided below.

Using hybridoma technology, antigen-specific human mAbs with the desired specificity can be produced and selected from the transgenic mice such as those described above. Such antibodies may be cloned and expressed using a suitable vector and host cell, or the antibodies can be harvested from cultured hybridoma cells.

Fully human antibodies can also be derived from phage-display libraries (as disclosed in Hoogenboom et al., 1991, *J. Mol. Biol.* 227:381; and Marks et al., 1991, *J. Mol. Biol.* 222:581). Phage display techniques mimic immune selection through the display of antibody repertoires on the surface of filamentous bacteriophage, and subsequent selection of phage by their binding to an antigen of choice. One such technique is described in PCT Publication No. WO 99/10494 (hereby incorporated by reference).

The Jagged1 binding protein can also be a variant, mimetic, derivative or oligomer based upon the structure of Jagged1 antigen binding proteins have the CDRs, variable regions and/or full length chains as described above.

In one embodiment, for instance, an antigen binding protein is a variant form of the antigen binding proteins disclosed above. For instance, some of the antigen binding proteins have one or more conservative amino acid substitutions in one or more of the heavy or light chains, variable regions or CDRs.

Naturally-occurring amino acids may be divided into classes based on common side chain properties:
1) hydrophobic: norleucine, Met, Ala, Val, Leu, Ile;
2) neutral hydrophilic: Cys, Ser, Thr, Asn, Gln;
3) acidic: Asp, Glu;
4) basic: His, Lys, Arg;
5) residues that influence chain orientation: Gly, Pro; and
6) aromatic: Trp, Tyr, Phe.

Conservative amino acid substitutions may involve exchange of a member of one of these classes with another member of the same class. Conservative amino acid substitutions may encompass non-naturally occurring amino acid residues, which are typically incorporated by chemical peptide synthesis rather than by synthesis in biological systems. These include peptidomimetics and other reversed or inverted forms of amino acid moieties.

Non-conservative substitutions may involve the exchange of a member of one of the above classes for a member from another class. Such substituted residues may be introduced into regions of the antibody that are homologous with human antibodies, or into the non-homologous regions of the molecule.

In making such changes, according to certain embodiments, the hydropathic index of amino acids may be considered. The hydropathic profile of a protein is calculated by assigning each amino acid a numerical value ("hydropathy index") and then repetitively averaging these values along the peptide chain. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic profile in conferring interactive biological function on a protein is understood in the art (see, e.g., Kyte et al., 1982, *J. Mol. Biol.* 157:105-131). It is known that certain amino acids may be substituted for other amino acids having a similar hydropathic index or score and still retain a similar biological activity. In making changes based upon the hydropathic index, in certain embodiments, the substitution of amino acids whose hydropathic indices are within ±2 is included. In some aspects, those which are within ±1 are included, and in other aspects, those within +0.5 are included.

It is also understood in the art that the substitution of like amino acids can be made effectively on the basis of hydrophilicity, particularly where the biologically functional protein or peptide thereby created is intended for use in immunological embodiments, as in the present case. In certain embodiments, the greatest local average hydrophilicity of a protein, as governed by the hydrophilicity of its adjacent amino acids, correlates with its immunogenicity and antigen-binding or immunogenicity, that is, with a biological property of the protein.

The following hydrophilicity values have been assigned to these amino acid residues: arginine (+3.0); lysine (+3.0); aspartate (+3.0±1); glutamate (+3.0+1); serine (+0.3); asparagine (+0.2); glutamine (+0.2); glycine (0); threonine (−0.4); proline (−0.5+1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within ±2 is included, in other embodiments, those which are within +1 are included, and in still other embodiments, those within +0.5 are included. In some instances, one may also identify epitopes from primary amino acid sequences on the basis of hydrophilicity. These regions are also referred to as "epitopic core regions."

Exemplary conservative amino acid substitutions are set forth in Table 5.

TABLE 5

| Conservative Amino Acid Substitutions | |
|---|---|
| Original Residue | Exemplary Substitutions |
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

A skilled artisan will be able to determine suitable variants of polypeptides as set forth herein using well-known techniques. One skilled in the art may identify suitable areas of the molecule that may be changed without destroying activity by targeting regions not believed to be important for activity. The skilled artisan also will be able to identify residues and portions of the molecules that are conserved among similar polypeptides. In further embodiments, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in a protein that correspond to amino acid residues important for activity or structure in similar proteins. One skilled in the art may opt for chemically similar amino acid substitutions for such predicted important amino acid residues.

One skilled in the art can also analyze the 3-dimensional structure and amino acid sequence in relation to that structure in similar polypeptides. In view of such information, one skilled in the art may predict the alignment of amino acid residues of an antibody with respect to its three dimensional structure. One skilled in the art may choose not to make radical changes to amino acid residues predicted to be on the surface of the protein, since such residues may be involved in important interactions with other molecules. Moreover, one skilled in the art may generate test variants containing a single amino acid substitution at each desired amino acid residue. These variants can then be screened using assays for Jagged1 activity, thus yielding information regarding which amino acids can be changed and which must not be changed. In other words, based on information gathered from such routine experiments, one skilled in the art can readily determine the amino acid positions where further substitutions should be avoided either alone or in combination with other mutations.

A number of scientific publications have been devoted to the prediction of secondary structure. See, Moult, 1996, *Curr. Op. in Biotech.* 7:422-427; Chou et al., 1974, *Biochem.* 13:222-245; Chou et al., 1974, *Biochemistry* 113:211-222; Chou et al., 1978, *Adv. Enzymol. Relat. Areas Mol. Biol.* 47:45-148; Chou et al., 1979, *Ann. Rev. Biochem.* 47:251-276; and Chou et al., 1979, *Biophys. J.* 26:367-384. Moreover, computer programs are currently available to assist with predicting secondary structure. One method of predicting secondary structure is based upon homology modeling. For example, two polypeptides or proteins that have a sequence identity of greater than 30%, or similarity greater than 40% can have similar structural topologies. The recent growth of the protein structural database (PDB) has provided enhanced predictability of secondary structure, including the potential number of folds within a polypeptide's or protein's structure. See, Holm et al., 1999, *Nucl. Acid. Res.* 27:244-247. It has been suggested (Brenner et al., 1997,

*Curr. Op. Struct. Biol.* 7:369-376) that there are a limited number of folds in a given polypeptide or protein and that once a critical number of structures have been resolved, structural prediction will become dramatically more accurate.

Additional methods of predicting secondary structure include "threading" (Jones, 1997, *Curr. Opin. Struct. Biol.* 7:377-387; Sippl et al., 1996, *Structure* 4:15-19), "profile analysis" (Bowie et al., 1991, *Science* 253:164-170; Gribskov et al., 1990, *Meth. Enzym.* 183:146-159; Gribskov et al., 1987, *Proc. Nat. Acad. Sci.* 84:4355-4358), and "evolutionary linkage" (See, Holm, 1999, supra; and Brenner, 1997, supra).

In some embodiments, amino acid substitutions are made that: (1) reduce susceptibility to proteolysis, (2) reduce susceptibility to oxidation, (3) alter binding affinity for forming protein complexes, (4) alter ligand or antigen binding affinities, and/or (4) confer or modify other physicochemical or functional properties on such polypeptides. For example, single or multiple amino acid substitutions (in certain embodiments, conservative amino acid substitutions) may be made in the naturally-occurring sequence. Substitutions can be made in that portion of the antibody that lies outside the domain(s) forming intermolecular contacts). In such embodiments, conservative amino acid substitutions can be used that do not substantially change the structural characteristics of the parent sequence (e.g., one or more replacement amino acids that do not disrupt the secondary structure that characterizes the parent or native antigen binding protein). Examples of art-recognized polypeptide secondary and tertiary structures are described in Proteins, Structures and Molecular Principles (Creighton, Ed.), 1984, W. H. New York: Freeman and Company; Introduction to Protein Structure (Branden and Tooze, eds.), 1991, New York: Garland Publishing; and Thornton et al., 1991, *Nature* 354:105, which are each incorporated herein by reference.

Additional preferred antibody variants include cysteine variants wherein one or more cysteine residues in the parent or native amino acid sequence are deleted from or substituted with another amino acid (e.g., serine). Cysteine variants are useful, inter alia when antibodies must be refolded into a biologically active conformation. Cysteine variants may have fewer cysteine residues than the native antibody, and typically have an even number to minimize interactions resulting from unpaired cysteines.

The heavy and light chains, variable regions domains and CDRs that are disclosed can be used to prepare polypeptides that contain an antigen binding region that can specifically bind to Jagged1. For example, one or more of the CDRs can be incorporated into a molecule (e.g., a polypeptide) covalently or noncovalently to make an immunoadhesion. An immunoadhesion may incorporate the CDR(s) as part of a larger polypeptide chain, may covalently link the CDR(s) to another polypeptide chain, or may incorporate the CDR(s) noncovalently. The CDR(s) enable the immunoadhesion to bind specifically to a particular antigen of interest (e.g., an Jagged1 polypeptide or epitope thereof).

Mimetics (e.g., "peptide mimetics" or "peptidomimetics") based upon the variable region domains and CDRs that are described herein are also provided. These analogs can be peptides, non-peptides or combinations of peptide and non-peptide regions. Fauchere, 1986, *Adv. Drug Res.* 15:29; Veber and Freidinger, 1985, *TINS* p. 392; and Evans et al., 1987, *J. Med. Chem.* 30:1229, which are incorporated herein by reference for any purpose. Peptide mimetics that are structurally similar to therapeutically useful peptides may be used to produce a similar therapeutic or prophylactic effect. Such compounds are often developed with the aid of computerized molecular modeling. Generally, peptidomimetics are proteins that are structurally similar to an antibody displaying a desired biological activity, such as here the ability to specifically bind Jagged1, but have one or more peptide linkages optionally replaced by a linkage selected from: $-CH_2NH-$, $-CH_2S-$, $-CH_2-CH_2-$, $-CH=CH-$(cis and trans), $-COCH_2-$, $-CH(OH)CH_2-$, and $-CH_2SO-$, by methods well known in the art. Systematic substitution of one or more amino acids of a consensus sequence with a D-amino acid of the same type (e.g., D-lysine in place of L-lysine) may be used in certain embodiments to generate more stable proteins. In addition, constrained peptides comprising a consensus sequence or a substantially identical consensus sequence variation may be generated by methods known in the art (Rizo and Gierasch, 1992, *Ann. Rev. Biochem.* 61:387), incorporated herein by reference), for example, by adding internal cysteine residues capable of forming intramolecular disulfide bridges which cyclize the peptide.

Derivatives of the antigen binding proteins that are described herein are also provided. The derivatized antigen binding proteins can comprise any molecule or substance that imparts a desired property to the antibody or fragment, such as increased half-life in a particular use. The derivatized antigen binding protein can comprise, for example, a detectable (or labeling) moiety (e.g., a radioactive, colorimetric, antigenic or enzymatic molecule, a detectable bead (such as a magnetic or electrodense (e.g., gold) bead), or a molecule that binds to another molecule (e.g., biotin or streptavidin)), a therapeutic or diagnostic moiety (e.g., a radioactive, cytotoxic, or pharmaceutically active moiety), or a molecule that increases the suitability of the antigen binding protein for a particular use (e.g., administration to a subject, such as a human subject, or other in vivo or in vitro uses). Examples of molecules that can be used to derivatize an antigen binding protein include albumin (e.g., human serum albumin) and polyethylene glycol (PEG). Albumin-linked and PEGylated derivatives of antigen binding proteins can be prepared using techniques well known in the art. Certain antigen binding proteins include a pegylated single chain polypeptide as described herein. In one embodiment, the antigen binding protein is conjugated or otherwise linked to transthyretin (TTR) or a TTR variant. The TTR or TTR variant can be chemically modified with, for example, a chemical selected from the group consisting of dextran, poly(n-vinyl pyrrolidone), polyethylene glycols, propropylene glycol homopolymers, polypropylene oxide/ethylene oxide co-polymers, polyoxyethylated polyols and polyvinyl alcohols.

Other derivatives include covalent or aggregative conjugates of Jagged1 antigen binding proteins with other proteins or polypeptides, such as by expression of recombinant fusion proteins comprising heterologous polypeptides fused to the N-terminus or C-terminus of an Jagged1 antigen binding protein. For example, the conjugated peptide may be a heterologous signal (or leader) polypeptide, e.g., the yeast alpha-factor leader, or a peptide such as an epitope tag. Jagged1 antigen binding protein-containing fusion proteins can comprise peptides added to facilitate purification or identification of the Jagged1 antigen binding protein (e.g., poly-His). A Jagged1 antigen binding protein also can be linked to the FLAG peptide as described in Hopp et al., 1988, *Bio/Technology* 6:1204; and U.S. Pat. No. 5,011,912. The FLAG peptide is highly antigenic and provides an epitope reversibly bound by a specific monoclonal antibody (mAb), enabling rapid assay and facile purification of expressed recombinant protein. Reagents useful for preparing fusion proteins in which the FLAG peptide is fused to a given polypeptide are commercially available (Sigma, St. Louis, Mo.).

In some embodiments, the antigen binding protein comprises one or more labels. The term "labeling group" or "label" means any detectable label. Examples of suitable labeling groups include, but are not limited to, the following: radioisotopes or radionuclides (e.g., $^{3}H$, $^{14}C$, $^{15}N$, $^{35}S$, $^{90}Y$, $^{99}Tc$, $^{111}In$, $^{125}I$, $^{131}I$), fluorescent groups (e.g., FITC, rhodamine, lanthanide phosphors), enzymatic groups (e.g., horseradish peroxidase, β-galactosidase, luciferase, alkaline phosphatase), chemiluminescent groups, biotinyl groups, or predetermined polypeptide epitopes recognized by a secondary reporter (e.g., leucine zipper pair sequences, binding sites for secondary antibodies, metal binding domains, epitope tags). In some embodiments, the labeling group is coupled to the antigen binding protein via spacer arms of various lengths to reduce potential steric hindrance. Various methods for labeling proteins are known in the art and may be used as is seen fit.

The term "effector group" means any group coupled to an antigen binding protein that acts as a cytotoxic agent. Examples for suitable effector groups are radioisotopes or radionuclides (e.g., $^{3}H$, $^{14}C$, $^{15}N$, $^{35}S$, $^{90}Y$, $^{99}Tc$, $^{111}In$, $^{125}I$, $^{131}I$). Other suitable groups include toxins, therapeutic groups, or chemotherapeutic groups. Examples of suitable groups include calicheamicin, auristatins, geldanamycin and maytansine. In some embodiments, the effector group is coupled to the antigen binding protein via spacer arms of various lengths to reduce potential steric hindrance.

In general, labels fall into a variety of classes, depending on the assay in which they are to be detected: a) isotopic labels, which may be radioactive or heavy isotopes; b) magnetic labels (e.g., magnetic particles); c) redox active moieties; d) optical dyes; enzymatic groups (e.g. horseradish peroxidase, β-galactosidase, luciferase, alkaline phosphatase); e) biotinylated groups; and f) predetermined polypeptide epitopes recognized by a secondary reporter (e.g., leucine zipper pair sequences, binding sites for secondary antibodies, metal binding domains, epitope tags, etc.). In some embodiments, the labeling group is coupled to the antigen binding protein via spacer arms of various lengths to reduce potential steric hindrance. Various methods for labeling proteins are known in the art.

Specific labels include optical dyes, including, but not limited to, chromophores, phosphors and fluorophores, with the latter being specific in many instances. Fluorophores can be either "small molecule" fluores, or proteinaceous fluores.

By "fluorescent label" is meant any molecule that may be detected via its inherent fluorescent properties. Suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade BlueJ, Texas Red, IAEDANS, EDANS, BODIPY FL, LC Red 640, Cy 5, Cy 5.5, LC Red 705, Oregon green, the Alexa-Fluor dyes (Alexa Fluor 350, Alexa Fluor 430, Alexa Fluor 488, Alexa Fluor 546, Alexa Fluor 568, Alexa Fluor 594, Alexa Fluor 633, Alexa Fluor 660, Alexa Fluor 680), Cascade Blue, Cascade Yellow and R-phycoerythrin (PE) (Molecular Probes, Eugene, Oreg.), FITC, Rhodamine, and Texas Red (Pierce, Rockford, Ill.), Cy5, Cy5.5, Cy7 (Amersham Life Science, Pittsburgh, Pa.). Suitable optical dyes, including fluorophores, are described in Molecular Probes Handbook by Richard P. Haugland, hereby expressly incorporated by reference.

Suitable proteinaceous fluorescent labels also include, but are not limited to, green fluorescent protein, including a *Renilla*, *Ptilosarcus*, or *Aequorea* species of GFP (Chalfie et al., 1994, *Science* 263:802-805), EGFP (Clontech Labs., Inc., Genbank Accession Number U55762), blue fluorescent protein (BFP, Quantum Biotechnologies, Inc., Quebec, Canada; Stauber, 1998, *Biotechniques* 24:462-471; Heim et al., 1996, *Curr. Biol.* 6:178-182), enhanced yellow fluorescent protein (EYFP, Clontech Labs., Inc.), luciferase (Ichiki et al., 1993, *J. Immunol.* 150:5408-5417), β galactosidase (Nolan et al., 1988, *Proc. Natl. Acad. Sci. U.S.A.* 85:2603-2607) and *Renilla* (WO92/15673, WO95/07463, WO98/14605, WO98/26277, WO99/49019, U.S. Pat. Nos. 5,292,658, 5,418,155, 5,683,888, 5,741,668, 5,777,079, 5,804,387, 5,874,304, 5,876,995, 5,925,558).

Nucleic acids that encode for the antigen binding proteins described herein, or portions thereof, are also provided, including nucleic acids encoding one or both chains of an antibody, or a fragment, derivative, mutein, or variant thereof, polynucleotides encoding heavy chain variable regions or only CDRs, polynucleotides sufficient for use as hybridization probes, PCR primers or sequencing primers for identifying, analyzing, mutating or amplifying a polynucleotide encoding a polypeptide, anti-sense nucleic acids for inhibiting expression of a polynucleotide, and complementary sequences of the foregoing. The nucleic acids can be any length. They can be, for example, 5, 10, 15, 20, 25, 30, 35, 40, 45, 50, 75, 100, 125, 150, 175, 200, 250, 300, 350, 400, 450, 500, 750, 1,000, 1,500, 3,000, 5,000 or more nucleotides in length, and/or can comprise one or more additional sequences, for example, regulatory sequences, and/or be part of a larger nucleic acid, for example, a vector. The nucleic acids can be single-stranded or double-stranded and can comprise RNA and/or DNA nucleotides, and artificial variants thereof (e.g., peptide nucleic acids). Any variable region provided herein may be attached to these constant regions to form complete heavy and light chain sequences. However, it should be understood that these constant regions sequences are provided as specific examples only. In some embodiments, the variable region sequences are joined to other constant region sequences that are known in the art.

Nucleic acids encoding certain antigen binding proteins, or portions thereof (e.g., full length antibody, heavy or light chain, variable domain, or CDRH1, CDRH2, CDRH3, CDRL1, CDRL2, or CDRL3) may be isolated from B-cells of mice that have been immunized with Jagged1 or an immunogenic fragment thereof. The nucleic acid may be isolated by conventional procedures such as polymerase chain reaction (PCR). Phage display is another example of a known technique whereby derivatives of antibodies and other antigen binding proteins may be prepared. In one approach, polypeptides that are components of an antigen binding protein of interest are expressed in any suitable recombinant expression system, and the expressed polypeptides are allowed to assemble to form antigen binding proteins.

An aspect further provides nucleic acids that hybridize to other nucleic acids under particular hybridization conditions. Methods for hybridizing nucleic acids are well-known in the art. See, e.g., Current Protocols in Molecular Biology, John Wiley & Sons, N.Y. (1989), 6.3.1-6.3.6. As defined herein, a moderately stringent hybridization condition uses a prewashing solution containing 5× sodium chloride/sodium citrate (SSC), 0.5% SDS, 1.0 mM EDTA (pH 8.0), hybridization buffer of about 50% formamide, 6×SSC, and a hybridization temperature of 55° C. (or other similar hybridization solutions, such as one containing about 50% formamide, with a hybridization temperature of 42° C.), and washing conditions of 60° C., in 0.5×SSC, 0.1% SDS. A stringent hybridization condition hybridizes in 6×SSC at 45° C., followed by one or more washes in 0.1×SSC, 0.2% SDS at 68° C. Furthermore, one of skill in the art can manipulate the hybridization and/or washing conditions to increase or decrease the stringency of hybridization such that nucleic acids comprising nucleotide sequences that are at least 65%, 70%, 75%, 80%, 85%, 90%, 95%, 98% or 99% identical to each other typically remain hybridized to each other.

The basic parameters affecting the choice of hybridization conditions and guidance for devising suitable conditions are set forth by, for example, Sambrook, Fritsch, and Maniatis (2001, Molecular Cloning: A Laboratory Manual, Cold Spring Harbor Laboratory Press, Cold Spring Harbor, N.Y., supra; and Current Protocols in Molecular Biology, 1995, Ausubel et al., eds., John Wiley & Sons, Inc., sections 2.10 and 6.3-6.4), and can be readily determined by those having ordinary skill in the art based on, e.g., the length and/or base composition of the nucleic acid.

Changes can be introduced by mutation into a nucleic acid, thereby leading to changes in the amino acid sequence of a polypeptide (e.g., an antibody or antibody derivative) that it encodes. Mutations can be introduced using any technique known in the art. In one embodiment, one or more particular amino acid residues are changed using, for example, a site-directed mutagenesis protocol. In another embodiment, one or more randomly selected residues is changed using, for example, a random mutagenesis protocol. However it is made, a mutant polypeptide can be expressed and screened for a desired property.

Mutations can be introduced into a nucleic acid without significantly altering the biological activity of a polypeptide that it encodes. For example, one can make nucleotide substitutions leading to amino acid substitutions at non-essential amino acid residues. Alternatively, one or more mutations can be introduced into a nucleic acid that selectively changes the biological activity of a polypeptide that it encodes. For example, the mutation can quantitatively or qualitatively change the biological activity. Examples of quantitative changes include increasing, reducing or eliminating the activity. Examples of qualitative changes include changing the antigen specificity of an antibody. In one embodiment, a nucleic acid encoding any antigen binding protein described herein can be mutated to alter the amino acid sequence using molecular biology techniques that are well-established in the art.

Another aspect provides nucleic acid molecules that are suitable for use as primers or hybridization probes for the detection of nucleic acid sequences. A nucleic acid molecule can comprise only a portion of a nucleic acid sequence encoding a full-length polypeptide, for example, a fragment that can be used as a probe or primer or a fragment encoding an active portion of a polypeptide.

Probes based on the sequence of a nucleic acid can be used to detect the nucleic acid or similar nucleic acids, for example, transcripts encoding a polypeptide. The probe can comprise a label group, e.g., a radioisotope, a fluorescent compound, an enzyme, or an enzyme co-factor. Such probes can be used to identify a cell that expresses the polypeptide.

Another aspect provides vectors comprising a nucleic acid encoding a polypeptide or a portion thereof (e.g., a fragment containing one or more CDRs or one or more variable region domains). Examples of vectors include, but are not limited to, plasmids, viral vectors, non-episomal mammalian vectors and expression vectors, for example, recombinant expression vectors. The recombinant expression vectors can comprise a nucleic acid in a form suitable for expression of the nucleic acid in a host cell. The recombinant expression vectors include one or more regulatory sequences, selected on the basis of the host cells to be used for expression, which is operably linked to the nucleic acid sequence to be expressed. Regulatory sequences include those that direct constitutive expression of a nucleotide sequence in many types of host cells (e.g., SV40 early gene enhancer, Rous sarcoma virus promoter and cytomegalovirus promoter), those that direct expression of the nucleotide sequence only in certain host cells (e.g., tissue-specific regulatory sequences, see, Voss et al., 1986, *Trends Biochem. Sci.* 11:287, Maniatis et al., 1987, *Science* 236:1237, incorporated by reference herein in their entireties), and those that direct inducible expression of a nucleotide sequence in response to particular treatment or condition (e.g., the metallothionin promoter in mammalian cells and the tet-responsive and/or streptomycin responsive promoter in both prokaryotic and eukaryotic systems (see, id.). It will be appreciated by those skilled in the art that the design of the expression vector can depend on such factors as the choice of the host cell to be transformed, the level of expression of protein desired, etc. The expression vectors can be introduced into host cells to thereby produce proteins or peptides, including fusion proteins or peptides, encoded by nucleic acids as described herein.

Another aspect provides host cells into which a recombinant expression vector has been introduced. A host cell can be any prokaryotic cell (for example, *E. coli*) or eukaryotic cell (for example, yeast, insect, or mammalian cells (e.g., CHO cells)). Vector DNA can be introduced into prokaryotic or eukaryotic cells via conventional transformation or transfection techniques. For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die), among other methods.

Expression systems and constructs in the form of plasmids, expression vectors, transcription or expression cassettes that comprise at least one polynucleotide as described above are also provided herein, as well host cells comprising such expression systems or constructs.

The antigen binding proteins provided herein may be prepared by any of a number of conventional techniques. For example, Jagged1 antigen binding proteins may be produced by recombinant expression systems, using any technique known in the art. See, e.g., Monoclonal Antibodies, Hybridomas: A New Dimension in Biological Analyses, Kennet et al. (eds.) Plenum Press, New York (1980); and Antibodies: A Laboratory Manual, Harlow and Lane (eds.), Cold Spring Harbor Laboratory Press, Cold Spring Harbor, N.Y. (1988).

Antigen binding proteins can be expressed in hybridoma cell lines (e.g., in particular antibodies may be expressed in hybridomas) or in cell lines other than hybridomas. Expression constructs encoding the antibodies can be used to transform a mammalian, insect or microbial host cell. Transformation can be performed using any known method for introducing polynucleotides into a host cell, including, for example packaging the polynucleotide in a virus or bacteriophage and transducing a host cell with the construct by transfection procedures known in the art, as exemplified by U.S. Pat. Nos. 4,399,216; 4,912,040; 4,740,461; 4,959,455. The optimal transformation procedure used will depend upon which type of host cell is being transformed. Methods for introduction of heterologous polynucleotides into mammalian cells are well known in the art and include, but are not limited to, dextran-mediated transfection, calcium phosphate precipitation, polybrene mediated transfection, protoplast fusion, electroporation, encapsulation of the polynucleotide(s) in liposomes, mixing nucleic acid with positively-charged lipids, and direct microinjection of the DNA into nuclei.

Recombinant expression constructs typically comprise a nucleic acid molecule encoding a polypeptide comprising one or more of the following: one or more CDRs provided herein; a light chain constant region; a light chain variable region; a heavy chain constant region (e.g., $C_H1$, $C_H2$ and/or $C_H3$); and/or another scaffold portion of a Jagged1 antigen binding protein. These nucleic acid sequences are inserted into an appropriate expression vector using standard ligation techniques. In one embodiment, the heavy or light chain constant region is appended to the C-terminus of the anti-Jagged1 specific heavy or light chain variable region and is ligated into an expression vector. The vector is typically selected to be functional in the particular host cell employed (i.e., the vector is compatible with the host cell machinery, permitting amplification and/or expression of the gene can occur). In some embodiments, vectors are used that employ protein-fragment complementation assays using protein reporters, such as dihydrofolate reductase (see, for example, U.S. Pat. No. 6,270,964, which is hereby incorporated by reference). Suitable expression vectors can be purchased, for example, from Invitrogen Life Technologies or BD Biosciences (formerly "Clontech"). Other useful vectors for cloning and expressing the antibodies and fragments include those described in Bianchi and McGrew, 2003, *Biotech. Biotechnol. Bioeng.* 84:439-44, which is hereby incorporated by reference. Additional suitable expression vectors are discussed, for example, in Methods Enzymol., vol. 185 (D. V. Goeddel, ed.), 1990, New York: Academic Press.

Typically, expression vectors used in any of the host cells will contain sequences for plasmid maintenance and for cloning and expression of exogenous nucleotide sequences. Such sequences, collectively referred to as "flanking sequences" in certain embodiments will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element. Each of these sequences is discussed below.

Optionally, the vector may contain a "tag"-encoding sequence, i.e., an oligonucleotide molecule located at the 5' or 3' end of the Jagged1 antigen binding protein coding sequence; the oligonucleotide sequence encodes polyHis (such as hexaHis), or another "tag" such as FLAG®, HA (hemaglutinin influenza virus), or myc, for which commercially available antibodies exist. This tag is typically fused to the polypeptide upon expression of the polypeptide, and can serve as a means for affinity purification or detection of the Jagged1 antigen binding protein from the host cell. Affinity purification can be accomplished, for example, by column chromatography using antibodies against the tag as an affinity matrix. Optionally, the tag can subsequently be removed from the purified Jagged1 antigen binding protein by various means such as using certain peptidases for cleavage.

Flanking sequences may be homologous (i.e., from the same species and/or strain as the host cell), heterologous (i.e., from a species other than the host cell species or strain), hybrid (i.e., a combination of flanking sequences from more than one source), synthetic or native. As such, the source of a flanking sequence may be any prokaryotic or eukaryotic organism, any vertebrate or invertebrate organism, or any plant, provided that the flanking sequence is functional in, and can be activated by, the host cell machinery.

Flanking sequences useful in the vectors may be obtained by any of several methods well known in the art. Typically, flanking sequences useful herein will have been previously identified by mapping and/or by restriction endonuclease digestion and can thus be isolated from the proper tissue source using the appropriate restriction endonucleases. In some cases, the full nucleotide sequence of a flanking sequence may be known. Here, the flanking sequence may be synthesized using the methods described herein for nucleic acid synthesis or cloning.

Whether all or only a portion of the flanking sequence is known, it may be obtained using polymerase chain reaction (PCR) and/or by screening a genomic library with a suitable probe such as an oligonucleotide and/or flanking sequence fragment from the same or another species. Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarose gel purification, Qiagen® column chromatography (Chatsworth, Calif.), or other methods known to the skilled artisan. The selection of suitable enzymes to accomplish this purpose will be readily apparent to one of ordinary skill in the art.

An origin of replication is typically a part of those prokaryotic expression vectors purchased commercially, and the origin aids in the amplification of the vector in a host cell. If the vector of choice does not contain an origin of replication site, one may be chemically synthesized based on a known sequence, and ligated into the vector. For example, the origin of replication from the plasmid pBR322 (New England Biolabs, Beverly, Mass.) is suitable for most gram-negative bacteria, and various viral origins (e.g., SV40, polyoma, adenovirus, vesicular stomatitus virus (VSV), or papillomaviruses such as HPV or BPV) are useful for cloning vectors in mammalian cells. Generally, the origin of replication component is not needed for mammalian expression vectors (for example, the SV40 origin is often used only because it also contains the virus early promoter).

A transcription termination sequence is typically located 3' to the end of a polypeptide coding region and serves to terminate transcription. Usually, a transcription termination sequence in prokaryotic cells is a G-C rich fragment followed by a poly-T sequence. While the sequence is easily cloned from a library or even purchased commercially as part of a vector, it can also be readily synthesized using methods for nucleic acid synthesis such as those described herein.

A selectable marker gene encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells; (b) complement auxotrophic deficiencies of the cell; or (c) supply critical nutrients not available from complex or defined media. Specific selectable markers are the kanamycin resistance gene, the ampicillin resistance gene, and the tetracycline resistance gene. Advantageously, a neomycin resistance gene may also be used for selection in both prokaryotic and eukaryotic host cells.

Other selectable genes may be used to amplify the gene that will be expressed. Amplification is the process wherein genes that are required for production of a protein critical for growth or cell survival are reiterated in tandem within the chromosomes of successive generations of recombinant cells. Examples of suitable selectable markers for mammalian cells include dihydrofolate reductase (DHFR) and promoterless thymidine kinase genes. Mammalian cell transformants are placed under selection pressure wherein only the transformants are uniquely adapted to survive by virtue of the selectable gene present in the vector. Selection pressure is imposed by culturing the transformed cells under conditions in which the concentration of selection agent in the medium is successively increased, thereby leading to the amplification of both the selectable gene and the DNA that encodes another gene, such as an antigen binding protein that binds Jagged1 polypeptide. As a result, increased quantities of a polypeptide such as an antigen binding protein are synthesized from the amplified DNA.

A ribosome-binding site is usually necessary for translation initiation of mRNA and is characterized by a Shine-Dalgarno sequence (prokaryotes) or a Kozak sequence (eukaryotes). The element is typically located 3' to the promoter and 5' to the coding sequence of the polypeptide to be expressed.

In some cases, such as where glycosylation is desired in a eukaryotic host cell expression system, one may manipulate the various pre- or pro-sequences to improve glycosylation or yield. For example, one may alter the peptidase cleavage site of a particular signal peptide, or add prosequences, which also may affect glycosylation. The final protein product may have, in the −1 position (relative to the first amino acid of the mature protein), one or more additional amino acids incident to expression, which may not have been totally removed. For example, the final protein product may have one or two amino acid residues found in the peptidase cleavage site, attached to the amino-terminus. Alternatively, use of some enzyme cleavage sites may result in a slightly truncated form of the desired polypeptide, if the enzyme cuts at such area within the mature polypeptide.

Expression and cloning will typically contain a promoter that is recognized by the host organism and operably linked to the molecule encoding the Jagged1 antigen binding protein. Promoters are untranscribed sequences located upstream (i.e., 5') to the start codon of a structural gene (generally within about 100 to 1000 bp) that control transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, uniformly transcribe a gene to which they are operably linked, that is, with little or no control over gene expression.

A large number of promoters, recognized by a variety of potential host cells, are well known. A suitable promoter is operably linked to the DNA encoding heavy chain or light chain comprising a Jagged1 antigen binding protein by removing the promoter from the source DNA by restriction enzyme digestion and inserting the desired promoter sequence into the vector.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus, retroviruses, hepatitis-B virus, and Simian Virus 40 (SV40). Other suitable mammalian promoters include heterologous mammalian promoters, for example, heat-shock promoters and the actin promoter.

An enhancer sequence may be inserted into the vector to increase transcription of DNA encoding light chain or heavy chain comprising a Jagged1 antigen binding protein by higher eukaryotes. Enhancers are cis-acting elements of DNA, usually about 10-300 bp in length, that act on the promoter to increase transcription. Enhancers are relatively orientation and position independent, having been found at positions both 5' and 3' to the transcription unit. Several enhancer sequences available from mammalian genes are known (e.g., globin, elastase, albumin, alpha-feto-protein and insulin). Typically, however, an enhancer from a virus is used. The SV40 enhancer, the cytomegalovirus early promoter enhancer, the polyoma enhancer, and adenovirus enhancers known in the art are exemplary enhancing elements for the activation of eukaryotic promoters. While an enhancer may be positioned in the vector either 5' or 3' to a coding sequence, it is typically located at a site 5' from the promoter. A sequence encoding an appropriate native or heterologous signal sequence (leader sequence or signal peptide) can be incorporated into an expression vector, to promote extracellular secretion of the antibody. The choice of signal peptide or leader depends on the type of host cells in which the antibody is to be produced, and a heterologous signal sequence can replace the native signal sequence. Examples of signal peptides that are functional in mammalian host cells include the following: the signal sequence for interleukin-7 (IL-7) described in U.S. Pat. No. 4,965,195; the signal sequence for interleukin-2 receptor described in Cosman et al., 1984, Nature 312:768; the interleukin-4 receptor signal peptide described in EP Patent No. 0367 566; the type I interleukin-1 receptor signal peptide described in U.S. Pat. No. 4,968,607; the type II interleukin-1 receptor signal peptide described in EP Patent No. 0 460 846.

In one embodiment the leader sequence comprises SEQ ID NO: 355 (MDMRVPAQLL GLLLLWLRGA RC) which is encoded by SEQ ID NO: 356 (atggacatga gagtgcctgc acagctgctg ggcctgctgc tgctgtggct gagaggegee agatgc).

In another embodiment the leader sequence comprises SEQ ID NO: 357 (MAWALLLLTL LTQGTGSWA) which is encoded by SEQ ID NO: 358(atggcctggg ctctgctgct cctcaccctc ctcactcagg gcacagggtc ctgggcc).

The expression vectors that are provided may be constructed from a starting vector such as a commercially available vector. Such vectors may or may not contain all of the desired flanking sequences. Where one or more of the flanking sequences described herein are not already present in the vector, they may be individually obtained and ligated into the vector. Methods used for obtaining each of the flanking sequences are well known to one skilled in the art.

After the vector has been constructed and a nucleic acid molecule encoding light chain, a heavy chain, or a light chain and a heavy, chain comprising a Jagged1 antigen binding sequence has been inserted into the proper site of the vector, the completed vector may be inserted into a suitable host cell for amplification and/or polypeptide expression. The transformation of an expression vector for an antigen-binding protein into a selected host cell may be accomplished by well-known methods including transfection, infection, calcium phosphate co-precipitation, electroporation, microinjection, lipofection, DEAE-dextran mediated transfection, or other known techniques. The method selected will in part be a function of the type of host cell to be used. These methods and other suitable methods are well known to the skilled artisan, and are set forth, for example, in Sambrook et al., 2001, supra.

A host cell, when cultured under appropriate conditions, synthesizes an antigen binding protein that can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule.

Mammalian cell lines available as hosts for expression are well known in the art and include, but are not limited to, immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), and a number of other cell lines. In certain embodiments, cell lines may be selected through determining which cell lines have high expression levels and constitutively produce antigen binding proteins with Jagged1 binding properties. In another embodiment, a cell line from the B cell lineage that does not make its own antibody but has a capacity to make and secrete a heterologous antibody can be selected.

In one embodiment, the present invention is directed to an antigen binding protein produced by a cell expressing one or more of the polynucleotides identified in Tables 2, 3, and 4.

In one aspect, a Jagged1 binding protein is administered for chronic treatment. In another aspect, the binding proteins are administered for acute therapy.

Pharmaceutical compositions that comprise a Jagged1 antigen binding protein are also provided and can be utilized in any of the preventive and therapeutic methods disclosed herein. In an embodiment, a therapeutically effective amount of one or a plurality of the antigen binding proteins and a pharmaceutically acceptable diluent, carrier, solubilizer, emulsifier, preservative, and/or adjuvant are also provided. Acceptable formulation materials are nontoxic to recipients at the dosages and concentrations employed.

In certain embodiments, the pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. In such embodiments, suitable formulation materials include, but are not limited to, amino acids (such as glycine, glutamine, asparagine, arginine or lysine); anti-microbials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. REMINGTON'S PHARMACEUTICAL SCIENCES, 18" Edition, (A. R. Genrmo, ed.), 1990, Mack Publishing Company provides additional details and options for suitable agents that can be incorporated into the pharmaceutical compositions.

In certain embodiments, the optimal pharmaceutical composition will be determined by one skilled in the art depending upon, for example, the intended route of administration, delivery format and desired dosage. See, for example, REMINGTON'S PHARMACEUTICAL SCIENCES, supra. In certain embodiments, such compositions may influence the physical state, stability, rate of in vivo release and rate of in vivo clearance of the antigen binding proteins disclosed. In certain embodiments, the primary vehicle or carrier in a pharmaceutical composition may be either aqueous or non-aqueous in nature. For example, a suitable vehicle or carrier may be water for injection or physiological saline solution. In certain embodiments, Jagged1 antigen binding protein compositions may be prepared for storage by mixing the selected composition having the desired degree of purity with optional formulation agents (REMINGTON'S PHARMACEUTICAL SCIENCES, supra) in the form of a lyophilized cake or an aqueous solution. Further, in certain embodiments, the Jagged1 antigen binding protein may be formulated as a lyophilizate using appropriate excipients such as sucrose.

The pharmaceutical compositions can be selected for parenteral delivery. Alternatively, the compositions may be selected for inhalation or for delivery through the digestive tract, such as orally. Preparation of such pharmaceutically acceptable compositions is within the skill of the art.

The formulation components are present preferably in concentrations that are acceptable to the site of administration. In certain embodiments, buffers are used to maintain the composition at physiological pH or at a slightly lower pH, typically within a pH range of from about 5 to about 8.

When parenteral administration is contemplated, the therapeutic compositions may be provided in the form of a pyrogen-free, parenterally acceptable aqueous solution comprising the desired human Jagged1 antigen binding protein in a pharmaceutically acceptable vehicle. A particularly suitable vehicle for parenteral injection is sterile distilled water in which the Jagged1 antigen binding protein is formulated as a sterile, isotonic solution, properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that may provide controlled or sustained release of the product which can be delivered via depot injection. In certain embodiments, hyaluronic acid may also be used, having the effect of promoting sustained duration in the circulation. In certain embodiments, implantable drug delivery devices may be used to introduce the desired antigen binding protein.

Certain pharmaceutical compositions are formulated for inhalation. In some embodiments, Jagged1 antigen binding proteins are formulated as a dry, inhalable powder. In specific embodiments, Jagged1 antigen binding protein inhalation solutions may also be formulated with a propellant for aerosol delivery. In certain embodiments, solutions may be nebulized. Pulmonary administration and formulation methods therefore are further described in International Patent Application No. PCT/US94/001875, which is incorporated by reference and describes pulmonary delivery of chemically modified proteins. Some formulations can be administered orally. Jagged1 antigen binding proteins that are administered in this fashion can be formulated with or without carriers customarily used in the compounding of solid dosage forms such as tablets and capsules. In certain embodiments, a capsule may be designed to release the active portion of the formulation at the point in the gastrointestinal tract when bioavailability is maximized and pre-systemic degradation is minimized. Additional agents can be included to facilitate absorption of the Jagged1 antigen binding protein. Diluents, flavorings, low melting point waxes, vegetable oils, lubricants, suspending agents, tablet disintegrating agents, and binders may also be employed.

Some pharmaceutical compositions comprise an effective quantity of one or a plurality of Jagged1 antigen binding proteins in a mixture with non-toxic excipients that are suitable for the manufacture of tablets. By dissolving the tablets in sterile water, or another appropriate vehicle, solutions may be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving Jagged1 binding proteins in sustained- or controlled-delivery formulations. Techniques for formulating a variety of other sustained- or controlled-delivery means, such as liposome carriers, bio-erodible microparticles or porous beads and depot injections, are also known to those skilled in the art. See, for example, International Patent Application No. PCT/US93/00829, which is incorporated by reference and describes controlled release of porous polymeric microparticles for delivery of pharmaceutical compositions. Sustained-release preparations may include semipermeable polymer matrices in the form of shaped articles, e.g., films, or microcapsules. Sustained release matrices may include polyesters, hydrogels, polylactides (as disclosed in U.S. Pat. No. 3,773,919 and European Patent Application Publication No. EP 058481, each of which is incorporated by reference), copolymers of L-glutamic acid and gamma ethyl-L-glutamate (Sidman et al., 1983, Biopolymers 2:547-556), poly (2-hydroxyethyl-inethacrylate) (Langer et al., 1981, *J. Biomed. Mater. Res.* 15:167-277 and Langer, 1982, *Chem. Tech.* 12:98-105), ethylene vinyl acetate (Langer et al., 1981, supra) or poly-D(–)-3-hydroxybutyric acid (European Patent Application Publication No. EP 133,988). Sustained release compositions may also include liposomes that can be prepared by any of several methods known in the art. See, e.g., Eppstein et al., 1985, *Proc. Natl. Acad. Sci. U.S.A.* 82:3688-3692; European Patent Application Publication Nos. EP 036,676; EP 088,046 and EP 143,949, incorporated by reference.

Pharmaceutical compositions used for in vivo administration are typically provided as sterile preparations. Sterilization can be accomplished by filtration through sterile filtration membranes. When the composition is lyophilized, sterilization using this method may be conducted either prior to or following lyophilization and reconstitution. Compositions for parenteral administration can be stored in lyophilized form or in a solution. Parenteral compositions generally are placed into a container having a sterile access port, for example, an intravenous solution bag or vial having a stopper pierceable by a hypodermic injection needle.

In certain formulations, an antigen binding protein has a concentration of at least 10 mg/mL, 20 mg/mL, 30 mg/mL, 40 mg/mL, 50 mg/mL, 60 mg/mL, 70 mg/mL, 80 mg/mL, 90 mg/mL, 100 mg/mL or 150 mg/mL. In one embodiment, a pharmaceutical composition comprises the antigen binding protein, a buffer and polysorbate. In other embodiments, the pharmaceutical composition comprises an antigen binding protein, a buffer, sucrose and polysorbate. An example of a pharmaceutical composition is one containing 50-100 mg/mL of antigen binding protein, 5-20 mM sodium acetate, 5-10% w/v sucrose, and 0.002-0.008% w/v polysorbate. Certain, compositions, for instance, contain 65-75 mg/mL of an antigen binding protein in 9-11 mM sodium acetate buffer, 8-10% w/v sucrose, and 0.005-0.006% w/v polysorbate. The pH of certain such formulations is in the range of 4.5-6. Other formulations have a pH of 5.0-5.5 (e.g., pH of 5.0, 5.2 or 5.4).

Once the pharmaceutical composition has been formulated, it may be stored in sterile vials as a solution, suspension, gel, emulsion, solid, crystal, or as a dehydrated or lyophilized powder. Such formulations may be stored either in a ready-to-use form or in a form (e.g., lyophilized) that is reconstituted prior to administration. Kits for producing a single-dose administration unit are also provided. Certain kits contain a first container having a dried protein and a second container having an aqueous formulation. In certain embodiments, kits containing single and multi-chambered pre-filled syringes (e.g., liquid syringes and lyosyringes) are provided. The therapeutically effective amount of a Jagged1 antigen binding protein-containing pharmaceutical composition to be employed will depend, for example, upon the therapeutic context and objectives. One skilled in the art will appreciate that the appropriate dosage levels for treatment will vary depending, in part, upon the molecule delivered, the indication for which the Jagged1 antigen binding protein is being used, the route of administration, and the size (body weight, body surface or organ size) and/or condition (the age and general health) of the patient. In certain embodiments, the clinician may titer the dosage and modify the route of administration to obtain the optimal therapeutic effect.

Dosing frequency will depend upon the pharmacokinetic parameters of the particular Jagged1 antigen binding protein in the formulation used. Typically, a clinician administers the composition until a dosage is reached that achieves the desired effect. The composition may therefore be administered as a single dose, or as two or more doses (which may or may not contain the same amount of the desired molecule) over time, or as a continuous infusion via an implantation device or catheter. Appropriate dosages may be ascertained through use of appropriate dose-response data. In certain embodiments, the antigen binding proteins can be administered to patients throughout an extended time period. In certain embodiments, the antigen binding protein is dosed every two weeks, every month, every two months, every three months, every four months, every five months, or every six months.

The route of administration of the pharmaceutical composition is in accord with known methods, e.g., orally, through injection by intravenous, intraperitoneal, intracerebral (intra-parenchymal), intracerebroventricular, intramuscular, intra-ocular, intraarterial, intraportal, or intralesional routes; by sustained release systems or by implantation devices. In certain embodiments, the compositions may be administered by bolus injection or continuously by infusion, or by implantation device.

The composition also may be administered locally via implantation of a membrane, sponge or another appropriate material onto which the desired molecule has been absorbed or encapsulated. In certain embodiments, where an implantation device is used, the device may be implanted into any suitable tissue or organ, and delivery of the desired molecule may be via diffusion, timed-release bolus, or continuous administration.

It also may be desirable to use Jagged1 antigen binding protein pharmaceutical compositions according to the disclosed ex vivo. In such instances, cells, tissues or organs that have been removed from the patient are exposed to Jagged1 antigen binding protein pharmaceutical compositions after which the cells, tissues and/or organs are subsequently implanted back into the patient.

A physician will be able to select an appropriate treatment indication and target lipid levels depending on the individual profile of a particular patient. One well-accepted standard for guiding treatment of hyperlipidemia is the Third Report of the National Cholesterol Education Program (NCEP) Expert Panel on Detection, Evaluation, and Treatment of the High Blood Cholesterol in Adults (Adult Treatment Panel III) Final Report, National Institutes of Health, NIH Publication No. 02-5215 (2002), the printed publication of which is hereby incorporated by reference in its entirety.

The efficacy of a particular dose can be assessed by reference to biomarkers or improvement in certain physiological parameters. Examples of suitable biomarkers include, the ratio of free cholesterol to plasma lipid, free cholesterol to membrane protein, phospatidylcholine to sphingomyelin, or HDL-C levels.

Also provided herein are compositions comprising a Jagged1 antigen binding protein and one or more additional therapeutic agents, as well as methods in which such agents are administered concurrently or sequentially with a Jagged1 antigen binding protein for use in the preventive and therapeutic methods disclosed herein. The one or more additional agents can be co-formulated with a Jagged1 antigen binding protein or can be co-administered with a Jagged1 antigen binding protein. In general, the therapeutic methods, compositions and compounds may also be employed in combination with other therapeutics in the treatment of various disease states, with the additional agents being administered concurrently.

The Jagged1 antigen binding proteins that are provided herein are useful for detecting Jagged1 in biological samples. For instance, the Jagged1 antigen binding proteins can be used in diagnostic assays, e.g., binding assays to detect and/or quantify Jagged1 expressed in serum.

The antigen binding proteins of the described can be used for diagnostic purposes to detect, diagnose, or monitor diseases and/or conditions associated with Jagged1. The disclosed antigen binding proteins provide a means for the detection of the presence of Jagged1 in a sample using classical immunohistological methods known to those of skill in the art (e.g., Tijssen, 1993, *Practice and Theory of Enzyme Immunoassays*, Vol 15 (Eds R. H. Burdon and P. H. van Knippenberg, Elsevier, Amsterdam); Zola, 1987, *Monoclonal Antibodies: A Manual of Techniques*, pp. 147-158 (CRC Press, Inc.); Jalkanen et al., 1985, *J. Cell. Biol.* 101:976-985; Jalkanen et al., 1987, *J. Cell Biol.* 105:3087-3096). The detection of Jagged1 can be performed in vivo or in vitro.

Diagnostic applications provided herein include use of the antigen binding proteins to detect expression of Jagged1. Examples of methods useful in the detection of the presence of Jagged1 include immunoassays, such as the enzyme linked immunosorbent assay (ELISA) and the radioimmunoassay (RIA).

For diagnostic applications, the antigen binding protein typically will be labeled with a detectable labeling group. Suitable labeling groups include, but are not limited to, the following: radioisotopes or radionuclides (e.g., $^3$H, $^{14}$C, $^{15}$N, $^{35}$S, $^{90}$Y, $^{99}$Tc, $^{111}$In, $^{125}$I, $^{131}$I), fluorescent groups (e.g., FITC, rhodamine, lanthanide phosphors), enzymatic groups (e.g., horseradish peroxidase, β-galactosidase, luciferase, alkaline phosphatase), chemiluminescent groups, biotinyl groups, or predetermined polypeptide epitopes recognized by a secondary reporter (e.g., leucine zipper pair sequences, binding sites for secondary antibodies, metal binding domains, epitope tags). In some embodiments, the labeling group is coupled to the antigen binding protein via spacer arms of various lengths to reduce potential steric hindrance. Various methods for labeling proteins are known in the art and may be used.

In some embodiments, the Jagged1 antigen binding protein is isolated and measured using techniques known in the art. See, for example, Harlow and Lane, 1988, *Antibodies: A Laboratory Manual*, New York: Cold Spring Harbor (ed. 1991 and periodic supplements); John E. Coligan, ed., 1993, *Current Protocols In Immunology* New York: John Wiley & Sons.

Another aspect of the disclosed provides for detecting the presence of a test molecule that competes for binding to Jagged1 with the antigen binding proteins provided. An example of one such assay would involve detecting the amount of free antigen binding protein in a solution containing an amount of Jagged1 in the presence or absence of the test molecule. An increase in the amount of free antigen binding protein (i.e., the antigen binding protein not bound to Jagged1) would indicate that the test molecule is capable of competing for Jagged1 binding with the antigen binding protein. In one embodiment, the antigen binding protein is labeled with a labeling group. Alternatively, the test molecule is labeled and the amount of free test molecule is monitored in the presence and absence of an antigen binding protein.

Jagged1 binding proteins can be used to treat, diagnose or ameliorate, a condition associated with lung disease. In various embodiments, the lung disease may be lung cancer, a respiratory tract or lung infection, a disease of the interstitium, a disorder of gas exchange or blood circulation, a disease of the airways or a disorder of the pleura. As used herein, a "lung cancer" refers to either a primary lung tumor (for example, bronchogenic carcinoma or bronchial carcinoid) or a metastasis from a primary tumor of another organ or tissue (for example, breast, colon, prostate, kidney, thyroid, stomach, cervix, rectum, testis, bone, or melanoma). As used herein, a "respiratory tract or lung infection" refers to any bacterial, viral, fungal, or parasite infection of any part of the respiratory system. As used herein, a "disease of the interstitium" includes any disorder of the interstitium including fibrosis (for example, interstitial pulmonary fibrosis, interstitial pneumonia, interstitial lung disease, Langerhans' cell granulomatosis, sarcoidosis, or idiopathic pulmonary hemosiderosis). As used herein, a "disorder of gas exchange or blood circulation", refers to any abnormality affecting the distribution and/or exchange of gases to/from the blood and lungs (for example, pulmonary edema, pulmonary embolism, respiratory failure (e.g., due to weak muscles), acute respiratory distress syndrome, or pulmonary hypertension). As used herein, a "disease of the airway" includes any disorder of regular breathing patterns, including disorders of genetic and environmental etiologies (for example, asthma, chronic bronchitis, bronchiolitis, cystic fibrosis, bronchiectasis, emphysema, chronic obstructive pulmonary disease, diffuse panbronchiolitis, or lymphangiomyonatosis). As used herein, a "disorder of the pleura" includes, for example, pleural effusion (e.g., hemothorax (blood into the pleural space), or emphysema (pus into the pleural space), pneumothorax (air, e.g., traumatic, spontaneous, or tension), pleurisy or pleural fibrosis or calcification.

In application, a condition associated with lung disease, can be treated by administering a therapeutically effective dose of a Jagged1 binding protein to a patient in need thereof. The administration can be performed as described herein, such as by IV injection, intraperitoneal (IP) injection, subcutaneous injection, intramuscular injection, nebulization, or orally in the form of a tablet or liquid formation. In some situations, a therapeutically effective or preferred dose of a Jagged1 binding protein can be determined by a clinician. A therapeutically effective dose of Jagged1 binding protein will depend, inter alia, upon the administration schedule, the unit dose of agent administered, whether the Jagged1 binding protein is administered in combination with other therapeutic agents, the immune status and the health of the recipient. The term "therapeutically effective dose," as used herein, means an amount of Jagged1 binding protein that elicits a biological or medicinal response in a tissue system, animal, or human being sought by a researcher, medical doctor, or other clinician, which includes alleviation or amelioration of the symptoms of the disease or disorder being treated.

It is noted that a pharmaceutical composition comprising a Jagged1 binding protein can be co-administered with another compound. The identity and properties of compound co-administered with the Jagged1 binding protein will depend on the nature of the condition to be treated or ameliorated.

Also provided are kits for practicing the disclosed methods. Such kits can comprise a pharmaceutical composition such as those described herein, including nucleic acids encoding the peptides or proteins provided herein, vectors and cells comprising such nucleic acids, and pharmaceutical compositions comprising such nucleic acid-containing compounds, which can be provided in a sterile container. Optionally, instructions on how to employ the provided pharmaceutical composition in the treatment of a metabolic disorder can also be included or be made available to a patient or a medical service provider.

In one aspect, a kit comprises (a) a pharmaceutical composition comprising a therapeutically effective amount of a Jagged1 binding protein; and (b) one or more containers for the pharmaceutical composition. Such a kit can also comprise instructions for the use thereof; the instructions can be tailored to the precise metabolic disorder being treated. The instructions can describe the use and nature of the materials provided in the kits Instructions can be printed on a substrate, such as paper or plastic, etc., and can be present in the kits as a package insert, in the labeling of the container of the kit or components thereof (e.g., associated with the packaging), etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, such as over the internet, are provided. An example of this embodiment is a kit that includes a web address where the instructions can be viewed and/or from which the instructions can be downloaded.

Often it will be desirable that some or all components of a kit are packaged in suitable packaging to maintain sterility. The components of a kit can be packaged in a kit containment element to make a single, easily handled unit, where the kit containment element, e.g., box or analogous structure, may or may not be an airtight container, e.g., to further preserve the sterility of some or all of the components of the kit.

EXAMPLES

Example 1: Immunization

Fully human antibodies to Jagged-1 were generated using XenoMouse technology, transgenic mice engineered to express diverse repertoires of fully human IgGK and IgGλ antibodies of the corresponding isotype (Mendez, M. J., Green, L. L., Corvalan, J. R., Jia, X. C., Maynard-Currie, C. E., Yang, X. D., Gallo, M. L., Louie, D. M., Lee, D. V., Erickson, K. L., Luna, J., Roy, C. M., Abderrahim, H., Kirschenbaum, F., Noguchi, M., Smith, D. H., Fukushima, A., Hales, J. F., Klapholz, S., Finer, M. H., Davis, C. G., Zsebo, K. M., and Jakobovits, A. (1997) Nature genetics 15, 146-156; Kellermann, S. A., and Green, L. L. (2002) *Current opinion in biotechnology* 13, 593-597). XMG2-KL and XMG4-KL strains of mice were immunized with two forms of Jagged-1 immunogen; 293T transfectants expressing full length human Jagged-1 and CHO transfectants expressing full length human Jagged-1. Cellular immunogens were dosed at $4.0 \times 10^6$ Jagged-1 transfected cells/mouse and subsequent boosts were of $2.0 \times 10^6$ Jagged-1 transfected cells/mouse. Injection sites used were combinations of subcutaneous base-of-tail and intraperitoneal. Adjuvant used was Alum (E. M. Sergent Pulp and Chemical Co., Clifton, N.J., cat. #1452-250) that was prepared according to manufacturers' instructions and mixed with antigen solution. Mice were immunized over a period of 8 weeks to 12 weeks.

Sera were collected at approximately 5 weeks after the first injection and specific titers were determined by FACs staining of recombinant BCMA receptor transiently expressed on CHO-S cells. The specific immune responses achieved using the CHO cell immunogen groups were determined to be superior. Two groups of immune animals were identified and used for two screening campaigns; the first group of animals including 5 XMG2-KL and 3 XMG2-KLs immunized with CHO cells transiently expressing Jagged-1 were pooled and advanced to antibody generation. The second group was 7 XMG4-KL animals immunized with CHO cells transiently expressing Jagged-1 were pooled and advanced to antibody generation.

Example 2: Preparation of Monoclonal Antibodies

Draining lymph nodes and spleens were harvested from immune animals and pooled for each cohort. Lymphocytes and splenocytes were dissociated from tissue in suitable medium RPMI (Invitrogen, Carlsbad, Calif.) to release the cells from the tissues, and suspended in RPMI. B cells were selected and/or expanded using a suitable method, and fused with suitable fusion partner, for example, non-secretory myeloma P3X63Ag8.653 cells (American Type Culture Collection CRL 1580; Kearney et al, J. Immunol. 123, 1979, 1548-1550).

B cells were mixed with fusion partner cells at a ratio of 1:4. The cell mixture was gently pelleted by centrifugation at 400×g for 4 minutes, the supernatant decanted, and the cell mixture gently mixed by using a 1 ml pipette. Fusion was induced with PEG/DMSO (polyethylene glycol/dimethyl sulfoxide; obtained from Sigma-Aldrich, St. Louis Mo.; 1 ml per 10 million of lymphocytes). PEG/DMSO was slowly added with gentle agitation over one minute followed, by one minute of mixing. IDMEM (DMEM without glutamine; 2 ml per 10 million of B cells), was then added over 2 minutes with gentle agitation, followed by additional IDMEM (8 ml per 10 million B-cells) which was added over 3 minutes.

The fused cells were gently pelleted (400×g 5 6 minutes) and resuspended in 20 ml Selection media (for example, DMEM containing Azaserine and Hypoxanthine [HA] and other supplemental materials as necessary) per 20 million B-cells. Cells were incubated for 20-30 minutes at 37° C. and then resuspended in 200 ml Selection media per 20 million B-cells and cultured for three to four days in T175 flasks prior to 96-well plating.

Cells were distributed into 96-well plates using standard techniques to maximize clonality of the resulting colonies. After several days of culture, the hybridoma supernatants were collected and subjected to screening assays as detailed in the examples below, including confirmation of binding to human Jagged-1 receptor, identification of Notch Ligand blocking antibodies by a ligand binding competition assay and evaluation of cross-reactivity with other receptors related to Jagged-1 receptor (for example, human Jagged-2 and human DLL-4 receptors). Hybridoma lines that were identified to have the binding properties for interest were then further selected with functional screens and subjected to standard cloning and subcloning techniques. Clonal lines were expanded in vitro, and the secreted human antibodies obtained for analysis and V gene sequencing was performed.

Example 3: Selection of Jagged-1 Receptor Specific Binding Antibodies by FMAT

After 14 days of culture, hybridoma supernatants were screened for human Jagged-1 specific monoclonal antibodies by Fluorometric Microvolume Assay Technology (FMAT) (Applied Biosystems, Foster City, Calif.). The supernatants were screened against 293T cells transiently transfected with human Jagged-1 and counter screened against 293T cells transiently transfected with the same expression plasmid that did not contain the Jagged-1 gene. Briefly, the cells in Freestyle media (Invitrogen, Carlsbad, Calif.) were seeded into 384-well FMAT plates in a volume of 50 µL/well at a density of approximately 4000 cells/well for the stable transfectants, and at a density of approximately 16,000 cells/well for the parental cells, and cells were incubated overnight at 37° C. Then, 10 µL/well of supernatant was added and plates were incubated for approximately one hour at 4° C., after which 10 µL/well of anti-human IgG-Cy5 secondary antibody (Jackson Immunoresearch, West Grove, Pa.) was added at a concentration of 2.8 µg/ml (400 ng/ml final concentration). Plates were then incubated for one hour at 4° C., and fluorescence was read using an FMAT plate reader (Applied Biosystems, Foster City, Calif.).

After two screening campaigns a panel of 495 (335 campaign #1, 160 campaign #2) anti-Jagged-1 binding hybridoma lines were identified and advanced to further characterization assays.

Example 4: Identification of Blocking Antibodies by Ligand Binding Competition Assay by FMAT A ligand binding competition method was developed to identify antibodies (in the hybridoma supernatants) that bind Jagged-1 receptor and block Notch-3 ligand binding. Briefly, the cells in Freestyle media (Invitrogen, Carlsbad, Calif.) were seeded into 384-well FMAT plates in a volume of 50 µL/well at a density of approximately 3000 cells/well for the stable transfectants, and at a density of approximately 15,000 cells/well for the parental cells, and pulse centrifuged. Then, 20 µL/well of supernatant was added and plates were incubated for approximately one hour at 4° C., after which 10 µL/well of human Notch-3/ALEXA647 (600 ng/ml final concentration). Plates were then incubated for three hours at 4° C., and fluorescence was read using an FMAT plate reader (Applied Biosystems, Foster City, Calif.).

The experiments included negative control hybridoma supernatants. The average signal observed in these negative control experiments was adopted as the maximum possible signal for the assay. Experimental supernatants were compared to this maximum signal and a percent inhibition was calculated for each well (% Inhibition=(1−(FL1 of the anti-BCMA hybridoma supernatant/Maximum FL1 signal).

For screening campaign #1, two replicates of the assay were completed and resulted in 49 antibodies of interest based on an activity of greater than 60% inhibition in at least one of the two replicates. These 49 hybridoma supernatants plus 10 non-blocking supernatants were carried forward to additional testing. For screening campaign #2, two replicates of the assay resulted in 4 hybridoma supernatants identified with greater than 60% inhibition, these were carried forward to additional characterization.

Example 5: Identification of Blocking Antibodies by Ligand Binding Competition Assay by FACs A ligand binding competition method was developed to identify antibodies (in the hybridoma supernatants) that bind Jagged-1 receptor and block binding of three ligands; Notch-3, Notch 2 and Notch-1. FACs assays were performed by incubating 20 ul of hybridoma supernatants with 50,000 cells transiently expressing at 4° C. for one hour followed by two washes with PBS/BSA. Cells were then treated with 5 ug/ml florochrome-labeled Notch-3 (#1559-NT, RnD Systems) ligand at 4° C. followed by two washes. The cells were resuspended in 1 ml PBS/BSA and antibody binding was analyzed using a FACSCalibur™ instrument. Similar assays were performed using Notch-2 (#3735-NT, RnD Systems) and Notch-1 (#3647-TK, RnD Systems).

The experiments included negative control hybridoma supernatants. The average signal observed in these negative control experiments was adopted as the maximum possible signal for the assay. Experimental supernatants were compared to this maximum signal and a percent inhibition was calculated for each well (% Inhibition=(1−(FL1 of the anti-BCMA hybridoma supernatant/Maximum FL1 signal)).

Example 6: Additional Binding Characterization by Flow Cytometry (FACs)

FACS binding assays were performed to evaluate the binding of the anti-Jagged-1 receptor specific antibodies to the murine Jagged-1 orthologue as well as related receptors human Jagged-2 and Human DLL-4. FACs assays were performed by incubating hybridoma supernatants with 50,000 cells at 4° C. for one hour followed by two washes with PBS/BSA. Cells were then treated with florochrome-labeled secondary antibodies at 4° C. followed by two washes. The cells were resuspended in 1 ml PBS/BSA and antibody binding was analyzed using a FACSCalibur™ instrument.

Example 7: Identification of Function Antagonists by Cellular Bioassay

Normal human bronchial epithelial cells and culture media were purchased from Lonza. Air liquid interface cultures using passage 2 cells were performed as per manufacturer instructions using the Lonza B-ALI protocol. Three weeks post airlift, cultures were treated with or without IL-13 (20 ng/ml) in combination with; IgG1 (10 ug/ml); anti-Jag-1 (15D11.1) (10 ug/ml or 1 ug/ml) for 7 days (added basolaterally to media). Fresh media (with or without treatment) was changed every other day. At 7 days, cultures were fixed in 4% PFA for 48 hrs@RT and then transferred to 70% EtOH and stored at 4C until processed for PAS/AB staining. See FIG. 1 and FIG. 2.

Example 8: PAS/AB Staining Methods and Quantification Method

Periodic Acid-Schiff/Alcian Blue staining in Air Liquid Interface Cultures:

Air Liquid Interface (ALI) bronchial epithelial cell cultures derived from NHBE donors were fixed in 4% paraformaldehyde for 48 hours at room temperature (RT) and embedded in paraffin. Four micron thick sections were stained for mucin/goblet cells with Alcian Blue/Periodic Acid-Schiff (AB/PAS) special stain.

Briefly, after de-paraffinization, sections were treated with acetic acid solution for 3 minutes at RT followed by Alcian Blue (pH2.5, Abcam, Cambridge Mass.; Cat #ab150662) staining for 30 minutes at RT. After rinsing in tap water for 2 minutes followed by rinsing in 2 changes of distilled water, sections were treated with 1% periodic acid solution (Sigma, St Louis, Mo.; Cat #3951) for 10 minutes at RT. Sections were rinsed once again in 2 changes of distilled water and subsequently stained with Schiff's Solution (American Master Tech, Lodi, Ca; Cat #STSSCHLT) for 10 minutes at RT. Sections were then rinsed in hot running tap water followed by distilled water and then counterstained in Modified Mayer's Hematoxylin (American Master Tech, Lodi Calif.; Cat #HSMMHLT) for 15 seconds. Sections were subsequently blued with TBS buffer, rinsed in distilled water, dehydrated in alcohols, cleared in Xylenes and then mounted with a coverslip using Tissue-Tek® Glas™ mounting media (Sakura, Torrance, Calif.; Cat #6419).

Periodic Acid-Schiff Staining in Murine Lungs:

Murine lungs were fixed in 10% Neutral Buffered Formalin for 24 hours at room temperature (RT) and embedded in paraffin. Five micron thick sections were stained for mucin/goblet cells with Periodic Acid-Schiff (PAS) special stain. Briefly, after de-paraffinization, sections were treated with freshly made 0.5% Periodic Acid for 7 minutes at RT. After rinsing in distilled water sections were immersed in Schiff's Solution (American Master Tech, Lodi, Ca; Cat #STSSCHLT) for 15 minutes at RT. Sections were then rinsed in warm running tap water for 5 minutes and subsequently counterstained with SelecTech Hematoxylin 560 (Leica Biosystems; Buffalo Grove, Ill.; Cat #3801575) for 3 minutes at RT. Sections were then treated with SelecTech Define (Leica Biosystems, Cat #3803590) and blued with Blue Buffer (Lieca Biosystems, Cat #3802915). Sections were then rinsed in distilled water, dehydrated in alcohols, cleared in Xylenes and then mounted with a coverslip using Tissue-Tek® Glas™ mounting media (Sakura, Torrance, Calif.; Cat #6419).

Quantification of Mucin Volumes and Goblet Cell Numbers in ALI Cultures

Figure 22:
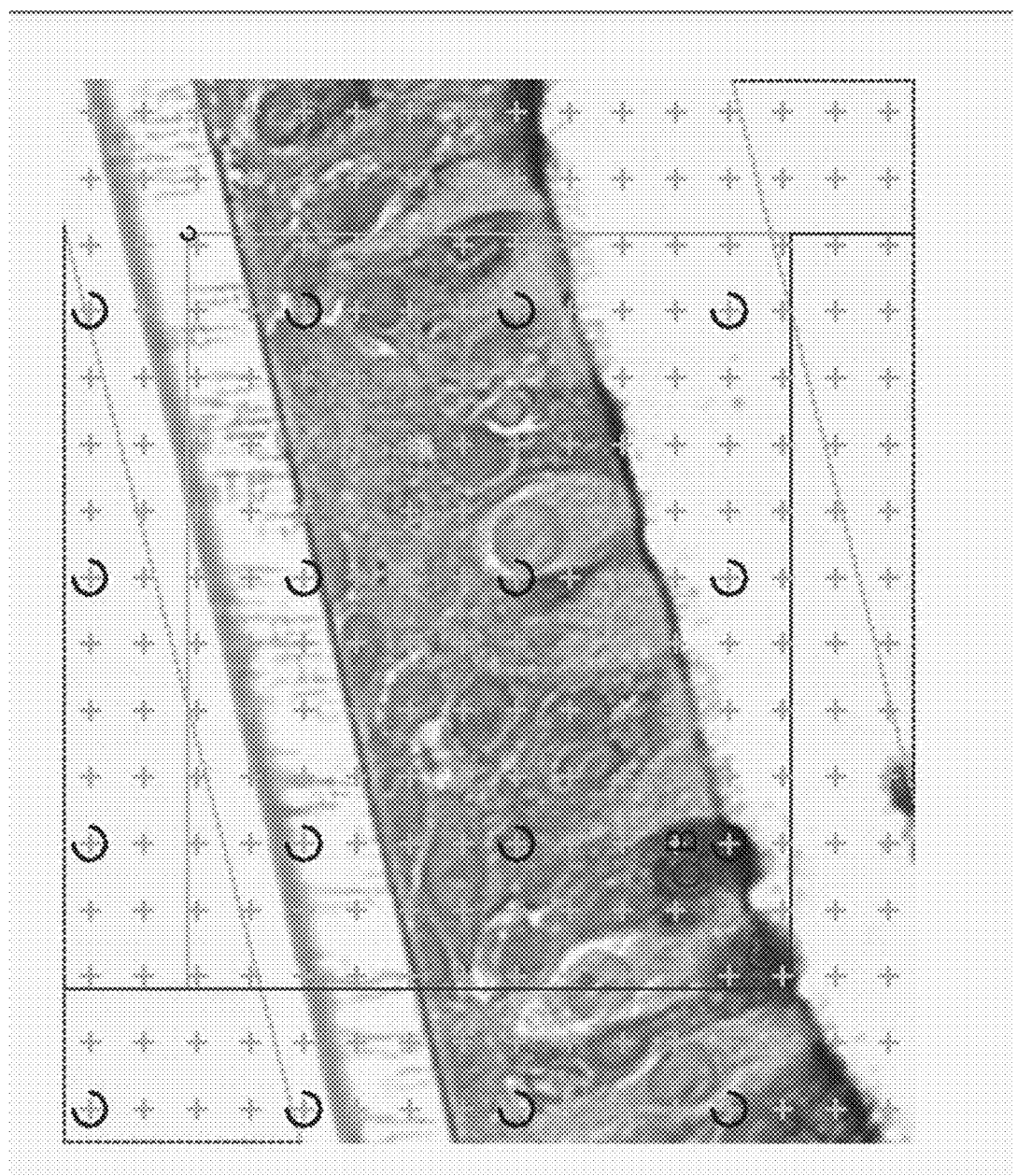
FIG. 22 shows four micron thick paraffin sections of Air Liquid Interface (ALI) bronchial epithelial cell cultures that have been stained for mucin/goblet cells using Alcian Blue/Periodic Acid-Schiff special stain were quantified for percent of mucin present as well as number of goblet cells present in the epithelium.

Four micron thick paraffin sections of Air Liquid Interface (ALI) bronchial epithelial cell cultures that have been stained for mucin/goblet cells using Alcian Blue/Periodic Acid-Schiff special stain were quantified for percent of mucin present as well as number of goblet cells present in the epithelium. Utilizing the Visiopharm Integrative Sofware package (Hoersholm, Denmark), the entire section of the ALI culture was delineated and randomly sampled for mucin content and goblet cell numbers in the epithelium by placing a point grid over each field of view at 100× magnification and counting the number of points that land on the total epithelium versus the number of points that land on the mucin stained by the AB/PAS special stain (See FIG. 22).

Approximately 75% of the total area of the section was uniformly randomly sampled in this manner, with the label A indicating all the points that hit the epithelium, B all the points that hit the mucin/goblet cell, and C which indicates a point count for each goblet cell (not all possible counts shown). After all counts are tabulated and added up, the following two calculations are performed using the calculator tool in the software:

Volume of mucin/volume of epi (percentage of mucin stores present in the epithelium):

$$V_v = P_{sub}/P_{ref}$$

Where:

$P_{sub}$=the total number of counts of mucin
$P_{ref}$=the total number of counts of total epithelium
The volume of total mucin is expressed as a percentage of mucin present in the total epithelium.

Number of goblet cells/volume of epithelium:

$$N_{goblet\ cells}/V_{epi} = \Sigma Q^-/BA \times (a/p) \times \Sigma P$$

Figure 23:
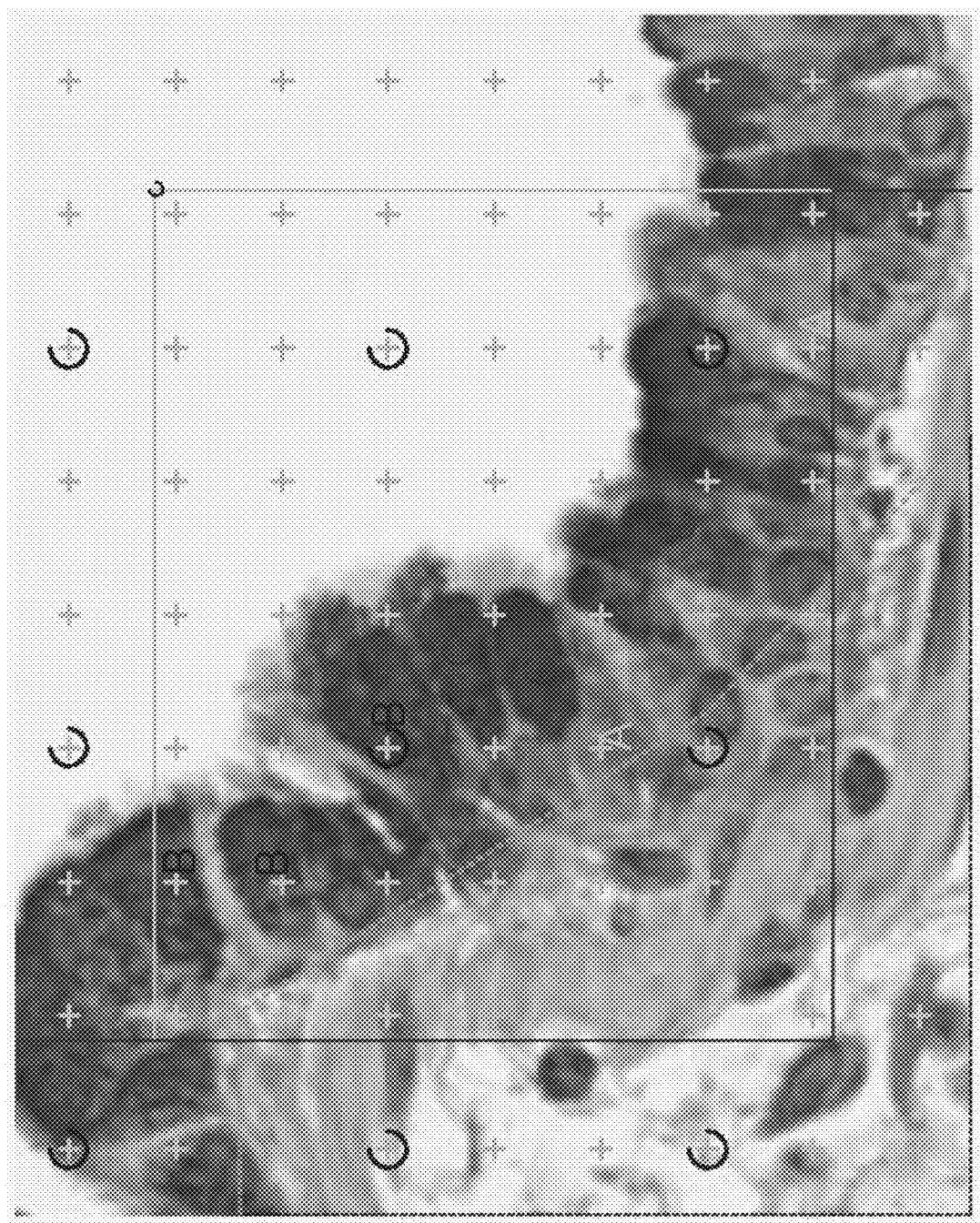
FIG. 23 shows five micron thick paraffin sections of murine lungs that have been stained for mucin/goblet cells using Periodic Acid-Schiff special stain were quantified for percent of mucin present as well as number of goblet cells present in the epithelium.

Where:

$\Sigma Q^-$=the number of goblet cells counted
BA=thickness of section
a/p=area per point
$\Sigma P$=number of area points counted
The number of goblet cells in the epithelium is expressed as the number of goblet cells per volume of epithelium in $mm^3$, or $N_{goblet\ cells}/mm^3$ of epi Quantification of Mucin Volumes and Goblet Cell Numbers in Murine Airways Five micron thick paraffin sections of murine lungs that have been stained for mucin/goblet cells using Periodic Acid-Schiff special stain were quantified for percent of mucin present as well as number of goblet cells present in the epithelium. Utilizing the Visiopharm Integrative Sofware package (Hoersholm, Denmark), the murine airways of interest were delineated and randomly sampled for mucin content and goblet cell numbers in the epithelium by placing a point grid over each field of view at 100× magnification and counting the number of points that land on the total epithelium versus the number of points that land on the mucin stained by the AB/PAS special stain (See FIG. 23).

Approximately 75% of the total area of the region of interest, i.e. the murine epithelium, was uniformly randomly sampled in this manner, with the label A indicating all the points that hit the epithelium, B all the points that hit the mucin/goblet cell, and C which indicates a point count for each goblet cell (not all possible counts shown). After all counts are tabulated and added up, the following two calculations are performed using the calculator tool in the software:

Percentage of mucin/area of epi (percentage of mucin stores present in the epithelium):

$$V_v = P_{sub}/P_{ref}$$

Where:
$P_{sub}$=the total number of counts of mucin
$P_{ref}$=the total number of counts of total epithelium
The volume of total mucin is expressed as a percentage of mucin present in the total murine airway epithelium.

Number of goblet cells/area of epithelium:

$$N_{goblet\ cells}/\text{Area}_{epi} = \Sigma Q^-/(a/p) \times \Sigma P$$

Where:
$\Sigma Q^-$=the number of goblet cells counted
a/p=area per point
$\Sigma P$=number of area points counted The number of goblet cells in the epithelium is expressed as the number of goblet cells per area of epithelium in $mm^2$, or $N_{goblet\ cells/mm^2}$ of epi Normal human bronchial epithelial cells and culture media were purchased from Lonza. 3D bronchosphere cultures using passage 2 cells were performed as described previously (ref Danahay et al). One week after plating, cultures were treated with or without IL-13 (1 ng/ml or 3.3 ng/ml) in combination with; IgG1 (10 ug/ml); anti-Jag-1 (15D11.1) (10 ug/ml or 1 ug/ml) for an additional 7 days. Fresh media (with or without treatment) was changed every other day and supplemented with fresh cytokine and treatment. At 7 days, bronchospheres were harvested from matrigel using the Cultrex 3D Culture Cell Harvesting Kit from Trevigen (Cat #3448-020-K) with a slightly modified manufacturers protocol. RNA was isolated using RNAeasy Kit from Qiagen (cat #74181) as per manufacturers protocol and qPCR was performed for MUC5AC (*see below); MUC5B (*see below) and FOXA3 (Hs00270130-m1). See FIG. 3. HPRT (*see below) was used as the housekeeping gene and gene expression is expressed relative to HPR Prophylactic Inhibition of Goblet Cell Metaplasia by Jag1 Neutralizing Ab in Ovalbumin Induced Asthma Model and Tissue Toxicology Assessment.

Mouse allergen induced pulmonary inflammation and airway remodeling (goblet cell metaplasia) were measured in the ovalbumin induced mouse model of asthma. Seven groups of eight mice (56 total mice) were used in this study. Adult female Balb/c mice (greater than 8 weeks of age) were sensitized and boosted by intraperitoneal (i.p.) injection of 0.2 ml of 2% aluminum hydroxide (ALUM) gel (Serva Electrophoretics, 12261, Heidelberg, Germany) with or without 10 µg of ovalbumin (OVA) antigen (Worthington Biochemical Corporation, LS003054, Lakewood, N.J.) on days 0 and 14. Groups A, B, and C, were sensitized and boosted with 0.2 ml i.p. injections of a solution of one ml of 0.9% saline in 50 ml of ALUM gel. Groups D, E, F, and G, were sensitized and boosted with 0.2 ml i.p. injections of a solution of 2.55 mg OVA dissolved in one ml of 0.9% saline in 50 ml of ALUM gel. Groups D, E, F, and G inhaled nebulized OVA to evoke antigen-induced lung inflammation and goblet cell metaplasia in the lungs. For nebulized OVA challenge, mice were placed in a plexiglass box and aerosolized OVA was nebulized into the box by a nebulizer (PARI Respiratory Equipment, LC STAR nebulizer and Proneb Ultra II compressor, Midlothian, VA) filled with 1% ovalbumin in saline (0.01 g/ml) for 20 minutes on days 21, 22, and 23. On day 26, a 20 minute nebulized OVA challenge with 5% ovalbumin in saline was conducted. Group A, B, and C inhaled nebulized saline with no OVA. Groups A and D were dosed with vehicle (A52SuT: 20 mM Sodium Acetate, 5% Sucrose, 0.04% Tween 20, adjusted to pH 5.2 with acetic acid), groups B and E were dosed with hu anti-<hu Jag-1> 15D11.1 Mab (80 mg/kg), group G was dosed with rat anti-<muTSLP> IgG2a (mTSLP-M702, 20 mg/kg)), and groups C and F were dosed with 655-341-G1 human IgG1 control antibody (80 mg/kg). All groups were dosed i.v. by the tail vein with a volume of 10 ml/kg on days 0, 7, 14, and 20. See FIG. 4. On day 27, the mice were euthanized and lungs were inflated with 10% neutral buffered formalin through a tracheal cannula. The inflated lungs were immersed in formalin for at least 24 h. After being processed into paraffin blocks, the lungs were sectioned (5 µm) and floated onto glass slides. The lung sections were stained with hematoxylin and eosin (H&E) for assessment of inflammatory cell infiltration or periodic acid-schiff (PAS) for assessment of mucin content. H&E stained slices from groups A, B, and C of the kidney, spleen, thymus, liver, heart, ovary, pancreas, colon, duodenum, stomach, ileum, jejunum, and femur were also prepared for assessment by a toxicologist.

Figure 5A:
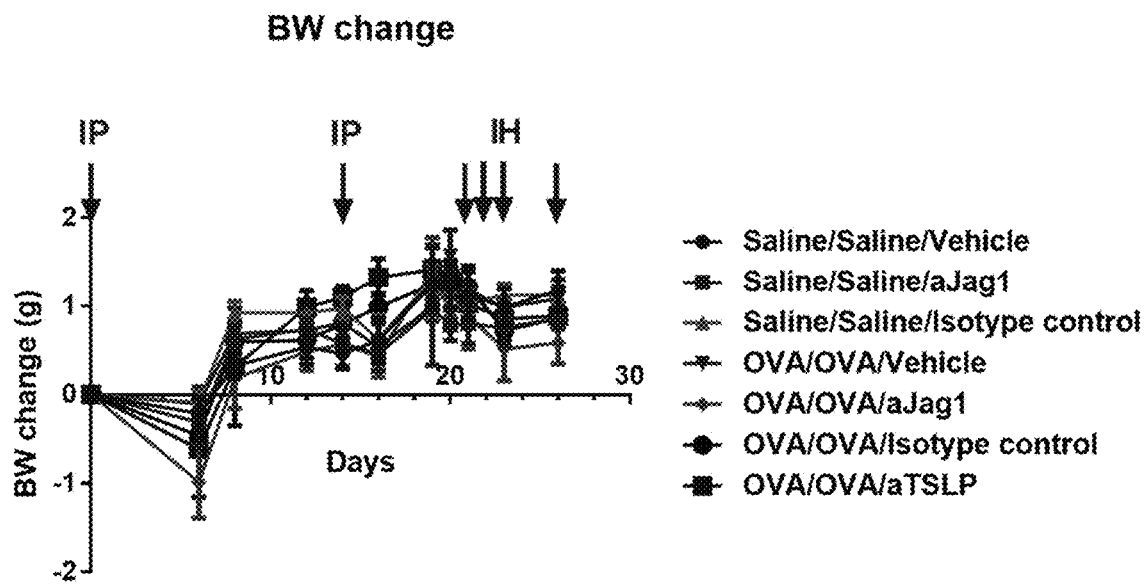
FIGS. 5A-5C.
Figure 5B:
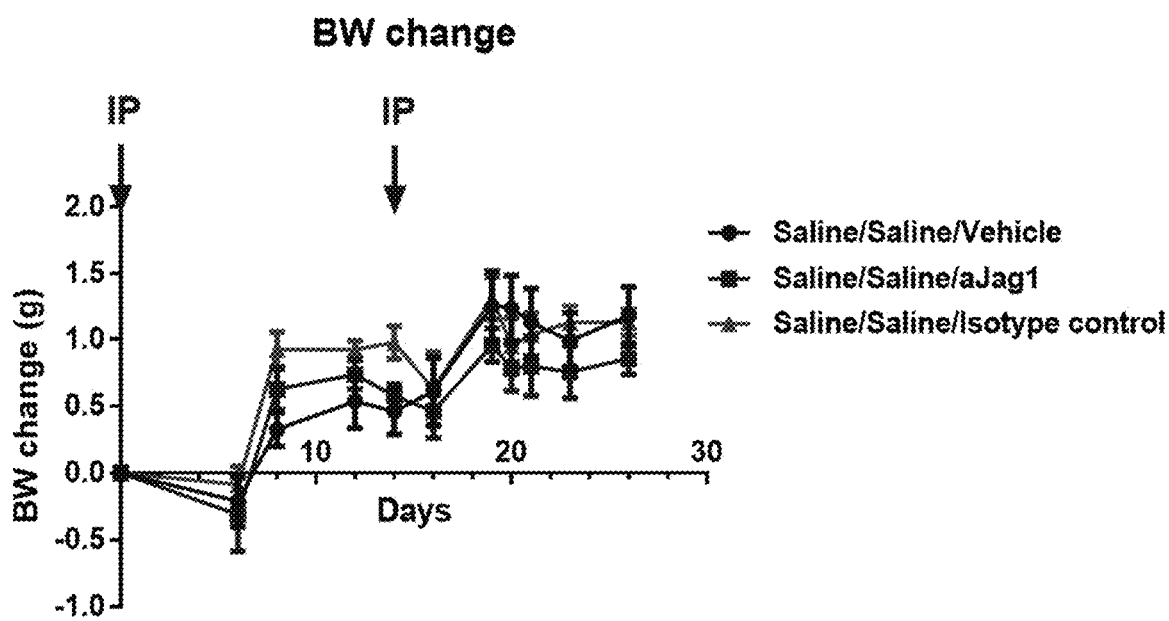
Figure 5C:
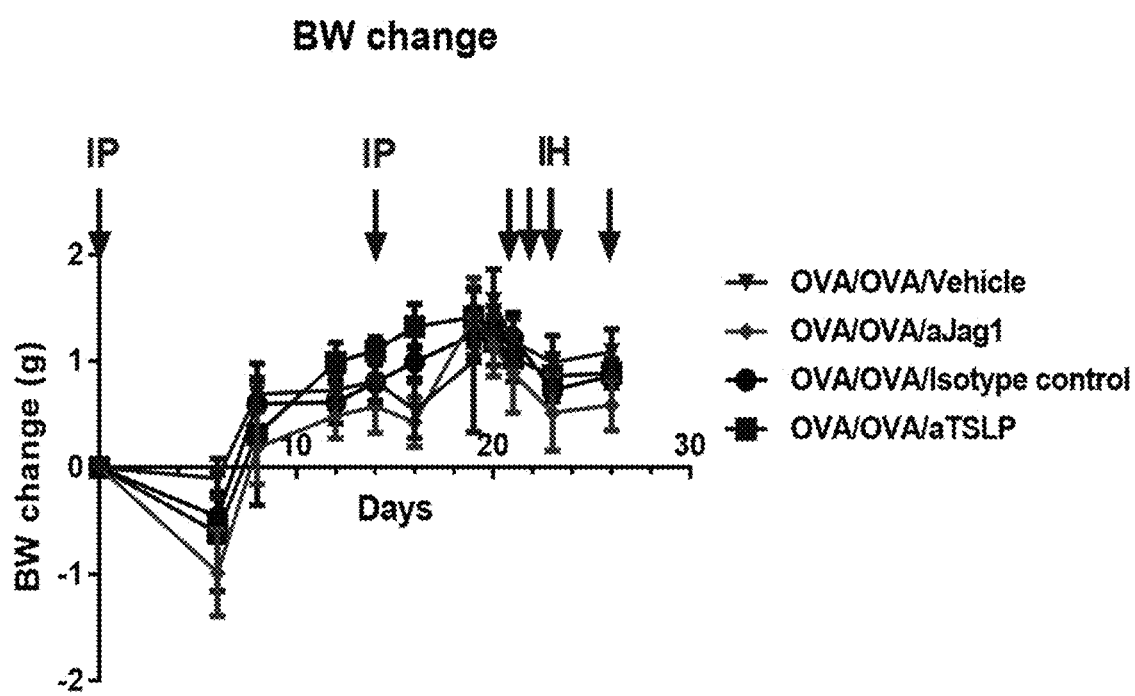

Four weeks of Jag1 blockade with 15D11.1 Mab did not cause body weight loss. Mice were sensitized and boosted by intraperitoneal (i.p.) injection of 0.2 ml of 2% aluminum hydroxide without or with 10 µg of ovalbumin (OVA) antigen on day 0 and 14, and then challenged with inhaled (IH) OVA to induce inflammation & goblet cell metaplasia. Vehicle, anti-Jag1 antibody 15D11.1 Mab (80 mg/kg of), isotype control antibody 655-341-G1 human IgG1 (80 mg/kg), or rat anti-<muTSLP> IgG2a (20 mg/kg) were dosed once per week on day 0, 7, 14 & 20. The average body weight changes (y-axis) from baseline are graphed over time (x-axis). Data are represent as mean±standard deviations (n=7-8). No weight loss was observed in anti-Jag1 antibody treated mice compare to vehicle or isotype control antibody treated mice. However i.p. sensitization & OVA IH causes transient weight loss in all groups. FIG. 5A: Body weight changes for all groups. The mice sensitized without & with OVA are displayed separately in graph FIG. 5B & FIG. 5C.

Example 9: Assessment of Human Anti-hJagged1 mAb 15D11.1 Binding Affinity to hJagged1

Figure 6:
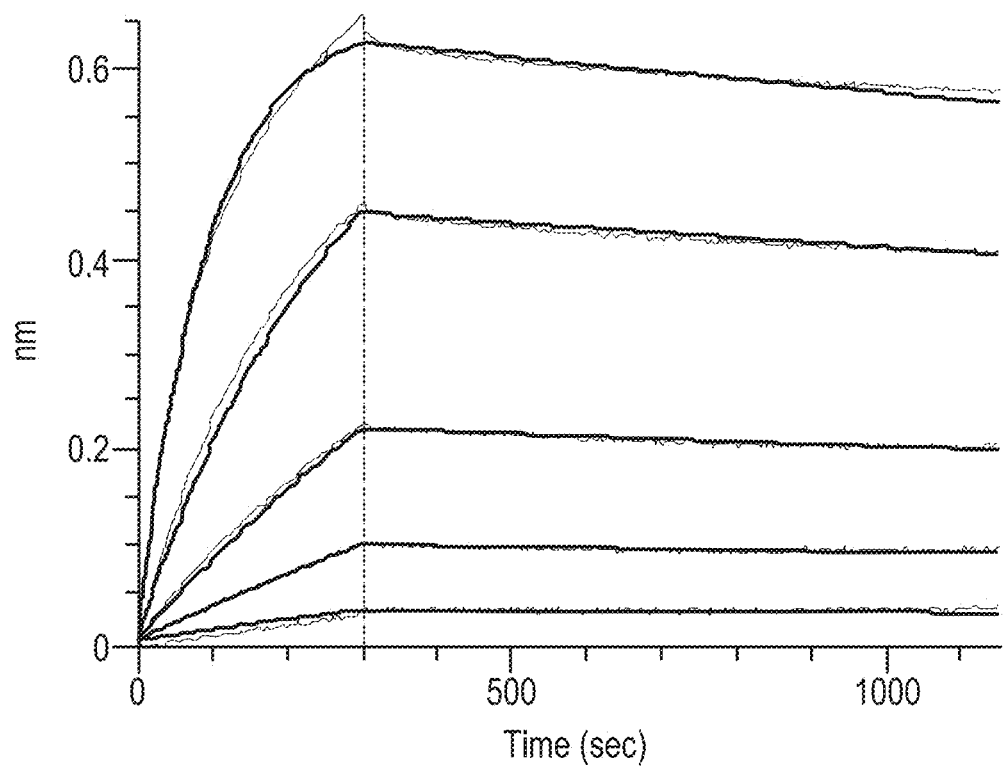
FIG. 6 shows Assessment of human anti-hJagged1 mAb 15D11.1 binding affinity to hJagged1

The anti-hJagged1 mAb 15D11.1 (PL-50432) was evaluated for its affinity to the recombinant human Jagged1 extracellular domain (Met 1-Ser 1046), fused with a polyhistidine tag at the C-terminus, and produced in human cell and obtained from Creative Biomart (Cat #JAG1-3226H). The binding kinetics and fit for an antigen concentration of 50, 15.3, 5.1, 1.7 and 0.56 nM and are shown in FIG. 6.

The affinity of the soluble recombinant hJagged1 was determined in Octet platform (Octet Red96) under the manufactures recommended kinetic measurement settings. Briefly, hJagged1 was diluted 1 to 3 from 150 nM to 0.5 nM in Octet buffer (10 mM Tris base, 150 mM NaCl, 1 mM CaCl2), 0.1 mg/ml BSA, 0.1% Triton X100) and 60 ul of this serial diluted samples were taken in 384 well tilted bottom (TW384) black polypropylene microplate (Forte Bio, Cat #18-0019) (sample plate). 3 ug/ml of anti-hJagged1 mAb 15D11.1 present in 60 ul in sample plate was used and captured on AHC—anti-HuFc (Kinetic) biosensors (cat #18-5060). A sample with buffer alone is used as a control.

The antibody was captured for 300 sec, the association and dissociation was measured for 300 and 1200 sec, respectively. ForteBio Data Analysis Software version 9.0.0.12 was used to interrogate the association (300 sec) and dissociation (900 sec) and measure the kinetics.

Example 10: On-Cell Affinity by Equilibrium Measurement Using KinExA

The anti-hJagged1 mAb 15D11.1 (PL-50432) was evaluated for its affinity to the native human Jagged1 expressed on a stable 293 cell line.

Figure 7A:
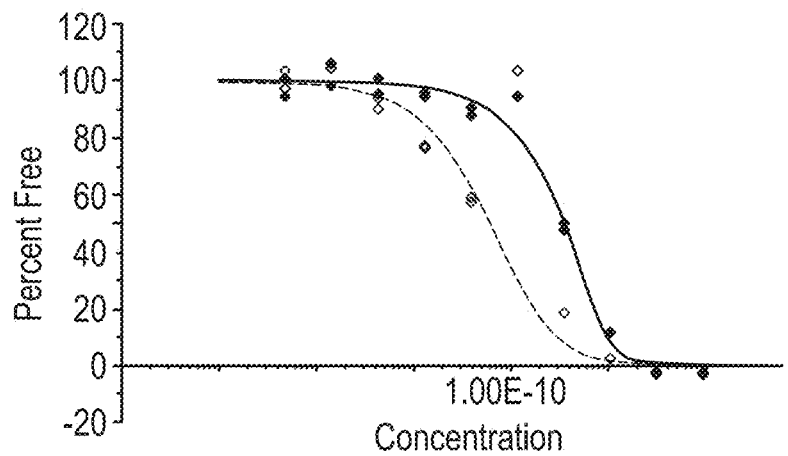
FIGS. 7A-7C show On-cell affinity by equilibrium measurement using KinExA.
Figure 7B:
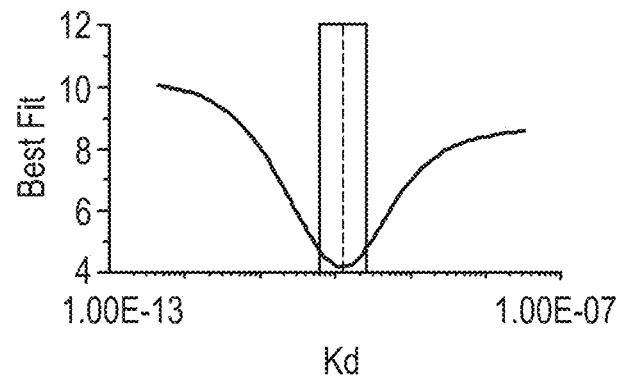
Figure 7C:
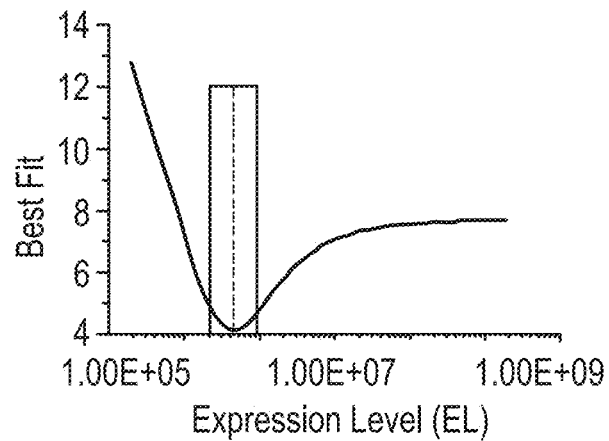

Cells in media were serially diluted and incubated with 30 pM or 1 nM active binding site concentration of antibody in media in the presence of 0.05% NaN3, and allowed to equilibrate. The free mAb left in the supernatant was measured as explained in the text. (FIG. 7A) The % free mAb (red curve for 30 pM and blue curve for 1 nM) is plotted against the cell concentration. N-curve analysis using the equilibrium, whole cell method was performed to determine optimal values for $K_d$ and the antigen expression level. (FIGS. 7B and 7C) The 95% confidence intervals were determined by changing iteratively the optimized value for $K_d$ or antigen expression level while keeping other parameters at their optimal values.

The affinity of mAb 15D11.1 was determined by measuring the equilibrium dissociation constant ($K_d$). Kinetic Exclusion Assay (KinExA) was used in which the $K_d$ was determined from the concentration of free antibody that remains in solution after equilibrium has been established between the antibody and the cell-surface-expressed antigen. The more-resource intensive, KinExA assay provides a more sensitive determination of binding affinity for the native form of Jagged1 than the soluble Jagged1-based Octet assay system. The Kinetic Exclusion Assay method of Rathanaswami et al. (2008) was followed. (Rathanaswami et al., High affinity binding measurements of antibodies to cell-surface-expressed antigens, Analytical Biochemistry 373:52-60 (2008)). Briefly, two different equilibrium sets were set up using doxycycline-induced Jagged1-expressing cells. The cells were cell dissociated with cell dissociation solution, washed twice with ice-cold 1×PBS and counted using a Hemocytometer. The cells were titrated and incubated with two different constant antibody concentrations, one at 30 pM and the other at 1 nM. Cell titrations and antibody solutions were set up in media with 0.05% Sodium Azide. Cells were titrated from 8.33 million per milliliter concentration, 1 to 3, for 10 points in 50-mL Falcon tubes. For the low [Ab] equilibrium set, 4.5 mL of 60 pM Ab was mixed with 4.5 mL of each cell titration solution diluting the final cell and Ab concentration in half. For the high [Ab] equilibrium set, 200 µL of 1 nM Ab was mixed with 200 µL. of each cell titration solution diluting the final cell and Ab concentration in half. For each equilibrium set a blank cell media only sample and no cell added sample would be included for reference points. The equilibrium sets were incubated for 44 hours at RT, with shaking.

After 44 hours of incubation, the supernatants were separated from the cell pellets via centrifugation at 500×g for 5 minutes. The supernatants of both high [Ab] and low [Ab] equilibrium sets were then run through a KinExA 3200 machine.

Each equilibrium sample set was read in duplicate on the KinExA machine. For low [Ab] equilibrium samples 4.1 mL was run of each sample in duplicate. For high [Ab] equilibrium samples 100 uL was run of each sample in duplicate. PMMA (Polymethyl Methacrylate Particles) beads were coated with Goat anti-human Fc Ab and subsequently blocked with a blocking solution (1×PBS pH7.4+10 mg/mL BSA+0.05% Sodium Azide). For each equilibrium sample the free [Ab] would be detected by running the equilibrium samples through the coated-beads followed by a quick wash with the running buffer (1×PBS pH7.4+1% BSA+0.05% Sodium Azide). Then the secondary detection Ab, Goat anti-huIgG (H+L) Dylight 649, was run through the flow cell at 680 ng/mL and 500 µL per run. The KinExA voltage output signal was then used in KinExA software to calculate the $K_d$. From the plots at two different initial total [Ab] concentrations the $K_d$ was obtained from curve fitting using n-curve analysis in KinExA Pro software (Sapidyne Instruments Inc., Boise Id.). The 95% confidence interval is given as $K_d$ low and $K_d$ high.

TABLE 6

Summary of 15D11.1 Binding Affinities

| | Octet | | | | KinExA | |
|---|---|---|---|---|---|---|
| | KD (M) | kon (1/Ms) | kdis (1/s) | KD (nM) | Kd (pM) | 95% CI (pM) |
| Mean | 6.14E−10 | 3.31E+05 | 1.89E−04 | 0.61 | 125 | 61-255 |
| SD | 2.37E−10 | 1.46E+05 | 5.90E−05 | 0.24 | | |

*Octet summary is the mean of 3 experiments

Example 11: ELISA Assay Results of 15D11.1 Cross Species Reactivity and Selectivity Against Notch Ligand Family Members 15D11.1 binds to recombinant human Jagged-1 and rat Jagged-1 but does not bind to Jagged-2, Dll1 or Dll4. Below are the summary of the IC50s.

TABLE 7

| | IC50 hJAG1 Fc (nM) | IC50 hJAG1 His (nM) | IC50 rJAG1 (nM) |
|---|---|---|---|
| 15D11.1 | 0.80 (n = 3) | 0.39 (n = 1) | 0.51 (n = 3) |

15D11.1 was tested for binding to recombinant purified Notch ligands using a standard ELISA assay format. 15D11.1 bound human and rat Jagged-1 (with IC50s ranging from 0.3 nM-0.9 nM) but did not bind to Jagged-2, Dll1 or Dll4.

Figure 8A:
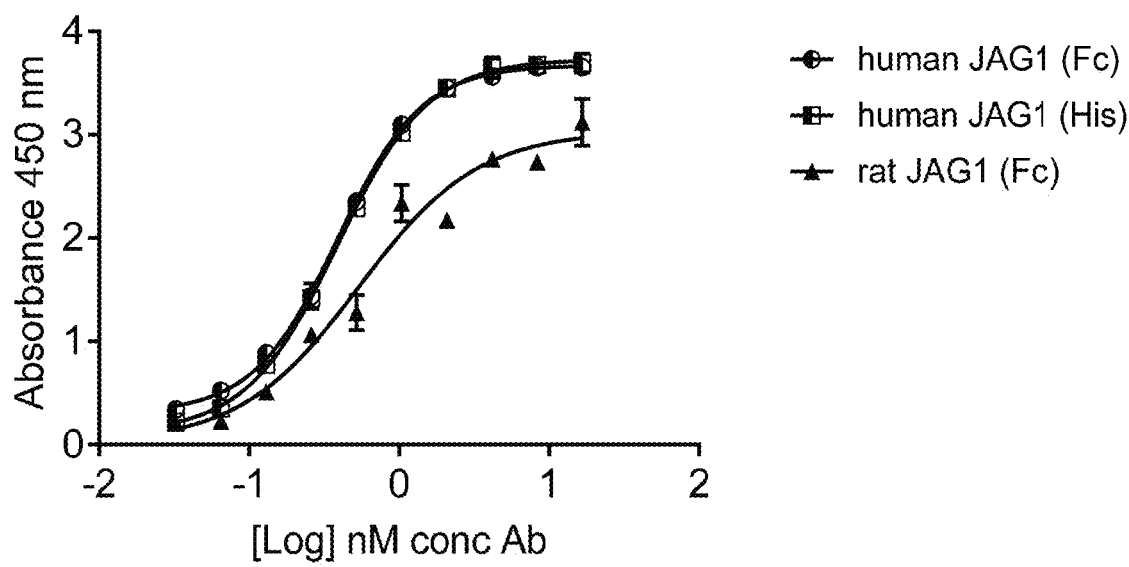
FIGS. 8A-8B show ELISA assay results of 15D11.1 cross species reactivity and selectivity against Notch ligand family members
Figure 8B:
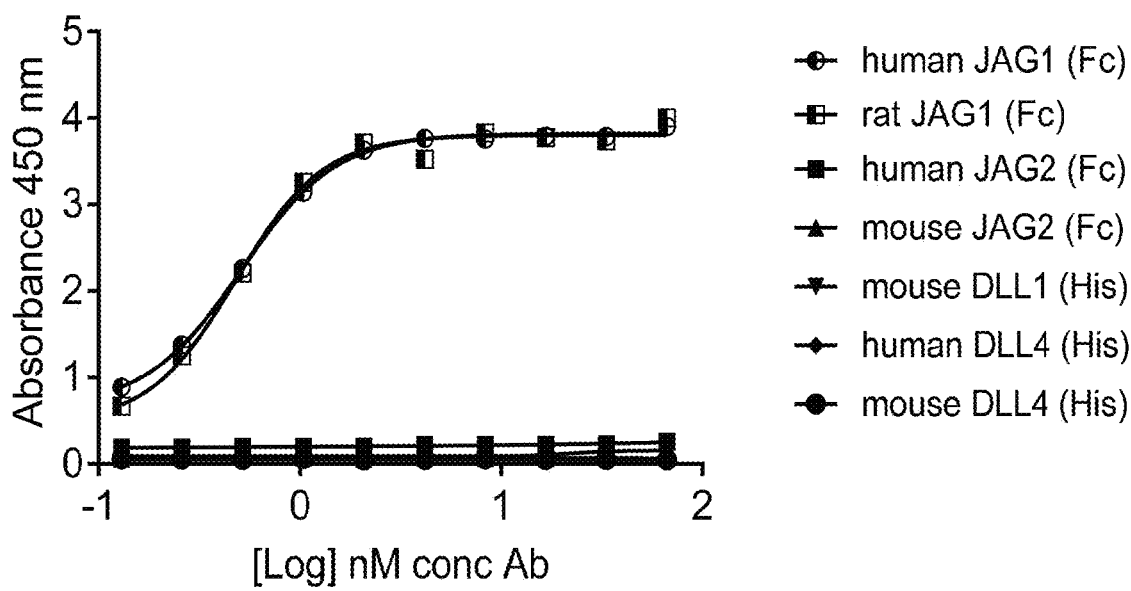

15D11.1 was tested for binding to recombinant purified Notch ligands; human Jagged1 Fc (Recombinant Human Jagged1 Fc chimera—R&D Systems Cat #: 1277-JG-050), human Jagged1 His (Human JAG1/Jagged1 His Tag Sino Biological Cat #: 11648-H08H), rat Jagged1 Fc (Recombinant Rat Jagged 1 Fc chimera—R&D Systems—Cat #: 599-JG-050), human Jagged2 (Recombinant Human Jagged 2 Fc chimera—R&D Systems Cat #: 1726-JG-050), murine Jagged2 (Recombinant Mouse Jagged 2 Fc chimera—R&D Systems Cat #: 4748-JG-0050), murine Delta-like 1 (Recombinant Mouse DLL1 His tag—Sino Biological Cat #: 50522-M08H-50), human Deltalike 4 (Recombinant Human DLL4 His tag—R&D Systems—Cat #: 1506-D4-050) and murine Deltalike 4 (Recombinant Mouse DLL4 His tag—R&D Systems—Cat #: 1389-D4-050) using a standard enzyme-linked immunosorbent assay (ELISA). 1 ug/ml of Notch ligand protein (as indicated) in PBS, pH7.4, was coated onto ELISA plates (Nunc Maxisorp) at 4° C. overnight. Plates were blocked with Casein blocker in PBS (Pierce) for one hour at room temperature. Serial 2-fold dilutions of 15D11.1
in PBST buffer (PBT buffer (PBS+0.05% (v/v) Tween 20) with 0.5% (w/v) BSA) were added to the plates and incubated for one hour at room temperature. The plates were then washed with PBST and bound antibodies were detected with peroxidase-conjugated goat anti-human Fab specific IgG (Sigma). TMB substrate (3,3',5,5'-tetramethylbenzidine) was used and absorbance at 450 nm was read using a standard ELISA plate reader. Absorbance was plotted against concentrations of 15D11.1 in FIGS. 8A and 8B.

Example 12: Binding of 15D11.1 to Human Jagged-1 Transfected 293T Cells

Figure 9:
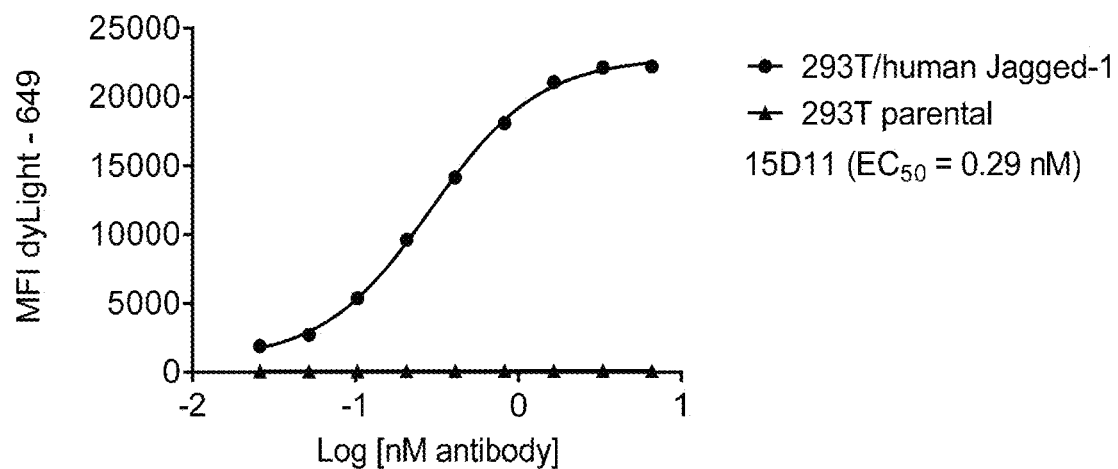
FIG. 9 shows Binding of 15D11.1 to human Jagged-1 transfected 293T cells.

15D11.1 bound to 293T cells stably transfected with human Jagged-1 with an $EC_{50}$ of 0.29 nM. Binding of 15D11.1 to 293T parental cells was used as a negative control Binding of 15D11.1 to human Jagged-1 was assessed by flow cytometry using 293T cells engineered to stably express human Jagged-1 in a Tet inducible manner. 15D11.1 bound to human Jagged-1 transfected 293T cells with an $EC_{50}$ of 0.29 nM. See FIG. 9.

Briefly, 293T cells @~60% confluency were grown overnight @ 37 C/5% $CO_2$ in the presence of 1 ug/ml Doxycycline to induce human Jagged-1 expression. The next morning cells were removed with non-enzymatic cell dissociation solution (Gibco), washed in PBS (Gibco) supplemented with 2% FBS (Hyclone), diluted to 1×10e5 cells/100 ul in PBS/2% FBS and aliquoted to 1.5 ml 96 well deep well plates (Nunc) for immunostaining. 1:2 serial dilutions of 15D11.1 were made ranging from 13.2 nM to 0.026 nM in concentration. 100 ul of antibody dilution was added to 1×10e5 cells and incubated on ice for 1 hr. Cells were washed 2× w/PBS/2% FBS and incubated with mouse anti-human Fc (clone 1.35.1) conjugated to dylight 649 at a conc of (0.1 ug/ml) for an additional 1 hr for detection of 15D11.1. After 2 additional washes cells were run on a BD LSRII flow cytometer using the APC channel.

Figure 10:
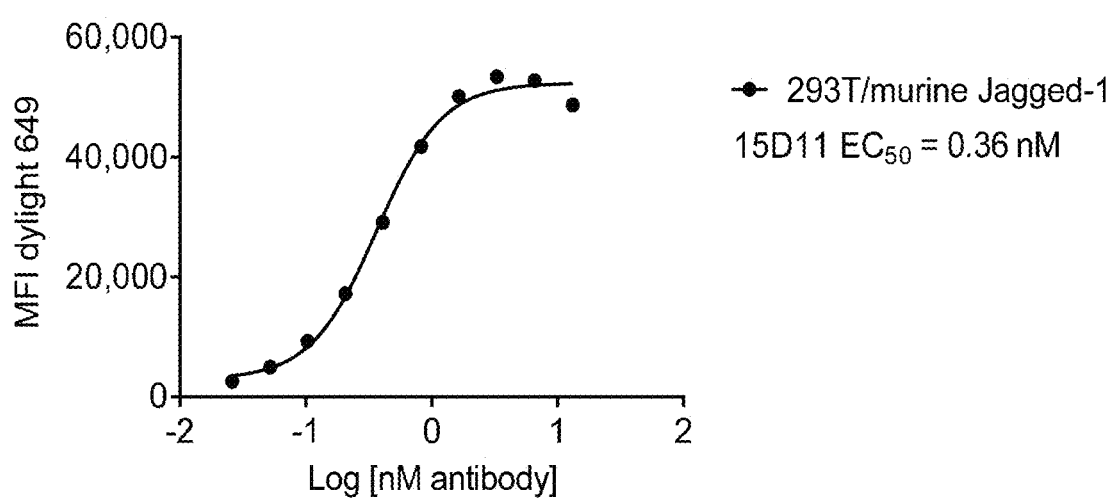
FIG. 10 shows Cross-species reactivity of 15D11.1 to murine Jagged-1 transfected 293T cells.

Example 13: Cross-Species Reactivity of 15D11.1 to Murine Jagged-1 Transfected 293T Cells 15D11.1 bound to 293T cells stably transfected with murine Jagged-1 with an $EC_{50}$ of 0.36 nM.
Cross-species reactivity of 15D11.1 to murine Jagged-1 was assessed by flow cytometry using 293T cells engineered to stably express murine Jagged-1. 15D11.1 bound to murine Jagged-1 transfected 293T cells with an $EC_{50}$ of 0.36 nM. See FIG. 10.

Briefly, 293T cells stably expressing murine Jagged-1 were removed with non-enzymatic cell dissociation solution (Gibco), washed in PBS (Gibco) supplemented with 2% FBS (Hyclone), diluted to 1×10e5 cells/100 ul in PBS/2% FBS and aliquoted to 1.5 ml 96 well deep well plates (Nunc) for immunostaining. 1:2 serial dilutions of 15D11.1 were made ranging from 13.2 nM to 0.026 nM in concentration. 100 ul of antibody dilution was added to 1×10e5 cells and incubated on ice for 1 hr. Cells were washed 2× w/PBS/2% FBS and incubated with mouse anti-human Fc (clone 1.35.1) conjugated to dylight 649 at a conc of (0.1 ug/ml) for an additional 1 hr for detection of 15D11.1. After 2 additional washes cells were run on a BD LSRII flow cytometer using the APC channel.

Example 14: Binding of 15D11.1 to Rat-Jagged-1 Transfected 293T Cells 293T cells were transiently transfected with rat Jagged-1 and 15D11.1 binding was assessed by flow cytometry. 15D11.1 bound to rat Jagged-1 transfected cells with an $EC_{50}$ of 0.25 nM. Binding of 15D11.1 to 293T parental cells was used as a negative control.

Figure 11:
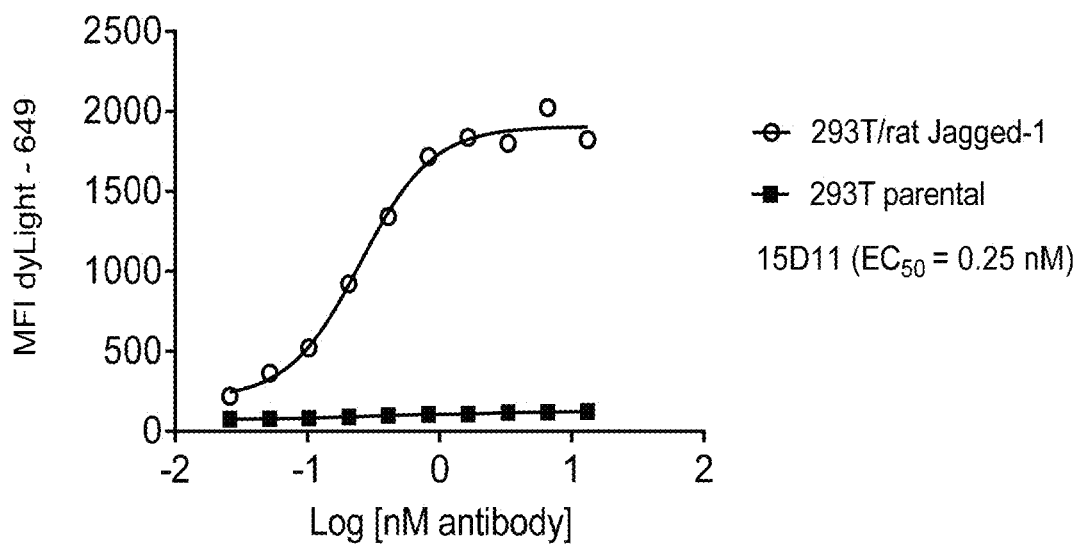
FIG. 11 shows Binding of 15D11.1 to rat-Jagged-1 transfected 293T cells.

Cross-species reactivity of 15D11.1 with rat Jagged-1 was assessed by flow cytometry using 293T cells transiently transfected with rat Jagged-1. 15D11.1 bound to rat Jagged-1 transfected 293T cells with an $EC_{50}$ of 0.25 nM. See FIG. 11.

Briefly, 293T cells @~60% confluency were transiently transduced with 8% (V/V) BacMam/rat Jagged1 overnight @ 37 C/5% $CO_2$. The next morning cells were removed with non-enzymatic cell dissociation solution (Gibco), washed in PBS (Gibco) supplemented with 2% FBS (Hyclone), diluted to 1×10e5 cells/100 ul in PBS/2% FBS and aliquoted to 1.5 ml 96 well deep well plates (Nunc) for immunostaining. 1:2 serial dilutions of 15D11.1 were made ranging from 13.2 nM to 0.026 nM in concentration. 100 ul of antibody dilution was added to 1×10e5 cells and incubated on ice for 1 hr. Cells were washed 2× w/PBS/2% FBS and incubated with mouse anti-human Fc (clone 1.35.1) conjugated to dylight 649 at a conc of (0.1 ug/ml) for an additional 1 hr for detection of 15D11.1. After 2 additional washes cells were run on a BD LSRII flow cytometer using the APC channel.

Figure 12:
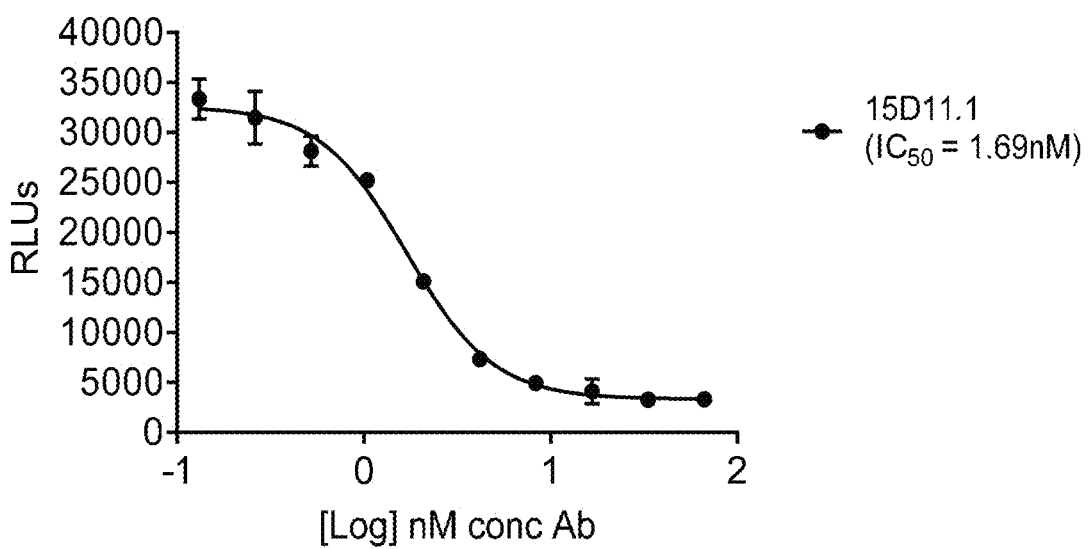
FIG. 12 shows Dose titration of anti-Jagged-1 mAb 15D11.1 in human Jagged-1 induced human Notch2 activation co-culture assay

Example 15: Dose Titration of Anti-Jagged-1 mAb 15D11.1 in Human Jagged-1 Induced Human Notch2 Activation Co-Culture Assay Anti Jagged-1 mAb 15D11.1 antagonizes human Jagged-1 induced human Notch activation in co-culture experiments in a dose dependent manner with an IC50 of 1.69 nM (avg $IC_{50}$ of 2.31 nM+/−0.56 Std Dev, from n=4 experiments). See FIG. 12.

293T cells engineered to stably express human Jagged-1 in a doxycycline induced manner were co-cultured with SK-MEL-28 cells stably transfected with a Notch responsive (12×CSL) firefly luciferase reporter (pGL4, Promega) with increasing amounts of anti-Jagged-1 mAb 15D11.1 (66.7 nM-0.131 nM). SK-MEL-28 cells were characterized by Flow cytometry and qPCR and demonstrated to express high levels of Notch 2 receptor endogenously (data not shown). Endogenous expression of other Notch family members was not detected (Notch 1 & Notch 3). 15D11.1 was able to inhibit Jagged-1 induced Notch signaling in a dose dependent manner with an avg $IC_{50}$ of 2.31 nM (+/−0.56 Std Dev) from n=4 experiments.

Briefly, 293T/human Jagged-1 Tet inducible cells were incubated with doxycycline (1 ug/ml) overnight at 37 C/5% $CO_2$ to induce human Jagged-1 expression. The next day doxycycline induced 293T/human Jagged-1 cells (2×10e4) were co-cultured with SK-MEL-28 cells (2×10e4) stably expressing the 12×CSL-firefly luciferase reporter (pGL4, Promega), in the presence of increasing amounts of anti-Jagged-1 mAb 15D11.1 (1:2 dilns ranging from 66.7 nM-0.131 nM) in a 96 well tissue culture dish. Cells were co-cultured overnight for ~18 hrs at 37 C/5% $CO_2$. The following day, an equal volume of One-Glo (Promega) was added to each well and plates were incubated @ RT for 10 min with gentle shaking and read on a luminometer.

Example 16: Dose Titration of Anti-Jagged-1 mAb 15D11.1 in Murine Jagged-1 Induced Murine Notch1 Activation Co-Culture Assay Anti Jagged-1 mAb 15D11.1 antagonizes murine Jagged-1 induced murine Notch 1 activation in co-culture experiments in a dose dependent manner with an $IC_{50}$ of 7.72 nM (avg $IC_{50}$ of 9.0 nM+/−1.47 Std Dev, from n=3 experiments).

Figure 13:
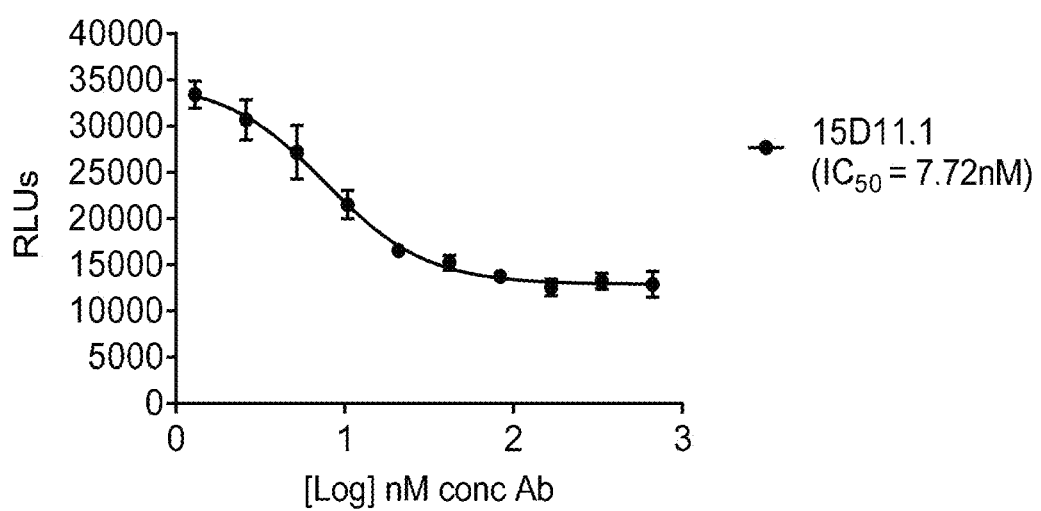
FIG. 13 shows Cross-species reactivity of 15D11.1 against mouse Jagged-1.

293T cells engineered to stably express murine Jagged-1 were co-cultured with 293T cells stably transfected with murine Notch1 and a Notch responsive (7×CSL) firefly luciferase reporter with increasing amounts of anti-Jagged-1 mAb 15D11.1 (667 nM-1.3 nM). 15D11.1 was able to inhibit murine Jagged-1 induced murine Notch1 signaling in a dose dependent manner with an avg $IC_{50}$ of 7.72 nM (+/−1.47 Std Dev) from n=3 experiments. See FIG. 13.

Briefly, 293T/murine Jagged-1 cells (2×10e4) were co-cultured with 293T/murine Notch1 cells (2×10e4) stably expressing a Notch responsive 7×CSL-firefly luciferase reporter, in the presence of increasing amounts of anti-Jagged-1 mAb 15D11.1 (1:2 dilns ranging from 667 nM-1.3 nM) in a 96 well tissue culture dish. Cells were co-cultured overnight for ~18 hrs at 37 C/5% $CO_2$. The following day, an equal volume of One-Glo (Promega) was added to each well and plates were incubated @ RT for 10 min with gentle shaking and read on a luminometer.

Example 17: Dose Titration of Anti-Jagged-1 mAb 15D11.1 in Unstimulated and Stimulated Bronchosphere Cultures The impact of anti-Jagged-1 mAb (15D11.1) treatment on airway epithelial cell differentiation was assessed using 3D bronchosphere cultures derived from normal healthy or diseased (CF & COPD) bronchial epithelial cells, either unstimulated or stimulated with IL-13 (1 ng/ml) for 7 days in the presence of increasing concentrations of 15D11.1 (66.7 nM-0.131 nM). 15D11.1 reduced secretory cell (SCGB1A1), goblet cell (MUC5AC) and Notch activation (NRARP) marker expression in a dose dependent manner after 7 day treatment in IL-13 (1 ng/ml) stimulated and unstimulated cultures and increased ciliated cell marker expression (DNAI2) in unstimulated cultures. Results were similar in normal healthy donor cells and diseased donor cells (CF and COPD). Expression levels are expressed relative to the housekeeping gene HPRT1.

Normal human bronchial epithelial cells and Chronic Obstructive Pulmonary Disease (COPD) bronchial epithelial cells were purchased from Lonza. Cystic Fibrosis (CF) bronchial epithelial cells and differentiation media (UNC ALI media) were obtained from University of North Carolina Chapel Hill (UNC). 3D bronchosphere cultures using passage 2 cells were performed as described previously (ref Danahay et al). Briefly, P1 human bronchial epithelial cells were expanded in BEGM media (Lonza) in a T75 tissue culture flask. Upon confluency, cells were trypsonized, resuspended in UNC differentiation media+3% matrigel (Corning) and plated at a density of 6000 cells/well onto 60 ul solidified UNC ALI media containing 25% matrigel, in 96 well flat bottom plates. The bronchospheres were grown 7 days with re-feeding three times a week. On day 7 cultures were stimulated+/−IL-13 (@1 ng/ml)+15D11.1 for an additional 7 days. Fresh media (with or without treatment) was changed every other day and supplemented with fresh cytokine and treatment. On day 14 the organoids were lysed and processed following the Affymetrix QuantiGene platform manufacturer's specifications to examine markers for secretory cells (SGB1A1; FIGS. 14A, 14E, 14I, 15A, 15E, and 15I), goblet cells (MUC5AC; FIGS. 14B, 14F, 14J, 15B, 15F, and 15J), ciliated cells (DNAI2 (FIGS. 14C, 14G, 14K, 15C, 15G, and 15K) and FOXJ1) and the Notch activation marker (NRARP; FIGS. 14D, 14H, 14L, 15D, 15H, and 15L).

Figure 14A:
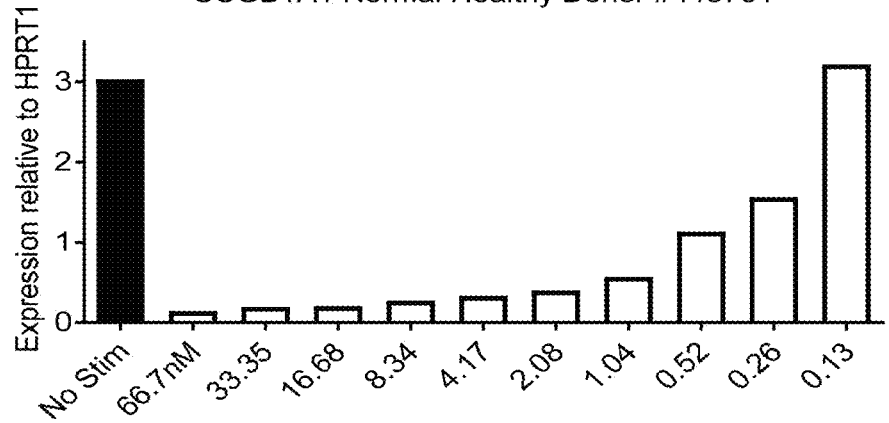
FIGS. 14A-14L show Dose titration of anti-Jagged-1 mAb 15D11.1 in unstimulated bronchosphere cultures
Figure 14B:
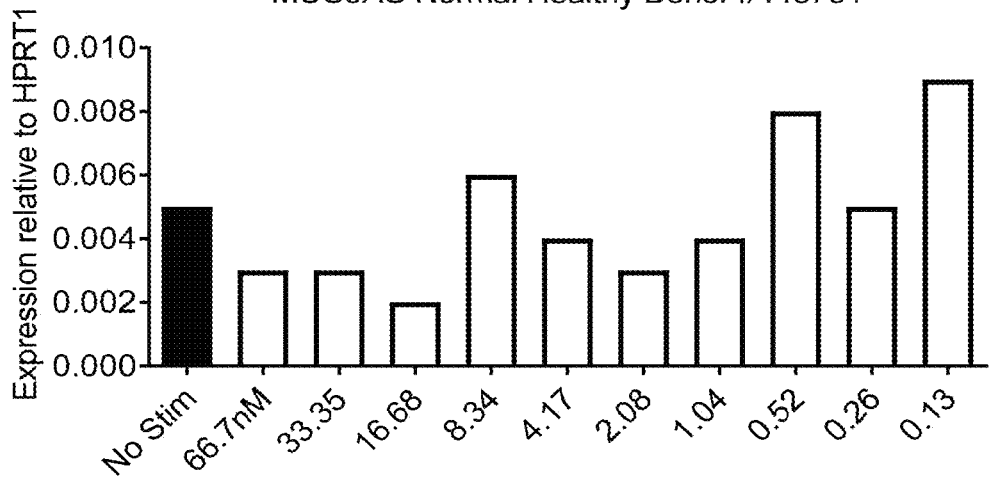
Figure 14C:
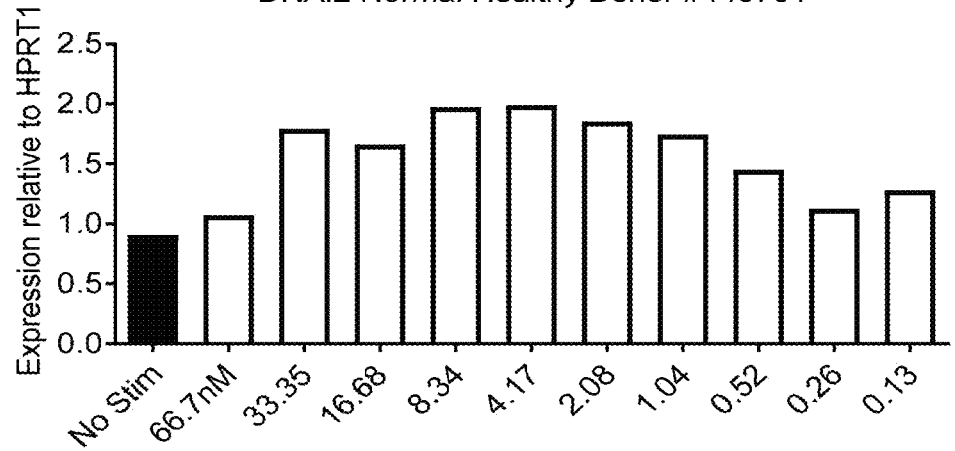
Figure 14D:
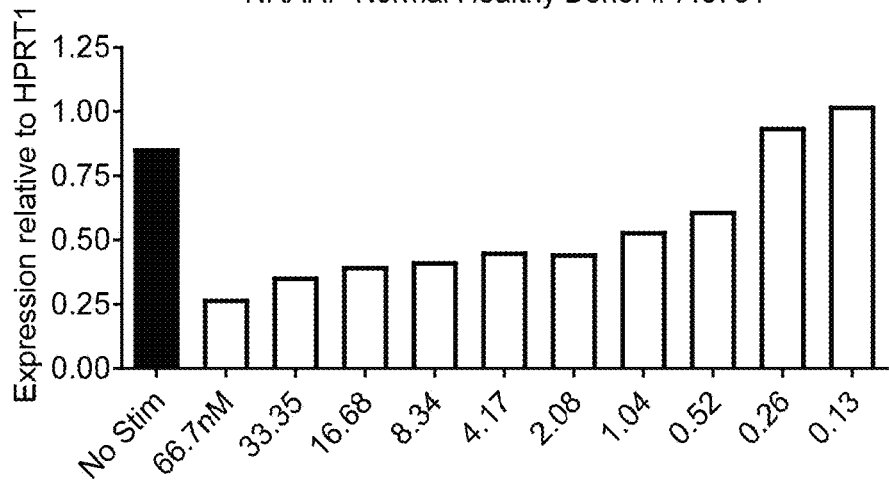
Figure 14E:
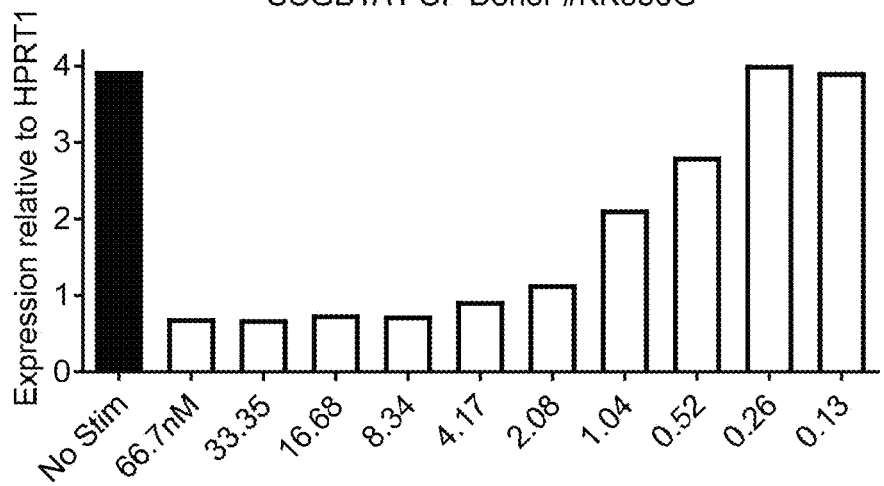
Figure 14F:
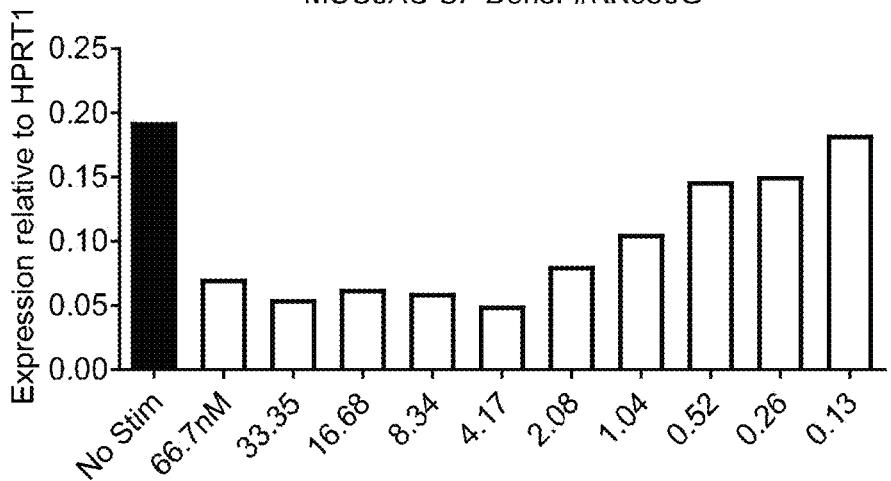
Figure 14G:
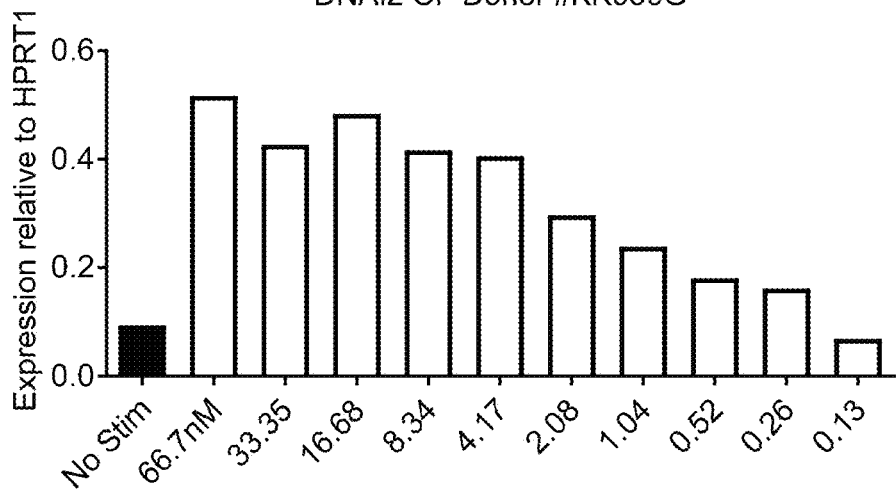
Figure 14H:
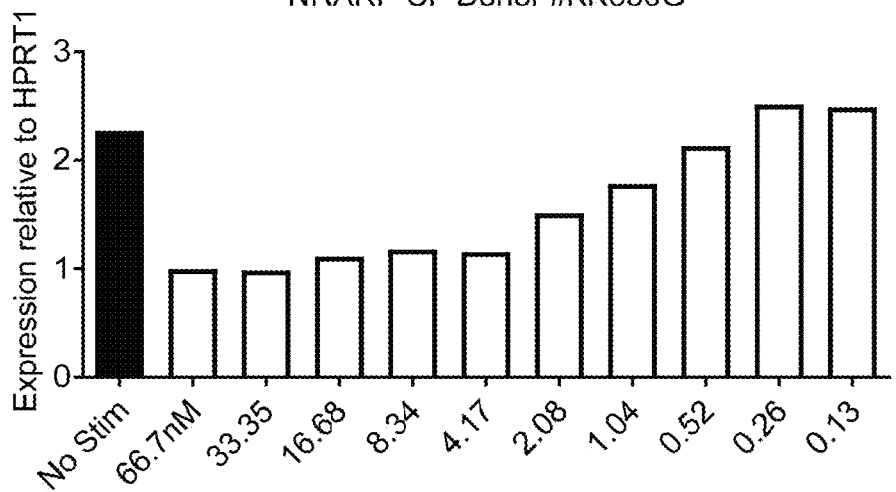
Figure 14I:
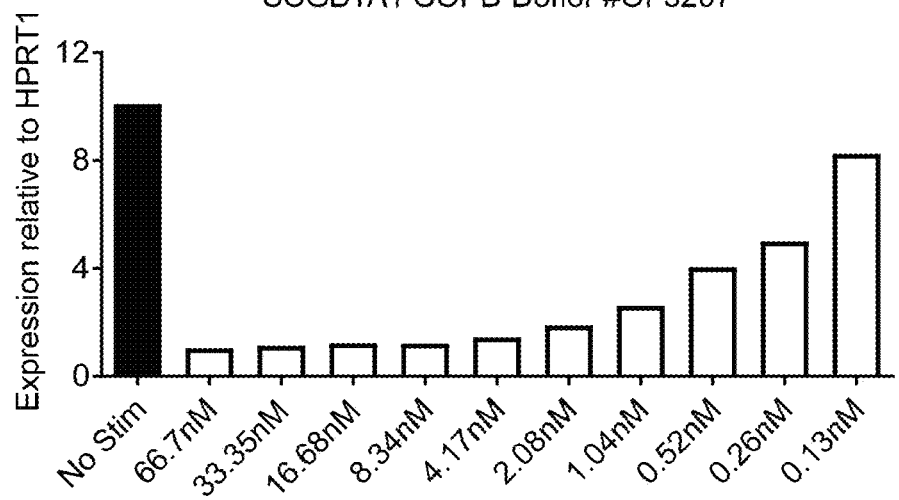
Figure 14J:
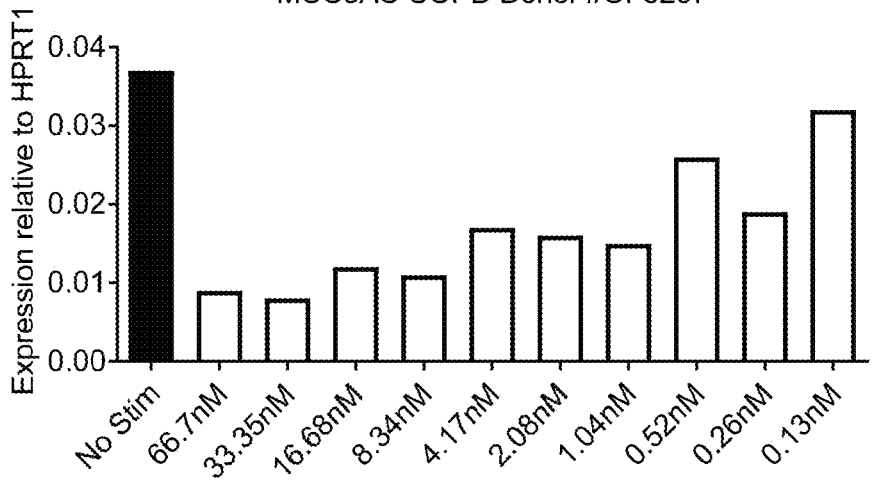
Figure 14K:
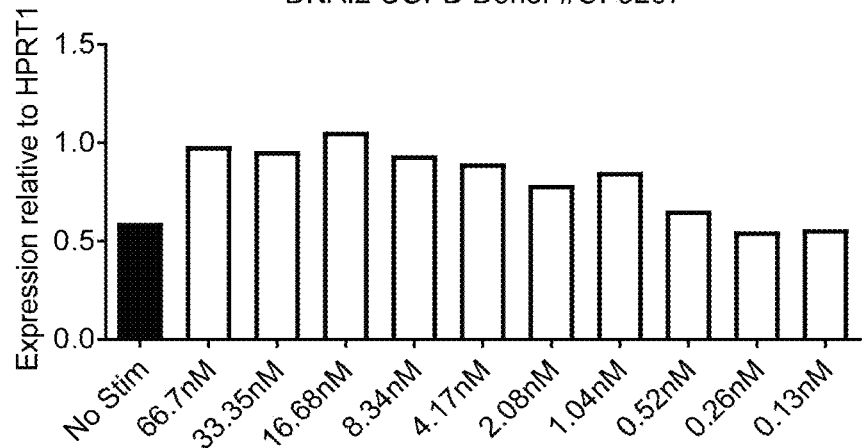
Figure 14L:
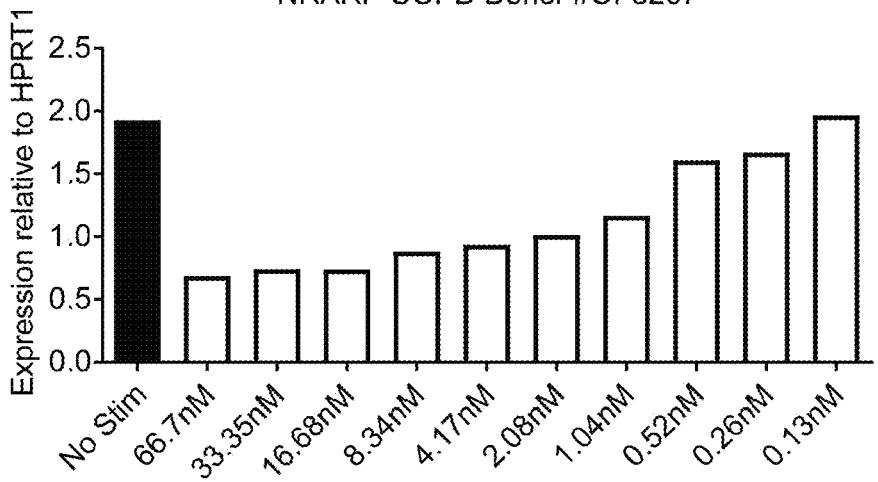

The anti-Jag1 mAb 15D11.1 reduced secretory cell (SCGB1A1; FIGS. 14A, E, and I), goblet cell (MUC5AC; FIGS. 14B, F, and J) and Notch activation (NRARP; FIGS. 14D, H, and L) marker expression while demonstrating increased ciliated cell (DNAI2; FIGS. 14C, G, and K) marker expression in a dose dependent manner after 7 day treatment in unstimulated bronchosphere cultures derived from normal (FIGS. 14A-D), or diseased (CF (FIGS. 14E-H) and COPD (FIGS. 14I-L)) bronchial epithelial cells. Expression levels are expressed relative to the housekeeping gene HPRT1

Figure 15A:
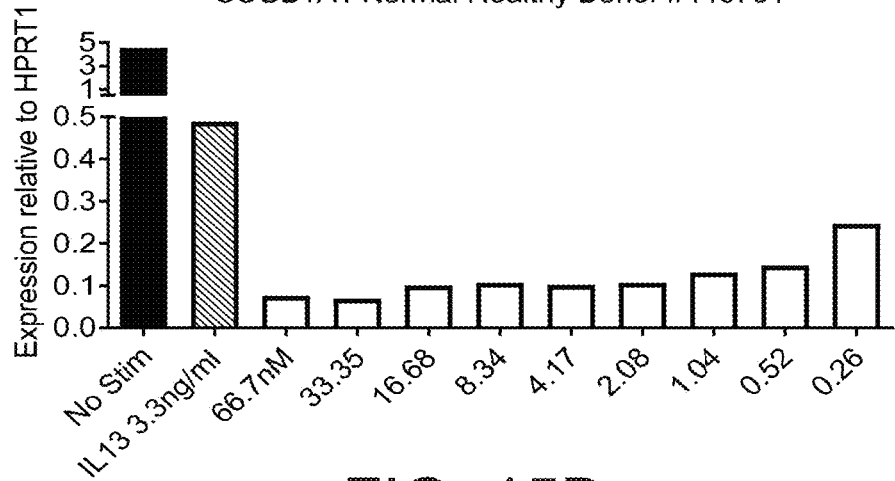
FIGS. 15A-15L show Dose titration of anti-Jagged-1 mAb 15D11.1 in IL-13 (1 ng/ml) stimulated bronchosphere cultures
Figure 15B:
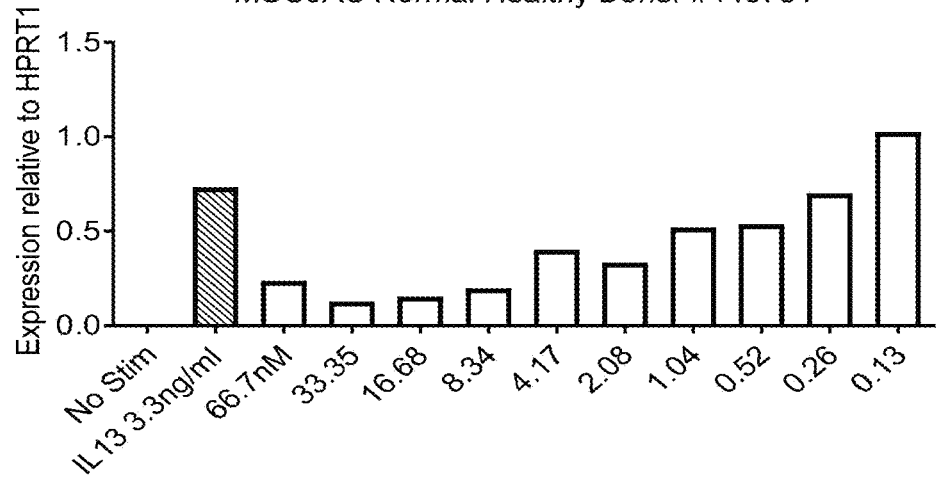
Figure 15C:
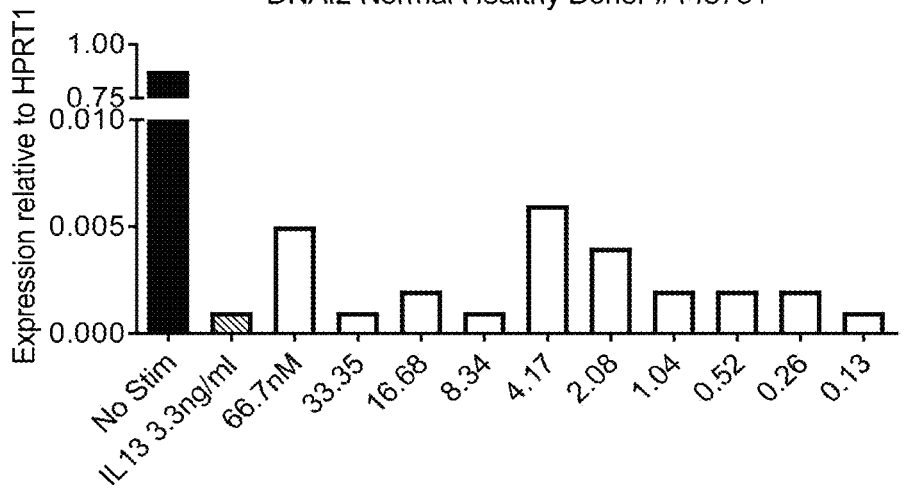
Figure 15D:
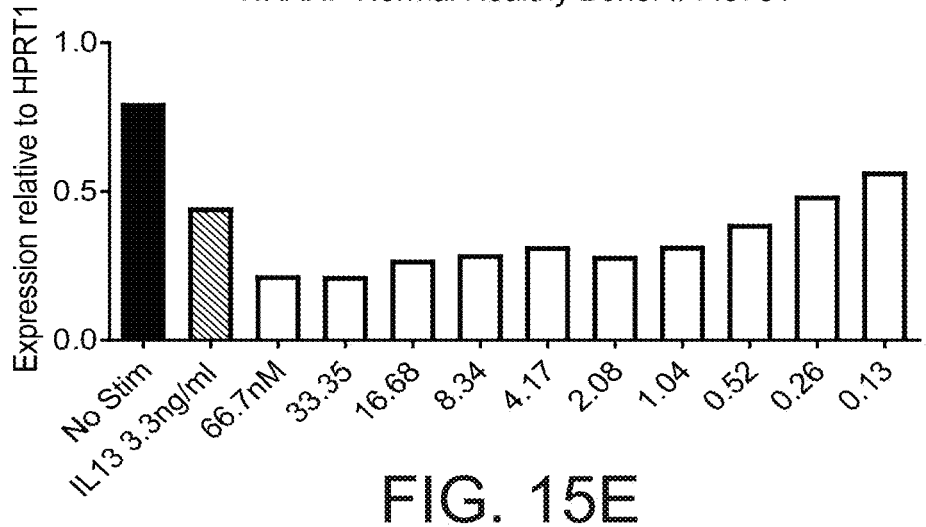
Figure 15E:
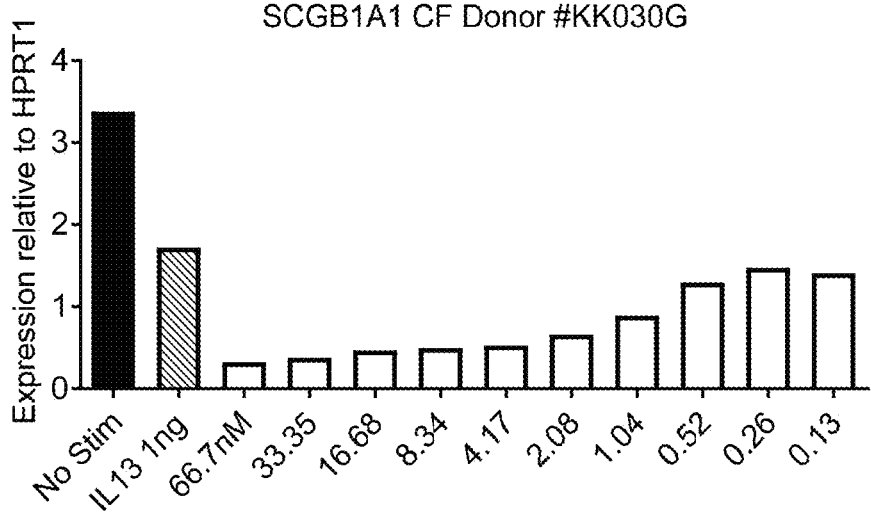
Figure 15F:
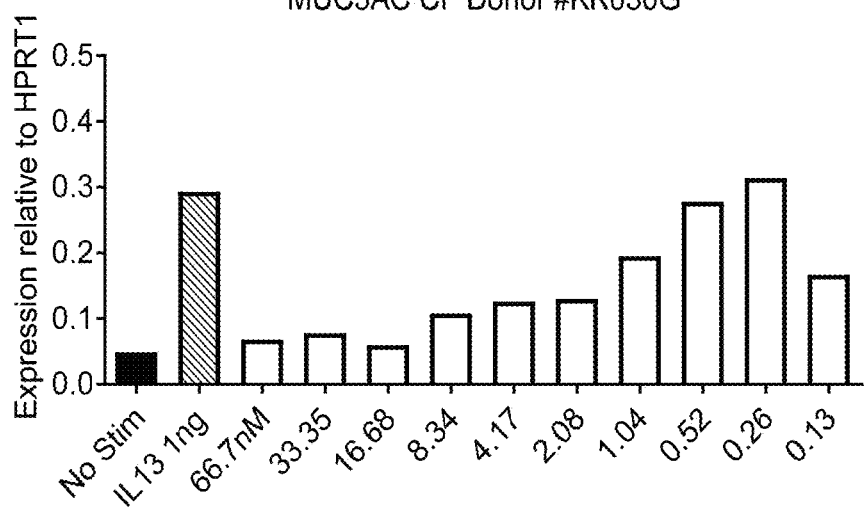
Figure 15G:
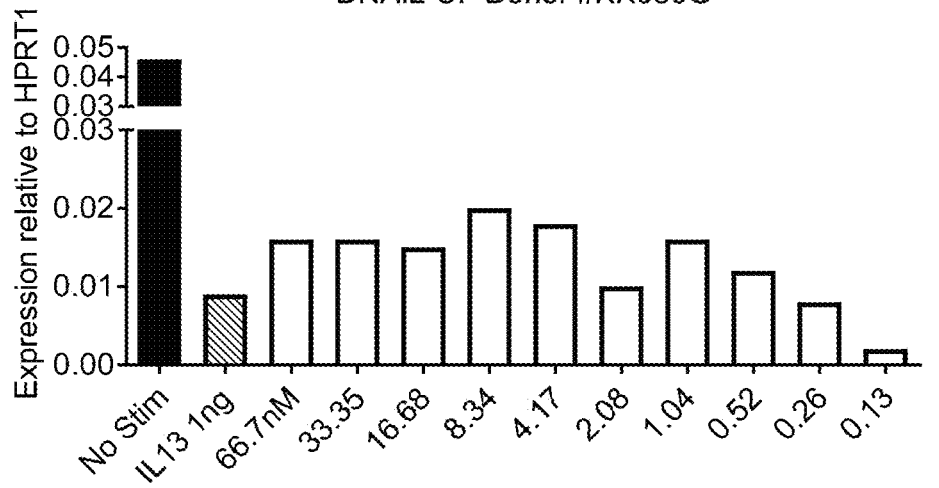
Figure 15H:
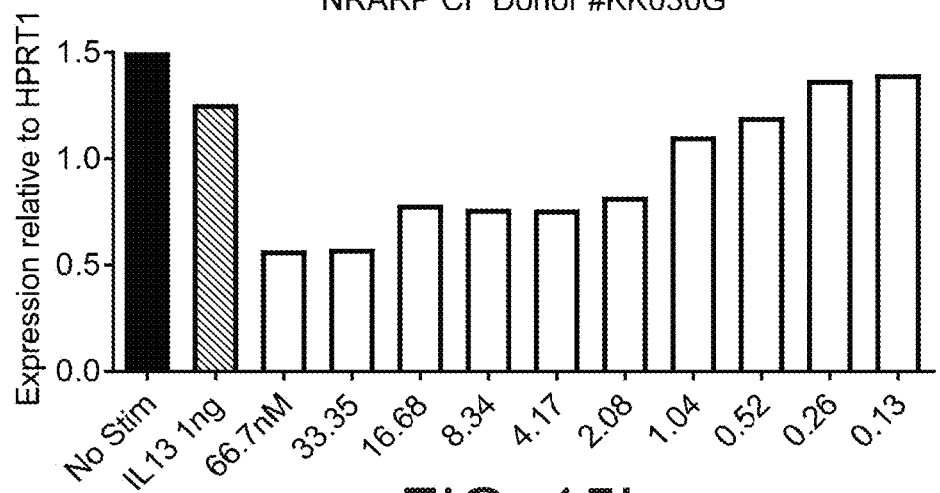
Figure 15I:
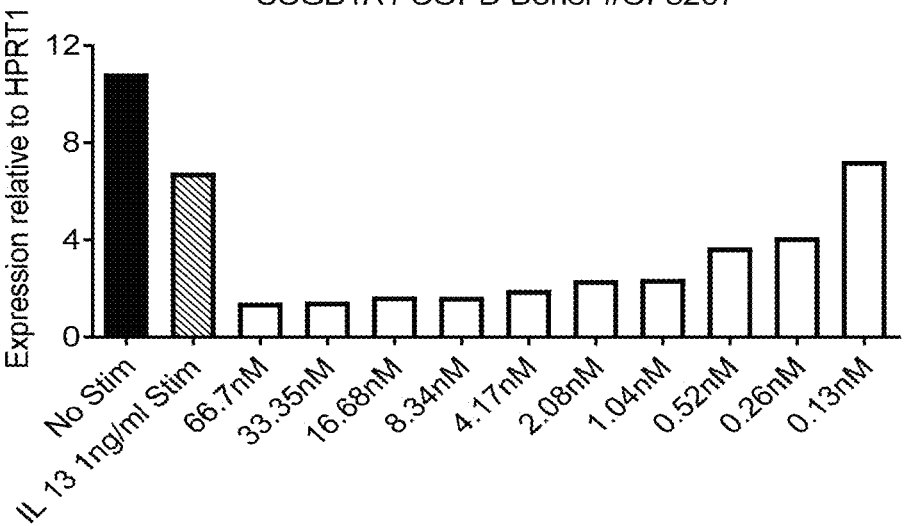
Figure 15J:
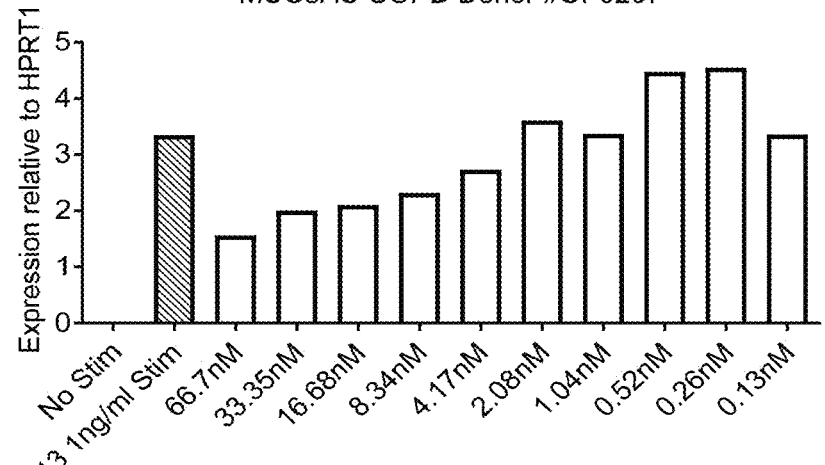
Figure 15K:
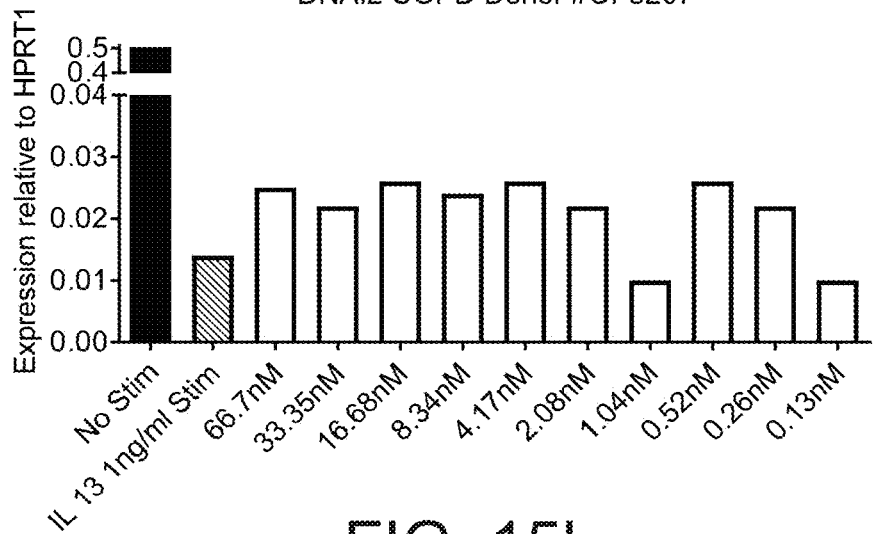
Figure 15L:
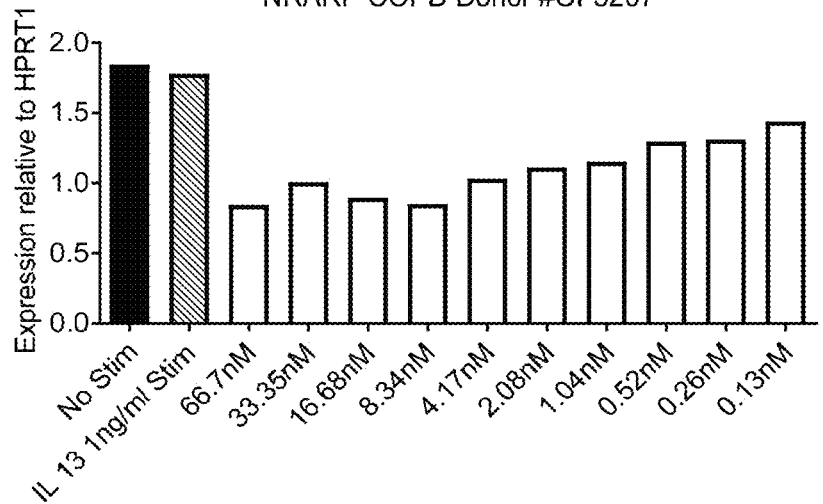

The anti-Jag1 mAb 15D11.1 reduced secretory cell (SCGB1A1; FIGS. 15A, E, and I), goblet cell (MUC5AC; FIGS. 15B, F, and J) and Notch activation (NRARP; FIGS. 14D, H, and L) marker expression in a dose dependent manner after 7 day treatment in IL-13 (1 ng/ml) stimulated bronchosphere cultures derived from normal, or diseased (CF and COPD) bronchial epithelial cells. Expression levels are expressed relative to the housekeeping gene HPRT1

Gene expression of 3D bronchosphere cultures was quantified using the QuantiGene Multiplex Assay (Affymetrix). 30 ul of Affymetrix lysis solution with Proteinase K was added to each well of 60 ul of bronchospheres at 2:1 ratio and incubated at 55 C for 30 min as per Danahay et al., 2015. A 80 ul sample of the lysates were transferred to 96 well plate provided by Affymetrix containing 20 ul of a hybridization solution with lysis mixture, proteinase K, blocking reagent and specific probe set and bead set 0/N at 55 C. The probe sets contained the target genes: DNAI2(NM_023036); FOXA3(NM_0044971); FOXJ1(NM_001454); HPRT1 (NM_000194); MUC5AC(NM_017511); MUC5B (NM_002458); NOTCH3(NM_000435); NRARP (NM_001004354); SCGB1A1(NM_003357) from Affymetrix Panel M17012501 or DNAI2(NM_023036); FOXJ1(NM_001454); HPRT1(NM_000194); MUC5AC (NM_017511); MUC5B(NM_002458); NRARP (NM_001004354); SCGB1A1(NM_003357); ANO1 (NM_018043); SLC26A4(NM_000441) from Afffymetrix Panel M18013101. The next day, wash solution, preamplifier solution, amplifier solution and label probe streptavidin-phycoerthythrin (SAPE) solution were prepared using the manufacturer's specifications. Plates were washed on a magnetic plate washer three times in between each step.

Each well was read on FlexMap 3D instrument (Luminex). To ensure that the levels were similar across the wells, the data was normalized against the house keeping gene HRPRT1.

Example 18: Prophylactic Dosing of Jag1 Antibody Inhibits the Expression of the Notch Signaling Pathway Gene NRARP and the Goblet Cell Marker Gene Muc5ac in the Mouse Goblet Cell Metaplasia Model Induced by Intratracheal Delivery of IL-13

Figure 16A:
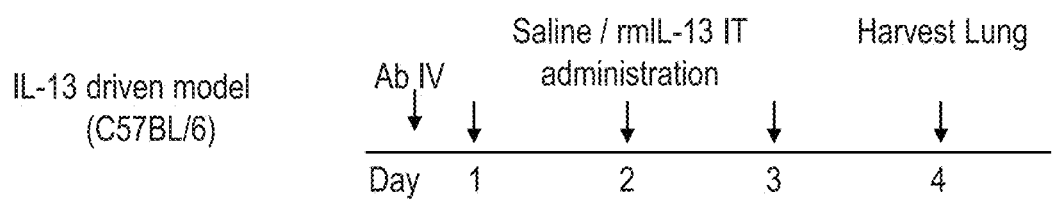
FIGS. 16A-16C show Prophylactic dosing of Jag1 antibody inhibits the expression of the Notch signaling pathway gene Nrarp and the goblet cell marker gene Muc5ac in the mouse goblet cell metaplasia model induced by intratracheal delivery of IL-13.
Figure 16B:
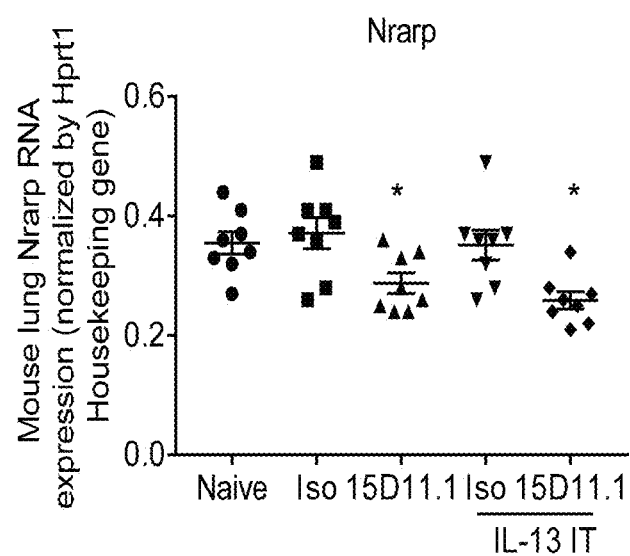
Figure 16C:
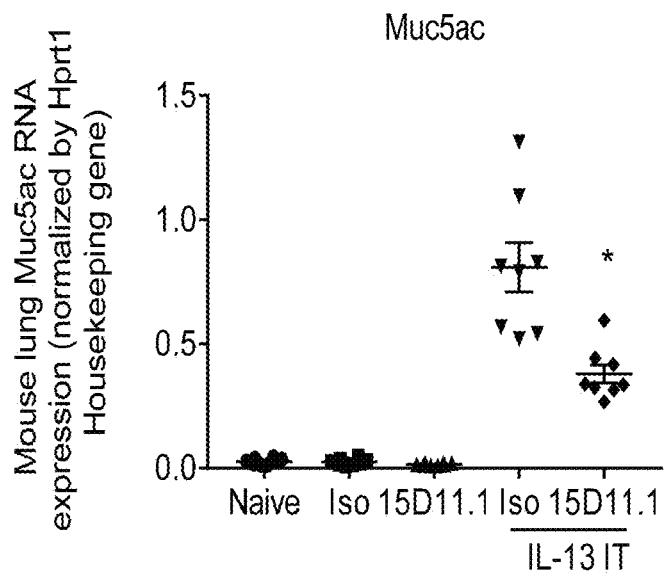

For intratracheal (IT) IL-13 administration, C57Bl/6 mice were anesthetized with 3-5% isoflurane to effect and dosed using a blunt gel loading pipette tip carefully inserted into the trachea through the mouth. Mice were suspended on a board using suture thread around the incisor as needed to visualize the trachea. 10 micrograms of mouse IL-13 was administered in 50 microliters of saline daily, for three days. On day 4 the lungs were harvested for RNA. Five groups of mice were used. Three groups were intratracheally administered saline and pretreated once on day 1 with nothing (Naïve), 100 mg/kg of isotype control antibody (Iso), or 100 mg/kg of 15D11.1. Two groups were intratracheally administered IL-13 and pretreated once on day 1 with 100 mg/kg of isotype control antibody (Iso) or 100 mg/kg of 15D11.1. A) The Notch signaling pathway gene Nrarp is down-regulated in the lungs of mice intratracheally challenged with saline or IL-13 when treated by 15D11.1 B) The goblet cell marker gene Muc5ac is upregulated in the lungs of mice intratracheally challenged with IL-13 and downregulated when treated by 15D11.1. See FIGS. 16A and B.

Example 19: Prophylactic Dosing of Jag1 Antibody Drives a Ciliated Airway Epithelial Cell Phenotype and Inhibits Goblet Cell Metaplasia in Ovalbumin Induced Asthma Model Mouse allergen induced pulmonary airway remodeling (goblet cell metaplasia) was measured in the ovalbumin induced mouse model of asthma. Five groups of eight mice (40 total mice) were used in this study. Adult female Balb/c mice (greater than 8 weeks of age) were sensitized and boosted by intraperitoneal (i.p.) injection of 0.2 ml of 2% aluminum hydroxide (ALUM) gel (Serva Electrophoretics, 12261, Heidelberg, Germany) with or without 10 µg of ovalbumin (OVA) antigen (Worthington Biochemical Corporation, LS003054, Lakewood, N.J.) on days 0 and 14. Group A was sensitized and boosted with 0.2 ml i.p. injections of a solution of one ml of 0.9% saline in 50 ml of ALUM gel. Groups B, C, D, and E were sensitized and boosted with 0.2 ml i.p. injections of a solution of 2.55 mg OVA dissolved in one ml of 0.9% saline in 50 ml of ALUM gel. Groups B, C, D, and E inhaled nebulized OVA to evoke antigen-induced lung inflammation and goblet cell metaplasia in the lungs. For nebulized OVA challenge, mice were placed in a plexiglass box and aerosolized OVA was nebulized into the box by a nebulizer (PARI Respiratory Equipment, LC STAR nebulizer and Proneb Ultra II compressor, Midlothian, VA) filled with 1% ovalbumin in saline (0.01 g/ml) for 20 minutes on days 21, 22, and 23. On day 26, a 20 minute nebulized OVA challenge with 5% ovalbumin in saline was conducted. Group A inhaled nebulized saline with no OVA. Groups A and B were dosed with Isotype control antibody (100 mg/kg, PL-35304) and groups, C (1 mg/kg), D (10 mg/kg) and E (100 mg/kg) were dosed with hu anti-<hu Jag-1> 15D11.1 Mab (PL-42541).mg/kg). All groups were dosed i.v. by the tail vein with a volume of 5 ml/kg on days 0, 7, 14, and 20. On day 27, the mice were euthanized and lungs were inflated with 10% neutral buffered formalin through a tracheal cannula. The inflated lungs were immersed in formalin for at least 24 h. After being processed into paraffin blocks, the lungs were sectioned (5 µm) and floated onto glass slides. The lung sections were stained with periodic acid-schiff (PAS) for assessment of mucin content.

Figure 17A:
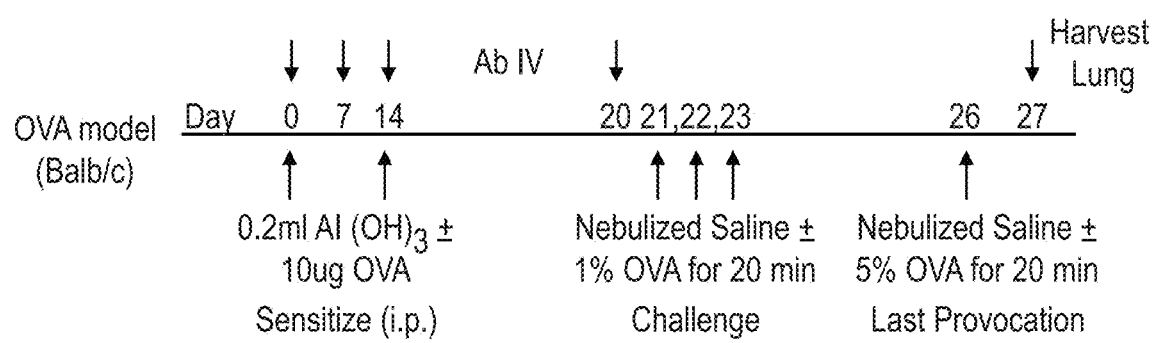
FIGS. 17A-17D show Prophylactic dosing of Jag1 antibody drives a ciliated airway epithelial cell phenotype and inhibits goblet cell metaplasia in ovalbumin induced asthma model.
Figure 17B:
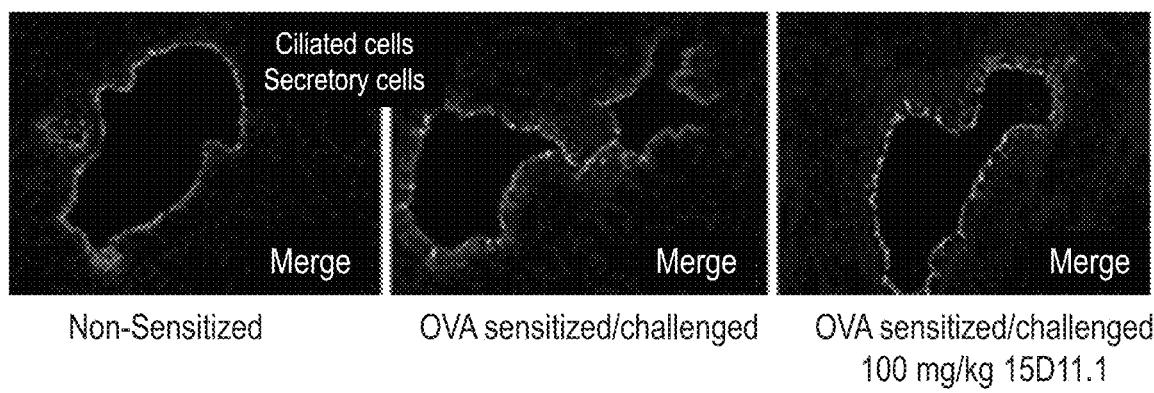
Figure 17C:
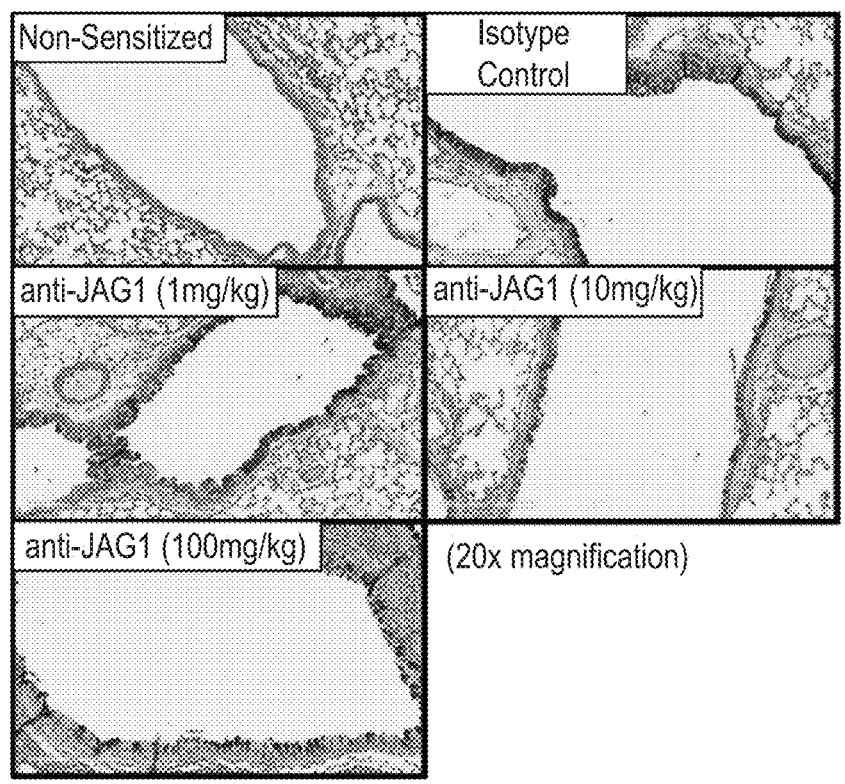
Figure 17D:
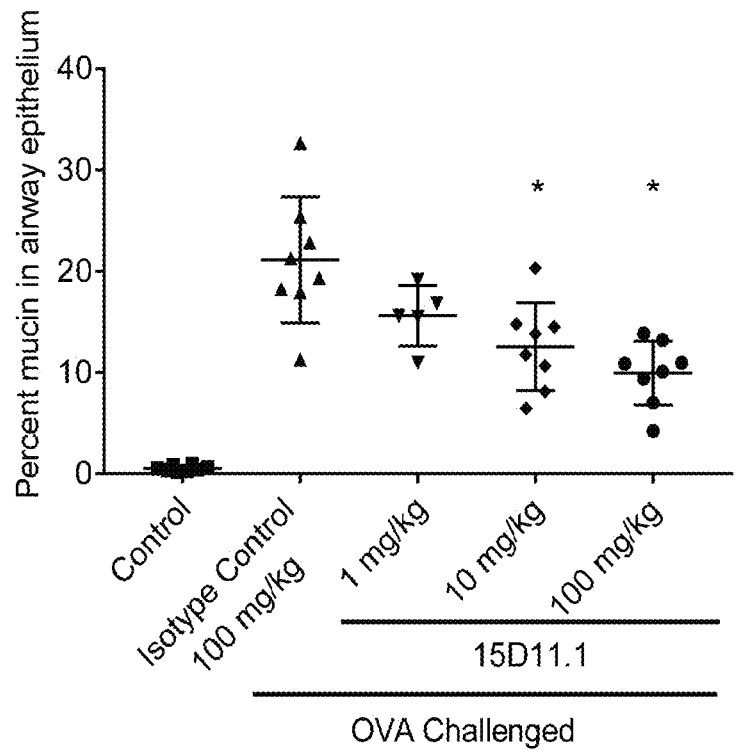

FIG. 17A) Dual immunofluorescent staining was used to visualize secretory and ciliated cell content of the airway epithelium. Non-sensitized and OVA sensitized/challenged airways have a predominately secretory cell phenotype where a more ciliated cell phenotype is observed in the OVA sensitized/challenged mice treated with 15D11.1. FIG. 17B) Representative images of airway epithelium with mucin stained by PAS. FIG. 17C) Mucin content, measured by stereologic technique, in the airway epithelium decreases in a dose dependent manner with 15D11.1 treatment.

Example 20: Therapeutic Dosing of Jag1 Neutralizing Ab in Ovalbumin Induced Asthma Model Inhibits Secretory Cell Gene Expression In the mouse OVA model of asthma, five groups of mice were dosed on day 22 (therapeutic dosing). One group was not sensitized to OVA and dosed with 100 mg/kg isotype control antibody (Saline-Iso). One group was sensitized/challenged with OVA and dosed 100 mg/kg isotype control antibody (Iso). Three groups of mice were sensitized/challenged with OVA and dosed with 10, 30, or 100 mg/kg of 15D11.1

Figure 18A:
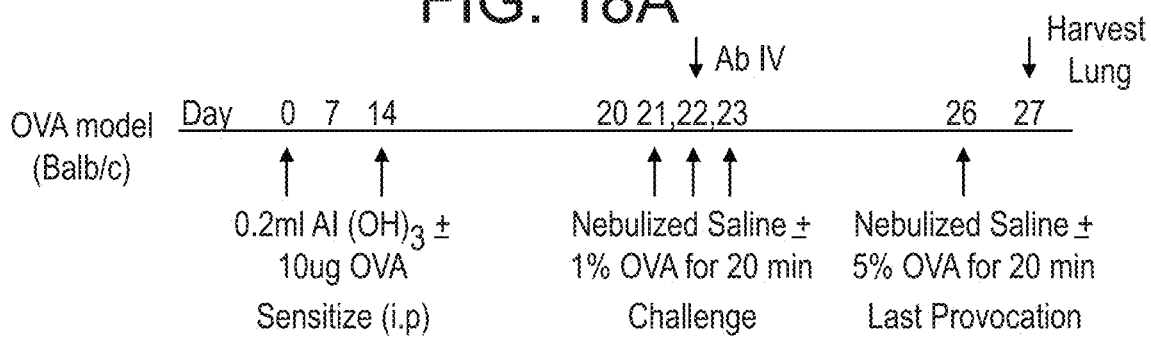
FIGS. 18A-18E show Therapeutic dosing of Jag1 neutralizing Ab in ovalbumin induced asthma model inhibits secretory cell gene expression.
Figure 18B:
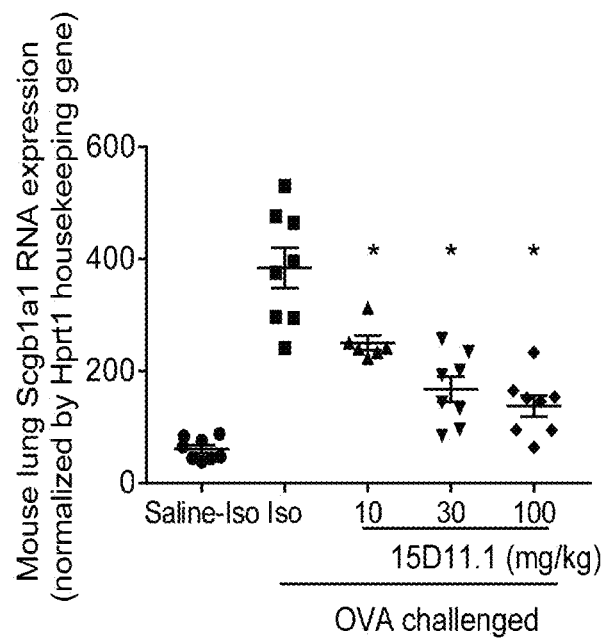
Figure 18C:
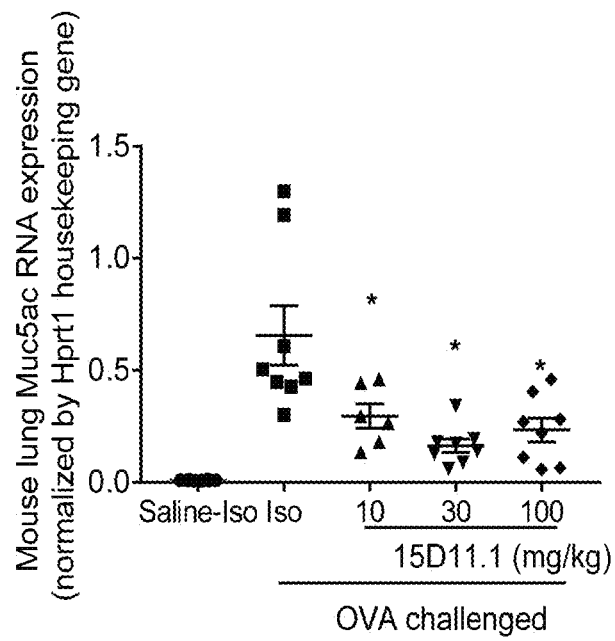
Figure 18D:
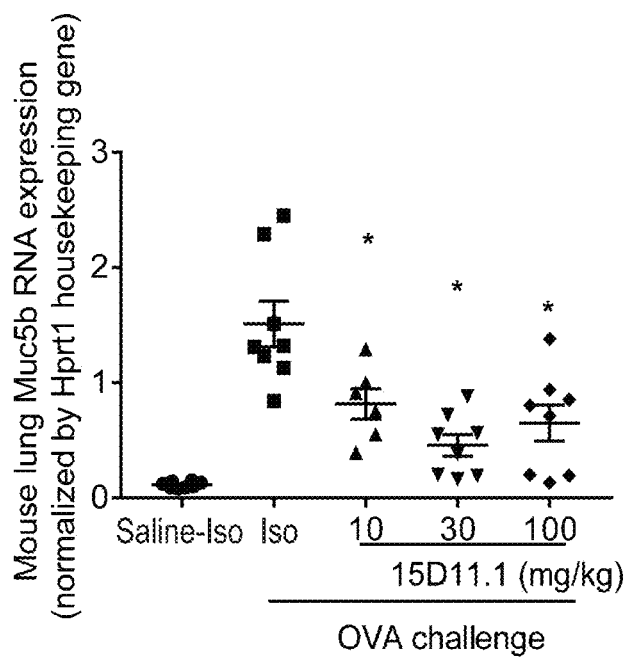
Figure 18E:
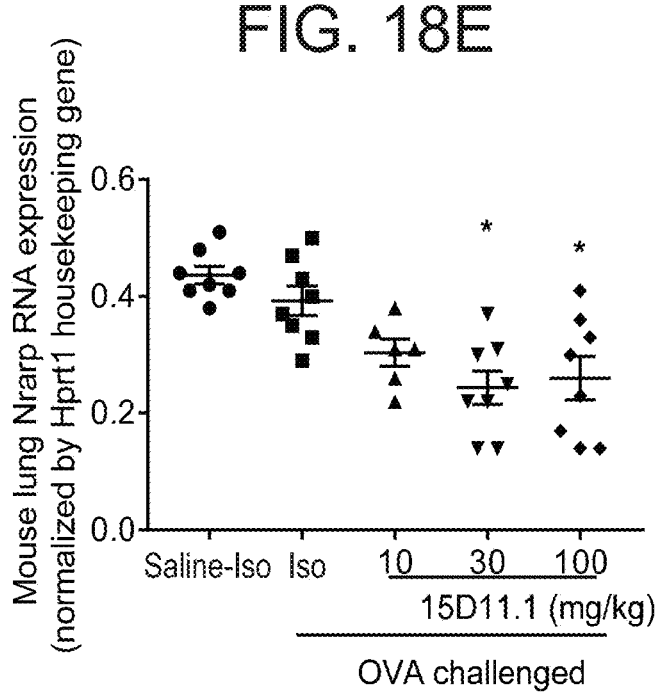

FIG. 18A) 15D11.1 inhibited expression of the secretory cell marker gene Scgb1a1 in mouse lung tissue in a dose dependent manner with an $ED_{50}$ between the 10 and 30 mg/kg doses. 15D11.1 also significantly inhibited the goblet cell marker genes FIG. 18B) Muc5ac, FIG. 18C) Muc5b, and FIG. 18D) the notch signaling pathway gene Nrarp.

Example 21: Jag1 Antibody Treatment Reduces Airway Mucus Obstruction in b-ENaC Transgenic Mouse Model of Muco-Obstructive Lung Disease b-ENaC transgenic (Tg) mice develop airway mucus obstruction (Livraghi-Butrico, A., et al., 2012, Genetically determined heterogeneity of lung disease in a mouse model of airway mucus obstruction. Physiol Genomics, 44: 470-484). 100 mg/kg of 15D11.1 or 100 mg/kg of isotype control antibody were delivered once a week for three weeks to b-ENaC transgenic (Tg) mice and wild type littermate controls. Lungs were harvested four weeks after the first antibody dose and embedded in paraffin, sectioned, and stained with PAS for mucus. The severity of lung pathology was graded semiquantitatively on a scale ranging from 0 to 3 for the airway mucus plug score: 0 normal lung, 1 scant PAS positive material lining epithelium in the medium/large airways, 2 mild amount of PAS positive material and no more than 1 obstructed medium sized airway, 3 moderate amount of PAS positive material and more than 1 obstructed medium sized airway.

Figure 19A:
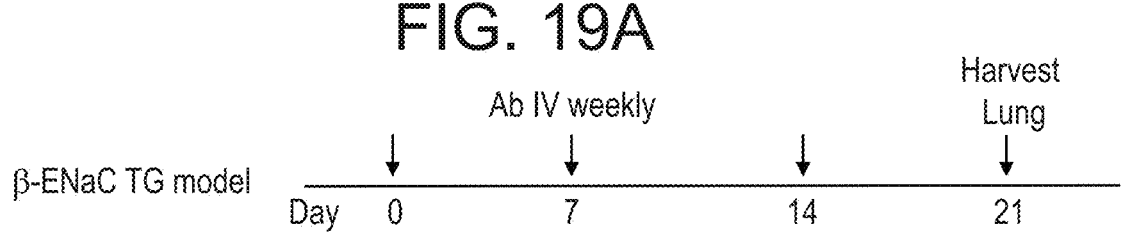
FIGS. 19A-19C show Jag1 antibody treatment reduces airway mucus obstruction in b-ENaC transgenic mouse model of muco-obstructive lung disease.
Figure 19B:
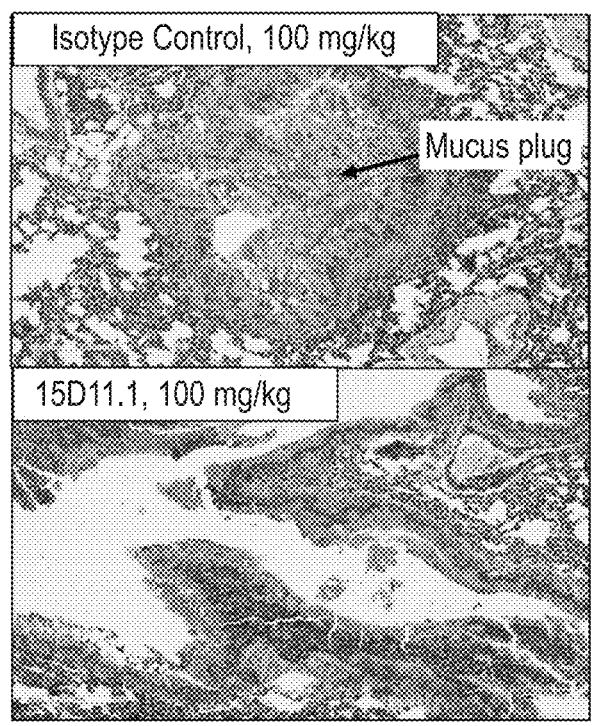
Figure 19C:
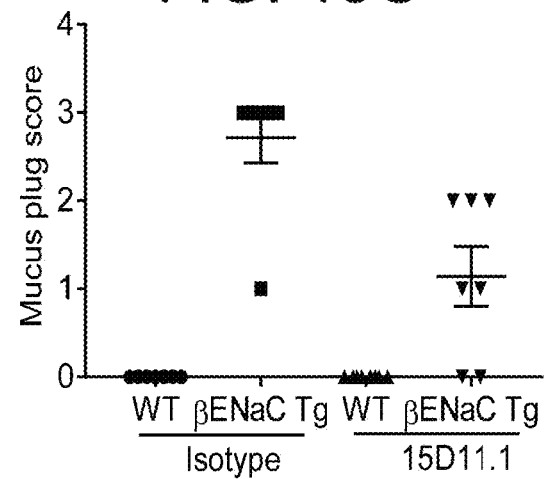

FIG. 19A) Representative images of airway epithelium with mucin stained by PAS. FIG. 19B) Mucus plug score was decreased in the lungs by 15D11.1 treatment.

Example 22: Dosing of Jag1 Antibody Inhibits Reduced Mucin Content in the Respiratory Epithelium of Monkeys 4 weekly doses of 15D11.1 50 mg/kg SC given to cynomolgus monkeys. On day 28 after the first dose, the monkeys were euthanized and lungs processed and stained with PAS for assessment of mucin content.

Representative images of cynomolgus monkey airway epithelium with mucin stained by PAS. 15D11.1 reduced mucin content (i.e. goblet cell number) in the respiratory epithelium (FIGS. 20D-F) compared to monkeys dosed with vehicle alone (FIGS. 20A-C).

Example 23: Pharmacokinetics of 15D11.1 Antibody

The pharmacokinetic profile of different dose levels of 15D11.1 antibody after a single intravenous (IV) or subcutaneous (SC) injection was evaluated in BALB/c mice and cynomologus monkeys. Serum samples were collected and antibody concentrations were analyzed by an enzyme linked immunosorbent assay.

Figure 21A:
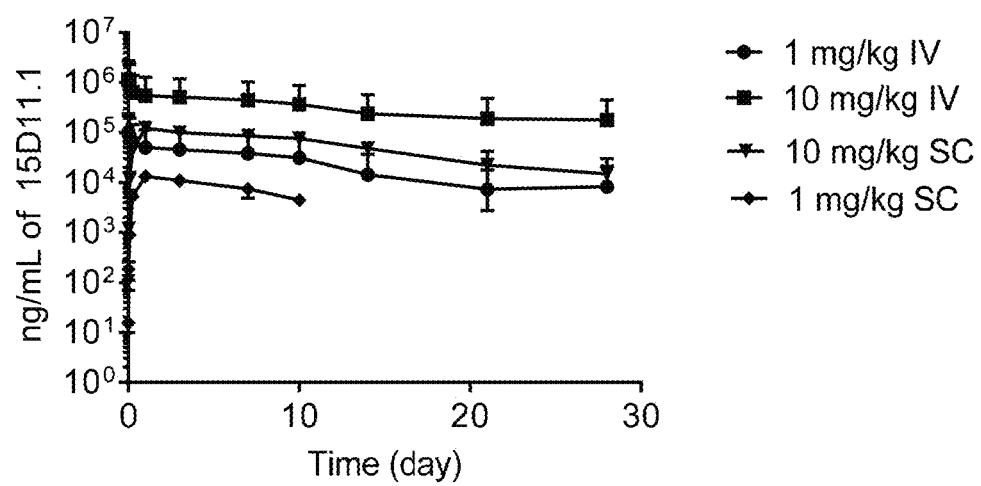
FIGS. 21A-21B show Pharmacokinetics of 15D11.1 antibody.
Figure 21B:
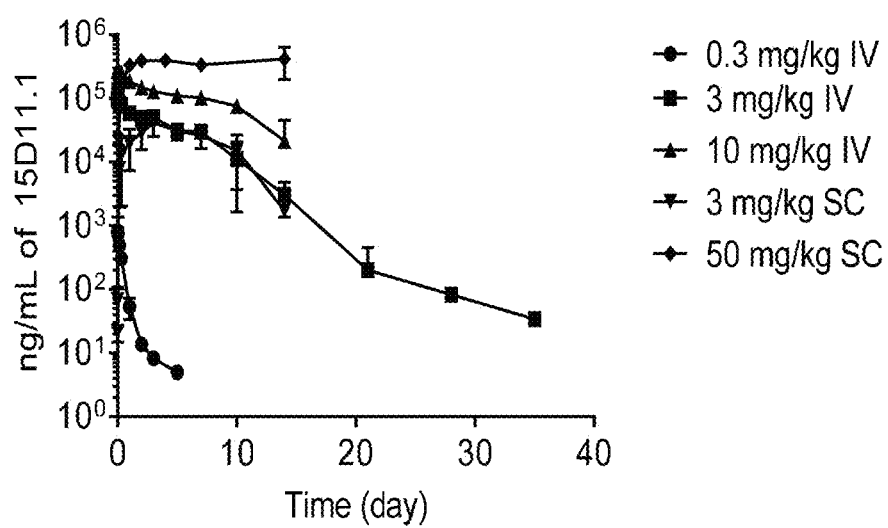

Clearance of 15D11.1 antibody after a single intravenous or subcutaneous administration of different doses of the antibody to FIG. 21A) mice and FIG. 21B) cynomolgus monkeys. The clearance profiles in cynomolgus monkeys exhibited target-mediated disposition at doses less than 10 mg/kg.

What is claimed is:

1. An isolated antigen binding protein that specifically binds to a human Jagged1 polypeptide, wherein the antigen binding protein is an antibody or a fragment thereof, and wherein the antibody comprises a CDRL1, a CDRL2, a CDRL3, a CDRH1, a CDRH2, and a CDRH3, wherein each CDRL1, CDRL2, CDRL3, CDRH1, CDRH2, and CDRH3, respectively, comprises a sequence selected from the group consisting of SEQ ID NO: 98, SEQ ID NO: 99, SEQ ID NO: 100, SEQ ID NO: 230, SEQ ID NO: 231, and SEQ ID NO: 232.

2. The isolated antigen binding protein of claim 1, wherein the human Jagged1 has a sequence comprising SEQ ID NO: 353.

3. The isolated antigen binding protein of claim 1, wherein the antigen binding protein is a monoclonal antibody, a polyclonal antibody, a recombinant antibody, a human antibody, a humanized antibody, a chimeric antibody, a multispecific antibody, or an antibody fragment thereof.

4. The isolated antigen binding protein of claim 3, wherein the antibody fragment is a Fab fragment, a Fab' fragment, or a F(ab')2 fragment.

5. The isolated antigen binding protein of claim 3, wherein the antigen binding protein is a human antibody.

6. The isolated antigen binding protein of claim 3, wherein the antigen binding protein is a monoclonal antibody.

7. The isolated antigen binding protein of claim 3, wherein the antigen binding protein is of the IgG1-, IgG2- IgG3- or IgG4-type.

8. The isolated antigen binding protein of claim 7, wherein the antigen binding protein is of the IgG1- or the IgG2-type.

9. The isolated antigen binding protein of claim 3, wherein the antigen binding protein is coupled to a labeling group.

10. The isolated antigen binding protein of claim 3, wherein the antigen binding protein is an antibody or a fragment thereof, and wherein the antibody or fragment thereof comprises a combination of a light chain variable region and a heavy chain variable region wherein the light chain variable region comprises SEQ ID NO: 7 and the heavy chain variable region comprises SEQ ID NO: 8.

11. A pharmaceutical composition comprising at least one antibody or fragment thereof according to claim 1, and pharmaceutically acceptable excipient.

* * * * *

```
                             SEQUENCE LISTING

<160> NUMBER OF SEQ ID NOS: 370

<210> SEQ ID NO 1
<211> LENGTH: 321
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 1
gacatccaga tgacccagtc tccatcttcc gtgtctgcat ctgtaggaga cagagtcacc    60
atcacttgtc gggcgagtca gggtattagc gactggttag cctggtatca gcagaaacca   120
gggaaagccc ctaagctcct gatctttgct gcatccagtt tgcaaagtgg ggtcccatcc   180
aggttcagcg gcagtgaatc tgggacagat ttcactctca ccatcagcag cctgcagcct   240
gaagattttg caacttacta ttgtcaacag gctaacagtt tcccgatcac cttcggccaa   300
gggacacgac tggagattca a                                             321

<210> SEQ ID NO 2
<211> LENGTH: 357
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 2
caggtgcagc tggtggagtc tgggggaggc gtggtccagc ctgggaggtc cctgagactc    60
tcctgtgcag cgtctggatt caccttcagt agttatggca tgcactgggt ccgccaggct   120
ccaggcaagg ggctggagtg ggtggcagtt atatggtatg atggaagtaa tgaatactat   180
gcagactccg tgaagggccg attcaccatc tccagagaca attccaagaa cacgctgtat   240
ctgcaaatga acagcctgag agccgaggac acggctgtgt attactgtgc gagacatgac   300
cacagtcact acggttttga ctactggggc cagggaaccc tggtcaccgt atcctca      357

<210> SEQ ID NO 3
<211> LENGTH: 107
<212> TYPE: PRT
<213> ORGANISM: ARTIFICIAL SEQUENCE
<220> FEATURE:
<223> OTHER INFORMATION: Antibody or a portion thereof.

<400> SEQUENCE: 3

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Asp Trp
            20                  25                  30
```

Leu Ala Trp Tyr Gln Gln Lys Pro Gly Lys Ala Pro Lys Leu Leu Ile
            35                  40                  45

Phe Ala Ala Ser Ser Leu Gln Ser Gly Val Pro Ser Arg Phe Ser Gly
        50                  55                  60

Ser Glu Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Ile
                85                  90                  95

Thr Phe Gly Gln Gly Thr Arg Leu Glu Ile Gln
            100                 105

<210> SEQ ID NO 4
<211> LENGTH: 119
<212> TYPE: PRT
<213> ORGANISM: ARTIFICIAL SEQUENCE
<220> FEATURE:
<223> OTHER INFORMATION: Antibody or a portion thereof.

<400> SEQUENCE: 4

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Glu Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Asp His Ser His Tyr Gly Phe Asp Tyr Trp Gly Gln Gly
            100                 105                 110

Thr Leu Val Thr Val Ser Ser
        115

<210> SEQ ID NO 5
<211> LENGTH: 330
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 5
cagtctgccc tgactcagcc tgcctccgtg tctgggtctc ctggacagtc gatcaccatc      60
tcctgcactg gaaccagcag tgccgttggt ggtcataact tgtctcctg gtaccaacag      120 tacccaggca agcccccaa actcatgatt tatgaggtca gtaatcggcc ctcaggggtt      180
tctactcgct tctctggctc caagtctggc aacacggcct ccctgaccat ctctgggctc      240
caggctgagg acgaggctga ttattactgc agctcttata caagcagcag cacttgggtg      300
ttcggcggag ggaccaggct gaccgtccta                                       330

<210> SEQ ID NO 6
<211> LENGTH: 360
<212> TYPE: DNA
<213> ORGANISM: ARTIFICIAL SEQUENCE
<220> FEATURE:

<223> OTHER INFORMATION: Polynucleotide encoding the antibody or a
      portion thereof.

<400> SEQUENCE: 6
caggtcacct tgaaggagtc tggtcctgtg ctggtgaaac ccacagagac cctcacgctg    60
acctgcaccg tctctgggtt ctcactcagc aatgctgaaa tgggtgtgag ctggatccgt   120
cagcccccag ggaaggccct ggagtggctt gcacaccttt tttcgaatga cgaaaaatcc   180
tacagcacat ctctgaagag caggctcacc atctccaagg acacctccaa aagccaggtg   240
gtccttacca tgaccgacct ggaccctgtg acacagcca cctattactg tgcacggtcg   300
tttaactgga actacgactt tgactactgg ggccagggaa ccctggtcac cgtctcctca   360

<210> SEQ ID NO 7
<211> LENGTH: 110
<212> TYPE: PRT
<213> ORGANISM: ARTIFICIAL SEQUENCE
<220> FEATURE:
<223> OTHER INFORMATION: Antibody or a portion thereof.

<400> SEQUENCE: 7

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Ala Val Gly Gly His
                20                  25                  30

Asn Phe Val Ser Trp Tyr Gln Gln Tyr Pro Gly Lys Ala Pro Lys Leu
            35                  40                  45

Met Ile Tyr Glu Val Ser Asn Arg Pro Ser Gly Val Ser Thr Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Trp Val Phe Gly Gly Gly Thr Arg Leu Thr Val Leu
                100                 105                 110

<210> SEQ ID NO 8
<211> LENGTH: 120
<212> TYPE: PRT
<213> ORGANISM: ARTIFICIAL SEQUENCE
<220> FEATURE:
<223> OTHER INFORMATION: Antibody or a portion thereof.

<400> SEQUENCE: 8

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Asn Ala
                20                  25                  30

Glu Met Gly Val Ser Trp Ile Arg Gln Pro Pro Gly Lys Ala Leu Glu
            35                  40                  45

Trp Leu Ala His Leu Phe Ser Asn Asp Glu Lys Ser Tyr Ser Thr Ser
    50                  55                  60

Leu Lys Ser Arg Leu Thr Ile Ser Lys Asp Thr Ser Lys Ser Gln Val
65                  70                  75                  80

Val Leu Thr Met Thr Asp Leu Asp Pro Val Asp Thr Ala Thr Tyr Tyr
                85                  90                  95

Cys Ala Arg Ser Phe Asn Trp Asn Tyr Asp Phe Asp Tyr Trp Gly Gln
                100                 105                 110

Gly Thr Leu Val Thr Val Ser Ser
        115                 120

<210> SEQ ID NO 9
<211> LENGTH: 318
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 9

| | | | | | |
|---|---|---|---|---|---|
| gaaatagtga | tgacgcagtc | tccagccacc | ctgtctgtgt | ctccagggga | aagagccacc | 60 |
| ctctcctgca | gggccagtca | gagtgttagg | agcaacttag | cctggtacca | gcagaaagct | 120 |
| ggccaggctc | ccaggctcct | catcgatggt | gcatccacca | gggccactgg | cataacagcc | 180 |
| aggttcagtg | gcagtgggtc | tgggacagag | ttcactctca | ccatcagcag | cctgcagtct | 240 |
| gaagattttg | cagtttatta | ctgtcagcag | tataataact | ggcctacttt | cggccctggg | 300 |
| accaaagtgg | atatcaaa | | | | | 318 |

<210> SEQ ID NO 10
<211> LENGTH: 354
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 10

| | | | | | |
|---|---|---|---|---|---|
| cagctgcagc | tgcaggagtc | gggcccagga | ctggtgaagc | cttcggagac | cctgtccctc | 60 |
| acctgcactg | tctctggtgg | ctccatcagc | agtggtagtt | actactgggg | ctggatccgc | 120 |
| cagcccccag | ggaaggggct | ggagtggatt | gggagtatct | attatggtgg | gaacacctac | 180 |
| tacaacccgt | ccctcaagag | tcgagtcacc | atatccatag | acacgtccaa | gaaccagttc | 240 |
| tccctgaagc | tgagctctgt | gaccgccgca | gacacggctg | tgtattactg | tgcgggagaa | 300 |
| ctgcggaggg | cttttgatat | ctggggccaa | gggacaatgg | tcaccgtctc | ttca | 354 |

<210> SEQ ID NO 11
<211> LENGTH: 106
<212> TYPE: PRT
<213> ORGANISM: ARTIFICIAL SEQUENCE
<220> FEATURE:
<223> OTHER INFORMATION: Antibody or a portion thereof.

<400> SEQUENCE: 11

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Arg Ser Asn
            20                  25                  30

Leu Ala Trp Tyr Gln Gln Lys Ala Gly Gln Ala Pro Arg Leu Leu Ile
        35                  40                  45

Asp Gly Ala Ser Thr Arg Ala Thr Gly Ile Thr Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Thr
                85                  90                  95

Phe Gly Pro Gly Thr Lys Val Asp Ile Lys
            100                 105

<210> SEQ ID NO 12
<211> LENGTH: 118
<212> TYPE: PRT
<213> ORGANISM: ARTIFICIAL SEQUENCE
<220> FEATURE:
<223> OTHER INFORMATION: Antibody or a portion thereof.

<400> SEQUENCE: 12

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Gly
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Gly Gly Asn Thr Tyr Tyr Asn Pro Ser
    50                  55                  60

Leu Lys Ser Arg Val Thr Ile Ser Ile Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Gly Glu Leu Arg Arg Ala Phe Asp Ile Trp Gly Gln Gly Thr
            100                 105                 110

Met Val Thr Val Ser Ser
        115

<210> SEQ ID NO 13
<211> LENGTH: 333
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 13
aattttatgc tgactcagcc ccactctgtg tcggagtctc cggggaagac ggtaaccatc      60
tcctgcaccc gcagcagtga cagcattgcc agcaactatg tgcagtggta ccagcagcgc    120
ccgggcagtt cccccaccac tgtgatcttt gaggataacc aaagacccct ctggggtccct   180 gatcggttct ctggctccat cgacagctcc tccaactctg cctccctcac catctctgga   240
ctgaagcctg aggacgaggc tgactactac tgtcagtctt atgatagcag caatcatgtg    300
gtattcggcg agggaccaa gctgaccgtc cta                                   333

<210> SEQ ID NO 14
<211> LENGTH: 363
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 14
caggtgcagc tggtggagtc tgggggaggc gtggtccagc ctggagggtc cctgagactc      60
tcctgtgcag cgtctggatt caccttcagt tactatggca tgcactgggt ccgccaggct    120
ccaggcaagg ggctggagtg ggtggcagtt atatggtatg atggaagtaa taaatactat    180
gcagactccg tgaagggccg attcaccatc tccagagaca attccaagaa cacgctgtat    240
ctgcaaatga acagcctgag agccgaggac acggctgtgt attactgtgc gagagatcat    300

```
gactacggtg tcctgtacta ctttgactac tggggccagg gaaccctggt caccgtctcc    360
tca                                                                  363
```

<210> SEQ ID NO 15
<211> LENGTH: 111
<212> TYPE: PRT
<213> ORGANISM: ARTIFICIAL SEQUENCE
<220> FEATURE:
<223> OTHER INFORMATION: Antibody or a portion thereof.

<400> SEQUENCE: 15

```
Asn Phe Met Leu Thr Gln Pro His Ser Val Ser Glu Ser Pro Gly Lys
1               5                   10                  15

Thr Val Thr Ile Ser Cys Thr Arg Ser Ser Asp Ser Ile Ala Ser Asn
            20                  25                  30

Tyr Val Gln Trp Tyr Gln Arg Pro Gly Ser Ser Pro Thr Thr Val
        35                  40                  45

Ile Phe Glu Asp Asn Gln Arg Pro Ser Gly Val Pro Asp Arg Phe Ser
    50                  55                  60

Gly Ser Ile Asp Ser Ser Asn Ser Ala Ser Leu Thr Ile Ser Gly
65                  70                  75                  80

Leu Lys Pro Glu Asp Glu Ala Asp Tyr Tyr Cys Gln Ser Tyr Asp Ser
                85                  90                  95

Ser Asn His Val Val Phe Gly Gly Gly Thr Lys Leu Thr Val Leu
            100                 105                 110
```

<210> SEQ ID NO 16
<211> LENGTH: 121
<212> TYPE: PRT
<213> ORGANISM: ARTIFICIAL SEQUENCE
<220> FEATURE:
<223> OTHER INFORMATION: Antibody or a portion thereof.

<400> SEQUENCE: 16

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Tyr Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp His Asp Tyr Gly Val Leu Tyr Tyr Phe Asp Tyr Trp Gly
            100                 105                 110

Gln Gly Thr Leu Val Thr Val Ser Ser
        115                 120
```

<210> SEQ ID NO 17
<211> LENGTH: 318
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 17

```
tcctttgaac tgacacagcc accctcggtg tcagtgtccc caggacagac ggccaggatc    60
acctgctctg gagatgcatt gccaaagcaa tatgcttatt ggtaccggca gaagccaggc   120 caggccctg tactggtaat atataaagac agtgagaggc cctcagggat ccatgagcga   180
ttctctggct ccacctcagg gacaacagtc acgttgacca tcagtggagt ccaggcagaa   240
gacgaggctg actattactg tcaatcaaca gacagaagag gtactgtgtt cggcggaggg   300
accaagttga ccgtccta                                                 318

<210> SEQ ID NO 18
<211> LENGTH: 369
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 18
cagatcacct tgaaggagtc tggtcctacg ctggtgaaac ccacacagac cctcacgctg    60
acctgcacct tctctgggtt ctcactcagc actagtggag tgggtgtggg ctggatccgt   120
cagcccccag gaaaggccct ggagtggctt gcactcattt attggaatga tgataagcgc   180
tacagcccat ctctgaagag caggctcacc atcaccaagg acacctccaa aaaccaggtg   240
gtccttacaa tgaccaacat ggaccctgtg gacacagcca catattactg tgcacacaga   300
catggctacg ataggatgcg tgatgctttt gatatctggg gccaaggggac aatggtcacc   360 gtctcttca                                                           369

<210> SEQ ID NO 19
<211> LENGTH: 106
<212> TYPE: PRT
<213> ORGANISM: ARTIFICIAL SEQUENCE
<220> FEATURE:
<223> OTHER INFORMATION: Antibody or a portion thereof.

<400> SEQUENCE: 19

Ser Phe Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
            20                  25                  30

Tyr Trp Tyr Arg Gln Lys Pro Gly Gln Ala Pro Val Leu Val Ile Tyr
        35                  40                  45

Lys Asp Ser Glu Arg Pro Ser Gly Ile His Glu Arg Phe Ser Gly Ser
    50                  55                  60

Thr Ser Gly Thr Thr Val Thr Leu Thr Ile Ser Gly Val Gln Ala Glu
65                  70                  75                  80

Asp Glu Ala Asp Tyr Tyr Cys Gln Ser Thr Asp Arg Arg Gly Thr Val
                85                  90                  95

Phe Gly Gly Gly Thr Lys Leu Thr Val Leu
            100                 105

<210> SEQ ID NO 20
<211> LENGTH: 123
<212> TYPE: PRT
<213> ORGANISM: ARTIFICIAL SEQUENCE
<220> FEATURE:
<223> OTHER INFORMATION: Antibody or a portion thereof.

<400> SEQUENCE: 20
```

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Leu Ile Tyr Trp Asn Asp Asp Lys Arg Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
            85                  90                  95

Cys Ala His Arg His Gly Tyr Asp Arg Met Arg Asp Ala Phe Asp Ile
            100                 105                 110

Trp Gly Gln Gly Thr Met Val Thr Val Ser Ser
        115                 120

<210> SEQ ID NO 21
<211> LENGTH: 321
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 21
gaaattgtgt tgacgcagtc tccagacacc ctgtctttgt ctccagggga aagagccacc      60
ctctcctgca gggccagtca gattttagc agcagttact tagcctggta ccagcagaaa     120
cctggccagg ctcccaggct cctcatctct ggtgcatcca gcagggccac tggcatccca    180
gacaggttca gtggcagtgg gtctgggtca gacttcactc tcaccatcag cagactggag    240
cctgaggatt ttgcagtgta ttactgtcag cagtatggta gctcatgcag ttttggccag    300
gggaccaagc tggagatcaa a                                              321

<210> SEQ ID NO 22
<211> LENGTH: 381
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 22
caggtgcagt tggtgcagtc tggggctgag gtgaagaagc ctggggcctc agtgaaggtt     60
tcctgcaagg catctggata caccttcacc agctacttta tacactgggt gcgacaggcc   120
cctggacaag gcttgagtg gatgggaata atcaaccctg tggtggtag cacaagctac    180 gcacagaagt tccagggcag agtcaccatg accaggggaca cgtccacgag tacagtctac    240
atggagctta gcagcctgag atctgaggac acggccgtgt attactgtgc gagagatcag    300
gagggagcag tggctggtac agactactac ttctacggta tggacgtctg gggccaaggg    360
accacggtca ccgtctcctc a                                             381

<210> SEQ ID NO 23
<211> LENGTH: 107
<212> TYPE: PRT
<213> ORGANISM: ARTIFICIAL SEQUENCE
<220> FEATURE:
<223> OTHER INFORMATION: Antibody or a portion thereof.

<400> SEQUENCE: 23

Glu Ile Val Leu Thr Gln Ser Pro Asp Thr Leu Ser Leu Ser Pro Gly
1               5                   10                  15

Glu Arg Ala Thr Leu Ser Cys Arg Ala Ser Gln Ile Phe Ser Ser Ser
            20                  25                  30

Tyr Leu Ala Trp Tyr Gln Gln Lys Pro Gly Gln Ala Pro Arg Leu Leu
        35                  40                  45

Ile Ser Gly Ala Ser Ser Arg Ala Thr Gly Ile Pro Asp Arg Phe Ser
    50                  55                  60

Gly Ser Gly Ser Gly Ser Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Cys
                85                  90                  95

Ser Phe Gly Gln Gly Thr Lys Leu Glu Ile Lys
            100                 105

<210> SEQ ID NO 24
<211> LENGTH: 127
<212> TYPE: PRT
<213> ORGANISM: ARTIFICIAL SEQUENCE
<220> FEATURE:
<223> OTHER INFORMATION: Antibody or a portion thereof.

<400> SEQUENCE: 24

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Phe Ile His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gln Glu Gly Ala Val Ala Gly Thr Asp Tyr Tyr Phe Tyr
            100                 105                 110

Gly Met Asp Val Trp Gly Gln Gly Thr Thr Val Thr Val Ser Ser
        115                 120                 125

<210> SEQ ID NO 25
<211> LENGTH: 336
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 25
gatattgtga tgactcagtc tccactctcc ctgcccgtca cccctggaga gccggcctcc      60
atctcctgca ggtctagtca gagcctccta catagtcatg gatacagcta tttgaattgg     120
tacctgcaga agccagggca gtctccacag ctcctgatcc atttgggttc taatcgggcc     180
tccggggtcc ctgacaggtt cagtggcagt ggatcaggca cagaatttac actgagaatc     240
agcagagtgg aggctgagga tgttgggggtt tattactgca tgcaagttct gctaactccg     300
atcaccctcg gccaagggac acgactggag attaaa         336

<210> SEQ ID NO 26
<211> LENGTH: 360
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 26
caggtgcagc tggtggagtc tgggggaggc gtggtccagc ctggagggtc cctgagactc      60
tcctgtgcag cctctggatt caccttcagt agctatggca tgcactgggt ccgccaggct     120
ccaggcaagg ggctggagtg ggtggcagtt atatcatatg atggaaataa taaatactat     180
gcagactccg tgaagggccg attcaccatc tccagagaca attccaagac cacgctgtat     240
ctgcaaatga acagcctgag acctgaggac acggctgtgt tttactgtgc gagagatgcc     300
agtgggagct ccctctacct tgactactgg ggccagggaa ccctggtcac cgtctcctca     360

<210> SEQ ID NO 27
<211> LENGTH: 112
<212> TYPE: PRT
<213> ORGANISM: ARTIFICIAL SEQUENCE
<220> FEATURE:
<223> OTHER INFORMATION: Antibody or a portion thereof.

<400> SEQUENCE: 27

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

His Gly Tyr Ser Tyr Leu Asn Trp Tyr Leu Gln Lys Pro Gly Gln Ser
        35                  40                  45

Pro Gln Leu Leu Ile His Leu Gly Ser Asn Arg Ala Ser Gly Val Pro
    50                  55                  60

Asp Arg Phe Ser Gly Ser Gly Ser Gly Thr Glu Phe Thr Leu Arg Ile
65                  70                  75                  80

Ser Arg Val Glu Ala Glu Asp Val Gly Val Tyr Tyr Cys Met Gln Val
                85                  90                  95

Leu Leu Thr Pro Ile Thr Leu Gly Gln Gly Thr Arg Leu Glu Ile Lys
            100                 105                 110

<210> SEQ ID NO 28
<211> LENGTH: 120
<212> TYPE: PRT
<213> ORGANISM: ARTIFICIAL SEQUENCE
<220> FEATURE:
<223> OTHER INFORMATION: Antibody or a portion thereof.

<400> SEQUENCE: 28

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Thr Thr Leu Tyr

```
                65                  70                  75                  80
Leu Gln Met Asn Ser Leu Arg Pro Glu Asp Thr Ala Val Phe Tyr Cys
                    85                  90                  95

Ala Arg Asp Ala Ser Gly Ser Ser Leu Tyr Leu Asp Tyr Trp Gly Gln
                100                 105                 110

Gly Thr Leu Val Thr Val Ser Ser
                115                 120
```

<210> SEQ ID NO 29
<211> LENGTH: 336
<212> TYPE: DNA
<213> ORGANISM: ARTIFICIAL SEQUENCE
<220> FEATURE:
<223> OTHER INFORMATION: Polynucleotide encoding the antibody or a portion thereof.

<400> SEQUENCE: 29

```
gatattgtga tgactcagtc tccactctcc ctgcccgtca cccctggaga gccggcctcc    60
atctcctgca ggtctagtca gagcctcctg catagtcatg gatacaacta tttgaattgg   120
tacctgcaga agccagggca gtctccacac ctcctgatct atttgggttc taatcgggcc   180
tccgggtcc ctgacaggtt cagtggcagt ggatcaggca cagaatttac actgaaaatc    240
agcagagtgg aggctgagga tgttggggtt tattactgca tgcaagttct acaaactccg   300
atcacccctcg gccaagggac acgactggag attaaa                            336
```

<210> SEQ ID NO 30
<211> LENGTH: 360
<212> TYPE: DNA
<213> ORGANISM: ARTIFICIAL SEQUENCE
<220> FEATURE:
<223> OTHER INFORMATION: Polynucleotide encoding the antibody or a portion thereof.

<400> SEQUENCE: 30

```
caggtgcagc tggtggagtc tgggggaggc gtggtccagc ctgggaggtc cctgagactc    60
tcctgtgcag cctctggatt caccttcagt aactatggca tgcactgggt ccgccaggct   120
ccaggcaagg ggctggagtg ggtggcagtt atatcatatg atggaagtaa aaatactat    180
gcagactccg tgaagggccg attcaccatc tccagagaca attccaagaa cacgctgtat   240
ctgcaaatga acagcctgag agctgaggac acggctgtgt attactgtgc gagagatgcc   300
agtgggagct ccctctactc tgactactgg ggccagggaa tcctggtcac cgtctcctca   360
```

<210> SEQ ID NO 31
<211> LENGTH: 112
<212> TYPE: PRT
<213> ORGANISM: ARTIFICIAL SEQUENCE
<220> FEATURE:
<223> OTHER INFORMATION: Antibody or a portion thereof.

<400> SEQUENCE: 31

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

His Gly Tyr Asn Tyr Leu Asn Trp Tyr Leu Gln Lys Pro Gly Gln Ser
                35                  40                  45

Pro His Leu Leu Ile Tyr Leu Gly Ser Asn Arg Ala Ser Gly Val Pro
            50                  55                  60
```

```
Asp Arg Phe Ser Gly Ser Gly Ser Gly Thr Glu Phe Thr Leu Lys Ile
 65                  70                  75                  80

Ser Arg Val Glu Ala Glu Asp Val Gly Val Tyr Tyr Cys Met Gln Val
                 85                  90                  95

Leu Gln Thr Pro Ile Thr Leu Gly Gln Gly Thr Arg Leu Glu Ile Lys
            100                 105                 110
```

<210> SEQ ID NO 32
<211> LENGTH: 120
<212> TYPE: PRT
<213> ORGANISM: ARTIFICIAL SEQUENCE
<220> FEATURE:
<223> OTHER INFORMATION: Antibody or a portion thereof.

<400> SEQUENCE: 32

```
Gln Val Gln Leu Val Glu Ser Gly Gly Val Val Gln Pro Gly Arg
  1               5                  10                  15

Ser Leu Arg Leu Ser Cys Ala Ala Ser Gly Phe Thr Phe Ser Asn Tyr
                 20                  25                  30

Gly Met His Trp Val Arg Gln Ala Pro Gly Lys Gly Leu Glu Trp Val
             35                  40                  45

Ala Val Ile Ser Tyr Asp Gly Ser Lys Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Ala Ser Gly Ser Ser Leu Tyr Ser Asp Tyr Trp Gly Gln
            100                 105                 110

Gly Ile Leu Val Thr Val Ser Ser
            115                 120
```

<210> SEQ ID NO 33
<211> LENGTH: 336
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 33

```
gatattgtga tgactcagtc tccactctcc ctgcccgtca cccctggaga gccggcctcc      60
atctcctgca ggtctagtca gggcctcctg catagtcatg gataccacta tttgaattgg     120
tacctgcaga agccagggca gtctccacag ctcctgatct atttgggttc taatcgggcc     180
tccggggtcc ctgacaggtt cagtggcagt ggatcaggca cagaatttac actgaaaatc     240
agcagagtgg aggctgagga tgttggggtt tattactgca tgcaagttct acaaactccg     300
atcaccctcg gccaagggac acgactggag attaaa                               336
```

<210> SEQ ID NO 34
<211> LENGTH: 360
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 34

```
caggtgcagc tggtggagtc tgggggaggc gtggtccagc ctggagggtc cctgagactc      60
```

-continued

```
tcctgtgcag cctctggatt caccttcagt agctatggca tgcactgggt ccgccaggct    120
ccaggcaagg ggctggagtg ggtgacagtt atatcaaaag atggaagtta taaatactat    180
gcggactccg tgaagggccg attcaccatc tccagagaca attccaagaa cacgctgtat    240
ctgcaaatga acagcctgag agctgaggac acggctgtgt attactgtgc gagggatgcc    300
agtgggagct ccctctactt agactactgg ggccaggta ccctggtcac cgtctcctca     360
```

<210> SEQ ID NO 35
<211> LENGTH: 112
<212> TYPE: PRT
<213> ORGANISM: ARTIFICIAL SEQUENCE
<220> FEATURE:
<223> OTHER INFORMATION: Antibody or a portion thereof.

<400> SEQUENCE: 35

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Gly Leu Leu His Ser
            20                  25                  30

His Gly Tyr His Tyr Leu Asn Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Glu Phe Thr Leu Lys Ile
65                  70                  75                  80

Ser Arg Val Glu Ala Glu Asp Val Gly Val Tyr Tyr Cys Met Gln Val
                85                  90                  95

Leu Gln Thr Pro Ile Thr Leu Gly Gln Gly Thr Arg Leu Glu Ile Lys
            100                 105                 110
```

<210> SEQ ID NO 36
<211> LENGTH: 120
<212> TYPE: PRT
<213> ORGANISM: ARTIFICIAL SEQUENCE
<220> FEATURE:
<223> OTHER INFORMATION: Antibody or a portion thereof.

<400> SEQUENCE: 36

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Thr Val Ile Ser Lys Asp Gly Ser Tyr Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Ser Gly Ser Ser Leu Tyr Leu Asp Tyr Trp Gly Gln
            100                 105                 110

Gly Thr Leu Val Thr Val Ser Ser
        115                 120
```

<210> SEQ ID NO 37
<211> LENGTH: 330
<212> TYPE: DNA

<213> ORGANISM: ARTIFICIAL SEQUENCE
<220> FEATURE:
<223> OTHER INFORMATION: Polynucleotide encoding the antibody or a
      portion thereof.

<400> SEQUENCE: 37

```
cagtctgtgc tgactcagcc accctcagcg tctgggaccc ccgggcagag ggtcaccatc    60
tcttgttctg gaagcagctc aacatcgga agaaatactg taaactggta ccagcagctc   120
ccaggaacgg cccccaaact cctcatctat agtaataatc agcggccctc aggggtccct   180
gaccgattct ctggctccaa gtctggcacc tcagtctccc tggccatcag tgggctccag   240
tctgaggatg aggctgatta ttactgtgca gcatgggatg acagcctgaa tggtgtggta   300
ttcggcggag ggaccaagtt gaccgtccta                                    330
```

<210> SEQ ID NO 38
<211> LENGTH: 360
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 38

```
caggtgcagc tggtggagtc tgggggaggc gtggtccagc ctgggaggtc cctgagactc    60
tcctgtgcag cgtctggatt caccttcagt agctatggca tgcactgggt ccgccaggct   120
ccaggcaagg ggctggagtg ggtggcagtt atatggtatg atggaagtaa taataccat   180 gcagactccg tgaagggccg attcaccatc tccagagaca attccaagga cacgctgtat   240
ctgcaaatga acagcctgag agccgaggac acggctgtgt attactgtgc gggggacttt   300
gcttacttct actacggtat ggacgtctgg ggccaaggga ccacggtcac cgtctcctca   360
```

<210> SEQ ID NO 39
<211> LENGTH: 110
<212> TYPE: PRT
<213> ORGANISM: ARTIFICIAL SEQUENCE
<220> FEATURE:
<223> OTHER INFORMATION: Antibody or a portion thereof.

<400> SEQUENCE: 39

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Arg Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Val Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Val Val Phe Gly Gly Gly Thr Lys Leu Thr Val Leu
            100                 105                 110
```

<210> SEQ ID NO 40
<211> LENGTH: 120
<212> TYPE: PRT
<213> ORGANISM: ARTIFICIAL SEQUENCE
<220> FEATURE:

<223> OTHER INFORMATION: Antibody or a portion thereof.

<400> SEQUENCE: 40

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr His Ala Asp Ser Val
    50                  55                  60

Lys Gly Arg Phe Thr Ile Ser Arg Asp Asn Ser Lys Asp Thr Leu Tyr
65                  70                  75                  80

Leu Gln Met Asn Ser Leu Arg Ala Glu Asp Thr Ala Val Tyr Tyr Cys
                85                  90                  95

Ala Gly Asp Phe Ala Tyr Phe Tyr Tyr Gly Met Asp Val Trp Gly Gln
            100                 105                 110

Gly Thr Thr Val Thr Val Ser Ser
        115                 120

<210> SEQ ID NO 41
<211> LENGTH: 318
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 41
tcctatgagc tgacccagcc accctcggtg tcagtgtccc caggacagac ggccaggatc      60
acctgctctg gagatgcttt gccaaggcaa tatacttatt ggtaccagca gaaaccaggc    120 caggccctg ttctggtgat atttaaagac actgcgaggc cctcagggat ccctgagcga     180
ttctctggct ccagctcagg gacaacagtc acgttgacca tcagtggagt ccaggcagaa    240
gacgaggctg actattactg tcaatcaaca gacagaagtg gtactgtgtt cggcggaggg    300
accaagctga ccgtccta                                                  318

<210> SEQ ID NO 42
<211> LENGTH: 369
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 42
cagatcacct tgaaggagtc tggtcctacg ctggtgaaac ccacacagac cctcacgctg      60
acctgcacct ctctgggtt ctcactcagc actagtggag tgggtgtggg ctggatccgt     120
cagcccccag gaaaggccct ggagtggctt gcactcattt attggaatga tgataagcgc    180
tacagcccat ctctgaagag caggctcacc atcaccaagg acacctccaa aaaccaggtg    240
gtccttacaa tgaccaacat ggaccctgtg gacagagcca catattactg tgcacacaga    300
catggctacg ataggatgcg tgatgctttt gatatctggg gccaagggac aatggtcacc    360
gtctcttca                                                            369

<210> SEQ ID NO 43
<211> LENGTH: 106

```
<212> TYPE: PRT
<213> ORGANISM: ARTIFICIAL SEQUENCE
<220> FEATURE:
<223> OTHER INFORMATION: Antibody or a portion thereof.

<400> SEQUENCE: 43
```

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Arg Gln Tyr Thr
            20                  25                  30

Tyr Trp Tyr Gln Gln Lys Pro Gly Gln Ala Pro Val Leu Val Ile Phe
        35                  40                  45

Lys Asp Thr Ala Arg Pro Ser Gly Ile Pro Glu Arg Phe Ser Gly Ser
50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Thr Asp Arg Ser Gly Thr Val
                85                  90                  95

Phe Gly Gly Gly Thr Lys Leu Thr Val Leu
            100                 105

```
<210> SEQ ID NO 44
<211> LENGTH: 123
<212> TYPE: PRT
<213> ORGANISM: ARTIFICIAL SEQUENCE
<220> FEATURE:
<223> OTHER INFORMATION: Antibody or a portion thereof.

<400> SEQUENCE: 44
```

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Leu Ile Tyr Trp Asn Asp Asp Lys Arg Tyr Ser Pro Ser
50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Arg His Gly Tyr Asp Arg Met Arg Asp Ala Phe Asp Ile
            100                 105                 110

Trp Gly Gln Gly Thr Met Val Thr Val Ser Ser
        115                 120

```
<210> SEQ ID NO 45
<211> LENGTH: 336
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 45
gaaattgtga tgacccagac tccattctct ctgtccgtca cccctggaca gccggcctcc      60
atctcctgca agtctagtca gagcctcctg catagtagtg gaaagaccta tttgtattgg     120
tacctgcaga agccaggcca gcctccacag ctcctgatct atgaagtttc caaccggttc     180
```

| | |
|---|---|
| tctggagtgc agataggtt cagtggcagc gggtcaggga cagatttcac actgaaaatc | 240 |
| agccgggtgg aggctgagga tgttggggtt tatttctgca tgcaaagtat acagcttccg | 300 |
| tggacgttcg gccaagggac caaggtggaa atcaaa | 336 |

```
<210> SEQ ID NO 46
<211> LENGTH: 363
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 46
```

| | |
|---|---|
| caggtgcagc tgcaggagtc gggcccagga ctggtgaagc cttcccagac cctgtccctc | 60 |
| acctgcactg tctctggtgg ctccatcaac agtggtggtt actactggag ctggatccgc | 120 |
| cagcacccag ggaagggcct ggagtggatt gggtacatct cttacagtgg gagcacctac | 180 |
| tacaacccgt ccctcaagag tcgagttacc atatcagtag acacgtctaa gaaccagttc | 240 |
| tccctgaggc tgagctctgt gactgccgcg gacacggccg tgtattactg cgagagag | 300 |
| agccctacgg tgactacggc ttttgatatc tggggccaag ggacaaaggt caccgtctct | 360 |
| tca | 363 |

```
<210> SEQ ID NO 47
<211> LENGTH: 112
<212> TYPE: PRT
<213> ORGANISM: ARTIFICIAL SEQUENCE
<220> FEATURE:
<223> OTHER INFORMATION: Antibody or a portion thereof.

<400> SEQUENCE: 47
```

Glu Ile Val Met Thr Gln Thr Pro Phe Ser Leu Ser Val Thr Pro Gly
1               5                   10                  15

Gln Pro Ala Ser Ile Ser Cys Lys Ser Ser Gln Ser Leu Leu His Ser
            20                  25                  30

Ser Gly Lys Thr Tyr Leu Tyr Trp Tyr Leu Gln Lys Pro Gly Gln Pro
        35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Met Gln Ser
                85                  90                  95

Ile Gln Leu Pro Trp Thr Phe Gly Gln Gly Thr Lys Val Glu Ile Lys
            100                 105                 110

```
<210> SEQ ID NO 48
<211> LENGTH: 121
<212> TYPE: PRT
<213> ORGANISM: ARTIFICIAL SEQUENCE
<220> FEATURE:
<223> OTHER INFORMATION: Antibody or a portion thereof.

<400> SEQUENCE: 48
```

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Asn Ser Gly
            20                  25                  30

Gly Tyr Tyr Trp Ser Trp Ile Arg Gln His Pro Gly Lys Gly Leu Glu

```
                  35                  40                  45
Trp Ile Gly Tyr Ile Ser Tyr Ser Gly Ser Thr Tyr Tyr Asn Pro Ser
         50                  55                  60

Leu Lys Ser Arg Val Thr Ile Ser Val Asp Thr Ser Lys Asn Gln Phe
 65                  70                  75                  80

Ser Leu Arg Leu Ser Ser Val Thr Ala Ala Asp Thr Ala Val Tyr Tyr
                 85                  90                  95

Cys Ala Arg Glu Ser Pro Thr Val Thr Thr Ala Phe Asp Ile Trp Gly
            100                 105                 110

Gln Gly Thr Lys Val Thr Val Ser Ser
        115                 120
```

<210> SEQ ID NO 49
<211> LENGTH: 321
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 49

```
gacatccagt tgacccagtc tccatcctcc ctgtgtgcat ctgtaggaga cagagtcacc      60
atcacttgcc gggtgagtca ggacattaac agttatttaa attggtgtcg gcagaaacca     120
gggaaagttc ctcagttcct gatctatagt gcatccaatt tgcaatctgg agtcccatct     180
cggttcagtg gcagtggatc tgggacagat ttcactctca ctttcagcgg cctgcagact     240
gaatatgttg cacgttatta cggtcaacgg acttacaatg cccttccgac gttcggccta    300
gggaccaggg cggaaatcaa a                                                321
```

<210> SEQ ID NO 50
<211> LENGTH: 378
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 50

```
caggtgcagc tgcaggagtc gggcccagga ctggtgaagc cctcacagac cctgtccctc      60
acctgcactg tctctggtgg ctccatcagc agtggtggtt acgactggag ctggatccgc     120
cagcacccag ggaagggcct ggagtggatt gggaacattt attacagtgg gaggacctac     180
tacaacccgt ccctcaagag tcgaattacc atatcagtag acacgtctaa gaaccagttc     240
tccctgaagc tgaggtctgt gactgccgcg gacacggccg tgtattactg cgagagat      300 cgcccttatg gaggtaattc cggctactac tacggtatgg acgtctgggg ccaagggacc     360
acggtcaccg tctcccca                                                   378
```

<210> SEQ ID NO 51
<211> LENGTH: 107
<212> TYPE: PRT
<213> ORGANISM: ARTIFICIAL SEQUENCE
<220> FEATURE:
<223> OTHER INFORMATION: Antibody or a portion thereof.

<400> SEQUENCE: 51

```
Asp Ile Gln Leu Thr Gln Ser Pro Ser Ser Leu Cys Ala Ser Val Gly
  1               5                  10                  15

Asp Arg Val Thr Ile Thr Cys Arg Val Ser Gln Asp Ile Asn Ser Tyr
```

```
                 20                  25                  30

Leu Asn Trp Cys Arg Gln Lys Pro Gly Lys Val Pro Gln Phe Leu Ile
         35                  40                  45

Tyr Ser Ala Ser Asn Leu Gln Ser Gly Val Pro Ser Arg Phe Ser Gly
     50                  55                  60

Ser Gly Ser Gly Thr Asp Phe Thr Leu Thr Phe Ser Gly Leu Gln Thr
 65                  70                  75                  80

Glu Tyr Val Ala Arg Tyr Tyr Gly Gln Arg Thr Tyr Asn Ala Leu Pro
                 85                  90                  95

Thr Phe Gly Leu Gly Thr Arg Ala Glu Ile Lys
            100                 105

<210> SEQ ID NO 52
<211> LENGTH: 126
<212> TYPE: PRT
<213> ORGANISM: ARTIFICIAL SEQUENCE
<220> FEATURE:
<223> OTHER INFORMATION: Antibody or a portion thereof.

<400> SEQUENCE: 52

Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
             20                  25                  30

Gly Tyr Asp Trp Ser Trp Ile Arg Gln His Pro Gly Lys Gly Leu Glu
         35                  40                  45

Trp Ile Gly Asn Ile Tyr Tyr Ser Gly Arg Thr Tyr Tyr Asn Pro Ser
     50                  55                  60

Leu Lys Ser Arg Ile Thr Ile Ser Val Asp Thr Ser Lys Asn Gln Phe
 65                  70                  75                  80

Ser Leu Lys Leu Arg Ser Val Thr Ala Ala Asp Thr Ala Val Tyr Tyr
                 85                  90                  95

Cys Ala Arg Asp Arg Pro Tyr Gly Gly Asn Ser Gly Tyr Tyr Tyr Gly
            100                 105                 110

Met Asp Val Trp Gly Gln Gly Thr Thr Val Thr Val Ser Pro
        115                 120                 125

<210> SEQ ID NO 53
<211> LENGTH: 327
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 53
gaaattgtgt tgacgcagtc tccaggcacc ctgtctttgt ctccagggga aagagccacc      60
ctctcctgca gggccagtca gactattagc agcagctact tagcctggta ccagcagaga     120
cctggccagg ctcccaggct ccttatgtat ggtgcatcca acagggtcat ggcatccca     180 gtcaggttca gtggcggtgg gtgtgggaca gacttcactt tcaccatcag cagactggat     240
cctgaagatt ttgcagtgta ttactgtcag cagtatggta actcacccat gtgcagtttt     300
ggccagggga ccaaggtgga gatcaaa                                        327

<210> SEQ ID NO 54
<211> LENGTH: 378
<212> TYPE: DNA
<213> ORGANISM: ARTIFICIAL SEQUENCE
```

<220> FEATURE:
<223> OTHER INFORMATION: Polynucleotide encoding the antibody or a
      portion thereof.

<400> SEQUENCE: 54
caggtgcagc tgcaggagtc gggcccagga ctggtgaagc cctcacagac cctgtccctc      60
acctgcactg tctctggtgg ctccatcagc agtggtggtt acgactggag ctggatccgc     120
cagcacccag ggaagggcct ggagtggatt gggaacattt attacagtgg gaggacctac     180
tacaacccgt ccctcaagag tcgaattacc atatcagtag acacgtctaa gaaccagttc     240
tccctgaagc tgaggtctgt gactgccgcg gacacggccg tgtattactg tgcgagagat     300
cgcccttatg gaggtaattc cggctactac tacggtatgg acgtctgggg ccaagggacc     360
acggtcaccg tctcccca                                                   378

<210> SEQ ID NO 55
<211> LENGTH: 109
<212> TYPE: PRT
<213> ORGANISM: ARTIFICIAL SEQUENCE
<220> FEATURE:
<223> OTHER INFORMATION: Antibody or a portion thereof.

<400> SEQUENCE: 55

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Thr Ile Ser Ser Ser
            20                  25                  30

Tyr Leu Ala Trp Tyr Gln Gln Arg Pro Gly Gln Ala Pro Arg Leu Leu
        35                  40                  45

Met Tyr Gly Ala Ser Asn Arg Val Ile Gly Ile Pro Val Arg Phe Ser
    50                  55                  60

Gly Gly Gly Cys Gly Thr Asp Phe Thr Phe Thr Ile Ser Arg Leu Asp
65                  70                  75                  80

Pro Glu Asp Phe Ala Val Tyr Tyr Cys Gln Gln Tyr Gly Asn Ser Pro
                85                  90                  95

Met Cys Ser Phe Gly Gln Gly Thr Lys Val Glu Ile Lys
            100                 105

<210> SEQ ID NO 56
<211> LENGTH: 126
<212> TYPE: PRT
<213> ORGANISM: ARTIFICIAL SEQUENCE
<220> FEATURE:
<223> OTHER INFORMATION: Antibody or a portion thereof.

<400> SEQUENCE: 56

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Asp Trp Ser Trp Ile Arg Gln His Pro Gly Lys Gly Leu Glu
        35                  40                  45

Trp Ile Gly Asn Ile Tyr Tyr Ser Gly Arg Thr Tyr Tyr Asn Pro Ser
    50                  55                  60

Leu Lys Ser Arg Ile Thr Ile Ser Val Asp Thr Ser Lys Asn Gln Phe
65                  70                  75                  80

Ser Leu Lys Leu Arg Ser Val Thr Ala Ala Asp Thr Ala Val Tyr Tyr
                85                  90                  95

Cys Ala Arg Asp Arg Pro Tyr Gly Gly Asn Ser Gly Tyr Tyr Tyr Gly
            100                 105                 110

Met Asp Val Trp Gly Gln Gly Thr Thr Val Thr Val Ser Pro
        115                 120                 125

<210> SEQ ID NO 57
<211> LENGTH: 318
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 57
gaaatagtga tgacgcagtc tccagccacc ctgtctgtgt ctccagggga gagagccacc      60
ctctcctgca gggccagtca gagtgttagg agcaacttag cctggtacca gcagaaacct     120
ggccaggctc ccaggctcct catcgatggt gcatccacca gggccactgg catcacagcc     180
aggttcagtg gcagtgggtc tgggacagag ttcactctca ccatcagcag cctgcagtct     240
gaagattttg cagtttatta ctgtcagcag tataataact ggcctacttt cggccctggg     300
accaaagtgg atatcaaa                                                   318

<210> SEQ ID NO 58
<211> LENGTH: 354
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 58
cagctgcagc tgcaggagtc gggcccagga ctggtgaagc cttcggagac cctgtccctc      60
acctgcactg tctctggtgg ctccatcagc agtagtagtt actattgggg ctggatccgc     120
cagcccccag ggaaggggct ggagtggatt ggagtatct attatggtgg aacaccctac     180
tacaacccgt ccctcaagag tcgagtcacc atatccgtag acacgtccaa gaaccagttc     240
tccctgaagc tgagctctgt gaccgccgca gacacggctg tgtattactg tgcgggagaa     300
ctgcggaggg cttttgatat ctgggggccaa gggacaatgg tcaccgtctc ttca          354

<210> SEQ ID NO 59
<211> LENGTH: 106
<212> TYPE: PRT
<213> ORGANISM: ARTIFICIAL SEQUENCE
<220> FEATURE:
<223> OTHER INFORMATION: Antibody or a portion thereof.

<400> SEQUENCE: 59

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Arg Ser Asn
            20                  25                  30

Leu Ala Trp Tyr Gln Gln Lys Pro Gly Gln Ala Pro Arg Leu Leu Ile
        35                  40                  45

Asp Gly Ala Ser Thr Arg Ala Thr Gly Ile Thr Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Thr
                85                  90                  95

Phe Gly Pro Gly Thr Lys Val Asp Ile Lys
              100                 105

<210> SEQ ID NO 60
<211> LENGTH: 118
<212> TYPE: PRT
<213> ORGANISM: ARTIFICIAL SEQUENCE
<220> FEATURE:
<223> OTHER INFORMATION: Antibody or a portion thereof.

<400> SEQUENCE: 60

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Gly Gly Asn Thr Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Gly Glu Leu Arg Arg Ala Phe Asp Ile Trp Gly Gln Gly Thr
            100                 105                 110

Met Val Thr Val Ser Ser
        115

<210> SEQ ID NO 61
<211> LENGTH: 318
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 61
gaaatagtga tgacgcagtc tccagccacc ctgtctgtgt ctccagggga aagagccacc      60
ctctcctgca gggccagtca gagtgttagg agcaacttag cctggtacca gcagaaacct    120
ggccaggctc ccaggctcct catcgatggt gcatccacca gggccactgg catcacagcc    180
aggttcagtg gcagtgggtc tgggacagag ttcactctca ccatcagcag cctgcagtct    240
gaagattttg cagtttatta ctgtcagcag tataataatt ggcctacttt cggccctggg    300
accaaagtgg atatcaaa                                                  318

<210> SEQ ID NO 62
<211> LENGTH: 354
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 62
cagctgcagc tgcaggagtc gggcccagga ctggtgaagc cttcggagac cctgtccctc      60
acctgcactg tctctggtgg ctccatcagc agtggtagtt actactgggg ctggatccgc    120
cagcccccag ggaaggggct ggagtggatt gggagtatct attatggtgg aaacacctac    180
tacaacccgt ccctcaagag tcgagtcacc atatccgtag acacgtccaa gaaccagttc    240

```
tccctgaagc tgagctctgt gaccgccgca gacacggctg tgtattactg tgcgggagaa      300
ctgcggaggg cttttgatat ctggggccaa gggacaatgg tcaccgtctc ttca            354
```

<210> SEQ ID NO 63
<211> LENGTH: 106
<212> TYPE: PRT
<213> ORGANISM: ARTIFICIAL SEQUENCE
<220> FEATURE:
<223> OTHER INFORMATION: Antibody or a portion thereof.

<400> SEQUENCE: 63

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Arg Ser Asn
            20                  25                  30

Leu Ala Trp Tyr Gln Gln Lys Pro Gly Gln Ala Pro Arg Leu Leu Ile
        35                  40                  45

Asp Gly Ala Ser Thr Arg Ala Thr Gly Ile Thr Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Thr
                85                  90                  95

Phe Gly Pro Gly Thr Lys Val Asp Ile Lys
            100                 105
```

<210> SEQ ID NO 64
<211> LENGTH: 118
<212> TYPE: PRT
<213> ORGANISM: ARTIFICIAL SEQUENCE
<220> FEATURE:
<223> OTHER INFORMATION: Antibody or a portion thereof.

<400> SEQUENCE: 64

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Gly
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Gly Gly Asn Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Gly Glu Leu Arg Arg Ala Phe Asp Ile Trp Gly Gln Gly Thr
            100                 105                 110

Met Val Thr Val Ser Ser
        115
```

<210> SEQ ID NO 65
<211> LENGTH: 321
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 65

```
gacatccaga tgacccagtc tccgtcctcc ctgtgtgcat ctgtaggaga cagagtcacc    60
atctcttgcc gggcaagtca ggacattaga aatgatttag ctggtatca gcagaaacca   120
gggaaagccc ctaagcgcct gatttatgtt gcatccagtt tgcaaagtgg ggtcccatca   180
aggttcagcg gcagtggatt tgggacagaa ttcactctca caatcagcag cctgcagcgt   240
gaagattttg caacttatta ctgtctacag cataatattt acccgtgcag ttttggccag   300
gggaccaagc tggagatcaa a                                            321
```

<210> SEQ ID NO 66
<211> LENGTH: 363
<212> TYPE: DNA
<213> ORGANISM: ARTIFICIAL SEQUENCE
<220> FEATURE:
<223> OTHER INFORMATION: Polynucleotide encoding the antibody or a portion thereof.

<400> SEQUENCE: 66

```
caggtgcagc tggtggagtc tgggggaggc gtggtccagc ctgggaggtc cctgagactc    60
tcctgtgcag cctctggatt caccttcagt agctttggca tgcactgggt ccgccaggct   120
ccaggcaagg ggctggagtg ggtggcaatt ttatcatttg atggaaataa taaatactat   180
gcagactccg tgaagggccg attcaccatc tccagagaca attccaagaa cacggtgtat   240
ctgcaaatga acagcctgag agctgaggac acggctgtgt attactgtgc gagagagggg   300
gggtataact ggaactacga ctttgactac tggggccagg gaaccctggt caccgtctcc   360
tca                                                                363
```

<210> SEQ ID NO 67
<211> LENGTH: 107
<212> TYPE: PRT
<213> ORGANISM: ARTIFICIAL SEQUENCE
<220> FEATURE:
<223> OTHER INFORMATION: Antibody or a portion thereof.

<400> SEQUENCE: 67

```
Asp Ile Gln Met Thr Gln Ser Pro Ser Ser Leu Cys Ala Ser Val Gly
1               5                   10                  15
Asp Arg Val Thr Ile Ser Cys Arg Ala Ser Gln Asp Ile Arg Asn Asp
            20                  25                  30
Leu Gly Trp Tyr Gln Gln Lys Pro Gly Lys Ala Pro Lys Arg Leu Ile
        35                  40                  45
Tyr Val Ala Ser Ser Leu Gln Ser Gly Val Pro Ser Arg Phe Ser Gly
    50                  55                  60
Ser Gly Phe Gly Thr Glu Phe Thr Leu Thr Ile Ser Ser Leu Gln Arg
65                  70                  75                  80
Glu Asp Phe Ala Thr Tyr Tyr Cys Leu Gln His Asn Ile Tyr Pro Cys
                85                  90                  95
Ser Phe Gly Gln Gly Thr Lys Leu Glu Ile Lys
            100                 105
```

<210> SEQ ID NO 68
<211> LENGTH: 121
<212> TYPE: PRT
<213> ORGANISM: ARTIFICIAL SEQUENCE
<220> FEATURE:
<223> OTHER INFORMATION: Antibody or a portion thereof.

<400> SEQUENCE: 68

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Phe
            20                  25                  30

Gly Met His Trp Val Arg Gln Ala Pro Gly Lys Gly Leu Glu Trp Val
            35                  40                  45

Ala Ile Leu Ser Phe Asp Gly Asn Asn Lys Tyr Tyr Ala Asp Ser Val
        50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Tyr Asn Trp Asn Tyr Asp Phe Asp Tyr Trp Gly
            100                 105                 110

Gln Gly Thr Leu Val Thr Val Ser Ser
            115                 120

<210> SEQ ID NO 69
<211> LENGTH: 324
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 69
tcttctgagc tgactcagga ccctgctgtg tctgtggcct tgggacagac agtcaggatc      60
acatgtcaag agacagcct cagaacctat tatgcaagct ggtaccagca gaagccagga     120 caggccctg tacttgtcat ctatggtaaa acatccggc cctcagggat cccagaccga     180
ttctctgcct ccaggtcagg aaatacagct gccttgacca tcactggggc tcaggcggaa    240
gatgaggctg actattactg taactcccgg gacagcagtg gtgaccatgt gatattcggc    300
ggagggacca aggtgaccgt ccta                                            324

<210> SEQ ID NO 70
<211> LENGTH: 360
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 70
caggtgcaac tgcaggagtc gggcccagga ctggtgaagc cttcggagac cctgtccctc     60
acctgcactg tctctggtgg ctccgtcagc agtggtggtg actactggag ctggatccgg    120
cagcccccag ggaagggact ggagtggatt ggttatatct attacactgg gagcaccaac    180
tacaacccct ccctcaagag tcgagtcacc atatcagtag acacgttcaa gcaccagttc    240
tccgtgaatc tgacctctgt gaccgctgcg gacacggccg tgtattattg cgcgagatcg    300
ggtgtagcaa tggctcgctt tgactactgg ggccagggaa ccctggtcac cgtctcctca    360

<210> SEQ ID NO 71
<211> LENGTH: 108
<212> TYPE: PRT
<213> ORGANISM: ARTIFICIAL SEQUENCE
<220> FEATURE:
<223> OTHER INFORMATION: Antibody or a portion thereof.
```

<400> SEQUENCE: 71

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Thr Tyr Tyr Ala
            20                  25                  30

Ser Trp Tyr Gln Gln Lys Pro Gly Gln Ala Pro Val Leu Val Ile Tyr
        35                  40                  45

Gly Lys Asn Ile Arg Pro Ser Gly Ile Pro Asp Arg Phe Ser Ala Ser
    50                  55                  60

Arg Ser Gly Asn Thr Ala Ala Leu Thr Ile Thr Gly Ala Gln Ala Glu
65                  70                  75                  80

Asp Glu Ala Asp Tyr Tyr Cys Asn Ser Arg Asp Ser Ser Gly Asp His
                85                  90                  95

Val Ile Phe Gly Gly Gly Thr Lys Val Thr Val Leu
            100                 105

<210> SEQ ID NO 72
<211> LENGTH: 120
<212> TYPE: PRT
<213> ORGANISM: ARTIFICIAL SEQUENCE
<220> FEATURE:
<223> OTHER INFORMATION: Antibody or a portion thereof.

<400> SEQUENCE: 72

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Gly Asp Tyr Trp Ser Trp Ile Arg Gln Pro Pro Gly Lys Gly Leu Glu
        35                  40                  45

Trp Ile Gly Tyr Ile Tyr Tyr Thr Gly Ser Thr Asn Tyr Asn Pro Ser
    50                  55                  60

Leu Lys Ser Arg Val Thr Ile Ser Val Asp Thr Phe Lys His Gln Phe
65                  70                  75                  80

Ser Val Asn Leu Thr Ser Val Thr Ala Ala Asp Thr Ala Val Tyr Tyr
                85                  90                  95

Cys Ala Arg Ser Gly Val Ala Met Ala Arg Phe Asp Tyr Trp Gly Gln
            100                 105                 110

Gly Thr Leu Val Thr Val Ser Ser
        115                 120

<210> SEQ ID NO 73
<211> LENGTH: 330
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 73
aattttatgc tgactcagcc ccactctgtg tcggagtctc cggggaagac ggtaaccatc      60
tcctgcaccc gcagcagtgg cagcattgtc agcaactatg tgcagtggta ccaacagcgc    120
ccgggcagtt cccccaccat tgtgatctat gaggataatc aaagaccctc tggggtccct    180
gatcggttct ctggctccat cgacagctcc tcgaactctg cctccctcac catctctgga    240
ctgaagactg aggacgaggc tgactactat tgtcagtctt atgatagcag caatcaggtg    300
ttcggcggag ggaccaagct gaccgtccta                                     330

-continued

<210> SEQ ID NO 74
<211> LENGTH: 363
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 74
caggtgcagc tgcaggagtc gggcccagga ctggtgaagc cttcacagac cctgtccctc      60
atctgcactg tctctggtgg ctccatcagc agtggtggct accactggag ctggatccgc     120
cagcacccag ggaagggcct ggagtggatt gggtacatct attacagtgg gagcacctac     180
tacaacccgt ccctcaagag tcgagttacc atatcagtag acacgtctaa gaaccagttc     240
tccctgaagc tgagctctgt gactgccgcg gacacggccg tatattactg tgcgagagag     300
actacggtgg taaaggggta cttcgatctc tggggccgtg gcaccctggt cactgtctcc     360
tca                                                                   363

<210> SEQ ID NO 75
<211> LENGTH: 110
<212> TYPE: PRT
<213> ORGANISM: ARTIFICIAL SEQUENCE
<220> FEATURE:
<223> OTHER INFORMATION: Antibody or a portion thereof.

<400> SEQUENCE: 75

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Val Ser Asn
            20                  25                  30

Tyr Val Gln Trp Tyr Gln Gln Arg Pro Gly Ser Ser Pro Thr Ile Val
        35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Ser Asn Gln Val Phe Gly Gly Gly Thr Lys Leu Thr Val Leu
            100                 105                 110

<210> SEQ ID NO 76
<211> LENGTH: 121
<212> TYPE: PRT
<213> ORGANISM: ARTIFICIAL SEQUENCE
<220> FEATURE:
<223> OTHER INFORMATION: Antibody or a portion thereof.

<400> SEQUENCE: 76

Gln Val Gln Leu Gln Glu Ser Gly Pro Gly Leu Val Lys Pro Ser Gln
1               5                   10                  15

Thr Leu Ser Leu Ile Cys Thr Val Ser Gly Gly Ser Ile Ser Ser Gly
            20                  25                  30

Gly Tyr His Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

```
Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Glu Thr Thr Val Val Lys Gly Tyr Phe Asp Leu Trp Gly
            100                 105                 110

Arg Gly Thr Leu Val Thr Val Ser Ser
        115                 120
```

<210> SEQ ID NO 77
<211> LENGTH: 330
<212> TYPE: DNA
<213> ORGANISM: ARTIFICIAL SEQUENCE
<220> FEATURE:
<223> OTHER INFORMATION: Polynucleotide encoding the antibody or a
     portion thereof.

<400> SEQUENCE: 77

```
cagtctgtgc tgactcagcc accctcagcg tctgggaccc ccgggcagag ggtcaccatc    60
tcttgttctg gaagcagctc caacatcgga agtaattatg tattctggta ccagcagctc   120
ccaggaacgg cccccaaact cctcatcttt aggaataatc agcggccctc agggtccct   180
gaccgattct ttggctccaa gtctggcacc tcagcctccc tggccatcag tgggctccgg   240
tccgaggatg aggctgatta ttactgtgca gcatgggatg acagcctgag tggttgggtg   300
ttcggcggag ggaccaagct gaccgtccta                                    330
```

<210> SEQ ID NO 78
<211> LENGTH: 360
<212> TYPE: DNA
<213> ORGANISM: ARTIFICIAL SEQUENCE
<220> FEATURE:
<223> OTHER INFORMATION: Polynucleotide encoding the antibody or a
     portion thereof.

<400> SEQUENCE: 78

```
gaggtgcagc tggtggagtc tgggggaggc ttggtaaagc ctgggggtc ccttagactc    60
tcctgtgcag cctctggatt cactttcagt tacgcctgga tgggctgggt ccgccaggct   120
ccagggaagg ggctggagtg gattggccgt attaaaagca aaactgatgg tgggacaaca   180
gactacgctg cacccgtgaa aggcagattc accatctcaa gagatgattc aaaaaacacg   240
ctgtatctgc aaatgaacag cctgaaaacc gaggacacag ccgtgtatta ctgtaccaca   300
gatggggcac tggccccca cggctactgg ggccagggaa ccctggtcac cgtctcctca   360
```

<210> SEQ ID NO 79
<211> LENGTH: 110
<212> TYPE: PRT
<213> ORGANISM: ARTIFICIAL SEQUENCE
<220> FEATURE:
<223> OTHER INFORMATION: Antibody or a portion thereof.

<400> SEQUENCE: 79

```
Gln Ser Val Leu Thr Gln Pro Pro Ser Ala Ser Gly Thr Pro Gly Gln
  1               5                  10                  15

Arg Val Thr Ile Ser Cys Ser Gly Ser Ser Ser Asn Ile Gly Ser Asn
                 20                  25                  30

Tyr Val Phe Trp Tyr Gln Gln Leu Pro Gly Thr Ala Pro Lys Leu Leu
             35                  40                  45

Ile Phe Arg Asn Asn Gln Arg Pro Ser Gly Val Pro Asp Arg Phe Phe
         50                  55                  60
```

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Trp Val Phe Gly Gly Gly Thr Lys Leu Thr Val Leu
            100                 105                 110

<210> SEQ ID NO 80
<211> LENGTH: 120
<212> TYPE: PRT
<213> ORGANISM: ARTIFICIAL SEQUENCE
<220> FEATURE:
<223> OTHER INFORMATION: Antibody or a portion thereof.

<400> SEQUENCE: 80

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Tyr Ala
            20                  25                  30

Trp Met Gly Trp Val Arg Gln Ala Pro Gly Lys Gly Leu Glu Trp Ile
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Asp Gly Ala Leu Ala Pro His Gly Tyr Trp Gly Gln
            100                 105                 110

Gly Thr Leu Val Thr Val Ser Ser
        115                 120

<210> SEQ ID NO 81
<211> LENGTH: 318
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 81
gaaatagtga tgacgcagtc tccagccacc ctgtctgtgt ctccagggga tagagccacc      60
ctctcctgca gggccagtca gagtgttaga agcaacttag cctggtacca gcagaaacct    120
ggccaggctc ccaggctcct catctatggt gcatccacca gggccactgg tatcccagcc    180
aggttcagtg gcagtgggtc tgggacagag ttcactctca ccatcagcag cctgcagtct    240
gaagattttg cagtttatta ctgtcagcaa tacactgact ggcccacttt cggcggaggg    300
accaaggtgg agatcaaa                                                  318

<210> SEQ ID NO 82
<211> LENGTH: 357
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 82
caggtgcagc tgcaggagtc gggcccagga ctggtgaagc cttcacagac cctgtccctc      60

```
acctgcactg tctctggtgg ctccatcagc agtggtggtt acttctggag ctggatccgc    120
cagcacccag ggaagggcct ggagtggatt gggtacatct attacagtgg gagcacctac    180
tacaacccgt ccctcaagag tcgagttacc atatcagtag acacgtctaa gaaccagttc    240
tccctgaagc tgagctctgt gactgccgcg gacacggccg tgtattactg tgcgagatgg    300
ggagcagcag ccggctttga ctattggggc cagggaaccc tggtcaccgt ctcctca      357
```

<210> SEQ ID NO 83
<211> LENGTH: 106
<212> TYPE: PRT
<213> ORGANISM: ARTIFICIAL SEQUENCE
<220> FEATURE:
<223> OTHER INFORMATION: Antibody or a portion thereof.

<400> SEQUENCE: 83

```
Glu Ile Val Met Thr Gln Ser Pro Ala Thr Leu Ser Val Ser Pro Gly
1               5                   10                  15

Asp Arg Ala Thr Leu Ser Cys Arg Ala Ser Gln Ser Val Arg Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Thr Asp Trp Pro Thr
                85                  90                  95

Phe Gly Gly Gly Thr Lys Val Glu Ile Lys
            100                 105
```

<210> SEQ ID NO 84
<211> LENGTH: 119
<212> TYPE: PRT
<213> ORGANISM: ARTIFICIAL SEQUENCE
<220> FEATURE:
<223> OTHER INFORMATION: Antibody or a portion thereof.

<400> SEQUENCE: 84

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Phe Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Trp Gly Ala Ala Ala Gly Phe Asp Tyr Trp Gly Gln Gly
            100                 105                 110

Thr Leu Val Thr Val Ser Ser
        115
```

<210> SEQ ID NO 85
<211> LENGTH: 336

```
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 85
gatattgtga tgactcagtc tccactctcc ctgcccgtca cccctggaga gccggcctcc      60
atctcctgca ggtctagtca gagcctccta catagtcatg gatacagcta tttgaattgg    120
tacctgcaga agccagggca gtctccacag ctcctgatcc atttgggttc taatcgggcc    180
tccggggtcc ctgacaggtt cagtggcagt ggatcaggca cagaatttac actgagaatc    240
agcagagtgg aggctgagga tgttggggtt tattattgca tgcaagttct gctaactccg    300 atcacccteg ccaagggac acgactggag attaaa                                336

<210> SEQ ID NO 86
<211> LENGTH: 360
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 86
caggtgcagc tggtggagtc tgggggaggc gtggtccagc ctgggaggtc cctgagactc      60
tcctgtgcag cctctggatt caccttcagt agctatggca tgcactgggt ccgccaggct    120
ccaggcaagg ggctggagtg ggtggcagtt atatcatatg atggaaataa taaatactat    180
gcagactccg tgaagggccg attcaccatc tccagagaca attccaagaa cacgctgtat    240
ctgcaaatga acagcctgag agctgaggac acggctgtgt attactgtgc gagagatgcc    300
agtgggagct ccctctacct tgactactgg ggccagggaa ccctggtcac cgtctcctca    360

<210> SEQ ID NO 87
<211> LENGTH: 112
<212> TYPE: PRT
<213> ORGANISM: ARTIFICIAL SEQUENCE
<220> FEATURE:
<223> OTHER INFORMATION: Antibody or a portion thereof.

<400> SEQUENCE: 87

Asp Ile Val Met Thr Gln Ser Pro Leu Ser Leu Pro Val Thr Pro Gly
1               5                   10                  15
Glu Pro Ala Ser Ile Ser Cys Arg Ser Ser Gln Ser Leu Leu His Ser
            20                  25                  30
His Gly Tyr Ser Tyr Leu Asn Trp Tyr Leu Gln Lys Pro Gly Gln Ser
        35                  40                  45
Pro Gln Leu Leu Ile His Leu Gly Ser Asn Arg Ala Ser Gly Val Pro
    50                  55                  60
Asp Arg Phe Ser Gly Ser Gly Ser Gly Thr Glu Phe Thr Leu Arg Ile
65                  70                  75                  80
Ser Arg Val Glu Ala Glu Asp Val Gly Val Tyr Tyr Cys Met Gln Val
                85                  90                  95
Leu Leu Thr Pro Ile Thr Leu Gly Gln Gly Thr Arg Leu Glu Ile Lys
            100                 105                 110

<210> SEQ ID NO 88
<211> LENGTH: 120
<212> TYPE: PRT
<213> ORGANISM: ARTIFICIAL SEQUENCE
```

<220> FEATURE:
<223> OTHER INFORMATION: Antibody or a portion thereof.

<400> SEQUENCE: 88

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Ser Gly Ser Ser Leu Tyr Leu Asp Tyr Trp Gly Gln
            100                 105                 110

Gly Thr Leu Val Thr Val Ser Ser
        115                 120

<210> SEQ ID NO 89
<211> LENGTH: 33
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 89
cgggcgagtc agggtattag cgactggtta gcc                                33

<210> SEQ ID NO 90
<211> LENGTH: 21
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 90
gctgcatcca gtttgcaaag t                                             21

<210> SEQ ID NO 91
<211> LENGTH: 27
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 91
caacaggcta acagtttccc gatcacc                                       27

<210> SEQ ID NO 92
<211> LENGTH: 11
<212> TYPE: PRT
<213> ORGANISM: ARTIFICIAL SEQUENCE
<220> FEATURE:
<223> OTHER INFORMATION: Antibody or a portion thereof.

<400> SEQUENCE: 92

Arg Ala Ser Gln Gly Ile Ser Asp Trp Leu Ala

```
<210> SEQ ID NO 93
<211> LENGTH: 7
<212> TYPE: PRT
<213> ORGANISM: ARTIFICIAL SEQUENCE
<220> FEATURE:
<223> OTHER INFORMATION: Antibody or a portion thereof.

<400> SEQUENCE: 93

Ala Ala Ser Ser Leu Gln Ser
1               5

<210> SEQ ID NO 94
<211> LENGTH: 9
<212> TYPE: PRT
<213> ORGANISM: ARTIFICIAL SEQUENCE
<220> FEATURE:
<223> OTHER INFORMATION: Antibody or a portion thereof.

<400> SEQUENCE: 94

Gln Gln Ala Asn Ser Phe Pro Ile Thr
1               5

<210> SEQ ID NO 95
<211> LENGTH: 42
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 95
actggaacca gcagtgccgt tggtggtcat aactttgtct cc                          42

<210> SEQ ID NO 96
<211> LENGTH: 21
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 96
gaggtcagta atcggccctc a                                                 21

<210> SEQ ID NO 97
<211> LENGTH: 30
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 97
agctcttata caagcagcag cacttgggtg                                        30

<210> SEQ ID NO 98
<211> LENGTH: 14
<212> TYPE: PRT
<213> ORGANISM: ARTIFICIAL SEQUENCE
<220> FEATURE:
<223> OTHER INFORMATION: Antibody or a portion thereof.

<400> SEQUENCE: 98

Thr Gly Thr Ser Ser Ala Val Gly Gly His Asn Phe Val Ser
1               5                   10
```

<210> SEQ ID NO 99
<211> LENGTH: 7
<212> TYPE: PRT
<213> ORGANISM: ARTIFICIAL SEQUENCE
<220> FEATURE:
<223> OTHER INFORMATION: Antibody or a portion thereof.

<400> SEQUENCE: 99

Glu Val Ser Asn Arg Pro Ser
1               5

<210> SEQ ID NO 100
<211> LENGTH: 10
<212> TYPE: PRT
<213> ORGANISM: ARTIFICIAL SEQUENCE
<220> FEATURE:
<223> OTHER INFORMATION: Antibody or a portion thereof.

<400> SEQUENCE: 100

Ser Ser Tyr Thr Ser Ser Ser Thr Trp Val
1               5                   10

<210> SEQ ID NO 101
<211> LENGTH: 33
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 101
agggccagtc agagtgttag gagcaactta gcc                                    33

<210> SEQ ID NO 102
<211> LENGTH: 21
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 102
ggtgcatcca ccagggccac t                                                 21

<210> SEQ ID NO 103
<211> LENGTH: 24
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 103
cagcagtata ataactggcc tact                                              24

<210> SEQ ID NO 104
<211> LENGTH: 11
<212> TYPE: PRT
<213> ORGANISM: ARTIFICIAL SEQUENCE
<220> FEATURE:
<223> OTHER INFORMATION: Antibody or a portion thereof.

<400> SEQUENCE: 104

Arg Ala Ser Gln Ser Val Arg Ser Asn Leu Ala
1               5                   10

<210> SEQ ID NO 105
<211> LENGTH: 7
<212> TYPE: PRT
<213> ORGANISM: ARTIFICIAL SEQUENCE
<220> FEATURE:
<223> OTHER INFORMATION: Antibody or a portion thereof.

<400> SEQUENCE: 105

Gly Ala Ser Thr Arg Ala Thr
1               5

<210> SEQ ID NO 106
<211> LENGTH: 8
<212> TYPE: PRT
<213> ORGANISM: ARTIFICIAL SEQUENCE
<220> FEATURE:
<223> OTHER INFORMATION: Antibody or a portion thereof.

<400> SEQUENCE: 106

Gln Gln Tyr Asn Asn Trp Pro Thr
1               5

<210> SEQ ID NO 107
<211> LENGTH: 39
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 107
acccgcagca gtgacagcat tgccagcaac tatgtgcag                              39

<210> SEQ ID NO 108
<211> LENGTH: 21
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 108
gaggataacc aaagaccctc t                                                 21

<210> SEQ ID NO 109
<211> LENGTH: 30
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 109
cagtcttatg atagcagcaa tcatgtggta                                        30

<210> SEQ ID NO 110
<211> LENGTH: 13
<212> TYPE: PRT
<213> ORGANISM: ARTIFICIAL SEQUENCE
<220> FEATURE:
<223> OTHER INFORMATION: Antibody or a portion thereof.

<400> SEQUENCE: 110

Thr Arg Ser Ser Asp Ser Ile Ala Ser Asn Tyr Val Gln
1               5                   10

```
<210> SEQ ID NO 111
<211> LENGTH: 7
<212> TYPE: PRT
<213> ORGANISM: ARTIFICIAL SEQUENCE
<220> FEATURE:
<223> OTHER INFORMATION: Antibody or a portion thereof.

<400> SEQUENCE: 111

Glu Asp Asn Gln Arg Pro Ser
1               5

<210> SEQ ID NO 112
<211> LENGTH: 10
<212> TYPE: PRT
<213> ORGANISM: ARTIFICIAL SEQUENCE
<220> FEATURE:
<223> OTHER INFORMATION: Antibody or a portion thereof.

<400> SEQUENCE: 112

Gln Ser Tyr Asp Ser Ser Asn His Val Val
1               5                   10

<210> SEQ ID NO 113
<211> LENGTH: 33
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 113
tctggagatg cattgccaaa gcaatatgct tat                            33

<210> SEQ ID NO 114
<211> LENGTH: 21
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 114
aaagacagtg agaggccctc a                                         21

<210> SEQ ID NO 115
<211> LENGTH: 27
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 115
caatcaacag acagaagagg tactgtg                                   27

<210> SEQ ID NO 116
<211> LENGTH: 11
<212> TYPE: PRT
<213> ORGANISM: ARTIFICIAL SEQUENCE
<220> FEATURE:
<223> OTHER INFORMATION: Antibody or a portion thereof.

<400> SEQUENCE: 116

Ser Gly Asp Ala Leu Pro Lys Gln Tyr Ala Tyr
1               5                   10

<210> SEQ ID NO 117
```

```
<211> LENGTH: 7
<212> TYPE: PRT
<213> ORGANISM: ARTIFICIAL SEQUENCE
<220> FEATURE:
<223> OTHER INFORMATION: Antibody or a portion thereof.

<400> SEQUENCE: 117

Lys Asp Ser Glu Arg Pro Ser
1               5

<210> SEQ ID NO 118
<211> LENGTH: 9
<212> TYPE: PRT
<213> ORGANISM: ARTIFICIAL SEQUENCE
<220> FEATURE:
<223> OTHER INFORMATION: Antibody or a portion thereof.

<400> SEQUENCE: 118

Gln Ser Thr Asp Arg Arg Gly Thr Val
1               5

<210> SEQ ID NO 119
<211> LENGTH: 36
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 119
agggccagtc agatttttag cagcagttac ttagcc                              36

<210> SEQ ID NO 120
<211> LENGTH: 21
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 120
ggtgcatcca gcagggccac t                                              21

<210> SEQ ID NO 121
<211> LENGTH: 24
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 121
cagcagtatg gtagctcatg cagt                                           24

<210> SEQ ID NO 122
<211> LENGTH: 12
<212> TYPE: PRT
<213> ORGANISM: ARTIFICIAL SEQUENCE
<220> FEATURE:
<223> OTHER INFORMATION: Antibody or a portion thereof.

<400> SEQUENCE: 122

Arg Ala Ser Gln Ile Phe Ser Ser Ser Tyr Leu Ala
1               5                   10

<210> SEQ ID NO 123
<211> LENGTH: 7
```

<212> TYPE: PRT
<213> ORGANISM: ARTIFICIAL SEQUENCE
<220> FEATURE:
<223> OTHER INFORMATION: Antibody or a portion thereof.

<400> SEQUENCE: 123

Gly Ala Ser Ser Arg Ala Thr
1               5

<210> SEQ ID NO 124
<211> LENGTH: 8
<212> TYPE: PRT
<213> ORGANISM: ARTIFICIAL SEQUENCE
<220> FEATURE:
<223> OTHER INFORMATION: Antibody or a portion thereof.

<400> SEQUENCE: 124

Gln Gln Tyr Gly Ser Ser Cys Ser
1               5

<210> SEQ ID NO 125
<211> LENGTH: 48
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 125
aggtctagtc agagcctcct acatagtcat ggatacagct atttgaat           48

<210> SEQ ID NO 126
<211> LENGTH: 21
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 126
ttgggttcta atcgggcctc c                                        21

<210> SEQ ID NO 127
<211> LENGTH: 27
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 127
atgcaagttc tgctaactcc gatcacc                                  27

<210> SEQ ID NO 128
<211> LENGTH: 16
<212> TYPE: PRT
<213> ORGANISM: ARTIFICIAL SEQUENCE
<220> FEATURE:
<223> OTHER INFORMATION: Antibody or a portion thereof.

<400> SEQUENCE: 128

Arg Ser Ser Gln Ser Leu Leu His Ser His Gly Tyr Ser Tyr Leu Asn
1               5                   10                  15

<210> SEQ ID NO 129
<211> LENGTH: 7
<212> TYPE: PRT

```
<213> ORGANISM: ARTIFICIAL SEQUENCE
<220> FEATURE:
<223> OTHER INFORMATION: Antibody or a portion thereof.

<400> SEQUENCE: 129

Leu Gly Ser Asn Arg Ala Ser
1               5

<210> SEQ ID NO 130
<211> LENGTH: 9
<212> TYPE: PRT
<213> ORGANISM: ARTIFICIAL SEQUENCE
<220> FEATURE:
<223> OTHER INFORMATION: Antibody or a portion thereof.

<400> SEQUENCE: 130

Met Gln Val Leu Leu Thr Pro Ile Thr
1               5

<210> SEQ ID NO 131
<211> LENGTH: 48
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 131
aggtctagtc agagcctcct gcatagtcat ggatacaact atttgaat                48

<210> SEQ ID NO 132
<211> LENGTH: 21
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 132
ttgggttcta atcgggcctc c                                             21

<210> SEQ ID NO 133
<211> LENGTH: 27
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 133
atgcaagttc tacaaactcc gatcacc                                       27

<210> SEQ ID NO 134
<211> LENGTH: 16
<212> TYPE: PRT
<213> ORGANISM: ARTIFICIAL SEQUENCE
<220> FEATURE:
<223> OTHER INFORMATION: Antibody or a portion thereof.

<400> SEQUENCE: 134

Arg Ser Ser Gln Ser Leu Leu His Ser His Gly Tyr Asn Tyr Leu Asn
1               5                   10                  15

<210> SEQ ID NO 135
<211> LENGTH: 7
<212> TYPE: PRT
<213> ORGANISM: ARTIFICIAL SEQUENCE
```

```
<220> FEATURE:
<223> OTHER INFORMATION: Antibody or a portion thereof.

<400> SEQUENCE: 135

Leu Gly Ser Asn Arg Ala Ser
1               5

<210> SEQ ID NO 136
<211> LENGTH: 9
<212> TYPE: PRT
<213> ORGANISM: ARTIFICIAL SEQUENCE
<220> FEATURE:
<223> OTHER INFORMATION: Antibody or a portion thereof.

<400> SEQUENCE: 136

Met Gln Val Leu Gln Thr Pro Ile Thr
1               5

<210> SEQ ID NO 137
<211> LENGTH: 48
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 137
aggtctagtc agggcctcct gcatagtcat ggataccact atttgaat                48

<210> SEQ ID NO 138
<211> LENGTH: 21
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 138
ttgggttcta atcgggcctc c                                             21

<210> SEQ ID NO 139
<211> LENGTH: 27
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 139
atgcaagttc tacaaactcc gatcacc                                       27

<210> SEQ ID NO 140
<211> LENGTH: 16
<212> TYPE: PRT
<213> ORGANISM: ARTIFICIAL SEQUENCE
<220> FEATURE:
<223> OTHER INFORMATION: Antibody or a portion thereof.

<400> SEQUENCE: 140

Arg Ser Ser Gln Gly Leu Leu His Ser His Gly Tyr His Tyr Leu Asn
1               5                   10                  15

<210> SEQ ID NO 141
<211> LENGTH: 7
<212> TYPE: PRT
<213> ORGANISM: ARTIFICIAL SEQUENCE
<220> FEATURE:
```

<223> OTHER INFORMATION: Antibody or a portion thereof.

<400> SEQUENCE: 141

Leu Gly Ser Asn Arg Ala Ser
1               5

<210> SEQ ID NO 142
<211> LENGTH: 9
<212> TYPE: PRT
<213> ORGANISM: ARTIFICIAL SEQUENCE
<220> FEATURE:
<223> OTHER INFORMATION: Antibody or a portion thereof.

<400> SEQUENCE: 142

Met Gln Val Leu Gln Thr Pro Ile Thr
1               5

<210> SEQ ID NO 143
<211> LENGTH: 39
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 143
tctggaagca gctccaacat cggaagaaat actgtaaac                              39

<210> SEQ ID NO 144
<211> LENGTH: 21
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 144
agtaataatc agcggccctc a                                                 21

<210> SEQ ID NO 145
<211> LENGTH: 33
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 145
gcagcatggg atgacagcct gaatggtgtg gta                                    33

<210> SEQ ID NO 146
<211> LENGTH: 13
<212> TYPE: PRT
<213> ORGANISM: ARTIFICIAL SEQUENCE
<220> FEATURE:
<223> OTHER INFORMATION: Antibody or a portion thereof.

<400> SEQUENCE: 146

Ser Gly Ser Ser Ser Asn Ile Gly Arg Asn Thr Val Asn
1               5                   10

<210> SEQ ID NO 147
<211> LENGTH: 7
<212> TYPE: PRT
<213> ORGANISM: ARTIFICIAL SEQUENCE
<220> FEATURE:
<223> OTHER INFORMATION: Antibody or a portion thereof.

<400> SEQUENCE: 147

Ser Asn Asn Gln Arg Pro Ser
1               5

<210> SEQ ID NO 148
<211> LENGTH: 11
<212> TYPE: PRT
<213> ORGANISM: ARTIFICIAL SEQUENCE
<220> FEATURE:
<223> OTHER INFORMATION: Antibody or a portion thereof.

<400> SEQUENCE: 148

Ala Ala Trp Asp Asp Ser Leu Asn Gly Val Val
1               5                   10

<210> SEQ ID NO 149
<211> LENGTH: 33
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 149
tctggagatg ctttgccaag gcaatatact tat                          33

<210> SEQ ID NO 150
<211> LENGTH: 21
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 150
aaagacactg cgaggccctc a                                       21

<210> SEQ ID NO 151
<211> LENGTH: 27
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 151
caatcaacag acagaagtgg tactgtg                                 27

<210> SEQ ID NO 152
<211> LENGTH: 11
<212> TYPE: PRT
<213> ORGANISM: ARTIFICIAL SEQUENCE
<220> FEATURE:
<223> OTHER INFORMATION: Antibody or a portion thereof.

<400> SEQUENCE: 152

Ser Gly Asp Ala Leu Pro Arg Gln Tyr Thr Tyr
1               5                   10

<210> SEQ ID NO 153
<211> LENGTH: 7
<212> TYPE: PRT
<213> ORGANISM: ARTIFICIAL SEQUENCE
<220> FEATURE:
<223> OTHER INFORMATION: Antibody or a portion thereof.

```
<400> SEQUENCE: 153

Lys Asp Thr Ala Arg Pro Ser
1               5

<210> SEQ ID NO 154
<211> LENGTH: 9
<212> TYPE: PRT
<213> ORGANISM: ARTIFICIAL SEQUENCE
<220> FEATURE:
<223> OTHER INFORMATION: Antibody or a portion thereof.

<400> SEQUENCE: 154

Gln Ser Thr Asp Arg Ser Gly Thr Val
1               5

<210> SEQ ID NO 155
<211> LENGTH: 48
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 155
aagtctagtc agagcctcct gcatagtagt ggaaagacct atttgtat              48

<210> SEQ ID NO 156
<211> LENGTH: 21
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 156
gaagtttcca accggttctc t                                           21

<210> SEQ ID NO 157
<211> LENGTH: 27
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 157
atgcaaagta tacagcttcc gtggacg                                     27

<210> SEQ ID NO 158
<211> LENGTH: 16
<212> TYPE: PRT
<213> ORGANISM: ARTIFICIAL SEQUENCE
<220> FEATURE:
<223> OTHER INFORMATION: Antibody or a portion thereof.

<400> SEQUENCE: 158

Lys Ser Ser Gln Ser Leu Leu His Ser Ser Gly Lys Thr Tyr Leu Tyr
1               5                   10                  15

<210> SEQ ID NO 159
<211> LENGTH: 7
<212> TYPE: PRT
<213> ORGANISM: ARTIFICIAL SEQUENCE
<220> FEATURE:
<223> OTHER INFORMATION: Antibody or a portion thereof.

<400> SEQUENCE: 159
```

Glu Val Ser Asn Arg Phe Ser
1               5

<210> SEQ ID NO 160
<211> LENGTH: 9
<212> TYPE: PRT
<213> ORGANISM: ARTIFICIAL SEQUENCE
<220> FEATURE:
<223> OTHER INFORMATION: Antibody or a portion thereof.

<400> SEQUENCE: 160

Met Gln Ser Ile Gln Leu Pro Trp Thr
1               5

<210> SEQ ID NO 161
<211> LENGTH: 33
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 161
cgggtgagtc aggacattaa cagttattta aat                                  33

<210> SEQ ID NO 162
<211> LENGTH: 21
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 162
agtgcatcca atttgcaatc t                                               21

<210> SEQ ID NO 163
<211> LENGTH: 27
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 163
caacggactt acaatgccct tccgacg                                         27

<210> SEQ ID NO 164
<211> LENGTH: 11
<212> TYPE: PRT
<213> ORGANISM: ARTIFICIAL SEQUENCE
<220> FEATURE:
<223> OTHER INFORMATION: Antibody or a portion thereof.

<400> SEQUENCE: 164

Arg Val Ser Gln Asp Ile Asn Ser Tyr Leu Asn
1               5                   10

<210> SEQ ID NO 165
<211> LENGTH: 7
<212> TYPE: PRT
<213> ORGANISM: ARTIFICIAL SEQUENCE
<220> FEATURE:
<223> OTHER INFORMATION: Antibody or a portion thereof.

<400> SEQUENCE: 165

Ser Ala Ser Asn Leu Gln Ser
1               5

<210> SEQ ID NO 166
<211> LENGTH: 9
<212> TYPE: PRT
<213> ORGANISM: ARTIFICIAL SEQUENCE
<220> FEATURE:
<223> OTHER INFORMATION: Antibody or a portion thereof.

<400> SEQUENCE: 166

Gln Arg Thr Tyr Asn Ala Leu Pro Thr
1               5

<210> SEQ ID NO 167
<211> LENGTH: 36
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 167
agggccagtc agactattag cagcagctac ttagcc                        36

<210> SEQ ID NO 168
<211> LENGTH: 21
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 168
ggtgcatcca acagggtcat t                                        21

<210> SEQ ID NO 169
<211> LENGTH: 30
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 169
cagcagtatg gtaactcacc catgtgcagt                               30

<210> SEQ ID NO 170
<211> LENGTH: 12
<212> TYPE: PRT
<213> ORGANISM: ARTIFICIAL SEQUENCE
<220> FEATURE:
<223> OTHER INFORMATION: Antibody or a portion thereof.

<400> SEQUENCE: 170

Arg Ala Ser Gln Thr Ile Ser Ser Ser Tyr Leu Ala
1               5                   10

<210> SEQ ID NO 171
<211> LENGTH: 7
<212> TYPE: PRT
<213> ORGANISM: ARTIFICIAL SEQUENCE
<220> FEATURE:
<223> OTHER INFORMATION: Antibody or a portion thereof.

<400> SEQUENCE: 171

Gly Ala Ser Asn Arg Val Ile

<210> SEQ ID NO 172
<211> LENGTH: 10
<212> TYPE: PRT
<213> ORGANISM: ARTIFICIAL SEQUENCE
<220> FEATURE:
<223> OTHER INFORMATION: Antibody or a portion thereof.

<400> SEQUENCE: 172

Gln Gln Tyr Gly Asn Ser Pro Met Cys Ser
1               5                   10

<210> SEQ ID NO 173
<211> LENGTH: 33
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 173
agggccagtc agagtgttag gagcaactta gcc                                    33

<210> SEQ ID NO 174
<211> LENGTH: 21
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 174
ggtgcatcca ccagggccac t                                                 21

<210> SEQ ID NO 175
<211> LENGTH: 24
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 175
cagcagtata ataactggcc tact                                              24

<210> SEQ ID NO 176
<211> LENGTH: 11
<212> TYPE: PRT
<213> ORGANISM: ARTIFICIAL SEQUENCE
<220> FEATURE:
<223> OTHER INFORMATION: Antibody or a portion thereof.

<400> SEQUENCE: 176

Arg Ala Ser Gln Ser Val Arg Ser Asn Leu Ala
1               5                   10

<210> SEQ ID NO 177
<211> LENGTH: 7
<212> TYPE: PRT
<213> ORGANISM: ARTIFICIAL SEQUENCE
<220> FEATURE:
<223> OTHER INFORMATION: Antibody or a portion thereof.

<400> SEQUENCE: 177

Gly Ala Ser Thr Arg Ala Thr
1               5

<210> SEQ ID NO 178
<211> LENGTH: 8
<212> TYPE: PRT
<213> ORGANISM: ARTIFICIAL SEQUENCE
<220> FEATURE:
<223> OTHER INFORMATION: Antibody or a portion thereof.

<400> SEQUENCE: 178

Gln Gln Tyr Asn Asn Trp Pro Thr
1               5

<210> SEQ ID NO 179
<211> LENGTH: 33
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 179
agggccagtc agagtgttag gagcaactta gcc                                33

<210> SEQ ID NO 180
<211> LENGTH: 21
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 180
ggtgcatcca ccagggccac t                                             21

<210> SEQ ID NO 181
<211> LENGTH: 24
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 181
cagcagtata ataattggcc tact                                          24

<210> SEQ ID NO 182
<211> LENGTH: 11
<212> TYPE: PRT
<213> ORGANISM: ARTIFICIAL SEQUENCE
<220> FEATURE:
<223> OTHER INFORMATION: Antibody or a portion thereof.

<400> SEQUENCE: 182

Arg Ala Ser Gln Ser Val Arg Ser Asn Leu Ala
1               5                   10

<210> SEQ ID NO 183
<211> LENGTH: 7
<212> TYPE: PRT
<213> ORGANISM: ARTIFICIAL SEQUENCE
<220> FEATURE:
<223> OTHER INFORMATION: Antibody or a portion thereof.

<400> SEQUENCE: 183

Gly Ala Ser Thr Arg Ala Thr
1               5

<210> SEQ ID NO 184
<211> LENGTH: 8
<212> TYPE: PRT
<213> ORGANISM: ARTIFICIAL SEQUENCE
<220> FEATURE:
<223> OTHER INFORMATION: Antibody or a portion thereof.

<400> SEQUENCE: 184

Gln Gln Tyr Asn Asn Trp Pro Thr
1               5

<210> SEQ ID NO 185
<211> LENGTH: 33
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 185
cgggcaagtc aggacattag aaatgattta ggc                               33

<210> SEQ ID NO 186
<211> LENGTH: 21
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 186
gttgcatcca gtttgcaaag t                                            21

<210> SEQ ID NO 187
<211> LENGTH: 27
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 187
ctacagcata atatttaccc gtgcagt                                      27

<210> SEQ ID NO 188
<211> LENGTH: 11
<212> TYPE: PRT
<213> ORGANISM: ARTIFICIAL SEQUENCE
<220> FEATURE:
<223> OTHER INFORMATION: Antibody or a portion thereof.

<400> SEQUENCE: 188

Arg Ala Ser Gln Asp Ile Arg Asn Asp Leu Gly
1               5                   10

<210> SEQ ID NO 189
<211> LENGTH: 7
<212> TYPE: PRT
<213> ORGANISM: ARTIFICIAL SEQUENCE
<220> FEATURE:
<223> OTHER INFORMATION: Antibody or a portion thereof.

<400> SEQUENCE: 189

Val Ala Ser Ser Leu Gln Ser
1               5

<210> SEQ ID NO 190
<211> LENGTH: 9
<212> TYPE: PRT
<213> ORGANISM: ARTIFICIAL SEQUENCE
<220> FEATURE:
<223> OTHER INFORMATION: Antibody or a portion thereof.

<400> SEQUENCE: 190

Leu Gln His Asn Ile Tyr Pro Cys Ser
1               5

<210> SEQ ID NO 191
<211> LENGTH: 33
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 191
caaggagaca gcctcagaac ctattatgca agc                                   33

<210> SEQ ID NO 192
<211> LENGTH: 21
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 192
ggtaaaaaca tccggccctc a                                                21

<210> SEQ ID NO 193
<211> LENGTH: 33
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 193
aactcccggg acagcagtgg tgaccatgtg ata                                   33

<210> SEQ ID NO 194
<211> LENGTH: 11
<212> TYPE: PRT
<213> ORGANISM: ARTIFICIAL SEQUENCE
<220> FEATURE:
<223> OTHER INFORMATION: Antibody or a portion thereof.

<400> SEQUENCE: 194

Gln Gly Asp Ser Leu Arg Thr Tyr Tyr Ala Ser
1               5                   10

<210> SEQ ID NO 195
<211> LENGTH: 7
<212> TYPE: PRT
<213> ORGANISM: ARTIFICIAL SEQUENCE
<220> FEATURE:
<223> OTHER INFORMATION: Antibody or a portion thereof.

<400> SEQUENCE: 195

Gly Lys Asn Ile Arg Pro Ser
1               5

<210> SEQ ID NO 196

```
<211> LENGTH: 11
<212> TYPE: PRT
<213> ORGANISM: ARTIFICIAL SEQUENCE
<220> FEATURE:
<223> OTHER INFORMATION: Antibody or a portion thereof.

<400> SEQUENCE: 196

Asn Ser Arg Asp Ser Ser Gly Asp His Val Ile
1               5                   10

<210> SEQ ID NO 197
<211> LENGTH: 39
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 197
acccgcagca gtggcagcat tgtcagcaac tatgtgcag                              39

<210> SEQ ID NO 198
<211> LENGTH: 21
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 198
gaggataatc aaagaccctc t                                                21

<210> SEQ ID NO 199
<211> LENGTH: 27
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 199
cagtcttatg atagcagcaa tcaggtg                                          27

<210> SEQ ID NO 200
<211> LENGTH: 13
<212> TYPE: PRT
<213> ORGANISM: ARTIFICIAL SEQUENCE
<220> FEATURE:
<223> OTHER INFORMATION: Antibody or a portion thereof.

<400> SEQUENCE: 200

Thr Arg Ser Ser Gly Ser Ile Val Ser Asn Tyr Val Gln
1               5                   10

<210> SEQ ID NO 201
<211> LENGTH: 7
<212> TYPE: PRT
<213> ORGANISM: ARTIFICIAL SEQUENCE
<220> FEATURE:
<223> OTHER INFORMATION: Antibody or a portion thereof.

<400> SEQUENCE: 201

Glu Asp Asn Gln Arg Pro Ser
1               5

<210> SEQ ID NO 202
<211> LENGTH: 9
```

<212> TYPE: PRT
<213> ORGANISM: ARTIFICIAL SEQUENCE
<220> FEATURE:
<223> OTHER INFORMATION: Antibody or a portion thereof.

<400> SEQUENCE: 202

Gln Ser Tyr Asp Ser Ser Asn Gln Val
1               5

<210> SEQ ID NO 203
<211> LENGTH: 39
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 203
tctggaagca gctccaacat cggaagtaat tatgtattc                            39

<210> SEQ ID NO 204
<211> LENGTH: 21
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 204
aggaataatc agcggccctc a                                              21

<210> SEQ ID NO 205
<211> LENGTH: 33
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 205
gcagcatggg atgacagcct gagtggttgg gtg                                 33

<210> SEQ ID NO 206
<211> LENGTH: 13
<212> TYPE: PRT
<213> ORGANISM: ARTIFICIAL SEQUENCE
<220> FEATURE:
<223> OTHER INFORMATION: Antibody or a portion thereof.

<400> SEQUENCE: 206

Ser Gly Ser Ser Ser Asn Ile Gly Ser Asn Tyr Val Phe
1               5                   10

<210> SEQ ID NO 207
<211> LENGTH: 7
<212> TYPE: PRT
<213> ORGANISM: ARTIFICIAL SEQUENCE
<220> FEATURE:
<223> OTHER INFORMATION: Antibody or a portion thereof.

<400> SEQUENCE: 207

Arg Asn Asn Gln Arg Pro Ser
1               5

<210> SEQ ID NO 208
<211> LENGTH: 11
<212> TYPE: PRT

```
<213> ORGANISM: ARTIFICIAL SEQUENCE
<220> FEATURE:
<223> OTHER INFORMATION: Antibody or a portion thereof.

<400> SEQUENCE: 208

Ala Ala Trp Asp Asp Ser Leu Ser Gly Trp Val
1               5                   10

<210> SEQ ID NO 209
<211> LENGTH: 33
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 209
agggccagtc agagtgttag aagcaactta gcc                                    33

<210> SEQ ID NO 210
<211> LENGTH: 21
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 210
ggtgcatcca ccagggccac t                                                 21

<210> SEQ ID NO 211
<211> LENGTH: 24
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 211
cagcaataca ctgactggcc cact                                              24

<210> SEQ ID NO 212
<211> LENGTH: 11
<212> TYPE: PRT
<213> ORGANISM: ARTIFICIAL SEQUENCE
<220> FEATURE:
<223> OTHER INFORMATION: Antibody or a portion thereof.

<400> SEQUENCE: 212

Arg Ala Ser Gln Ser Val Arg Ser Asn Leu Ala
1               5                   10

<210> SEQ ID NO 213
<211> LENGTH: 7
<212> TYPE: PRT
<213> ORGANISM: ARTIFICIAL SEQUENCE
<220> FEATURE:
<223> OTHER INFORMATION: Antibody or a portion thereof.

<400> SEQUENCE: 213

Gly Ala Ser Thr Arg Ala Thr
1               5

<210> SEQ ID NO 214
<211> LENGTH: 8
<212> TYPE: PRT
<213> ORGANISM: ARTIFICIAL SEQUENCE
```

```
<220> FEATURE:
<223> OTHER INFORMATION: Antibody or a portion thereof.

<400> SEQUENCE: 214

Gln Gln Tyr Thr Asp Trp Pro Thr
1               5

<210> SEQ ID NO 215
<211> LENGTH: 48
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 215
aggtctagtc agagcctcct acatagtcat ggatacagct atttgaat                 48

<210> SEQ ID NO 216
<211> LENGTH: 21
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 216
ttgggttcta atcgggcctc c                                              21

<210> SEQ ID NO 217
<211> LENGTH: 27
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 217
atgcaagttc tgctaactcc gatcacc                                        27

<210> SEQ ID NO 218
<211> LENGTH: 16
<212> TYPE: PRT
<213> ORGANISM: ARTIFICIAL SEQUENCE
<220> FEATURE:
<223> OTHER INFORMATION: Antibody or a portion thereof.

<400> SEQUENCE: 218

Arg Ser Ser Gln Ser Leu Leu His Ser His Gly Tyr Ser Tyr Leu Asn
1               5                   10                  15

<210> SEQ ID NO 219
<211> LENGTH: 7
<212> TYPE: PRT
<213> ORGANISM: ARTIFICIAL SEQUENCE
<220> FEATURE:
<223> OTHER INFORMATION: Antibody or a portion thereof.

<400> SEQUENCE: 219

Leu Gly Ser Asn Arg Ala Ser
1               5

<210> SEQ ID NO 220
<211> LENGTH: 9
<212> TYPE: PRT
<213> ORGANISM: ARTIFICIAL SEQUENCE
<220> FEATURE:
```

<223> OTHER INFORMATION: Antibody or a portion thereof.

<400> SEQUENCE: 220

Met Gln Val Leu Leu Thr Pro Ile Thr
1               5

<210> SEQ ID NO 221
<211> LENGTH: 15
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 221
agttatggca tgcac                                                    15

<210> SEQ ID NO 222
<211> LENGTH: 51
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 222
gttatatggt atgatggaag taatgaatac tatgcagact ccgtgaaggg c             51

<210> SEQ ID NO 223
<211> LENGTH: 30
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 223
catgaccaca gtcactacgg ttttgactac                                    30

<210> SEQ ID NO 224
<211> LENGTH: 5
<212> TYPE: PRT
<213> ORGANISM: ARTIFICIAL SEQUENCE
<220> FEATURE:
<223> OTHER INFORMATION: Antibody or a portion thereof.

<400> SEQUENCE: 224

Ser Tyr Gly Met His
1               5

<210> SEQ ID NO 225
<211> LENGTH: 17
<212> TYPE: PRT
<213> ORGANISM: ARTIFICIAL SEQUENCE
<220> FEATURE:
<223> OTHER INFORMATION: Antibody or a portion thereof.

<400> SEQUENCE: 225

Val Ile Trp Tyr Asp Gly Ser Asn Glu Tyr Tyr Ala Asp Ser Val Lys
1               5                   10                  15

Gly

<210> SEQ ID NO 226
<211> LENGTH: 10
<212> TYPE: PRT
<213> ORGANISM: ARTIFICIAL SEQUENCE

```
<220> FEATURE:
<223> OTHER INFORMATION: Antibody or a portion thereof.

<400> SEQUENCE: 226

His Asp His Ser His Tyr Gly Phe Asp Tyr
1               5                   10

<210> SEQ ID NO 227
<211> LENGTH: 21
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 227
aatgctgaaa tgggtgtgag c                                              21

<210> SEQ ID NO 228
<211> LENGTH: 48
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 228 caccttttt cgaatgacga aaatcctac agcacatctc tgaagagc                   48

<210> SEQ ID NO 229
<211> LENGTH: 30
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 229
tcgtttaact ggaactacga ctttgactac                                     30

<210> SEQ ID NO 230
<211> LENGTH: 7
<212> TYPE: PRT
<213> ORGANISM: ARTIFICIAL SEQUENCE
<220> FEATURE:
<223> OTHER INFORMATION: Antibody or a portion thereof.

<400> SEQUENCE: 230

Asn Ala Glu Met Gly Val Ser
1               5

<210> SEQ ID NO 231
<211> LENGTH: 16
<212> TYPE: PRT
<213> ORGANISM: ARTIFICIAL SEQUENCE
<220> FEATURE:
<223> OTHER INFORMATION: Antibody or a portion thereof.

<400> SEQUENCE: 231

His Leu Phe Ser Asn Asp Glu Lys Ser Tyr Ser Thr Ser Leu Lys Ser
1               5                   10                  15

<210> SEQ ID NO 232
<211> LENGTH: 10
<212> TYPE: PRT
<213> ORGANISM: ARTIFICIAL SEQUENCE
<220> FEATURE:
```

```
<223> OTHER INFORMATION: Antibody or a portion thereof.

<400> SEQUENCE: 232

Ser Phe Asn Trp Asn Tyr Asp Phe Asp Tyr
1               5                   10

<210> SEQ ID NO 233
<211> LENGTH: 21
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 233
agtggtagtt actactgggg c                                              21

<210> SEQ ID NO 234
<211> LENGTH: 48
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 234
agtatctatt atggtgggaa cacctactac aacccgtccc tcaagagt                 48

<210> SEQ ID NO 235
<211> LENGTH: 24
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 235
gaactgcgga gggcttttga tatc                                           24

<210> SEQ ID NO 236
<211> LENGTH: 7
<212> TYPE: PRT
<213> ORGANISM: ARTIFICIAL SEQUENCE
<220> FEATURE:
<223> OTHER INFORMATION: Antibody or a portion thereof.

<400> SEQUENCE: 236

Ser Gly Ser Tyr Tyr Trp Gly
1               5

<210> SEQ ID NO 237
<211> LENGTH: 16
<212> TYPE: PRT
<213> ORGANISM: ARTIFICIAL SEQUENCE
<220> FEATURE:
<223> OTHER INFORMATION: Antibody or a portion thereof.

<400> SEQUENCE: 237

Ser Ile Tyr Tyr Gly Gly Asn Thr Tyr Tyr Asn Pro Ser Leu Lys Ser
1               5                   10                  15

<210> SEQ ID NO 238
<211> LENGTH: 8
<212> TYPE: PRT
<213> ORGANISM: ARTIFICIAL SEQUENCE
<220> FEATURE:
<223> OTHER INFORMATION: Antibody or a portion thereof.
```

<400> SEQUENCE: 238

Glu Leu Arg Arg Ala Phe Asp Ile
1               5

<210> SEQ ID NO 239
<211> LENGTH: 15
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 239
tactatggca tgcac                                                    15

<210> SEQ ID NO 240
<211> LENGTH: 51
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 240
gttatatggt atgatggaag taataaatac tatgcagact ccgtgaaggg c             51

<210> SEQ ID NO 241
<211> LENGTH: 36
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 241
gatcatgact acggtgtcct gtactacttt gactac                             36

<210> SEQ ID NO 242
<211> LENGTH: 5
<212> TYPE: PRT
<213> ORGANISM: ARTIFICIAL SEQUENCE
<220> FEATURE:
<223> OTHER INFORMATION: Antibody or a portion thereof.

<400> SEQUENCE: 242

Tyr Tyr Gly Met His
1               5

<210> SEQ ID NO 243
<211> LENGTH: 17
<212> TYPE: PRT
<213> ORGANISM: ARTIFICIAL SEQUENCE
<220> FEATURE:
<223> OTHER INFORMATION: Antibody or a portion thereof.

<400> SEQUENCE: 243

Val Ile Trp Tyr Asp Gly Ser Asn Lys Tyr Tyr Ala Asp Ser Val Lys
1               5                   10                  15

Gly

<210> SEQ ID NO 244
<211> LENGTH: 12
<212> TYPE: PRT
<213> ORGANISM: ARTIFICIAL SEQUENCE
<220> FEATURE:

<223> OTHER INFORMATION: Antibody or a portion thereof.

<400> SEQUENCE: 244

Asp His Asp Tyr Gly Val Leu Tyr Tyr Phe Asp Tyr
1               5                   10

<210> SEQ ID NO 245
<211> LENGTH: 21
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 245
actagtggag tgggtgtggg c                                              21

<210> SEQ ID NO 246
<211> LENGTH: 48
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 246
ctcatttatt ggaatgatga taagcgctac agcccatctc tgaagagc                 48

<210> SEQ ID NO 247
<211> LENGTH: 39
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 247
agacatggct acgataggat gcgtgatgct tttgatatc                           39

<210> SEQ ID NO 248
<211> LENGTH: 7
<212> TYPE: PRT
<213> ORGANISM: ARTIFICIAL SEQUENCE
<220> FEATURE:
<223> OTHER INFORMATION: Antibody or a portion thereof.

<400> SEQUENCE: 248

Thr Ser Gly Val Gly Val Gly
1               5

<210> SEQ ID NO 249
<211> LENGTH: 16
<212> TYPE: PRT
<213> ORGANISM: ARTIFICIAL SEQUENCE
<220> FEATURE:
<223> OTHER INFORMATION: Antibody or a portion thereof.

<400> SEQUENCE: 249

Leu Ile Tyr Trp Asn Asp Asp Lys Arg Tyr Ser Pro Ser Leu Lys Ser
1               5                   10                  15

<210> SEQ ID NO 250
<211> LENGTH: 13
<212> TYPE: PRT
<213> ORGANISM: ARTIFICIAL SEQUENCE
<220> FEATURE:
<223> OTHER INFORMATION: Antibody or a portion thereof.

<400> SEQUENCE: 250

Arg His Gly Tyr Asp Arg Met Arg Asp Ala Phe Asp Ile
1               5                   10

<210> SEQ ID NO 251
<211> LENGTH: 15
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 251
agctacttta tacac                                                    15

<210> SEQ ID NO 252
<211> LENGTH: 51
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 252
ataatcaacc ctagtggtgg tagcacaagc tacgcacaga gttccaggg c              51

<210> SEQ ID NO 253
<211> LENGTH: 54
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 253
gatcaggagg gagcagtggc tggtacagac tactacttct acggtatgga cgtc          54

<210> SEQ ID NO 254
<211> LENGTH: 5
<212> TYPE: PRT
<213> ORGANISM: ARTIFICIAL SEQUENCE
<220> FEATURE:
<223> OTHER INFORMATION: Antibody or a portion thereof.

<400> SEQUENCE: 254

Ser Tyr Phe Ile His
1               5

<210> SEQ ID NO 255
<211> LENGTH: 17
<212> TYPE: PRT
<213> ORGANISM: ARTIFICIAL SEQUENCE
<220> FEATURE:
<223> OTHER INFORMATION: Antibody or a portion thereof.

<400> SEQUENCE: 255

Ile Ile Asn Pro Ser Gly Gly Ser Thr Ser Tyr Ala Gln Lys Phe Gln
1               5                   10                  15

Gly

<210> SEQ ID NO 256
<211> LENGTH: 18
<212> TYPE: PRT
<213> ORGANISM: ARTIFICIAL SEQUENCE
<220> FEATURE:

<223> OTHER INFORMATION: Antibody or a portion thereof.

<400> SEQUENCE: 256

Asp Gln Glu Gly Ala Val Ala Gly Thr Asp Tyr Tyr Phe Tyr Gly Met
1               5                   10                  15

Asp Val

<210> SEQ ID NO 257
<211> LENGTH: 15
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 257
agctatggca tgcac                                                    15

<210> SEQ ID NO 258
<211> LENGTH: 51
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 258
gttatatcat atgatggaaa taataaatac tatgcagact ccgtgaaggg c             51

<210> SEQ ID NO 259
<211> LENGTH: 33
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 259
gatgccagtg ggagctccct ctaccttgac tac                                33

<210> SEQ ID NO 260
<211> LENGTH: 5
<212> TYPE: PRT
<213> ORGANISM: ARTIFICIAL SEQUENCE
<220> FEATURE:
<223> OTHER INFORMATION: Antibody or a portion thereof.

<400> SEQUENCE: 260

Ser Tyr Gly Met His
1               5

<210> SEQ ID NO 261
<211> LENGTH: 17
<212> TYPE: PRT
<213> ORGANISM: ARTIFICIAL SEQUENCE
<220> FEATURE:
<223> OTHER INFORMATION: Antibody or a portion thereof.

<400> SEQUENCE: 261

Val Ile Ser Tyr Asp Gly Asn Asn Lys Tyr Tyr Ala Asp Ser Val Lys
1               5                   10                  15

Gly

<210> SEQ ID NO 262
<211> LENGTH: 11

```
<212> TYPE: PRT
<213> ORGANISM: ARTIFICIAL SEQUENCE
<220> FEATURE:
<223> OTHER INFORMATION: Antibody or a portion thereof.

<400> SEQUENCE: 262

Asp Ala Ser Gly Ser Ser Leu Tyr Leu Asp Tyr
1               5                   10

<210> SEQ ID NO 263
<211> LENGTH: 15
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 263
aactatggca tgcac                                                      15

<210> SEQ ID NO 264
<211> LENGTH: 51
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 264
gttatatcat atgatggaag taaaaaatac tatgcagact ccgtgaaggg c               51

<210> SEQ ID NO 265
<211> LENGTH: 33
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 265
gatgccagtg ggagctccct ctactctgac tac                                  33

<210> SEQ ID NO 266
<211> LENGTH: 5
<212> TYPE: PRT
<213> ORGANISM: ARTIFICIAL SEQUENCE
<220> FEATURE:
<223> OTHER INFORMATION: Antibody or a portion thereof.

<400> SEQUENCE: 266

Asn Tyr Gly Met His
1               5

<210> SEQ ID NO 267
<211> LENGTH: 17
<212> TYPE: PRT
<213> ORGANISM: ARTIFICIAL SEQUENCE
<220> FEATURE:
<223> OTHER INFORMATION: Antibody or a portion thereof.

<400> SEQUENCE: 267

Val Ile Ser Tyr Asp Gly Ser Lys Lys Tyr Tyr Ala Asp Ser Val Lys
1               5                   10                  15
Gly

<210> SEQ ID NO 268
```

```
<211> LENGTH: 11
<212> TYPE: PRT
<213> ORGANISM: ARTIFICIAL SEQUENCE
<220> FEATURE:
<223> OTHER INFORMATION: Antibody or a portion thereof.

<400> SEQUENCE: 268

Asp Ala Ser Gly Ser Ser Leu Tyr Ser Asp Tyr
1               5                   10

<210> SEQ ID NO 269
<211> LENGTH: 15
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 269
agctatggca tgcac                                                        15

<210> SEQ ID NO 270
<211> LENGTH: 51
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 270
gttatatcaa agatggaag ttataaatac tatgcggact ccgtgaaggg c                 51

<210> SEQ ID NO 271
<211> LENGTH: 33
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 271
gatgccagtg ggagctccct ctacttagac tac                                    33

<210> SEQ ID NO 272
<211> LENGTH: 5
<212> TYPE: PRT
<213> ORGANISM: ARTIFICIAL SEQUENCE
<220> FEATURE:
<223> OTHER INFORMATION: Antibody or a portion thereof.

<400> SEQUENCE: 272

Ser Tyr Gly Met His
1               5

<210> SEQ ID NO 273
<211> LENGTH: 17
<212> TYPE: PRT
<213> ORGANISM: ARTIFICIAL SEQUENCE
<220> FEATURE:
<223> OTHER INFORMATION: Antibody or a portion thereof.

<400> SEQUENCE: 273

Val Ile Ser Lys Asp Gly Ser Tyr Lys Tyr Tyr Ala Asp Ser Val Lys
1               5                   10                  15

Gly
```

<210> SEQ ID NO 274
<211> LENGTH: 11
<212> TYPE: PRT
<213> ORGANISM: ARTIFICIAL SEQUENCE
<220> FEATURE:
<223> OTHER INFORMATION: Antibody or a portion thereof.

<400> SEQUENCE: 274

Asp Ala Ser Gly Ser Ser Leu Tyr Leu Asp Tyr
1               5                   10

<210> SEQ ID NO 275
<211> LENGTH: 15
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 275
agctatggca tgcac                                               15

<210> SEQ ID NO 276
<211> LENGTH: 51
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 276
gttatatggt atgatggaag taataaatac catgcagact ccgtgaaggg c        51

<210> SEQ ID NO 277
<211> LENGTH: 33
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 277
gactttgctt acttctacta cggtatggac gtc                           33

<210> SEQ ID NO 278
<211> LENGTH: 5
<212> TYPE: PRT
<213> ORGANISM: ARTIFICIAL SEQUENCE
<220> FEATURE:
<223> OTHER INFORMATION: Antibody or a portion thereof.

<400> SEQUENCE: 278

Ser Tyr Gly Met His
1               5

<210> SEQ ID NO 279
<211> LENGTH: 17
<212> TYPE: PRT
<213> ORGANISM: ARTIFICIAL SEQUENCE
<220> FEATURE:
<223> OTHER INFORMATION: Antibody or a portion thereof.

<400> SEQUENCE: 279

Val Ile Trp Tyr Asp Gly Ser Asn Lys Tyr His Ala Asp Ser Val Lys
1               5                   10                  15

Gly

<210> SEQ ID NO 280
<211> LENGTH: 11
<212> TYPE: PRT
<213> ORGANISM: ARTIFICIAL SEQUENCE
<220> FEATURE:
<223> OTHER INFORMATION: Antibody or a portion thereof.

<400> SEQUENCE: 280

Asp Phe Ala Tyr Phe Tyr Tyr Gly Met Asp Val
1               5                   10

<210> SEQ ID NO 281
<211> LENGTH: 21
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 281
actagtggag tgggtgtggg c                                             21

<210> SEQ ID NO 282
<211> LENGTH: 48
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 282
ctcatttatt ggaatgatga taagcgctac agcccatctc tgaagagc                48

<210> SEQ ID NO 283
<211> LENGTH: 39
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 283
agacatggct acgataggat gcgtgatgct tttgatatc                          39

<210> SEQ ID NO 284
<211> LENGTH: 7
<212> TYPE: PRT
<213> ORGANISM: ARTIFICIAL SEQUENCE
<220> FEATURE:
<223> OTHER INFORMATION: Antibody or a portion thereof.

<400> SEQUENCE: 284

Thr Ser Gly Val Gly Val Gly
1               5

<210> SEQ ID NO 285
<211> LENGTH: 16
<212> TYPE: PRT
<213> ORGANISM: ARTIFICIAL SEQUENCE
<220> FEATURE:
<223> OTHER INFORMATION: Antibody or a portion thereof.

<400> SEQUENCE: 285

Leu Ile Tyr Trp Asn Asp Asp Lys Arg Tyr Ser Pro Ser Leu Lys Ser
1               5                   10                  15

```
<210> SEQ ID NO 286
<211> LENGTH: 13
<212> TYPE: PRT
<213> ORGANISM: ARTIFICIAL SEQUENCE
<220> FEATURE:
<223> OTHER INFORMATION: Antibody or a portion thereof.

<400> SEQUENCE: 286

Arg His Gly Tyr Asp Arg Met Arg Asp Ala Phe Asp Ile
1               5                   10

<210> SEQ ID NO 287
<211> LENGTH: 21
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 287
agtggtggtt actactggag c                                              21

<210> SEQ ID NO 288
<211> LENGTH: 48
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 288
tacatctctt acagtgggag cacctactac aacccgtccc tcaagagt                 48

<210> SEQ ID NO 289
<211> LENGTH: 33
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 289
gagagcccta cggtgactac ggcttttgat atc                                 33

<210> SEQ ID NO 290
<211> LENGTH: 7
<212> TYPE: PRT
<213> ORGANISM: ARTIFICIAL SEQUENCE
<220> FEATURE:
<223> OTHER INFORMATION: Antibody or a portion thereof.

<400> SEQUENCE: 290

Ser Gly Gly Tyr Tyr Trp Ser
1               5

<210> SEQ ID NO 291
<211> LENGTH: 16
<212> TYPE: PRT
<213> ORGANISM: ARTIFICIAL SEQUENCE
<220> FEATURE:
<223> OTHER INFORMATION: Antibody or a portion thereof.

<400> SEQUENCE: 291

Tyr Ile Ser Tyr Ser Gly Ser Thr Tyr Tyr Asn Pro Ser Leu Lys Ser
1               5                   10                  15

<210> SEQ ID NO 292
```

```
<211> LENGTH: 11
<212> TYPE: PRT
<213> ORGANISM: ARTIFICIAL SEQUENCE
<220> FEATURE:
<223> OTHER INFORMATION: Antibody or a portion thereof.

<400> SEQUENCE: 292

Glu Ser Pro Thr Val Thr Thr Ala Phe Asp Ile
1               5                   10

<210> SEQ ID NO 293
<211> LENGTH: 21
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 293
agtggtggtt acgactggag c                                                   21

<210> SEQ ID NO 294
<211> LENGTH: 48
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 294
aacatttatt acagtgggag gacctactac aacccgtccc tcaagagt                       48

<210> SEQ ID NO 295
<211> LENGTH: 48
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 295
gatcgccctt atggaggtaa ttccggctac tactacggta tggacgtc                       48

<210> SEQ ID NO 296
<211> LENGTH: 7
<212> TYPE: PRT
<213> ORGANISM: ARTIFICIAL SEQUENCE
<220> FEATURE:
<223> OTHER INFORMATION: Antibody or a portion thereof.

<400> SEQUENCE: 296

Ser Gly Gly Tyr Asp Trp Ser
1               5

<210> SEQ ID NO 297
<211> LENGTH: 16
<212> TYPE: PRT
<213> ORGANISM: ARTIFICIAL SEQUENCE
<220> FEATURE:
<223> OTHER INFORMATION: Antibody or a portion thereof.

<400> SEQUENCE: 297

Asn Ile Tyr Tyr Ser Gly Arg Thr Tyr Tyr Asn Pro Ser Leu Lys Ser
1               5                   10                  15

<210> SEQ ID NO 298
<211> LENGTH: 16
```

```
<212> TYPE: PRT
<213> ORGANISM: ARTIFICIAL SEQUENCE
<220> FEATURE:
<223> OTHER INFORMATION: Antibody or a portion thereof.

<400> SEQUENCE: 298

Asp Arg Pro Tyr Gly Gly Asn Ser Gly Tyr Tyr Tyr Gly Met Asp Val
1               5                   10                  15

<210> SEQ ID NO 299
<211> LENGTH: 21
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 299
agtggtggtt acgactggag c                                               21

<210> SEQ ID NO 300
<211> LENGTH: 48
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 300
aacatttatt acagtgggag gacctactac aacccgtccc tcaagagt                  48

<210> SEQ ID NO 301
<211> LENGTH: 48
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 301
gatcgccctt atggaggtaa ttccggctac tactacggta tggacgtc                  48

<210> SEQ ID NO 302
<211> LENGTH: 7
<212> TYPE: PRT
<213> ORGANISM: ARTIFICIAL SEQUENCE
<220> FEATURE:
<223> OTHER INFORMATION: Antibody or a portion thereof.

<400> SEQUENCE: 302

Ser Gly Gly Tyr Asp Trp Ser
1               5

<210> SEQ ID NO 303
<211> LENGTH: 16
<212> TYPE: PRT
<213> ORGANISM: ARTIFICIAL SEQUENCE
<220> FEATURE:
<223> OTHER INFORMATION: Antibody or a portion thereof.

<400> SEQUENCE: 303

Asn Ile Tyr Tyr Ser Gly Arg Thr Tyr Tyr Asn Pro Ser Leu Lys Ser
1               5                   10                  15

<210> SEQ ID NO 304
<211> LENGTH: 16
<212> TYPE: PRT
```

<213> ORGANISM: ARTIFICIAL SEQUENCE
<220> FEATURE:
<223> OTHER INFORMATION: Antibody or a portion thereof.

<400> SEQUENCE: 304

Asp Arg Pro Tyr Gly Gly Asn Ser Gly Tyr Tyr Tyr Gly Met Asp Val
1               5                   10                  15

<210> SEQ ID NO 305
<211> LENGTH: 21
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 305
agtagtagtt actattgggg c                                          21

<210> SEQ ID NO 306
<211> LENGTH: 48
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 306
agtatctatt atggtgggaa cacctactac aacccgtccc tcaagagt              48

<210> SEQ ID NO 307
<211> LENGTH: 24
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 307
gaactgcgga gggcttttga tatc                                       24

<210> SEQ ID NO 308
<211> LENGTH: 7
<212> TYPE: PRT
<213> ORGANISM: ARTIFICIAL SEQUENCE
<220> FEATURE:
<223> OTHER INFORMATION: Antibody or a portion thereof.

<400> SEQUENCE: 308

Ser Ser Ser Tyr Tyr Trp Gly
1               5

<210> SEQ ID NO 309
<211> LENGTH: 16
<212> TYPE: PRT
<213> ORGANISM: ARTIFICIAL SEQUENCE
<220> FEATURE:
<223> OTHER INFORMATION: Antibody or a portion thereof.

<400> SEQUENCE: 309

Ser Ile Tyr Tyr Gly Gly Asn Thr Tyr Tyr Asn Pro Ser Leu Lys Ser
1               5                   10                  15

<210> SEQ ID NO 310
<211> LENGTH: 8
<212> TYPE: PRT
<213> ORGANISM: ARTIFICIAL SEQUENCE

<220> FEATURE:
<223> OTHER INFORMATION: Antibody or a portion thereof.

<400> SEQUENCE: 310

Glu Leu Arg Arg Ala Phe Asp Ile
1               5

<210> SEQ ID NO 311
<211> LENGTH: 21
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 311
agtggtagtt actactgggg c                                           21

<210> SEQ ID NO 312
<211> LENGTH: 48
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 312
agtatctatt atggtgggaa cacctactac aacccgtccc tcaagagt              48

<210> SEQ ID NO 313
<211> LENGTH: 24
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 313
gaactgcgga gggcttttga tatc                                        24

<210> SEQ ID NO 314
<211> LENGTH: 7
<212> TYPE: PRT
<213> ORGANISM: ARTIFICIAL SEQUENCE
<220> FEATURE:
<223> OTHER INFORMATION: Antibody or a portion thereof.

<400> SEQUENCE: 314

Ser Gly Ser Tyr Tyr Trp Gly
1               5

<210> SEQ ID NO 315
<211> LENGTH: 16
<212> TYPE: PRT
<213> ORGANISM: ARTIFICIAL SEQUENCE
<220> FEATURE:
<223> OTHER INFORMATION: Antibody or a portion thereof.

<400> SEQUENCE: 315

Ser Ile Tyr Tyr Gly Gly Asn Thr Tyr Tyr Asn Pro Ser Leu Lys Ser
1               5                   10                  15

<210> SEQ ID NO 316
<211> LENGTH: 8
<212> TYPE: PRT
<213> ORGANISM: ARTIFICIAL SEQUENCE
<220> FEATURE:

<223> OTHER INFORMATION: Antibody or a portion thereof.

<400> SEQUENCE: 316

Glu Leu Arg Arg Ala Phe Asp Ile
1               5

<210> SEQ ID NO 317
<211> LENGTH: 15
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 317
agctttggca tgcac                                                    15

<210> SEQ ID NO 318
<211> LENGTH: 51
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 318
attttatcat tgatggaaa taataaatac tatgcagact ccgtgaaggg c              51

<210> SEQ ID NO 319
<211> LENGTH: 36
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 319
gagggggggt ataactggaa ctacgacttt gactac                             36

<210> SEQ ID NO 320
<211> LENGTH: 5
<212> TYPE: PRT
<213> ORGANISM: ARTIFICIAL SEQUENCE
<220> FEATURE:
<223> OTHER INFORMATION: Antibody or a portion thereof.

<400> SEQUENCE: 320

Ser Phe Gly Met His
1               5

<210> SEQ ID NO 321
<211> LENGTH: 17
<212> TYPE: PRT
<213> ORGANISM: ARTIFICIAL SEQUENCE
<220> FEATURE:
<223> OTHER INFORMATION: Antibody or a portion thereof.

<400> SEQUENCE: 321

Ile Leu Ser Phe Asp Gly Asn Asn Lys Tyr Tyr Ala Asp Ser Val Lys
1               5                   10                  15
Gly

<210> SEQ ID NO 322
<211> LENGTH: 12
<212> TYPE: PRT
<213> ORGANISM: ARTIFICIAL SEQUENCE

<220> FEATURE:
<223> OTHER INFORMATION: Antibody or a portion thereof.

<400> SEQUENCE: 322

Glu Gly Gly Tyr Asn Trp Asn Tyr Asp Phe Asp Tyr
1               5                   10

<210> SEQ ID NO 323
<211> LENGTH: 21
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 323
agtggtggtg actactggag c                                              21

<210> SEQ ID NO 324
<211> LENGTH: 48
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 324
tatatctatt acactgggag caccaactac aacccctccc tcaagagt                 48

<210> SEQ ID NO 325
<211> LENGTH: 30
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 325
tcgggtgtag caatggctcg ctttgactac                                     30

<210> SEQ ID NO 326
<211> LENGTH: 7
<212> TYPE: PRT
<213> ORGANISM: ARTIFICIAL SEQUENCE
<220> FEATURE:
<223> OTHER INFORMATION: Antibody or a portion thereof.

<400> SEQUENCE: 326

Ser Gly Gly Asp Tyr Trp Ser
1               5

<210> SEQ ID NO 327
<211> LENGTH: 16
<212> TYPE: PRT
<213> ORGANISM: ARTIFICIAL SEQUENCE
<220> FEATURE:
<223> OTHER INFORMATION: Antibody or a portion thereof.

<400> SEQUENCE: 327

Tyr Ile Tyr Tyr Thr Gly Ser Thr Asn Tyr Asn Pro Ser Leu Lys Ser
1               5                   10                  15

<210> SEQ ID NO 328
<211> LENGTH: 10
<212> TYPE: PRT
<213> ORGANISM: ARTIFICIAL SEQUENCE
<220> FEATURE:

<223> OTHER INFORMATION: Antibody or a portion thereof.

<400> SEQUENCE: 328

Ser Gly Val Ala Met Ala Arg Phe Asp Tyr
1               5                   10

<210> SEQ ID NO 329
<211> LENGTH: 21
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 329
agtggtggct accactggag c                                           21

<210> SEQ ID NO 330
<211> LENGTH: 48
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 330
tacatctatt acagtgggag cacctactac aacccgtccc tcaagagt              48

<210> SEQ ID NO 331
<211> LENGTH: 33
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 331
gagactacgg tggtaaaggg gtacttcgat ctc                              33

<210> SEQ ID NO 332
<211> LENGTH: 7
<212> TYPE: PRT
<213> ORGANISM: ARTIFICIAL SEQUENCE
<220> FEATURE:
<223> OTHER INFORMATION: Antibody or a portion thereof.

<400> SEQUENCE: 332

Ser Gly Gly Tyr His Trp Ser
1               5

<210> SEQ ID NO 333
<211> LENGTH: 16
<212> TYPE: PRT
<213> ORGANISM: ARTIFICIAL SEQUENCE
<220> FEATURE:
<223> OTHER INFORMATION: Antibody or a portion thereof.

<400> SEQUENCE: 333

Tyr Ile Tyr Tyr Ser Gly Ser Thr Tyr Tyr Asn Pro Ser Leu Lys Ser
1               5                   10                  15

<210> SEQ ID NO 334
<211> LENGTH: 11
<212> TYPE: PRT
<213> ORGANISM: ARTIFICIAL SEQUENCE
<220> FEATURE:
<223> OTHER INFORMATION: Antibody or a portion thereof.

-continued

<400> SEQUENCE: 334

Glu Thr Thr Val Val Lys Gly Tyr Phe Asp Leu
1               5                   10

<210> SEQ ID NO 335
<211> LENGTH: 15
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 335
tacgcctgga tgggc                                                         15

<210> SEQ ID NO 336
<211> LENGTH: 57
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 336
cgtattaaaa gcaaaactga tggtgggaca acagactacg ctgcacccgt gaaaggc           57

<210> SEQ ID NO 337
<211> LENGTH: 27
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 337
gatggggcac tggcccccca cggctac                                            27

<210> SEQ ID NO 338
<211> LENGTH: 5
<212> TYPE: PRT
<213> ORGANISM: ARTIFICIAL SEQUENCE
<220> FEATURE:
<223> OTHER INFORMATION: Antibody or a portion thereof.

<400> SEQUENCE: 338

Tyr Ala Trp Met Gly
1               5

<210> SEQ ID NO 339
<211> LENGTH: 19
<212> TYPE: PRT
<213> ORGANISM: ARTIFICIAL SEQUENCE
<220> FEATURE:
<223> OTHER INFORMATION: Antibody or a portion thereof.

<400> SEQUENCE: 339

Arg Ile Lys Ser Lys Thr Asp Gly Gly Thr Thr Asp Tyr Ala Ala Pro
1               5                   10                  15

Val Lys Gly

<210> SEQ ID NO 340
<211> LENGTH: 9
<212> TYPE: PRT
<213> ORGANISM: ARTIFICIAL SEQUENCE
<220> FEATURE:

```
<223> OTHER INFORMATION: Antibody or a portion thereof.

<400> SEQUENCE: 340

Asp Gly Ala Leu Ala Pro His Gly Tyr
1               5

<210> SEQ ID NO 341
<211> LENGTH: 21
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 341
agtggtggtt acttctggag c                                              21

<210> SEQ ID NO 342
<211> LENGTH: 48
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 342
tacatctatt acagtgggag cacctactac aacccgtccc tcaagagt                 48

<210> SEQ ID NO 343
<211> LENGTH: 27
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 343
tggggagcag cagccggctt tgactat                                        27

<210> SEQ ID NO 344
<211> LENGTH: 7
<212> TYPE: PRT
<213> ORGANISM: ARTIFICIAL SEQUENCE
<220> FEATURE:
<223> OTHER INFORMATION: Antibody or a portion thereof.

<400> SEQUENCE: 344

Ser Gly Gly Tyr Phe Trp Ser
1               5

<210> SEQ ID NO 345
<211> LENGTH: 16
<212> TYPE: PRT
<213> ORGANISM: ARTIFICIAL SEQUENCE
<220> FEATURE:
<223> OTHER INFORMATION: Antibody or a portion thereof.

<400> SEQUENCE: 345

Tyr Ile Tyr Tyr Ser Gly Ser Thr Tyr Tyr Asn Pro Ser Leu Lys Ser
1               5                   10                  15

<210> SEQ ID NO 346
<211> LENGTH: 9
<212> TYPE: PRT
<213> ORGANISM: ARTIFICIAL SEQUENCE
<220> FEATURE:
<223> OTHER INFORMATION: Antibody or a portion thereof.
```

```
<400> SEQUENCE: 346

Trp Gly Ala Ala Ala Gly Phe Asp Tyr
1               5

<210> SEQ ID NO 347
<211> LENGTH: 15
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 347
agctatggca tgcac                                                          15

<210> SEQ ID NO 348
<211> LENGTH: 51
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 348
gttatatcat atgatggaaa taataaatac tatgcagact ccgtgaaggg c                   51

<210> SEQ ID NO 349
<211> LENGTH: 33
<212> TYPE: DNA
<213> ORGANISM: ARTIFICIAL SEQUENCE
<220> FEATURE:
<223> OTHER INFORMATION: Polynucleotide encoding the antibody or a
      portion thereof.

<400> SEQUENCE: 349
gatgccagtg ggagctccct ctaccttgac tac                                       33

<210> SEQ ID NO 350
<211> LENGTH: 5
<212> TYPE: PRT
<213> ORGANISM: ARTIFICIAL SEQUENCE
<220> FEATURE:
<223> OTHER INFORMATION: Antibody or a portion thereof.

<400> SEQUENCE: 350

Ser Tyr Gly Met His
1               5

<210> SEQ ID NO 351
<211> LENGTH: 17
<212> TYPE: PRT
<213> ORGANISM: ARTIFICIAL SEQUENCE
<220> FEATURE:
<223> OTHER INFORMATION: Antibody or a portion thereof.

<400> SEQUENCE: 351

Val Ile Ser Tyr Asp Gly Asn Asn Lys Tyr Tyr Ala Asp Ser Val Lys
1               5                   10                  15

Gly

<210> SEQ ID NO 352
<211> LENGTH: 11
<212> TYPE: PRT
<213> ORGANISM: ARTIFICIAL SEQUENCE
<220> FEATURE:
```

<223> OTHER INFORMATION: Antibody or a portion thereof.

<400> SEQUENCE: 352

```
Asp Ala Ser Gly Ser Ser Leu Tyr Leu Asp Tyr
1               5                   10
```

<210> SEQ ID NO 353
<211> LENGTH: 1218
<212> TYPE: PRT
<213> ORGANISM: Homo sapiens
<220> FEATURE:
<221> NAME/KEY: MISC_FEATURE
<223> OTHER INFORMATION: HUMAN JAGGED1

<400> SEQUENCE: 353

```
Met Arg Ser Pro Arg Thr Arg Gly Arg Ser Gly Arg Pro Leu Ser Leu
1               5                   10                  15

Leu Leu Ala Leu Leu Cys Ala Leu Arg Ala Lys Val Cys Gly Ala Ser
                20                  25                  30

Gly Gln Phe Glu Leu Glu Ile Leu Ser Met Gln Asn Val Asn Gly Glu
            35                  40                  45

Leu Gln Asn Gly Asn Cys Cys Gly Gly Ala Arg Asn Pro Gly Asp Arg
        50                  55                  60

Lys Cys Thr Arg Asp Glu Cys Asp Thr Tyr Phe Lys Val Cys Leu Lys
65                  70                  75                  80

Glu Tyr Gln Ser Arg Val Thr Ala Gly Gly Pro Cys Ser Phe Gly Ser
                85                  90                  95

Gly Ser Thr Pro Val Ile Gly Gly Asn Thr Phe Asn Leu Lys Ala Ser
            100                 105                 110

Arg Gly Asn Asp Arg Asn Arg Ile Val Leu Pro Phe Ser Phe Ala Trp
        115                 120                 125

Pro Arg Ser Tyr Thr Leu Leu Val Glu Ala Trp Asp Ser Ser Asn Asp
130                 135                 140

Thr Val Gln Pro Asp Ser Ile Ile Glu Lys Ala Ser His Ser Gly Met
145                 150                 155                 160

Ile Asn Pro Ser Arg Gln Trp Gln Thr Leu Lys Gln Asn Thr Gly Val
                165                 170                 175

Ala His Phe Glu Tyr Gln Ile Arg Val Thr Cys Asp Asp Tyr Tyr Tyr
            180                 185                 190

Gly Phe Gly Cys Asn Lys Phe Cys Arg Pro Arg Asp Asp Phe Phe Gly
        195                 200                 205

His Tyr Ala Cys Asp Gln Asn Gly Asn Lys Thr Cys Met Glu Gly Trp
    210                 215                 220

Met Gly Arg Glu Cys Asn Arg Ala Ile Cys Arg Gln Gly Cys Ser Pro
225                 230                 235                 240

Lys His Gly Ser Cys Lys Leu Pro Gly Asp Cys Arg Cys Gln Tyr Gly
                245                 250                 255

Trp Gln Gly Leu Tyr Cys Asp Lys Cys Ile Pro His Pro Gly Cys Val
            260                 265                 270

His Gly Ile Cys Asn Glu Pro Trp Gln Cys Leu Cys Glu Thr Asn Trp
        275                 280                 285

Gly Gly Gln Leu Cys Asp Lys Asp Leu Asn Tyr Cys Gly Thr His His
    290                 295                 300

Pro Cys Leu Asn Gly Gly Thr Cys Ser Asn Thr Gly Pro Asp Lys Tyr
305                 310                 315                 320

Gln Cys Ser Cys Pro Glu Gly Tyr Ser Gly Pro Asn Cys Glu Ile Ala
```

-continued

```
            325                 330                 335
Glu His Ala Cys Leu Ser Asp Pro Cys His Asn Arg Gly Ser Cys Lys
            340                 345                 350
Glu Thr Ser Leu Gly Phe Glu Cys Glu Cys Ser Pro Gly Trp Thr Gly
            355                 360                 365
Pro Thr Cys Ser Thr Asn Ile Asp Asp Cys Ser Pro Asn Asn Cys Ser
        370                 375                 380
His Gly Gly Thr Cys Gln Asp Leu Val Asn Gly Phe Lys Cys Val Cys
385                 390                 395                 400
Pro Pro Gln Trp Thr Gly Lys Thr Cys Gln Leu Asp Ala Asn Glu Cys
                405                 410                 415
Glu Ala Lys Pro Cys Val Asn Ala Lys Ser Cys Lys Asn Leu Ile Ala
                420                 425                 430
Ser Tyr Tyr Cys Asp Cys Leu Pro Gly Trp Met Gly Gln Asn Cys Asp
                435                 440                 445
Ile Asn Ile Asn Asp Cys Leu Gly Gln Cys Gln Asn Asp Ala Ser Cys
        450                 455                 460
Arg Asp Leu Val Asn Gly Tyr Arg Cys Ile Cys Pro Pro Gly Tyr Ala
465                 470                 475                 480
Gly Asp His Cys Glu Arg Asp Ile Asp Glu Cys Ala Ser Asn Pro Cys
                485                 490                 495
Leu Asp Gly Gly His Cys Gln Asn Glu Ile Asn Arg Phe Gln Cys Leu
            500                 505                 510
Cys Pro Thr Gly Phe Ser Gly Asn Leu Cys Gln Leu Asp Ile Asp Tyr
            515                 520                 525
Cys Glu Pro Asn Pro Cys Gln Asn Gly Ala Gln Cys Tyr Asn Arg Ala
        530                 535                 540
Ser Asp Tyr Phe Cys Lys Cys Pro Glu Asp Tyr Glu Gly Lys Asn Cys
545                 550                 555                 560
Ser His Leu Lys Asp His Cys Arg Thr Thr Pro Cys Glu Val Ile Asp
                565                 570                 575
Ser Cys Thr Val Ala Met Ala Ser Asn Asp Thr Pro Glu Gly Val Arg
            580                 585                 590
Tyr Ile Ser Ser Asn Val Cys Gly Pro His Gly Lys Cys Lys Ser Gln
            595                 600                 605
Ser Gly Gly Lys Phe Thr Cys Asp Cys Asn Lys Gly Phe Thr Gly Thr
        610                 615                 620
Tyr Cys His Glu Asn Ile Asn Asp Cys Glu Ser Asn Pro Cys Arg Asn
625                 630                 635                 640
Gly Gly Thr Cys Ile Asp Gly Val Asn Ser Tyr Lys Cys Ile Cys Ser
                645                 650                 655
Asp Gly Trp Glu Gly Ala Tyr Cys Glu Thr Asn Ile Asn Asp Cys Ser
            660                 665                 670
Gln Asn Pro Cys His Asn Gly Gly Thr Cys Arg Asp Leu Val Asn Asp
            675                 680                 685
Phe Tyr Cys Asp Cys Lys Asn Gly Trp Lys Gly Lys Thr Cys His Ser
        690                 695                 700
Arg Asp Ser Gln Cys Asp Glu Ala Thr Cys Asn Asn Gly Gly Thr Cys
705                 710                 715                 720
Tyr Asp Glu Gly Asp Ala Phe Lys Cys Met Cys Pro Gly Gly Trp Glu
                725                 730                 735
Gly Thr Thr Cys Asn Ile Ala Arg Asn Ser Ser Cys Leu Pro Asn Pro
            740                 745                 750
```

-continued

Cys His Asn Gly Gly Thr Cys Val Val Asn Gly Glu Ser Phe Thr Cys
            755                 760                 765

Val Cys Lys Glu Gly Trp Glu Gly Pro Ile Cys Ala Gln Asn Thr Asn
770                 775                 780

Asp Cys Ser Pro His Pro Cys Tyr Asn Ser Gly Thr Cys Val Asp Gly
785                 790                 795                 800

Asp Asn Trp Tyr Arg Cys Glu Cys Ala Pro Gly Phe Ala Gly Pro Asp
                805                 810                 815

Cys Arg Ile Asn Ile Asn Glu Cys Gln Ser Ser Pro Cys Ala Phe Gly
                820                 825                 830

Ala Thr Cys Val Asp Glu Ile Asn Gly Tyr Arg Cys Val Cys Pro Pro
            835                 840                 845

Gly His Ser Gly Ala Lys Cys Gln Glu Val Ser Gly Arg Pro Cys Ile
850                 855                 860

Thr Met Gly Ser Val Ile Pro Asp Gly Ala Lys Trp Asp Asp Cys
865                 870                 875                 880

Asn Thr Cys Gln Cys Leu Asn Gly Arg Ile Ala Cys Ser Lys Val Trp
                885                 890                 895

Cys Gly Pro Arg Pro Cys Leu Leu His Lys Gly His Ser Glu Cys Pro
            900                 905                 910

Ser Gly Gln Ser Cys Ile Pro Ile Leu Asp Asp Gln Cys Phe Val His
                915                 920                 925

Pro Cys Thr Gly Val Gly Glu Cys Arg Ser Ser Leu Gln Pro Val
            930                 935                 940

Lys Thr Lys Cys Thr Ser Asp Ser Tyr Tyr Gln Asp Asn Cys Ala Asn
945                 950                 955                 960

Ile Thr Phe Thr Phe Asn Lys Glu Met Met Ser Pro Gly Leu Thr Thr
                965                 970                 975

Glu His Ile Cys Ser Glu Leu Arg Asn Leu Asn Ile Leu Lys Asn Val
            980                 985                 990

Ser Ala Glu Tyr Ser Ile Tyr Ile Ala Cys Glu Pro Ser Pro Ser Ala
            995                 1000                1005

Asn Asn Glu Ile His Val Ala Ile Ser Ala Glu Asp Ile Arg Asp
    1010                1015                1020

Asp Gly Asn Pro Ile Lys Glu Ile Thr Asp Lys Ile Ile Asp Leu
    1025                1030                1035

Val Ser Lys Arg Asp Gly Asn Ser Ser Leu Ile Ala Ala Val Ala
    1040                1045                1050

Glu Val Arg Val Gln Arg Arg Pro Leu Lys Asn Arg Thr Asp Phe
    1055                1060                1065

Leu Val Pro Leu Leu Ser Ser Val Leu Thr Val Ala Trp Ile Cys
    1070                1075                1080

Cys Leu Val Thr Ala Phe Tyr Trp Cys Leu Arg Lys Arg Arg Lys
    1085                1090                1095

Pro Gly Ser His Thr His Ser Ala Ser Glu Asp Asn Thr Thr Asn
    1100                1105                1110

Asn Val Arg Glu Gln Leu Asn Gln Ile Lys Asn Pro Ile Glu Lys
    1115                1120                1125

His Gly Ala Asn Thr Val Pro Ile Lys Asp Tyr Glu Asn Lys Asn
    1130                1135                1140

Ser Lys Met Ser Lys Ile Arg Thr His Asn Ser Glu Val Glu Glu
    1145                1150                1155

| | | | |
|---|---|---|---|
| Asp | Asp Met Asp Lys His Gln | Gln Lys Ala Arg Phe | Ala Lys Gln |
| 1160 | 1165 | 1170 | |

Pro Ala Tyr Thr Leu Val Asp Arg Glu Glu Lys Pro Pro Asn Gly
　　1175　　　　　　　　1180　　　　　　　　1185

Thr Pro Thr Lys His Pro Asn Trp Thr Asn Lys Gln Asp Asn Arg
　　1190　　　　　　　　1195　　　　　　　　1200

Asp Leu Glu Ser Ala Gln Ser Leu Asn Arg Met Glu Tyr Ile Val
　　1205　　　　　　　　1210　　　　　　　　1215

```
<210> SEQ ID NO 354
<211> LENGTH: 3657
<212> TYPE: DNA
<213> ORGANISM: Homo sapiens
<220> FEATURE:
<221> NAME/KEY: misc_feature
<223> OTHER INFORMATION: JAGGED1 DNA

<400> SEQUENCE: 354
```

| | | | | | |
|---|---|---|---|---|---|
| atgcgttccc | cacggacgcg | cggccggtcc | gggcgccccc | taagcctcct | gctcgccctg | 60 |
| ctctgtgccc | tgcgagccaa | ggtgtgtggg | gcctcgggtc | agttcgagtt | ggagatcctg | 120 |
| tccatgcaga | acgtgaacgg | ggagctgcag | aacgggaact | gctgcggcgg | cgcccggaac | 180 |
| ccgggagacc | gcaagtgcac | ccgcgacgag | tgtgacacat | acttcaaagt | gtgcctcaag | 240 |
| gagtatcagt | cccgcgtcac | ggccgggggg | ccctgcagct | tcggctcagg | gtccacgcct | 300 |
| gtcatcgggg | gcaacacctt | caacctcaag | gccagccgcg | gcaacgaccg | caaccgcatc | 360 |
| gtgctgcctt | tcagtttcgc | ctggccgagg | tcctatacgt | tgcttgtgga | ggcgtgggat | 420 |
| tccagtaatg | acaccgttca | acctgacagt | attattgaaa | aggcttctca | ctcgggcatg | 480 |
| atcaacccca | gccggcagtg | gcagacgctg | aagcagaaca | cgggcgttgc | ccactttgag | 540 |
| tatcagatcc | gcgtgacctg | tgatgactac | tactatggct | ttggctgcaa | taagttctgc | 600 |
| cgccccagag | atgacttctt | tggacactat | gcctgtgacc | agaatggcaa | caaaacttgc | 660 |
| atggaaggct | ggatgggccg | cgaatgtaac | agagctattt | gccgacaagg | ctgcagtcct | 720 |
| aagcatggt | cttgcaaaact | cccaggtgac | tgcaggtgcc | agtacggctg | gcaaggcctg | 780 |
| tactgtgata | agtgcatccc | acacccggga | tgcgtccacg | gcatctgtaa | tgagccctgg | 840 |
| cagtgcctct | gtgagaccaa | ctggggcggc | cagctctgtg | acaaagatct | caattactgt | 900 |
| gggactcatc | agccgtgtct | caacgggggg | acttgtagca | acacaggccc | tgacaaatat | 960 |
| cagtgttcct | gccctgaggg | gtattcagga | cccaactgtg | aaattgctga | gcacgcctgc | 1020 |
| ctctctgatc | cctgtcacaa | cagaggcagc | tgtaaggaga | cctccctggg | ctttgagtgt | 1080 |
| gagtgttccc | caggctggac | cggccccaca | tgctctacaa | acattgatga | ctgttctcct | 1140 |
| aataactgtt | cccacggggg | cacctgccag | gacctggtta | acggatttaa | gtgtgtgtgc | 1200 |
| cccccacagt | ggactgggaa | aacgtgccag | ttagatgcaa | atgaatgtga | ggccaaacct | 1260 |
| tgtgtaaacg | ccaaatcctg | taagaatctc | attgccagct | actactgcga | ctgtcttccc | 1320 |
| ggctggatgg | gtcagaattg | tgacataaat | attaatgact | gccttggcca | gtgtcagaat | 1380 |
| gacgcctcct | gtcgggattt | ggttaatggt | tatcgctgta | tctgtccacc | tggctatgca | 1440 |
| ggcgatcact | gtgagagaga | catcgatgaa | tgtgccagca | acccctgttt | ggatgggggt | 1500 |
| cactgtcaga | atgaaatcaa | cagattccag | tgtctgtgtc | ccactggttt | ctctggaaac | 1560 |
| ctctgtcagc | tggacatcga | ttattgtgag | cctaatcccT | gccagaacgg | tgcccagtgc | 1620 |
| tacaaccgtg | ccagtgacta | tttctgcaag | tgccccgagg | actatgaggg | caagaactgc | 1680 |

```
tcacacctga aagaccactg ccgcacgacc ccctgtgaag tgattgacag ctgcacagtg    1740
gccatggctt ccaacgacac acctgaaggg gtgcggtata tttcctccaa cgtctgtggt    1800
cctcacggga agtgcaagag tcagtcggga ggcaaattca cctgtgactg taacaaaggc    1860
ttcacgggaa catactgcca tgaaaatatt aatgactgtg agagcaaccc ttgtagaaac    1920
ggtggcactt gcatcgatgg tgtcaactcc tacaagtgca tctgtagtga cggctgggag    1980
ggggcctact gtgaaaccaa tattaatgac tgcagccaga accccctgcca caatgggggc    2040
acgtgtcgcg acctggtcaa tgacttctac tgtgactgta aaaatgggtg gaaaggaaag    2100
acctgccact cacgtgacag tcagtgtgat gaggccacgt gcaacaacgg tggcacctgc    2160
tatgatgagg gggatgctttt aagtgcatg tgtcctggcg gctgggaagg aacaacctgt    2220
aacatagccc gaaacagtag ctgcctgccc aaccccctgcc ataatggggg cacatgtgtg    2280
gtcaacggcg agtcctttac gtgcgtctgc aaggaaggct gggaggggcc catctgtgct    2340
cagaatacca atgactgcag ccctcatccc tgttacaaca gcggcacctg tgtggatgga    2400
gacaactggt accggtgcga atgtgccccg ggttttgctg gcccgactg cagaataaac    2460
atcaatgaat gccagtcttc accttgtgcc tttggagcga cctgtgtgga tgagatcaat    2520
ggctaccggt gtgtctgccc tccagggcac agtggtgcca agtgccagga agttccaggg    2580
agaccttgca tcaccatggg gagtgtgata ccagatgggg ccaaatggga tgatgactgt    2640
aatacctgcc agtgcctgaa tggacggatc gcctgctcaa aggtctggtg tggccctcga    2700
ccttgcctgc tccacaaagg gcacagcgag tgccccagcg ggcagagctg catccccatc    2760
ctggacgacc agtgcttcgt ccaccccctgc actggtgtgg gcgagtgtcg gtcttccagt    2820
ctccagccgg tgaagacaaa gtgcacctct gactcctatt accaggataa ctgtgcgaac    2880
atcacatttta cctttaacaa ggagatgatg tcaccaggtc ttactacgga gcacatttgc    2940
agtgaattga ggaatttgaa tattttgaag aatgtttccg ctgaatattc aatctacatc    3000
gcttgcgagc cttccccttc agcgaacaat gaaatacatg tggccatttc tgctgaagat    3060
atacgggatg atgggaaccc gatcaaggaa atcactgaca aaataattga tcttgttagt    3120
aaacgtgatg gaaacagctc gctgattgct gccgttgcag aagtaagagt tcagaggcgg    3180
cctctgaaga acagaacaga tttccttgtt cccttgctga gctctgtctt aactgtggct    3240
tggatctgtt gcttggtgac ggccttctac tggtgcctgc ggaagcggcg gaagccgggc    3300
agccacacac actcagcctc tgaggacaac accaccaaca acgtgcggga gcagctgaac    3360
cagatcaaaa accccattga gaacatggg gccaacacgg tccccatcaa ggattacgag    3420
aacaagaact ccaaaatgtc taaataagg acacacaatt ctgaagtaga agaggacgac    3480
atggacaaac accagcagaa agcccggttt gccaagcagc cggcgtatac gctggtagac    3540
agagaagaga agccccccaa cggcacgccg acaaacacc caaactggac aaacaaacag    3600
gacaacagag acttggaaag tgcccagagc ttaaaccgaa tggagtacat cgtatag      3657
```

<210> SEQ ID NO 355
<211> LENGTH: 22
<212> TYPE: PRT
<213> ORGANISM: ARTIFICIAL SEQUENCE
<220> FEATURE:
<223> OTHER INFORMATION: Leader Sequence

<400> SEQUENCE: 355

Met Asp Met Arg Val Pro Ala Gln Leu Leu Gly Leu Leu Leu Leu Trp
1               5                   10                  15

Leu Arg Gly Ala Arg Cys
            20

<210> SEQ ID NO 356
<211> LENGTH: 66
<212> TYPE: DNA
<213> ORGANISM: ARTIFICIAL SEQUENCE
<220> FEATURE:
<223> OTHER INFORMATION: Leader Sequence

<400> SEQUENCE: 356
atggacatga gagtgcctgc acagctgctg ggcctgctgc tgctgtggct gagaggcgcc    60
agatgc                                                              66

<210> SEQ ID NO 357
<211> LENGTH: 19
<212> TYPE: PRT
<213> ORGANISM: ARTIFICIAL SEQUENCE
<220> FEATURE:
<223> OTHER INFORMATION: Leader Sequence

<400> SEQUENCE: 357

Met Ala Trp Ala Leu Leu Leu Leu Thr Leu Leu Thr Gln Gly Thr Gly
1               5                   10                  15

Ser Trp Ala

<210> SEQ ID NO 358
<211> LENGTH: 57
<212> TYPE: DNA
<213> ORGANISM: ARTIFICIAL SEQUENCE
<220> FEATURE:
<223> OTHER INFORMATION: Leader Sequence

<400> SEQUENCE: 358
atggcctggg ctctgctgct cctcaccctc ctcactcagg gcacagggtc ctgggcc       57

<210> SEQ ID NO 359
<211> LENGTH: 9
<212> TYPE: DNA
<213> ORGANISM: Artificial Sequence
<220> FEATURE:
<223> OTHER INFORMATION: Probe

<400> SEQUENCE: 359 tccaaagat                                                            9

<210> SEQ ID NO 360
<211> LENGTH: 15
<212> TYPE: DNA
<213> ORGANISM: Artificial Sequence
<220> FEATURE:
<223> OTHER INFORMATION: Probe

<400> SEQUENCE: 360
ggtcaaggtc gcaag                                                     15

<210> SEQ ID NO 361
<211> LENGTH: 19
<212> TYPE: DNA
<213> ORGANISM: Artificial Sequence
<220> FEATURE:
<223> OTHER INFORMATION: Primer

<400> SEQUENCE: 361
acttcctccc ctcccttttc                                                19

<210> SEQ ID NO 362
<211> LENGTH: 20
<212> TYPE: DNA
<213> ORGANISM: Artificial Sequence
<220> FEATURE:
<223> OTHER INFORMATION: Primer

<400> SEQUENCE: 362
ctttgctttc cttggtcagg                                          20

<210> SEQ ID NO 363
<211> LENGTH: 9
<212> TYPE: DNA
<213> ORGANISM: Artificial Sequence
<220> FEATURE:
<223> OTHER INFORMATION: Probe

<400> SEQUENCE: 363 cgtttgacg                                                       9

<210> SEQ ID NO 364
<211> LENGTH: 15
<212> TYPE: DNA
<213> ORGANISM: Artificial Sequence
<220> FEATURE:
<223> OTHER INFORMATION: Probe

<400> SEQUENCE: 364
ggaagcaata cacgg                                               15

<210> SEQ ID NO 365
<211> LENGTH: 20
<212> TYPE: DNA
<213> ORGANISM: Artificial Sequence
<220> FEATURE:
<223> OTHER INFORMATION: Primer

<400> SEQUENCE: 365
tacctgctct gtgcttggag                                          20

<210> SEQ ID NO 366
<211> LENGTH: 19
<212> TYPE: DNA
<213> ORGANISM: Artificial Sequence
<220> FEATURE:
<223> OTHER INFORMATION: Primer

<400> SEQUENCE: 366
agggcttggt cagcacata                                           19

<210> SEQ ID NO 367
<211> LENGTH: 9
<212> TYPE: DNA
<213> ORGANISM: Artificial Sequence
<220> FEATURE:
<223> OTHER INFORMATION: Probe

<400> SEQUENCE: 367 aaccccgta                                                       9

<210> SEQ ID NO 368
<211> LENGTH: 14
<212> TYPE: DNA
<213> ORGANISM: Artificial Sequence
<220> FEATURE:

```
<223> OTHER INFORMATION: Probe

<400> SEQUENCE: 368
gaaggtgcca ttgt                                                     14

<210> SEQ ID NO 369
<211> LENGTH: 20
<212> TYPE: DNA
<213> ORGANISM: Artificial Sequence
<220> FEATURE:
<223> OTHER INFORMATION: Primer

<400> SEQUENCE: 369
ccagagaggc aggtacacat                                               20

<210> SEQ ID NO 370
<211> LENGTH: 18
<212> TYPE: DNA
<213> ORGANISM: Artificial Sequence
<220> FEATURE:
<223> OTHER INFORMATION: Primer

<400> SEQUENCE: 370
gcagacctca gctgtgtt                                                 18
```